United States Patent
Spiegel et al.

(10) Patent No.: US 12,364,766 B2
(45) Date of Patent: Jul. 22, 2025

(54) BIFUNCTIONAL SMALL MOLECULES TO TARGET THE SELECTIVE DEGRADATION OF CIRCULATING PROTEINS

(71) Applicant: YALE UNIVERSITY, New Haven, CT (US)

(72) Inventors: David Spiegel, New Haven, CT (US); David Caianiello, Brooklyn, NY (US); Mengwen Zhang, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 1162 days.

(21) Appl. No.: 17/046,221

(22) PCT Filed: Apr. 8, 2019

(86) PCT No.: PCT/US2019/026260
§ 371 (c)(1),
(2) Date: Oct. 8, 2020

(87) PCT Pub. No.: WO2019/199634
PCT Pub. Date: Oct. 17, 2019

(65) Prior Publication Data
US 2021/0145974 A1    May 20, 2021

Related U.S. Application Data

(60) Provisional application No. 62/655,055, filed on Apr. 9, 2018, provisional application No. 62/788,040, filed on Jan. 3, 2019.

(51) Int. Cl.
*A61K 47/64* (2017.01)
*A61K 45/06* (2006.01)
(Continued)

(52) U.S. Cl.
CPC .............. *A61K 47/64* (2017.08); *A61K 45/06* (2013.01); *C07D 261/20* (2013.01);
(Continued)

(58) Field of Classification Search
None
See application file for complete search history.

(56) References Cited

U.S. PATENT DOCUMENTS

| 5,958,408 A | 9/1999 | Griffiths et al. |
| 9,181,224 B2 | 11/2015 | Spiegel et al. |

(Continued)

FOREIGN PATENT DOCUMENTS

| EP | 2191849 A1 | 6/2010 |
| WO | 2006024175 A1 | 3/2006 |

(Continued)

OTHER PUBLICATIONS

Monaco. International Immunology, 2015, 27(1), 55-62 (Year: 2015).*

(Continued)

*Primary Examiner* — Noble E Jarrell
(74) *Attorney, Agent, or Firm* — Saul Ewing LLP; Kathryn Doyle; Domingos J. Silva

(57) ABSTRACT

The present invention is directed to bifunctional small molecules which contain a circulating protein binding moiety (CPBM) linked through a linker group to a cellular receptor binding moiety (CRBM) which is a membrane receptor of degrading cell such as a hepatocyte or other degrading cell. In embodiments, the (CRBM) is a moiety which binds to asialoglycoprotein receptor (an asialoglycoprotein receptor binding moiety, or ASGPRBM) of a hepatocyte. In additional embodiments, the (CRBM) is a moiety which binds to a receptor of other cells which can degrade proteins, such as a LRP1, LDLR, FcγRI, FcRN, Transferrin (Continued)

or Macrophage Scavenger receptor. Pharmaceutical compositions based upon these bifunctional small molecules represent an additional aspect of the present invention. These compounds and/or compositions may be used to treat disease states and conditions by removing circulating proteins through degradation in the hepatocytes or macrophages of a patient or subject in need of therapy. Methods of treating disease states and/or conditions in which circulating proteins are associated with the disease state and/or condition are also described herein.

16 Claims, 152 Drawing Sheets

Specification includes a Sequence Listing.

(51) Int. Cl.
| | | |
|---|---|---|
| C07D 261/20 | (2006.01) | |
| C07D 309/04 | (2006.01) | |
| C07D 413/02 | (2006.01) | |
| C07D 419/02 | (2006.01) | |
| C07H 15/04 | (2006.01) | |

(52) U.S. Cl.
    CPC ......... *C07D 309/04* (2013.01); *C07D 413/02* (2013.01); *C07D 419/02* (2013.01); *C07H 15/04* (2013.01)

(56) References Cited

U.S. PATENT DOCUMENTS

| | | |
|---|---|---|
| 9,296,708 B2 | 3/2016 | Spiegel et al. |
| 9,556,167 B2 | 1/2017 | Spiegel et al. |
| 10,016,412 B2 | 7/2018 | Spiegel et al. |
| 10,066,026 B2 | 9/2018 | Spiegel et al. |
| 10,633,375 B2 | 4/2020 | Yang et al. |
| 10,703,823 B2 | 7/2020 | Spiegel et al. |
| 10,912,836 B2 | 2/2021 | Spiegel et al. |
| 11,014,992 B2 | 5/2021 | Spiegel et al. |
| 11,725,064 B2 | 8/2023 | Spiegel et al. |
| 11,767,301 B2 | 9/2023 | Spiegel et al. |
| 12,083,181 B2 | 9/2024 | Spiegel et al. |
| 2004/0009907 A1 | 1/2004 | Alsobrook et al. |
| 2007/0077197 A1 | 4/2007 | Wedeking et al. |
| 2007/0249682 A1 | 10/2007 | Zheng et al. |
| 2013/0259882 A1 | 10/2013 | Liu |
| 2016/0082112 A1 | 3/2016 | Spiegel et al. |
| 2016/0136299 A1 | 5/2016 | Avila et al. |
| 2016/0207953 A1 | 7/2016 | Liras et al. |
| 2016/0362450 A1 | 12/2016 | Schteingart et al. |
| 2018/0094017 A1 | 4/2018 | Kitade et al. |
| 2018/0155332 A1 | 6/2018 | Spiegel et al. |
| 2018/0327419 A1 | 11/2018 | Bradner et al. |
| 2022/0023434 A1 | 1/2022 | Bertozzi et al. |
| 2023/0090282 A1* | 3/2023 | Spiegel ............... A61K 47/549 424/181.1 |
| 2023/0097887 A1 | 3/2023 | Spiegel et al. |
| 2024/0083859 A1 | 3/2024 | Spiegel et al. |

FOREIGN PATENT DOCUMENTS

| | | |
|---|---|---|
| WO | 2006045505 A1 | 5/2006 |
| WO | 2011038234 A2 | 3/2011 |
| WO | 2015143091 A1 | 9/2015 |
| WO | 2016040305 A1 | 3/2016 |
| WO | 2016057769 A2 | 4/2016 |
| WO | 2017024318 A1 | 2/2017 |
| WO | 2017058944 A1 | 4/2017 |
| WO | 2018146199 A1 | 8/2018 |
| WO | 2019199621 A1 | 10/2019 |
| WO | 2019199634 A1 | 10/2019 |
| WO | 2021072246 A1 | 4/2021 |
| WO | WO-2021072269 A1 * | 4/2021 ............ A61K 38/00 |
| WO | 2021142377 A2 | 7/2021 |
| WO | 2021155317 A1 | 8/2021 |

OTHER PUBLICATIONS

International Search Report and Written Opinion of International Application No. PCT/US2023/064473 issued on Jul. 25, 2023.
International Search Report and Written Opinion of International Application No. PCT/US2023/064470 issued on Aug. 14, 2023.
International Search Report and Written Opinion of International Application No. PCT/US2023/064436 issued on Aug. 15, 2023.
International Search Report and Written Opinion of International Application No. PCT/US2023/064467 issued on Aug. 15, 2023.
Buckley, et al. "Epidermal growth factor receptor expression and gene copy number in conventional hepatocellular carcinoma." American journal of clinical pathology 129.2 (2008): 245-251.
Guerrab, et al. "Anti-EGFR monoclonal antibodies and EGFR tyrosine kinase inhibitors as combination therapy for triple-negative breast cancer." Oncotarget 7.45 (2016): 73618.
Jakobsche, et al. "Exploring binding and effector functions of natural human antibodies using synthetic immunomodulators." ACS chemical biology 8.11 (2013): 2404-2411.
Khorev, et al. "Trivalent, Gal/GalNAc-containing ligands designed for the asialoglycoprotein receptor." Bioorganic & medicinal chemistry 16.9 (2008): 5216-5231.
Palit, et al. "Interaction of a Triantennary Quinoline Glycoconjugate with the Asialoglycoprotein Receptor." ChemMedChem 16.14 (2021): 2211-2216.
Semple, et al. "Synthesis and facile end-group quantification of functionalized PEG azides." Journal of Polymer Science Part A: Polymer Chemistry 54.18 (2016): 2888-2895.
Zhu, et al. "Dendronized DNA Chimeras Harness Scavenger Receptors To Degrade Cell Membrane Proteins." Angewandte Chemie International Edition 62.13 (2023): e202300694.
Goetze, et al. "High-mannose glycans on the Fc region of therapeutic IgG antibodies increase serum clearance in humans." Glycobiology 21.7 (2011): 949-959.
Extended European Search Report for European Patent Application No. EP 20875230.3 issued on Feb. 9, 2024.
"International Search Report and Written Opinion issued by the International Searching Authority (RU) on Aug. 15, 2019 for PCT/US2019/026260."
"International Search Report and Written Opinion issued by the International Searching Authority (RU) on Aug. 8, 2019 for PCT/US2019/026239."
"International Search Report and Written Opinion issued by the International Searching Authority (US) on Mar. 22, 2021 for PCT/US2020/055078."
Benedek , et al., "MIF and D-DT are potential disease severity modifiers in male MS subjects", Proceedings of the National Academy of Sciences, 114, 2017, E8421-E8429.
Bonetto , et al., "Identification of cyclic peptides able to mimic the functional epitope of IgG1-Fc for human FcγRI", The FASEB Journal, 23(2), 2009, 575-585.
Braisted , et al., "Discovery of a Potent Small Molecule IL-2 Inhibitor through Fragment Assembly", J. Am. Chem. Soc, 2003, 3714-3715.
Burmester , et al., "Small Molecule Antagonists of the TGF-pl/TGF-p Receptor Binding Interaction", Medical Oncology, 2006, 553-562.
Calandra , et al., "Protection from septic shock by neutralization of macrophage migration inhibitory factor", Nature Medicine, 6, 2000, 164-170.
Camperi , et al., "Monoclonal antibody purification by affinity chromatography with ligands derived from the screening of peptide combinatory libraries", Biotechnol. Lett, 25, 2003, 1545-1548.
Choe, Weonu , et al., "Fc-Binding Ligands of Immunoglobulin G: An Overview of High Affinity Proteins and Peptides", Materials (994), Dec. 8, 2016, 1-17.

(56) References Cited

OTHER PUBLICATIONS

Cisneros, "A Fluorescence Polarization Assay for Binding to Macrophage Migration Inhibitory Factor and Crystal Structures for Complexes of Two Potent Inhibitors", J. Am. Chem. Soc. (138), Jun. 14, 2016, 1-27.
Croy, et al., "Two Apolipoprotein E Mimetic Peptides, ApoE(130-149) and ApoE(141-155)2, Bind to LRP1", Biochemistry, 2004, 43(23):, 2004, 7328-7335.
David, et al., "Identification and characterization of highly versatile peptide-vectors that bind non-competitively to the low-density lipoprotein receptor for in vivo targeting and delivery of small molecules and protein cargos", PLOS One, 13(2):e0191052, 2018, 1-30.
Delano, et al., "Convergent Solutions to Binding at a Protein-Protein Interface", Science, 287, 2000, 1279-1283.
Dias, et al., "Protein ligand design: from phage display to synthetic protein epitope mimetics in human antibody Fc-binding peptidomimetics", J. Am. Chem. Soc., 128, 2006, 2726-2732.
Dinon, et al., "Structural refinement of protein A mimetic peptide", J. Mol. Recognit.,24, 2011, 1087-1094.
D'souza, Aniash A., et al., "Asialoglycoprotein receptor mediated hepatocyte targeting—Strategies and applications", Jrl. of Controlled Release (203), Apr. 10, 2015, 126-139.
Ehrlich, et al., "Identification of model peptides as affinity ligands for the purification of humanized monoclonal antibodies by means of phage display", J. Biochem. Biophys. Method, 49, 2001, 443-454.
Fairbrother, et al., "Novel Peptides Selected to Bind Vascular Endothelial Growth Factor Target the Receptor-Binding Site.", Biochemistry, 1998, 17754-7764.
Fassina, et al., "Protein a mimetic peptide ligand for affinity purification of antibodies", J. Mol. Recognit, 1996, 564-569.
Geuze, et al., "Intracellular site of asialoglycoprotein receptor-ligand uncoupling: double-label immunoelectron microscopy during receptor-mediated endocytosis", Cell, 32, 1983, 277-287.
Gong, et al., "Development of the double cyclic peptide ligand for antibody purification and protein detection", Bioconjug. Chem., 27, 2016, 1569-1573.
Hussain, et al., "Human anti-macrophage migration inhibitory factor antibodies inhibit growth of human prostate cancer cells in vitro and in vivo", Molecular Cancer Therapeutics, 12, 2013, 1223-1234.
Jacquot, Guillaume, et al., "Optimization and in Vivo Validation of Peptide Vectors Targeting the LDL Receptor" Molecular Pharmaceutics, 3(12), 2016, 4094-4105.
Kang, et al., "Cyclic peptide ligand with high binding capacity for affinity purification of immunoglobulin G", J. Chromatogr. A, 1466, 2016, 105-112.
Kim, et al., "Presumed LRP1-targeting transport peptide delivers B-secretase inhibitor to neurons in vitro with limited efficiency", Scientific Reports, 6, 34297, 2016.
Kim, et al., "Macrophage migration inhibitory factor: a potential therapeutic target for rheumatoid arthritis", The Korean Journal of Internal Medicine, 31, 2016, 634.
Krook, et al., "Novel peptides binding to the Fc-portion of immunoglobulins obtained from a combinatorial phage display peptide library", J. Immunol. Methods, 221, 1998, 51-157.
Landry, et al., "Discovering small molecule ligands of vascular endothelial growth factor that block VEGF-KDR binding using label-free microarray-based assays.", Assay and Drug Development Technologies, 2013, 326-332.
Lee, et al., "Receptor mediated uptake of peptides that bind the human transferrin receptor", European Journal of Biochemistry, 268(7), 2001, 2004-2012.
Lund, et al., "Novel peptide ligand with high binding capacity for antibody purification", J. Chromatogr. A, 1225, 2012, 158-167.
Mcenaney, Patrick J., et al., "Antibody-Recruiting Molecules: An Emerging Paradigm for Engaging Immune Function in Treating Human Disease", ACS Chem. Biol. (7), Jul. 3, 2012, 1139-1151.

Menegatti, et al., "Design of protease-resistant peptide ligands for the purification of antibodies from human plasma", J. Chromatogr. A, 1445, 2016, 93-104.
Menegatti, et al., "mRNA display selection and solid-phase synthesis of Fc-binding cyclic peptide affinity ligands", Biotechnol. Bioeng, 110, 2013, 857-870.
Menegatti, et al., "Reversible cyclic peptide libraries for the discovery of affinity ligands", Anal. Chem., 85, 2013, 9229-9237.
Mezo, et al., "Reduction of IgG in nonhuman primates by a peptide antagonist of the neonatal Fc receptor FcRn", Proceedings of the National Academy of Sciences105(7), 2008, 2337-2342.
Molino, et al., "Use of LDL receptor—targeting peptide vectors for in vitro and in vivo cargo transport across the blood-brain barrier", The FASEB Journal, 31(5), 2017, 1807-1827.
Mu, et al., "Lipid vesicles containing transferrin receptor binding peptide TfR-T12 and octa-arginine conjugate stearyl-R8 efficiently treat brain glioma along with glioma stem cells", Scientific Reports, 7(1), 2017, 3487.
Nalawansha, Dhanusha A., et al., "Targeted Protein Internalization and Degradation by ENDosome TArgeting Chimeras", ACS Central Science 5(6), May 9, 2019, 1079-1084.
Neven, et al., "Macrophage Scavenger Receptor A Mediates Adhesion to Apolipoproteins A-I and E", Biochemistry 48(50), 2009, 11858-11871.
Parker, et al., "Illuminating HIV gp 120-ligand recognition through computationally-driven optimization of antibody-recruiting molecules", Chem. Sci., 2014, 2311-2317.
Reidy, et al., "Homotrimeric macrophage migration inhibitory factor (MIF) drives inflammatory responses in the corneal epithelium by promoting caveolin-rich platform assembly in response to infection", Journal of Biological Chemistry, 288:, 2013, 8269-8278.
Ribeiro, et al., "The Activation Sequence of Thrombospondin-1 Inter-acts with the Latency-associated Peptide to Regulate Activation of Latent Transforming Growth Factor", The Journal of Biological Chemistry, 1999, 13586-13593.
Roseng, Lars, et al., "Uptake, Intracellular Transport, and Degradation of Polyethylene Glycol-modified Asialofetuin in Hepatocytes", The Journal of Biological Chemistry, Jul. 15, 1992, 22987-22930.
Ruan, et al., "A novel peptide ligand RAP12 of LRP1 for glioma targeted drug delivery,", Journal of Controlled Release, 279, 2018, 306-315.
Rullo, et al., "e-engineering the Immune Response to Metastatic Cancer: Antibody-Recruiting Small Molecules Targeting the Urokinase Receptor", Angew. Chem. Int. Ed, 2016, 3642-3646.
Sakamoto, et al., "A novel LRP1-binding peptide L57 that crosses the blood brain barrier", Biochemistry and Biophysics Reports, 12, 2017, 135-139.
Sanhueza, et al., "Efficient Liver Targeting by Polyvalent Display of a Compact Ligand for the Asialoglycoprotein Receptor", Journal of the American Chemical Society, 139, 2017, 3528-3536.
Santi, et al., "Rational design of a transferrin-binding peptide sequence tailored to targeted nanoparticle internalization", Bioconjugate Chemistry, 28(2), 2016, 471-480.
Schwartz, et al., "Characterization of the asialoglycoprotein receptor in a continuous hepatoma line", Journal of Biological Chemistry, 256, 1981, 8878-8881.
Segers, et al., "Scavenger Receptor-AI—Targeted Iron Oxide Nanoparticles for In Vivo MRI Detection of Atherosclerotic Lesions", Arteriosclerosis, Thrombosis, and Vascular Biology, 32(4), 2012, 971-978.
Stokmaier, "Targeting Hepatocytes via the Asialoglycoprotein-Receptor", Basel, 2010, 3-140, 3-141, 3-142, 3.143, 3-149.
Sugita, et al., "Screening of peptide ligands that bind to the Fc region of IgG using peptide array and its application to affinity purification of antibody", Biochem. Eng. J, 79, 2013, 33-40.
Toldo, et al., "Low-Density Lipoprotein Receptor-Related Protein-1 Is a Therapeutic Target in Acute Myocardial Infarction", JACC: Basic to Translational Science, 2.5, 2017, 561-574.
Tsai, et al., "Strategy of Fc-recognizable peptide ligand design for oriented immobilization of antibody", Anal. Chem.,86, 2014, 2931-2938.

(56) References Cited

OTHER PUBLICATIONS

Verdoliva, "A new ligand for immunoglobulin G subdomains by screening of a synthetic peptide library", ChemBioChem, 6, 2005, 1242-1253.

Verdoliva, et al., "Affinity purification of polyclonal antibodies using a new all-D synthetic peptide ligand: comparison with protein A and protein G", J. Immunol. Methods, 271, 2002, 77-88.

Wängler, et al., "In Vitro and Initial In Vivo Evaluation of 68Ga-Labeled Transferrin Receptor (TfR) Binding Peptides as Potential Carriers for Enhanced Drug Transport into TfR Expressing Cells", Molecular Imaging and Biology,13(2), 2011, 332-341.

Watarai, et al., "Posttranslational modification of the glycosylation inhibiting factor (GIF) gene product generates bioactive GIF", Proceedings of the National Academy of Sciences, 97, 2000, 13251-13256.

Willis, et al., "Macrophage migration inhibitory factor mediates late cardiac dysfunction after burn injury", American Journal of Physiology-Heart and Circulatory Physiology, 288, 2005, H795-H804.

Yang, et al., "Hexamer peptide affinity resins that bind the Fc region of human immunoglobulin G", J. Peptide Res, 66, 2005, 120-137.

Yang, et al., "Purification of human immunoglobulin G via Fc-specific small peptide ligand affinity chromatography", J. Chromatogr. A, 1216, 2009, 910-918.

Yoo, et al., "Identification of a peptide ligand for antibody immobilization on biosensor surfaces", Anal. Chem. 86, 2014, 2931-2938.

Zhang, et al., "Identification of a Small Peptide That Inhibits PCSK9 Protein Binding to the Low Density Lipoprotein Receptor", The Journal of Biological Chemistry, 2014, 942-955.

Zhao, et al., "Biomimetic design of affinity peptide ligands for human IgG based on protein A-IgG complex", Biochem. Eng. J, 88, 2014, 1-11.

Zhao, et al., "Dual-ligand affinity systems with octapeptide ligands for affinity chromatography of hIgG and monoclonal antibody", J. Chromatogr. A., 1359, 2014, 64-72.

Zhao, et al., "FYWHCLDE-based affinity chromatography of IgG: effect of ligand density and purifications of human IgG and monoclonal antibody", J. Chromatogr. A, 1355, 2014, 107-114.

Zhao, et al., "Octapeptide-based affinity chromatography of human immunoglobulin G: comparisons of three different ligands", J. Chromatogr. A, 1359, 2014, 100-111.

Supplementary European Search Report for European Patent Application No. 19784404.6 issued on Mar. 8, 2022.

Supplementary European Search Report for European Patent Application No. 19785819.4 issued on Mar. 5, 2022.

Qiao, et al. "PH-dependent antigen-binding antibody accelerates the clearance of antigen in vivo." European Journal of Immunology. vol. 49. 111 River St, Hoboken 07030-5774, NJ USA: Wiley, 2019. vol. 49, issue 10, p. 1741.

Berntzen, et al. "Identification of a High Affinity Fc gamma RIIA-binding Peptide That Distinguishes Fc gamma RIIA from Fc gamma RIIB and Exploits Fc gamma RIIA-mediated Phagocytosis and Degradation." Journal of Biological Chemistry 284.2 (2009): 1126-1135.

Liu "Antibody glycosylation and its impact on the pharmacokinetics and pharmacodynamics of monoclonal antibodies and Fc-fusion proteins." Journal of pharmaceutical sciences 104.6 (2015): 1866-1884.

Wright, et al. "In vivo trafficking and catabolism of IgG1 antibodies with Fc associated carbohydrates of differing structure." Glycobiology 10.12 (2000): 1347-1355.

Berhani, et al. "Human anti-NKp46 antibody for studies of NKp46-dependent NK cell function and its applications for type 1 diabetes and cancer research." European journal of immunology 49.2 (2019): 228-241.

Tampellini, et al. "Internalized Antibodies to the AB Domain of APP Reduce Neuronal Aβ and Protect against Synaptic Alterations." Journal of Biological Chemistry 282.26 (2007): 18895-18906.

Handlogten, et al. "Design of a heterobivalent ligand to inhibit IgE clustering on mast cells." Chemistry & biology 18.9 (2011): 1179-1188.

Banik, et al. "Lysosome-targeting chimaeras for degradation of extracellular proteins." Nature 584.7820 (2020): 291-297.

Springer, et al. "GalNAc-siRNA conjugates: leading the way for delivery of RNAi therapeutics." Nucleic acid therapeutics 28.3 (2018): 109-118.

Huang, et al. "Well-defined multivalent ligands for hepatocytes targeting via asialoglycoprotein receptor." Bioconjugate chemistry 28.2 (2017): 283-295.

Caianiello, et al. "Bifunctional small molecules that mediate the degradation of extracellular proteins." Nature chemical biology 17.9 (2021): 947-953.

Monk et al. Salvage bevacizumab (rhuMAB VEGF)-based therapy after multiple prior cytotoxic regimens in advanced refractory epithelial ovarian cancer. Gynecologic Oncology. 2006; 102: 140-144. (Year: 2006).

Skogh et al. Hepatic uptake of circulating IgG immune complexes. Immunology. 1985; 55: 585-594. (Year: 1985).

Non-Final Office Action issued on Jan. 6, 2025 for U.S. Appl. No. 18/161,712.

Written Opinion for Singapore Patent Application No. 11202204583Q issued by the Intellectual Property Office of Singapore on Jan. 10, 2025.

\* cited by examiner 3w (negative control MIF inhibitor)

MIF-FITC (fluorescent MIF binder)

MIF-AcF3-2

DNP-AcF3-3

<br>

1) HBTU, DIPEA, DMF,
2) 1M HCl

Exemplary R₁ and R₃ substituents/moieties for the [ASGPRBM] group

Exemplary R₁ and R₃ substituents/moieties for the [ASGPRBM] group

Exemplary R₂ substituents/moieties for the [ASGPRBM] group

FIGURE 89

| Target | Binding molecules | Indications | Example of in vitro assays | Example of in vivo assays |
|---|---|---|---|---|
| Circulating proteins | Soluble CD40L | HIV-associated neurocognitive disorders; cardiovascular complications | CD40L ELISA | |
| | BIO8898<br>ACS Chem. Biol. 2011, 6, 636-647 | | | |
| MIF | NVS-2<br>Patent no. WO 2006/045505 A1 | Tumor progression; systemic inflammation; atherosclerosis; Rheumatoid arthritis; Systemic lupus erythematosus | MIF ELISA Cell lines overexpressing MIF. | Diet induced atherosclerosis is in ApoE-/- mice |

FIGURE 89 (Cont'd)

| | | | | |
|---|---|---|---|---|
| TNF-alpha | 4-IPP (structure); C87 (structure)<br>Reference: J Biol Chem 2014, 289 (18), 12457-66.<br>Patent WO 2011/038234 A2 | Rheumatoid arthritis; inflammatory bowel disease; graft-vs-host disease; ankylosing spondylitis; psoriasis; hidradenitis suppurativa; refractory asthma; systemic lupus erythematosus | TNF-alpha ELISA; Cell lines overexpressing TNF-alpha; | Tg197 transgenic mouse model |

FIGURE 89 (Cont'd)

| | | | | |
|---|---|---|---|---|
| PCSK-9 | SP307<br>Science 310, 1022-1025.<br>YCWSQYLCY (Disulfide bridge: 2 - 8)<br>WP9QY<br>Nat Biotechnol. 1997 Nov;15(12):1266-70.<br>SBC-110,424<br>SBC-110,076<br>Reference: Patent WO 2016/040305 A1<br>Pep2-8 TVFTSWEEYLDWV<br>Reference: J Biol Chem. 2014 Jan 10;289(2):942-55 | High blood cholesterol; cardiovascular disease | Rescue of LDLR level of HepG2 cell lines | Cholesterol regulation in PCSK9 mice |

FIGURE 89 (Cont'd)

| | | | | |
|---|---|---|---|---|
| TSP-1 | 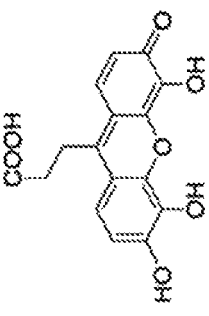LSKL peptide (J. Biol. Chem, Vol. 274, No. 19, pp. 13586–13593, 1999)<br>nsc 119915<br>Medical Oncology, 2006, col 23, 553-562 | Activation of latent TGF-beta | Inhibition of TSP-1 mediated activation of recombinant latent TGF-beta | LL2 lung tumor model in C57BL/6 mice |
| IL-17 | | Psoriasis; rheumatoid arthritis; inflammatory bowel disease; multiple sclerosis; asthma | | |
| Soluble uPAR | 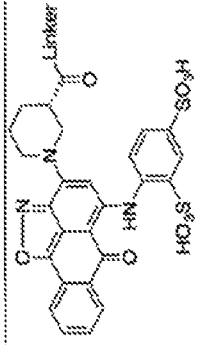Substructure of ARM-U2<br>Angew. Chem. Int. Ed. 2018, 55, 3642-3646 | Cancer therapy resistance; cancer angiogenesis | uPAR ELISA/Western blot | Synergy with ARM-U2 in tumor growth inhibition in a B16 mouse melanoma allograft model expressing |

FIGURE 89 (Cont'd)

| | | | | human uPAR Hu-PBL-NOD/SCID mice bearing xenograft human LNCaP tumors |
|---|---|---|---|
| Soluble PSMA | glutamate urea J. AM. CHEM. SOC. 2009, 131, 17090-17092 | Cancer therapy resistance | PSMA enzyme activity/ELISA/Western blot |
| IL-1 | | Rheumatoid arthritis; inflammatory bowel disease; graft-vs-host disease; heart disease | |
| IL-2 | Compound 13 J. AM. CHEM. SOC. 2003, 125, 3714-3715 | Potential immunosupressive drug; rejection of organ transplantation | Inhibition of T cell proliferation |
| IL-6 | | Thrombosis; hypercoagulation; Rheumatoid arthritis; cancer progression and metastasis | |
| IL- | | Colorectal cancer; | |

FIGURE 89 (Cont'd)

| R/CXCL-8 | | |
|---|---|---|
| IL-12 | | |
| IL-13 | cystic fibrosis; psoriasis; gingivitis | |
| | Autoimmune diseases | |
| | Allergic lung disease; Progression of parasite Schistosoma mansoni infection | |
| CXCL-1 | Cancer, inflammation, angiogenesis | |
| CXCL-2 | Cancer, inflammation, angiogenesis | |
| CXCL-3 | Atherosclerosis; multiple sclerosis; pulmonary fibrosis; type 1 diabetes; autoimmune myasthenia gravis; nephrotoxic nephritis; acute cardiac allograft rejection | |
| CXCL-4 | Systemic sclerosis | |
| CXCL-10 | Infectious diseases; chronic | |

FIGURE 89 (Cont'd)

| | | | | |
|---|---|---|---|---|
| | CXCL-12 | DCAWHLGELVWCT<br>Fc-III<br>Science, 2000, vol 287, 18, pp 1279 | inflammation; immune dysfunction; tumor development; metastasis and dissemination<br>Cancer metastasis | |
| | IgG | | Autoimmune diseases like systemic lupus erythematosus | IgG ELISA/Western blot |
| Bacteria virulent factors | Hemolysins, cytolysins | | Bacteria infections | |
| Virus | HIV (gp120) | BMS-378806 / Compound 7<br>Chem. Sci., 2014, 5, 2311-2317 | HIV | |
| | Dengue | Molecules targeting E protein, capsid protein | Dengue fever | |

BIFUNCTIONAL SMALL MOLECULES TO TARGET THE SELECTIVE DEGRADATION OF CIRCULATING PROTEINS

CROSS-REFERENCE TO RELATED APPLICATIONS

This application is a 35 U.S.C. § 371 national phase application from, and claiming priority to, International Application No. PCT/US2019/026260, filed Apr. 8, 2019, which claims the benefit of priority under 35 U.S.C. § 119(e) to U.S. Provisional Patent Application No. 62/655,055, filed Apr. 9, 2018 and U.S. Provisional Patent Application No. 62/788,040, filed Jan. 3, 2019, all of which applications are incorporated herein by reference in their entireties.

STATEMENT REGARDING FEDERALLY SPONSORED RESEARCH

This invention was made with government support under GM067543 awarded by National Institutes of Health and under W81XWH-13-1-0062 awarded by the United States Army Medical Research and Material Command. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 15, 2021, is named 047162-7239US1_replacement_Sequence_Listing.txt and is 28.9 kilobytes in size.

FIELD OF THE INVENTION

The present invention is directed to bifunctional small molecules which contain a circulating protein binding moiety (CPBM) linked through a linker group to a cellular receptor binding moiety (collectively, CRBM), preferably a moiety which binds to asialoglycoprotein receptor (an asialoglycoprotein receptor binding moiety, or ASGPRBM) of a hepatocyte. Pharmaceutical compositions based upon these bifunctional small molecules represent an additional aspect of the present invention. These compounds and/or compositions may be used to treat disease states and conditions by removing circulating proteins through degradation inside of cells of a patient or subject in need of therapy. Methods of treating disease states and/or conditions in which circulating proteins are associated with the disease state and/or condition are also described herein.

BACKGROUND/OVERVIEW OF THE INVENTION

Various diseases are associated with elevated levels of certain proteins in circulation, which play a role in disease progression. For example, increased levels of multiple circulating pro-inflammatory cytokines (i.e., signaling proteins that promote inflammatory effect) contribute to a variety of systemic inflammatory conditions and autoimmune diseases, such as Rheumatoid Arthritis (RA), systemic lupus erythematosus (SLE) and atherosclerosis. Studies have also linked chronic inflammation to an increased risk of heart disease, stroke, cancer and Alzheimer's disease. In particular, increased levels of cytokines such as TNFα or MIF are associated with Rheumatoid arthritis (RA), atherosclerosis and other diseases. Taken together, the diseases and/or conditions which are associated with circulating proteins impact the lives of millions of people. There is a strong need for novel treatments to address these diseases.

Current strategies to target circulating proteins include the use of inhibiting antibodies, which possess excellent specificity and affinity for target proteins. Despite these advantages, antibody-based therapies have several drawbacks that relate primarily to their high molecular weights and/or peptidic structures the likelihood of invoking immunogenicity, their high cost, short shelf life and low oral bioavailability. The small molecule based strategy pursuant to the present invention has the potential to combine the beneficial attributes of antibody-based therapies while overcoming their most significant disadvantages.

The high prevalence of inflammatory diseases in the population presents a considerable economic burden to the healthcare system. The high demand and high cost of current antibody-based treatments is reflected in the 34.4 billion USD global sales of TNF-α antibodies. In contrast, the bifunctional small molecule according to the present invention is readily prepared by organic synthesis, and has the potential to substantially lower the cost of manufacturing, storage and treatment. Similarly, these bifunctional chemical constructs are easier to produce in large quantity to ultimately meet high demand of treatments.

BRIEF DESCRIPTION OF THE INVENTION

Conceptually, the present invention is directed to bifunctional small molecules which can be used to remove circulating proteins, which mediate disease states and/or conditions in subjects. The present invention aims to establish a general small molecule strategy to target the selective degradation of disease-related circulating proteins. The bifunctional molecule construct contains a protein targeting motif derived from known small molecule ligands of the proteins of interest. The inventors refer to this moiety generically as a circulating protein binding moiety (CPBM). The other end of the bifunctional molecule is a cellular receptor binding moiety (CRBM) that binds to a cell surface receptor and leads to internalization of the circulating protein and bifunctional molecule. The two motifs are covalently linked via a linker such as a polyethylene glycol (PEG) linker with adjustable length and optionally contains one or more connector molecule which connects the linker to the CPBM and/or the CRBM.

The presently claimed bifunctional compounds selectively bind to the protein of interest in circulation and form a protein complex that then binds a cellular receptor and is endocytosed and degraded. As a consequence of this mechanism, the protein of interest is eliminated from circulation by hepatocytes, macrophages, or another cell type, thus resulting in lowered level of the protein of interest with the potential of attenuating the corresponding disease symptoms. In certain instances, the protein of interest may be eliminated, resulting in substantially reduced symptoms or even a cure or elimination of the disease state or condition.

The approach pursuant to the present invention is inherently advantageous compared to the classical antibody-based strategy to target disease-related circulating proteins of the prior art. The small molecule based approach of the current invention overcomes limitations of traditional antibody-based strategies, including lack of oral bioavailability, low-temperature storage requirements, immunogenicity, and high-cost.

Furthermore, the present invention is expected to have a more lasting effect compared to the conventional inhibitory approach because the disease relevant proteins are eliminated by degradation inside hepatocytes rather than simply inhibited by reversibly blocking the protein-receptor interaction. The bifunctional molecule construct pursuant to the present invention is also versatile in the sense that different disease related proteins can be targeted by simply switching the protein targeting motif in the construct. Thus, previously discovered non-inhibitory protein binders can be potentially therapeutically useful in these small molecules.

In one embodiment, the present invention is directed to compounds which are useful for removing circulating proteins which are associated with a disease state or condition in a patient or subject according to the general chemical structure:

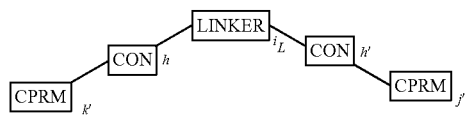

Wherein [CPBM] is a Circulating Protein Binding Moiety which binds respectively to circulating proteins as identified herein, which are related to and/or mediate a disease state and/or condition and is to be removed by the action of hepatocytes or other cells on the circulating protein (the compounds preferably selectively binding to the CPBM in plasma of the subject or patient);
[CRBM] is a Cellular Receptor binding moiety, preferably an [ASGPRBM] group, which is a binding moiety which binds to hepatocytes or other cells through asialoglycoprotein receptors or other receptors as identified herein which are on the surface of hepatocytes and other degrading cells, preferably in a patient or subject;
Each [CON] is an optional connector chemical moiety which, when present, connects directly to [CPBM] or to [CRBM] or connects the [LINKER] to [CPBM] or to [CRBM] and
[LINKER] is a chemical moiety having a valency from 1 to 15, often 1 to 10, more often 1 to 5 or 1, 2 or 3, which covalently attaches to one or more [CRBM] and/or [CPBM] group, optionally through a [CON], including a [MULTI-CON] group, wherein said [LINKER] optionally itself contains one or more [CON] or [MULTICON] group(s);
k' is 1 to 15, 1 to 10, 1 to 5, 1 to 3 or 1, 2 or 3;
j' is 1 to 15, 1 to 10, 1 to 5, 1 to 3 or 1, 2 or 3;
h and h' are each independently 0 to 15, 1 to 15, 1 to 10, 1 to 5, 1 to 3 or 1, 2 or 3, preferably h and/or h' is at least 1;
$i_L$ is 0 to 15, often 1 to 15, 1 to 10, 1 to 5, 1 to 3, or 1, 2 or 3, preferably $i_L$ is 1 to 5 or 1, 2 or 3 with the proviso that at least one of h, h' and $i_L$ is preferably at least 1, or a pharmaceutically acceptable salt, stereoisomer, solvate or polymorph thereof.

In an embodiment the present invention is directed to compounds where [CPBM] is a [MIFBM] moiety according to the chemical structure:

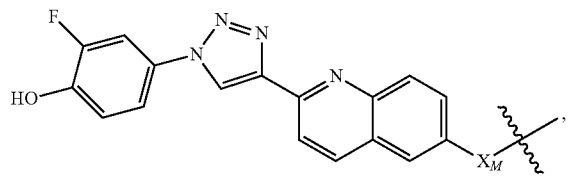

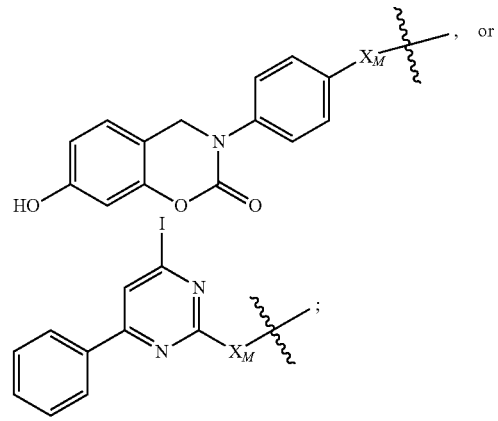

wherein $X_M$ is $-(CH_2)_{IM}$, $-O-(CH_2)_{IM}$, $S-(CH_2)_{IM}$, $NR_M-(CH_2)_{IM}$, $C(O)-(CH_2)_{IM}-$, a PEG group containing from 1 to 8, preferably 1-4 ethylene glycol residues or a $-C(O)(CH_2)_{IM}NR_M$ group;
$R_M$ is H or a $C_1$-$C_3$ alkyl group which is optionally substituted with one or two hydroxyl groups;
IM is 0-6, preferably 1, 2, 3 or 4, more preferably 1; or
[CPBM] is a [IgGMB] group according to the chemical structure:

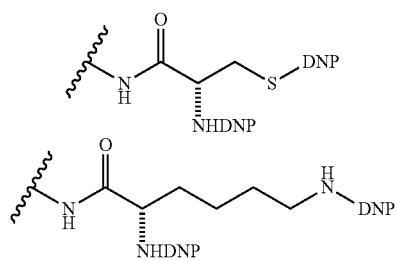

Where DNP is a 2,4-dinitrophenyl group; or a group according to the chemical structure:

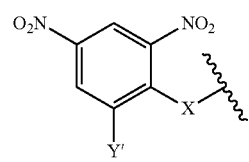

Where Y' is H or $NO_2$ (preferably H);
X is O, $CH_2$, $NR^1$, S(O), $S(O)_2$, $-S(O)_2O$, $-OS(O)_2$, or $OS(O)_2O$; and
$R^1$ is H, a $C_1$-$C_3$ alkyl group, or a $-C(O)(C_1$-$C_3)$ group; or a group according to the chemical structure:

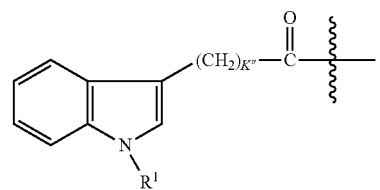

where $R^1$ is the same as above; and
κ" is 1-5 (preferably 3-5, most often 4), or
a group represented by the chemical formula:

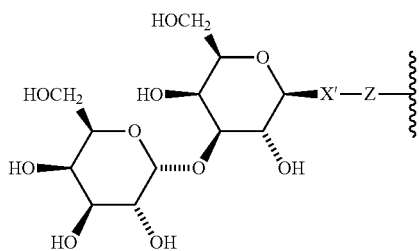

Where X' is $CH_2$, O, N—$R^{1'}$, or S, preferably O;
$R^{1'}$ is H or $C_1$-$C_3$ alkyl; and
Z is a bond, a monosaccharide, disaccharide, oligosaccharide, more preferably a sugar group selected from the monosaccharides, including aldoses and ketoses, and disaccharides, including those disaccharides described herein. Monosaccharide aldoses include monosaccharides such as aldotriose (D-glyceraldehyde, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiuose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others; or

[CPBM] is a [IgGBM] group according to the chemical structure:

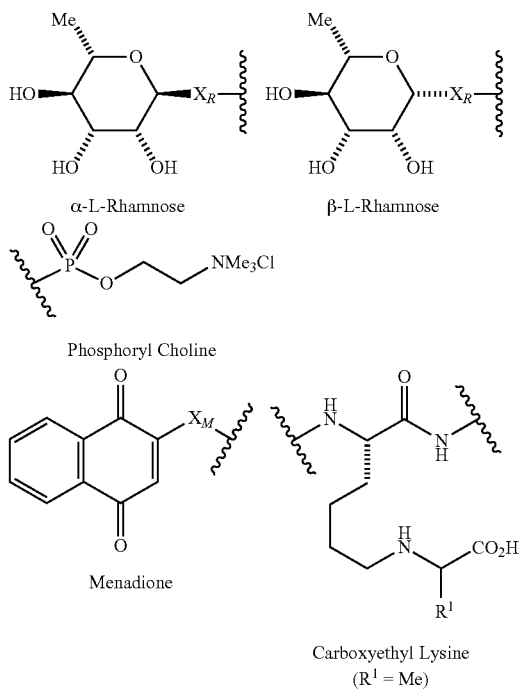

Where $X_R$ is O, S or $NR^1$; and
$X_M$ is O, $NR^1$ or S, and
$R^1$ is H or a $C_1$-$C_3$ alkyl group; or
[CPBM] is a [IgGBM] group according to the chemical structure:

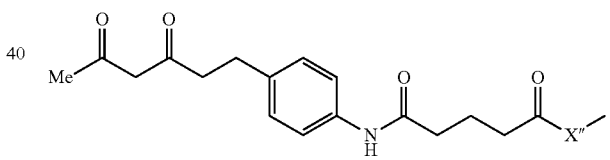

Where X" is O, $CH_2$, S; and
$R^1$ is H, a $C_1$-$C_3$ alkyl group or a —C(O)($C_1$-$C_3$) group; or

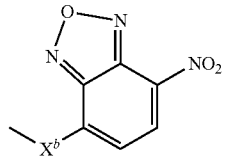

Where $X^b$ is a bond, O, $CH_2$ or $NR^1$ or S; and
$R^1$ is the same as above; or
a group according to the chemical structure:

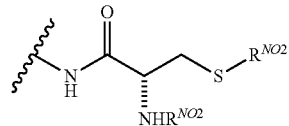

-continued

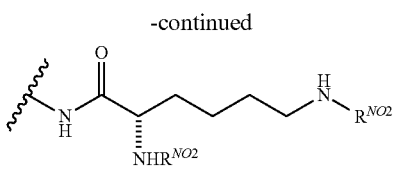

Where $R^{NO2}$ is a dinitrophenyl group optionally linked through $CH_2$, $S(O)$, $S(O)_2$, $—S(O)_2O$, $—OS(O)_2$, or $OS(O)_2O$; or a dinitrophenyl group according to the chemical structure:

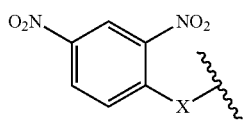

X is O, $CH_2$, $NR^1$, $S(O)$, $S(O)_2$, $—S(O)_2O$, $—OS(O)_2$, or $OS(O)_2O$; and $R^1$ is H, a $C_1$-$C_3$ alkyl group, or a $—C(O)(C_1$-$C_3)$ group, or

[CPBM] is a [IgGBM] group which is a 3-indoleacetic acid group according to the chemical structure:

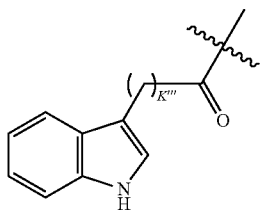

where κ''' is 1-4 (preferably 2-3, most often 3), or a

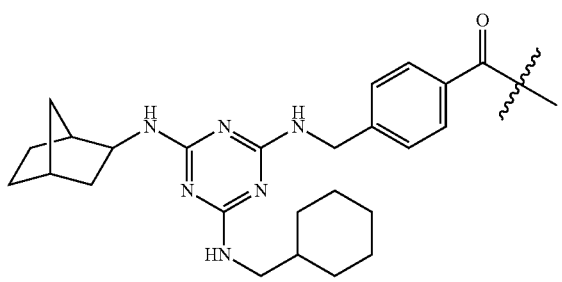 [SMILES: *C(=O)c1ccc(CNc2nc(NCC3CCCCC3)nc(NC3CC4CCC3C4)n2)cc1]

group, or a a group according to a chemical structure which is set forth in FIG. 67 hereof which is covalently attached to a [CON] group, a [LINKER] group or a [CRBM] group which includes an [ASGPRBM] group through an amine group, preferably a primary or secondary alkyl amine group which is optionally substituted on the amine group with a $C_1$-$C_3$ alkyl group; or

[CPBM] is a [IgGBM] group which is a peptide according to the sequence (all references cited are incorporated by reference herein):

PAM (Fassina, et al., *J. Mol. Recognit.* 1996, 9, 564-569);

D-PAM (Verdoliva, et al., *J. Immunol. Methods,* 2002, 271, 77-88);

D-PAM-Φ (Dinon, et al. *J. Mol. Recognit.* 2011, 24, 1087-1094);

TWKTSRISIF (Krook, et al., *J. Immunol. Methods* 1998, 221, 151-157) SEQ ID NO:1;

FGRLVSSIRY (Krook, et al., *J. Immunol. Methods* 1998, 221, 151-157) SEQ ID NO:2;

Fc-III (DeLano, et al., *Science* 2000, 287, 1279-1283);

FcBP-1 (Kang, et al., *J. Chromatogr. A* 2016, 1466, 105-112);

FcBP-2 (Dias, et al., *J. Am. Chem. Soc.* 2006, 128, 2726-2732);

Fc-III-4c (Gong, et al., *Bioconjug. Chem.* 2016, 27, 1569-1573);

EPIHRSTLTALL (Ehrlich, et al., *J. Biochem. Biophys. Method* 2001, 49, 443-454) SEQ ID NO:3;

APAR (Camperi, et al., *Biotechnol. Lett.* 2003, 25, 1545-1548) SEQ ID NO:4;

FcRM (Fc Receptor Mimetic, Verdoliva, et al., *ChemBioChem* 2005, 6, 1242-1253);

HWRGWV (Yang, et al., *J. Peptide Res.* 2006, 66, 110-137) SEQ ID NO:5;

HYFKFD (Yang, et al., *J. Chromatogr. A* 2009, 1216, 910-918) SEQ ID NO:6;

HFRRHL (Menegatti, et al., *J. Chromatogr. A* 2016, 1445, 93-104) SEQ ID NO:7;

HWCitGWV (Menegatti, et al., *J. Chromatogr. A* 2016, 1445, 93-104) SEQ ID NO:8;

D2AAG (Small Synthetic peptide ligand, Lund, et al., *J. Chromatogr. A* 2012, 1225, 158-167);

DAAG (Small Synthetic peptide ligand, Lund, et al., *J. Chromatogr. A* 2012, 1225, 158-167);

cyclo[(N—Ac)S(A)-RWHYFK-Lact-E] (Menegatti, et al., *Anal. Chem.* 2013, 85, 9229-9237) (SEQ ID NO:9-Lact-E);

cyclo[(N—Ac)-Dap(A)-RWHYFK-Lact-E] (Menegatti, et al., *Anal. Chem.* 2013, 85, 9229-9237) (SEQ ID NO:10-Lact-E);

cyclo[Link-M-WFRHYK] (Menegatti, et al., *Biotechnol. Bioeng.* 2013, 110, 857-870) SEQ ID NO:11;

NKFRGKYK (Sugita, et al., *Biochem. Eng. J.* 2013, 79, 33-40) SEQ ID NO:12;

NARKFYKG (Sugita, et al., *Biochem. Eng. J.* 2013, 79, 33-40) SEQ ID NO:13;

FYWHCLDE (Zhao, et al., *Biochem. Eng. J.* 2014, 88, 1-11) SEQ ID NO:14;

FYCHWALE (Zhao, et al., *J. Chromatogr. A* 2014, 1355, 107-114) SEQ ID NO:15;

FYCHTIDE (Zhao, et al., *J. Chromatogr. A* 2014, 1359, 100-111) SEQ ID NO:16;

Dual 1/3 (Zhao, et al., *J. Chromatogr. A* 2014, 1369, 64-72);

RRGW (Tsai, et al., *Anal. Chem.* 2014, 86, 2931-2938) SEQ ID NO:17;

KHRFNKD (Yoo and Choi, *BioChip J.* 2015, 10, 88-94) SEQ ID NO:18; or

[CPBM] is a CD40L-targeting motif according to the chemical structure:
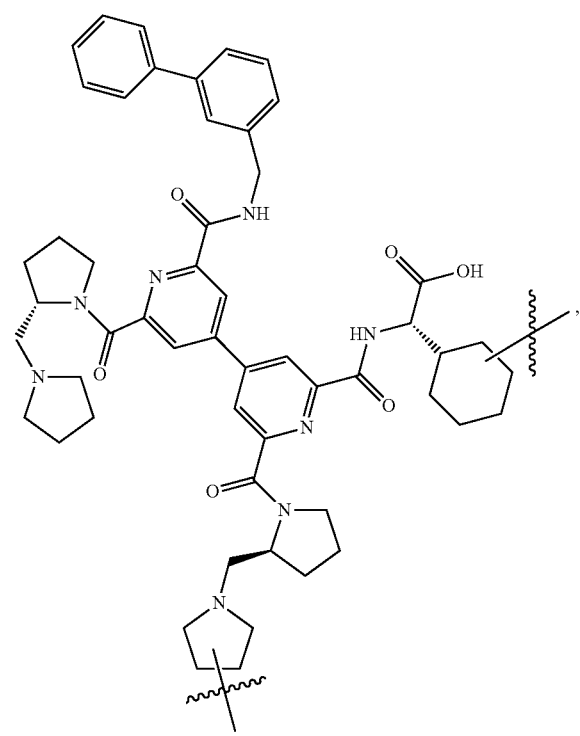
or
[CPBM] is a TNF alpha-targeting motif according to chemical structure:
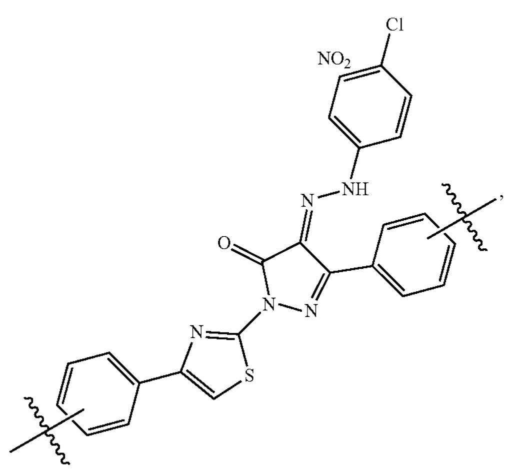
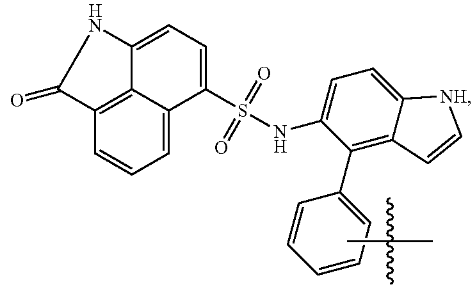
-continued
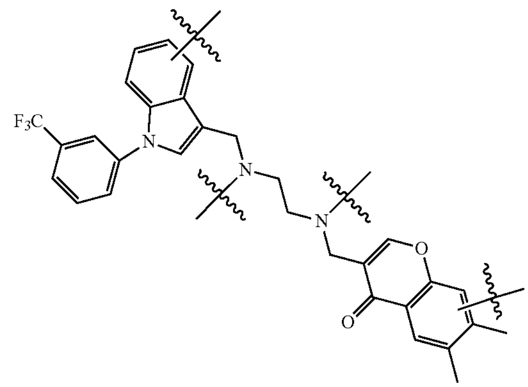
or
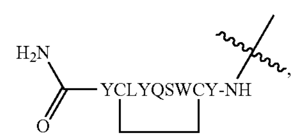
or
[CPBM] is a PCSK9-targeting motif according to the chemical structure:

-continued

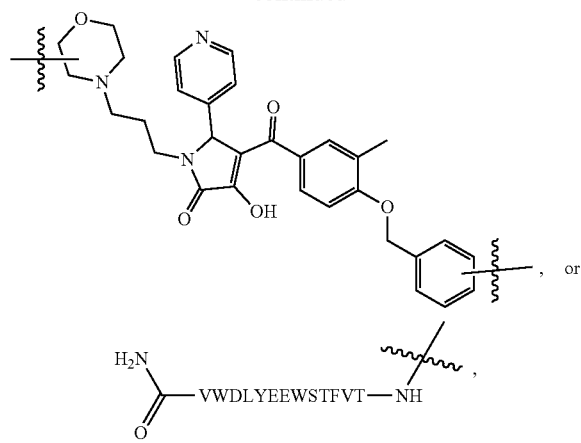, or

, or

[CPBM] is a VEGF-targeting motif according to the chemical structure:

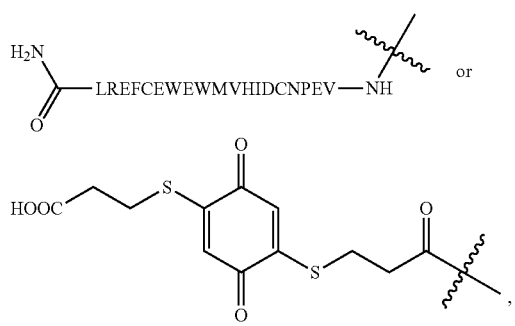

or

[CPBM] is a TGF beta-targeting motif according to the chemical structure:

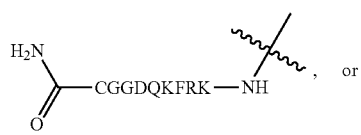, or

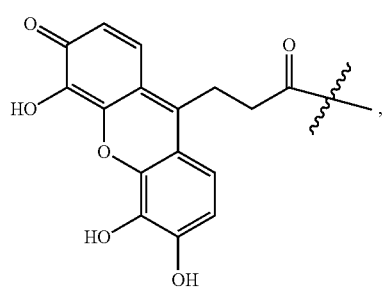, or

[CPBM] is a TSP-1 targeting motif according to the chemical structure:

[Image of LRLKSLIQGR peptide structure], or

[CPBM] is a soluble uPAR targeting motif according to the chemical structure:

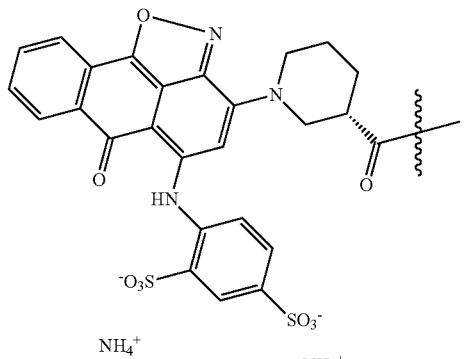

or

[CPBM] is a soluble PSMA targeting motif according to the chemical structure:

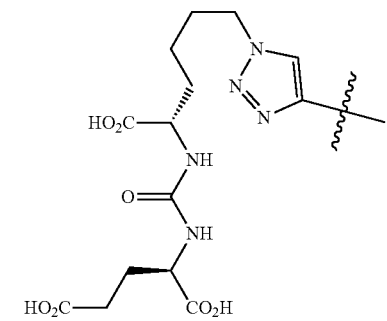, or

[CPBM] is a IL-2 targeting motif according to the chemical structure:

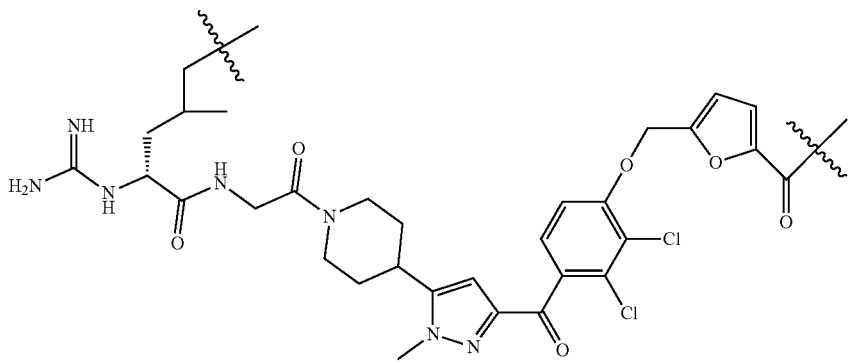

or

[CPBM] is a GP120-targeting motif according to the chemical structure:

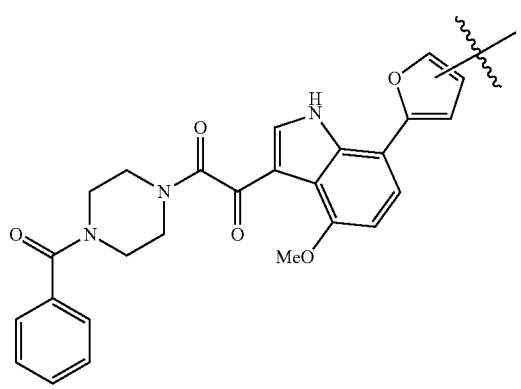

or

[CRBM] is an [ASGPRBM] is a group according to the chemical structure:

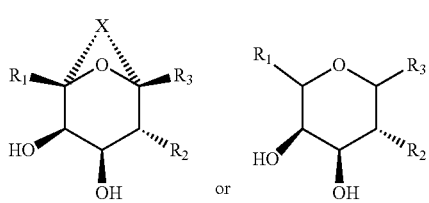

where X is 1-4 atoms in length and comprises O, S, N($R^{N1}$) or C($R^{N1}$)($R^{N1}$) groups such that
when X is 1 atom in length, X is O, S, N($R^{N1}$) or C($R^{N1}$)($R^{N1}$), when X is 2 atoms in length, no more than 1 atom of X is O, S or N($R^{N1}$), when X is 3 or 4 atoms in length, no more than 2 atoms of X are O, S or N($R^{N1}$);

where $R^{N1}$ is H or a $C_1$-$C_3$ alkyl group optionally substituted with from 1-3 halo groups, preferably F ($R^{N1}$ is preferably H or methyl, more often H);

$R_1$ and $R_3$ are each independently H, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —$(CH_2)_K$vinyl, O—$(CH_2)_K$vinyl, —$(CH_2)_K$alkynyl, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R_1$ and $R_3$ are each independently a

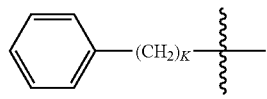

group, which is optionally substituted with up to three (preferably 1) halo groups (preferably F), $C_1$-$C_4$ alkyl groups, each of which is optionally substituted with from one to three halo groups, preferably F, or one or two hydroxyl groups, or O—$C_1$-$C_4$ alkyl groups, each of which alkyl groups is optionally substituted with from one to three halo groups, preferably F, or one or two hydroxyl groups, and K is independently 0-4 (0, 1, 2, 3 or 4), or $R_1$ and $R_3$ are each independently a group according to the chemical structure:

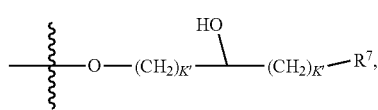

where $R^7$ is O—$C_1$-$C_4$ alkyl, which is optionally substituted with from 1 to 3 halo groups, preferably F and 1 or 2 hydroxy groups, or $R^7$ is a —$NR^{N3}R^{N4}$ group or a

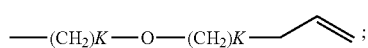
or R$_1$ and R$_3$ are each independently a group according to the structure:
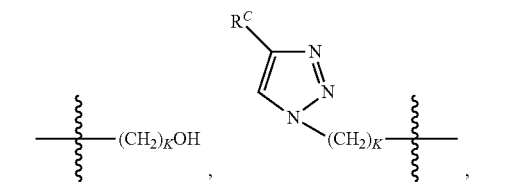
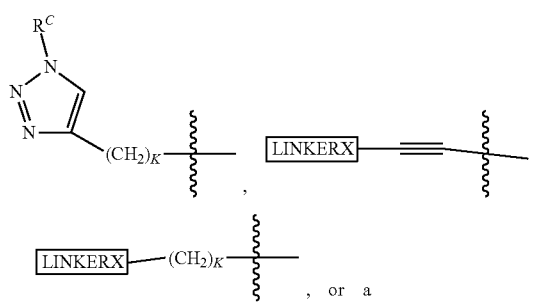
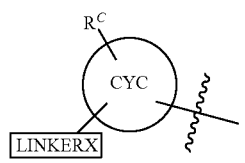
group according to the chemical structure:
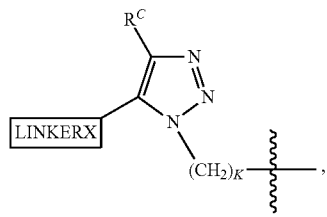
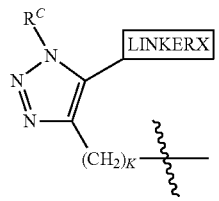
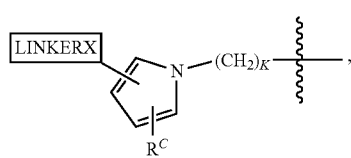
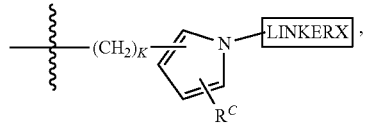
-continued
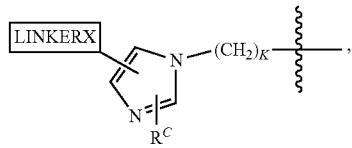
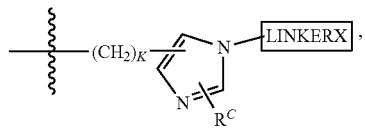
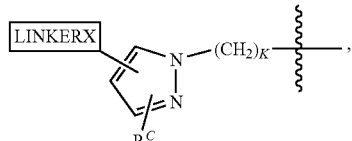
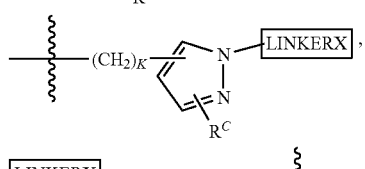
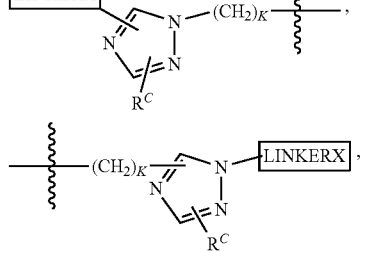
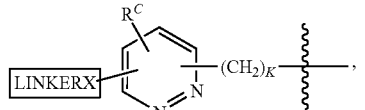
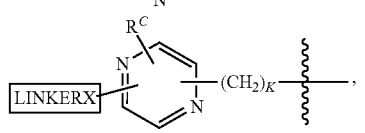
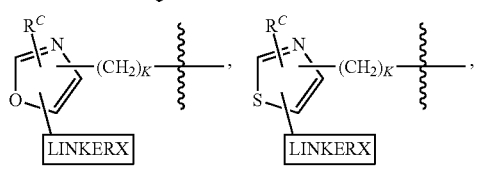
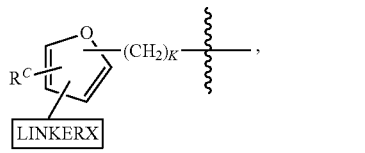
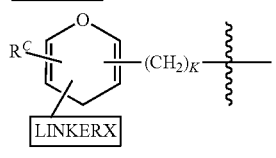
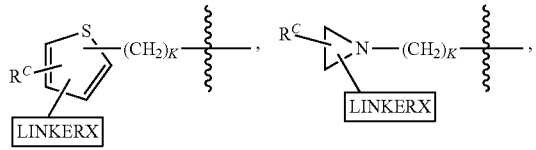

-continued

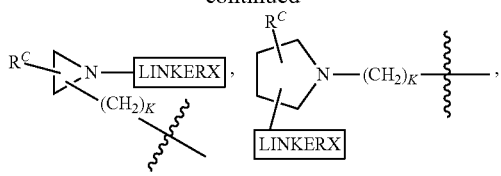
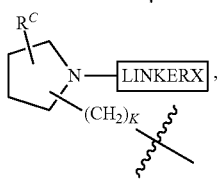
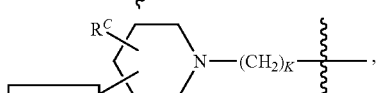
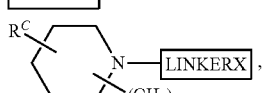
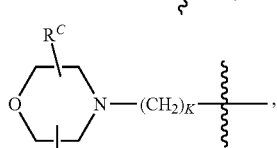
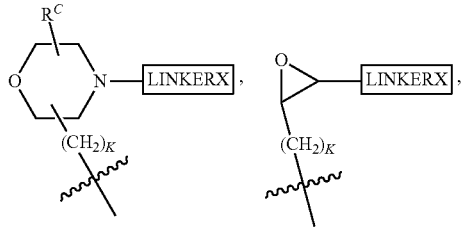
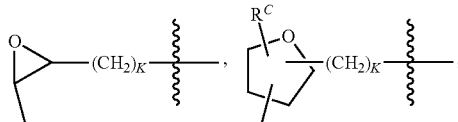
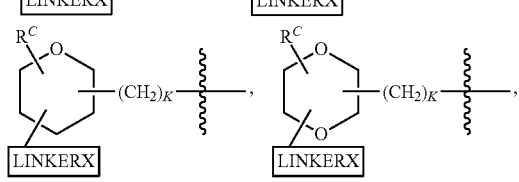
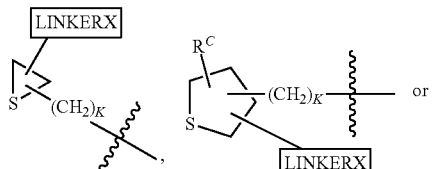
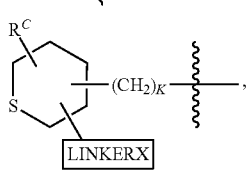

or $R_1$ and $R_3$ are each independently a

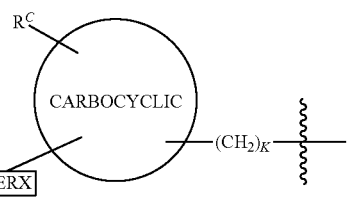

group, where

is a $C_3$-$C_8$ saturated carbocyclic group;

$R^C$ is absent, H, $C_1$-$C_4$ alkyl which is optionally substituted with from 1-3 halo (preferably fluoro) groups or 1-2 hydroxyl groups, or a group according to the structure:

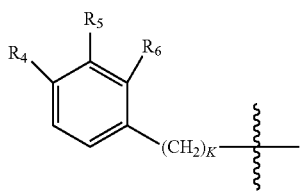

where $R_4$, $R_5$ and $R_6$ are each independently, H, halo (F, Cl, Br, I), CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups, —O—$C_1$-$C_3$-alkyl, which is optionally substituted with from 1-3 halo, preferably F groups, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^C$ is a

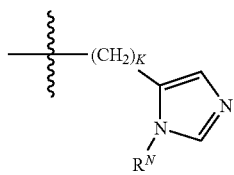

group, a

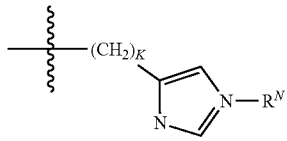

group a

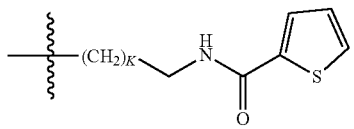

group or a

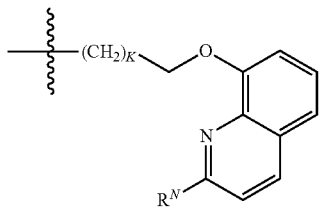

group, where $R^N$, $R^{N1}$ and $R^{N2}$ are each independently H or a $C_1$-$C_3$ alkyl group which is optionally substituted with from one to three halo groups, preferably F, or one or two hydroxyl groups;

K is independently 0-4 (0, 1, 2, 3 or 4), preferably 0 or 1;

K' is 1-4, preferably 1;

$R^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

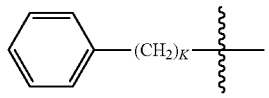

group, where K is preferably 1; LINKERX is a linker group which comprises at least one [CPBM] group and links the [CPBM] group to the [CRBM] through one or more optional [CON] groups, or LINKERX is a linker group which contains at least one or more functional groups which can be used to covalently bond the linker group to at least one [CPBM] group or optional [CON] group;

$R_2$ is a

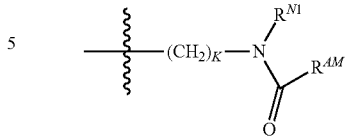

group where $R^{N1}$ and K are the same as above;

$R^{AM}$ is H, a $C_1$-$C_4$ alkyl group optionally substituted with up to 3 halo groups (preferably F) and one or two hydroxyl groups, a —$(CH_2)_K$COOH group, a —$(CH_2)_K$C(O)O—$C_1$-$C_4$ alkyl group which is optionally substituted with from 1-3 halo, preferably F groups, a O—C(O)—$C_1$-$C_4$ alkyl group, which is optionally substituted with from 1-3 halo, preferably F groups, a —C(O)—$C_1$-$C_4$ alkyl group, which is optionally substituted with from 1-3 halo, preferably F groups, a —$(CH_2)_K$—$NR^{N3}R^{N4}$ group where $R^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

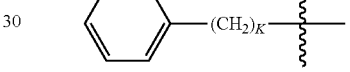

group (K is preferably 1), or $R_2$ is a

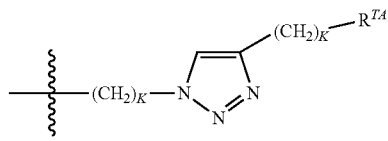

group, where $R^{TA}$ is H, CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^{TA}$ is a $C_3$-$C_{10}$ aryl or a three- to ten-membered heteroaryl group containing up to 5 heteroaryl atoms, each of said aryl or heteroaryl groups being optionally substituted with up to three (preferably 1) CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups or 1 or 2 hydroxy groups, —O—$C_1$-$C_3$-alkyl, which is optionally substituted with from 1-3 halo, preferably F groups, —$(CH_2)_K$COOH, —$(CH_2)_K$C(O)O—$C_1$-$C_4$ alkyl which is optionally substituted with from 1-3 halo, preferably F groups, O—C(O)—C$_1$-C$_4$ alkyl, which is optionally substituted with from 1-3 halo, preferably F groups or —(CH$_2$)$_K$C(O)—C$_1$-C$_4$ alkyl which is optionally substituted with from 1-3 halo, preferably F groups, or R$^{TA}$ is a

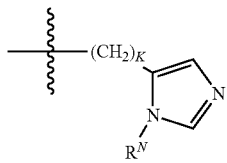

group, a

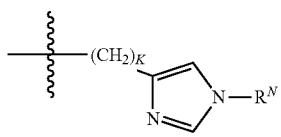

group, a

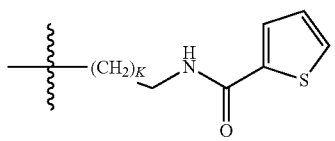

group or a

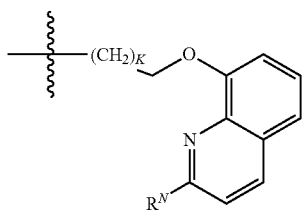

group,
(preferably, R$^{TA}$ is a

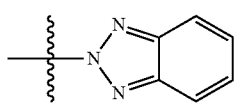 [SMILES: *n1nc2ccccc2n1]

group which is optionally substituted with up to three, preferably 1 C$_1$-C$_3$ alkyl groups which are optionally substituted with up to three halo (preferably F) groups, or R$^{TA}$ is a

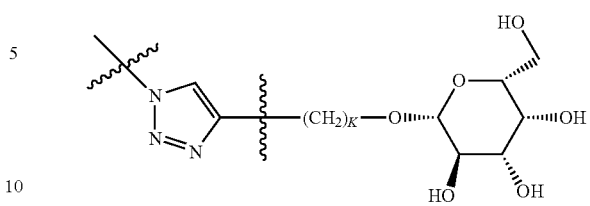

group,
wherein R$^N$, R$^{N1}$ and R$^{N2}$ are each independently H or a C$_1$-C$_3$ alkyl group which is optionally substituted with from one to three halo groups, preferably F, or one or two hydroxyl groups and
wherein each —(CH$_2$)$_K$ group is optionally substituted with 1-4, preferably 1 or 2, C$_1$-C$_3$ alkyl groups which are optionally substituted with from 1-3 fluoro groups or 1-2 hydroxyl groups; and K is independently 0-4 (0, 1, 2, 3 or 4), preferably 0 or 1; or
[CRBM] is a LRP1 (Low density lipoprotein receptor-related protein 1 or alpha-2-macroglobulin receptor) peptide binding group according to the peptide sequence (it is noted that in each case where a peptide is used, the amino end or the carboxylic acid end of the peptide is preferably linked, and more preferably the carboxylic acid terminus of the peptide is a non-reactive carboxamide group and the amine terminus is covalently linked to a CON, LINKER or CPBM group):

Ac-VKFNKPFVFLNleIEQNTK-NH$_2$ SEQ ID NO: 19 (See, Toldo, Stefano, et al. *JACC: Basic to Translational Science* 2.5 (2017): 561-574) where Nle is norleucine;

VKFNKPFVFLMIEQNTK SEQ ID NO:20 (See, Toldo, Stefano, et al. *JACC: Basic to Translational Science* 2.5 (2017): 561-574), TWPKHFDKHTFYSILKLGKH-OH SEQ ID NO: 21 (See, Sakamoto, Kotaro, et al. *Biochemistry and biophysics reports* 12 (2017): 135-139), Angiopep-2: TFFYGGSRGKRNNFKTEEY-OH SEQ ID NO:22 (See, Sakamoto, Kotaro, et al. *Biochemistry and biophysics reports* 12 (2017): 135-139), LRKLRKRLLRDADDLLRKLRKRLLRDADDL SEQ ID NO:23 (See, Croy, Johnny E., Theodore Brandon, and Elizabeth A. Komives. *Biochemistry* 43.23 (2004): 7328-7335.)

TEELRVRLASHLRKLRKRLL SEQ ID NO:24 (Croy, Johnny E., Theodore Brandon, and Elizabeth A. Komives. *Biochemistry* 43.23 (2004): 7328-7335.)

Rap12: EAKIEKHNHYQK (Ruan, Huitong, et al. "A novel peptide ligand RAP12 of LRP1 for glioma targeted drug delivery." *Journal of Controlled Release* 279 (2018): 306-315.)

Rap22: EAKIEKHNHYQKQLEIAHEKLR SEQ ID NO: 25 (Ruan, Huitong, et al. "A novel peptide ligand RAP12 of LRP1 for glioma targeted drug delivery." *Journal of Controlled Release* 279 (2018): 306-315.)

ANG: TFFYGGSRGKRNNFKTEEY SEQ ID NO:26 (Kim, Jong Ah, et al. *Scientific reports* 6 (2016): 34297), or

[CRBM] is a LDLR (low density lipoprotein receptor) binding group according to the peptide sequence:

VH4127: cM"Thz"RLRG"Pen" (cyclized c-Pen) SEQ ID NO:27 (See, Molino, Yves, et al. *The FASEB Journal* 31.5 (2017): 1807-1827) where Pen is Penicillamine and Thz is thiazolidine-4-carboxylic acid, VH434: CMPRLRGC (cyclized C—C) SEQ ID NO:28 (Molino, Yves, et al. *The FASEB Journal* 31.5 (2017): 1807-1827), VH101: HLDCMPRGCFRN (cyclized C—C) SEQ ID NO:29 David, Marion, et al. *PloS one* 13.2 (2018): e0191052, VH202: CQVKSMPRC (cyclized C—C) SEQ ID NO:30 (David, Marion, et al. *PloS one* 13.2 (2018): e0191052), VH203: CTTPMPRLC (cyclized C—C) SEQ ID NO:31 (David, Marion, et al. *PloS one* 13.2 (2018): e0191052), VH204: CKAPQMPRC (cyclized C—C) SEQ ID NO:32 (David, Marion, et al. *PloS one* 13.2 (2018): e0191052), VH205: CLNPSMPRC (cyclized C—C) SEQ ID NO:33 (David, Marion, et al. *PloS one* 13.2 (2018): e0191052), VH306: CLVSSMPRC (cyclized C—C) SEQ ID NO:34 (David, Marion, et al. *PloS one* 13.2 (2018): e0191052), VH307: CLQPMPRLC (cyclized C—C) SEQ ID NO:35 (David, Marion, et al. *PloS one* 13.2 (2018): e0191052), VH308: CPVSSMPRC (cyclized C—C) SEQ ID NO:36 (David, Marion, et al. *PloS one* 13.2 (2018): e0191052).

VH309: CQSPMPRLC (cyclized C—C) SEQ ID NO:37 (David, Marion, et al. *PloS one* 13.2 (2018): e0191052), VH310: CLTPMPRLC (cyclized C—C) SEQ NO:38 (David, Marion, et al. *PloS one* 13.2 (2018): e0191052), VH411: DSGLCMPRLRGCDPR (cyclized C—C) SEQ ID NO:39 (David, Marion, et al. *PloS one* 13.2 (2018): e0191052), VH549: TPSAHAMALQSLSVG SEQ ID NO:40 (David, Marion, et al. *PloS one* 13.2 (2018): e0191052), AcVH411: Ac-DSGLCMPRLRGCDPR-NH$_2$ (cyclized C—C) SEQ ID NO:41 (David Marion, et al. *PloS one* 13.2 (2018): e0191052), Pr VH434: Pr-CMPRLRGC-NH$_2$ (cyclized C—C) SEQ ID NO:42 (David, Marion, et al. *PloS one* 13.2 (2018): e0191052), VH445: Pr-cMPRLRGC-NH$_2$ (cyclized C—C) SEQ ID NO:43 (David, Marion, et al. *PloS one* 13.2 (2018): e0191052), VH4127: Pr-cMThzRLRG"Pen"-NH$_2$ (cyclized C-Pen) SEQ ID NO:44 (David, Marion, et al. *PloS one* 13.2 (2018): e0191052), where Pen is penacillamine, Ac VH434: Ac-CMPRLRGC-NH$_2$ (cyclized C—C) SEQ ID NO:45 (Jacquot, Guillaume, et al. *Molecular pharmaceutics* 13.12 (2016): 4094-4105), Ac VH445: Ac-cMPRLRGC-NH$_2$ (cyclized C—C) SEQ ID NO:46 (Jacquot, Guillaume, et al. *Molecular pharmaceutics* 13.12 (2016): 4094-4105), VH4106: Ac-$_D$-"Pen"M"Thz"RLRGC-NH$_2$ (cyclized Pen-C) SEQ ID NO:47 (Jacquot, Guillaume, et al. *Molecular pharmaceutics* 1312 (2016): 4094-4105), where Pen is penacillamine and Thz is thiazolidine-4-carboxylic acid, VH4127: Pr-cM"Thz"RLRG"Pen-NH$_2$ (cyclized c-Pen) SEQ ID NO:48 (Jacquot, Guillaume, et al. *Molecular pharmaceutics* 13.12 (2016): 4094-4105) where Pen is penacillamine and Thz is thiazolidine-4-carboxylic acid, VH4128: Pr-cM"Thz"RLR"Sar" "Pen"-NH$_2$ (cyclized C-Pen) SEQ ID NO:49 (Jacquot, Guillaume, et al. *Molecular pharmaceutics* 13.12 (2016): 4094-4105), where Pen is Penicillamine, Thz is thiazolidine-4-carboxylic acid, and Sar is Sarcosine, VH4129: Pr-cM"Pip"RLR"Sar"C-NH$_2$ (cyclized C—C) SEQ ID NO:50 (Jacquot, Guillaume, et al. *Molecular pharmaceutics* 13.12 (2016): 4094-4105), where Pip is a Pipecolic group and Sar is a sarcosine group, VH4130: Pr-cM"Pip"RLRG"Pen"-NH$_2$ (cyclized c-Pen) SEQ ID NO:51 (Jacquot, Guillaume, et al. *Molecular pharmaceutics* 13.12 (2016): 4094-4105), or VH4131: Pr-[cM"Pip"RLR"Sar" "Pen"-NH$_2$ (cyclized c-Pen) SEQ ID NO:52 (Jacquot, Guillaume, et al. *Molecular pharmaceutics* 13.12 (2016): 4094-4105), where Pen is Penicillamine, Thz is thiazolidine-4-carboxylic acid, Pip is pipecolic acid and Sar is sarcosine, or

[CRBM] is a FcγRI binding group according to the peptide sequence:

Cp22: TDT C LMLPLLLG C DEE (cyclized C—C) SEQ ID NO:53, Bonetto, Stephane, et al. *The FASEB Journal* 23.2 (2009): 575-585, Cp21: DPI C WYFPRLLG C TTL (cyclized C—C) SEQ ID NO:54, Bonetto, Stephane, et al. *The FASEB Journal* 23.2 (2009): 575-585, Cp23: WYP C YIYPRLLG C DGD (cyclized C—C) SEQ ID NO:55, Bonetto, Stephane, et al. *The FASEB Journal* 23.2 (2009): 575-585, Cp24: GNI C MLIPGLLG C SYE (cyclized C—C) SEQ ID NO:56 Bonetto, Stephane, et al. *The FASEB Journal* 23.2 (2009): 575-585, Cp33: VNS C LLLPNLLG C GDD (cyclized C—C) SEQ ID NO:57 Bonetto, Stephane, et al. *The FASEB Journal* 23.2 (2009): 575-585, Cp25: TPV C ILLPSLLG C DTQ (cyclized C—C) SEQ ID NO:58 Bonetto, Stephane, et al. *The FASEB Journal* 23.2 (2009): 575-585, Cp26: TVL C SLWPELLG C PPE (cyclized C—C) SEQ ID NO:59 Bonetto, Stephane, et al. *The FASEB Journal* 23.2 (2009): 575-585, Cp27: TFS C LMWPWLLG C ESL (cyclized C—C) SEQ ID NO:60 Bonetto, Stephane, et al. *The FASEB Journal* 23.2 (2009): 575-585, Cp32: FGT C YTWPWLLG C EGF (cyclized C—C) SEQ ID NO:61 Bonetto, Stephane, et al. *The FASEB Journal* 23.2 (2009): 575-585, Cp34: SLF C RLLLTPVG C VSQ (cyclized C—C) SEQ ID NO:62 Bonetto, Stephane, et al. *The FASEB Journal* 23.2 (2009): 575-585, P35: HLL V LPRGLLG C TTLA (cyclized C—C) SEQ ID NO:63 Bonetto, Stephane, et al. *The FASEB Journal* 23.2 (2009): 575-585, Cp28: TSL C SMFPDLLG C FNL (cyclized C—C) SEQ ID NO:64 Bonetto, Stephane, et al. *The FASEB Journal* 23.2 (2009): 575-585, Cp29: SHP C GRLPMLLG C AES (cyclized C—C) SEQ ID NO:65 Bonetto, Stephane, et al. *The FASEB Journal* 23.2 (2009): 575-585, P37: TST C SMVPGPLGAV STW (cyclized C—C) SEQ ID NO:66 Bonetto, Stephane, et al. *The FASEB Journal* 23.2 (2009): 575-585, Cp30: KDP C TRWAMLLG C DGE (cyclized C—C) SEQ ID NO:67 Bonetto, Stephane, et al. *The FASEB Journal* 23.2 (2009): 575-585, Cp31: IMT C SVYPFLLG C VDK (cyclized C—C) SEQ ID NO:68 Bonetto, Stephane, et al. *The FASEB Journal* 23.2 (2009): 575-585, or Cp36: IHS C AHVMRLLG C WSR (cyclized C—C) SEQ ID NO:69 Bonetto, Stephane, et al. *The FASEB Journal* 23.2 (2009): 575-585, or

[CRBM] is a FcRN binding moiety according to the peptide sequence:

SYN746: Ac—NH-QRFCTGHFGGLYPCNGP-CONH$_2$ (cyclized C—C) SEQ ID NO:70 (Mezo, Adam R., et al. *Proceedings of National Academy of Sciences* 105.7 (2008): 2337-2342), SYN1327: Ac—NH—RF-Pen-TGHFG-Sar-NMeLeu-YPC—CONH$_2$ (cyclized C—C) SEQ ID NO:71 (Mezo, Adam R., et al. *Proceedings of the National Academy of Sciences* 105.7 (2008): 2337-2342), where Pen is Penacillamine, Sar is a sarcosine and NMeLeu is N-methylleucine, or SYN1436: succinic anhydride N—N dimerized SYN1327 (each cyclized C—C) (Mezo, Adam R., et al. *Proceedings of the National Academy of Sciences* 105.7 (2008): 2337-2342), or

[CRBM] is a Transferrin Receptor binding group according to the peptide sequence:

Tf1: CGGGPFWWWP SEQ ID NO:72 (Santi, Melissa, et al. "Rational design of a transferrin-binding peptide sequence tailored to targeted nanoparticle internalization." *Bioconjugate chemistry* 28.2 (2016): 471-480), Tf2: CGGGHKYLRW SEQ ID NO:73 (Santi, Melissa, et al. "Rational design of a transferrin-binding peptide sequence tailored to targeted nanoparticle internalization." *Bioconjugate chemistry* 28.2 (2016): 471-480), Tf3: CGGGKRIFMV SEQ ID NO:74 (Santi, Melissa, et al. "Rational design of a transferrin-binding peptide sequence tailored to targeted nanoparticle internalization." *Bioconjugate chemistry* 28.2 (2016): 471-480), Tf2-scr: CGGGKWHYLR SEQ ID NO:75 (Santi, Melissa, et al. "Rational design of a transferrin-binding peptide sequence tailored to targeted nanoparticle internalization." *Bioconjugate chemistry* 28.2 (2016): 471-480), TfR-T$_{12}$: THRPPMWSPVWP SEQ ID NO:76 (Mu, Li-Min, et al. *Scientific reports* 7.1 (2017): 3487), HAIYPRH SEQ ID NO:77 (Lee, Jae H., et al. *European journal of biochemistry* 268.7 (2001): 2004-2012), THRPPMWSPVWP SEQ ID NO:78 (Lee, Jae H et al. *European journal of biochemistry* 268.7 (2001): 2004-2012), THRPPMWSPVWP SEQ ID NO:79 (Wängler, Carmen, et al. *Molecular Imaging and Biology* 13.2 (2011): 332-341), or

[CRBM] is a Macrophage Scavenger Receptor Binding Moiety according to the peptide sequence:

PP1: LSLERFLRCWSDAPA SEQ ID NO:80 (Segers, Filip M E, et al. Arteriosclerosis, thrombosis, and vascular biology 32.4 (2012): 971-978), PP1-13: LERFLRCWSDAPA SEQ ID NO:81 (Segers, Filip M E, et al. Arteriosclerosis, thrombosis, and vascular biology 32.4 (2012): 971-978), PP1-11: RFLRCWSDAPA SEQ ID NO:82 (Segers, Filip M E, et al. Arteriosclerosis, thrombosis, and vascular biology 32.4 (2012): 971-978), PP1-9: LRCWSDAPA SEQ ID NO:83 (Segers, Filip M E, et al. Arteriosclerosis, thrombosis, and vascular biology 32.4 (2012): 971-978.)

PP1-7: CWSDAPA SEQ ID NO:84 (Segers, Filip M E, et al. Arteriosclerosis, thrombosis, and vascular biology 32.4 (2012): 971-978.)

4F: DWFKAFYDKVAEKFKEAF SEQ ID NO:85 (Neyen, Claudine, et al. Biochemistry 48.50 (2009): 11858-11871);

[CON] is a connector moiety (including a [MULTICON]) as otherwise described herein; and

[LINKER] is a linking moiety as otherwise described herein which links [CPBM] to the [CRBM] group and optionally contains one or more connector moieties (which optionally connect(s) more than one chemical moiety to provide said linking moiety or which connects said linking moiety to said [CPBM] group or said [CRBM] group, or a pharmaceutically acceptable salt, stereoisomer, solvate or polymorph thereof.

In embodiments of the present invention X of the [CRBM]/[ASGPRBM] group is often —O—C($R^{N1}$)($R^{N1}$), C($R^{N1}$)($R^{N1}$)—O—, —S—C($R^{N1}$)($R^{N1}$), C($R^{N1}$)($R^{N1}$)—S—, N($R^{N1}$)—C($R^{N1}$)($R^{N1}$), C($R^{N1}$)($R^{N1}$)—N($R^{N1}$) or C($R^{N1}$)($R^{N1}$)—C($R^{N1}$)($R^{N1}$) when X is 2 atoms in length, X is —O—C($R^{N1}$)($R^{N1}$)—C($R^{N1}$)($R^{N1}$), C($R^{N1}$)($R^{N1}$)—O—C($R^{N1}$)($R^{N1}$)—, —O—C($R^{N1}$)($R^{N1}$)—O—, —O—C($R^{N1}$)($R^{N1}$)—S—, —O—C($R^{N1}$)($R^{N1}$)—N($R^{N1}$)—, —S—C($R^{N1}$)($R^{N1}$)—C($R^{N1}$)($R^{N1}$), C($R^{N1}$)($R^{N1}$)—S—C($R^{N1}$)($R^{N1}$)—, C($R^{N1}$)($R^{N1}$)—C($R^{N1}$)($R^{N1}$)—S, —S—C($R^{N1}$)($R^{N1}$)—S—, —S—C($R^{N1}$)($R^{N1}$)—O—, —S—C($R^{N1}$)($R^{N1}$)—N($R^{N1}$)—, N($R^{N1}$)—C($R^{N1}$)($R^{N1}$)—C($R^{N1}$)($R^{N1}$), C($R^{N1}$)($R^{N1}$)—N($R^{N1}$)—C($R^{N1}$)($R^{N1}$), C($R^{N1}$)($R^{N1}$)—C($R^{N1}$)($R^{N1}$)—N($R^{N1}$), N($R^{N1}$)—C($R^{N1}$)($R^{N1}$)—N($R^{N1}$) or C($R^{N1}$)($R^{N1}$)—C($R^{N1}$)($R^{N1}$)—C($R^{N1}$)($R^{N1}$) when X is 3 atoms in length, and X is —O—C($R^{N1}$)($R^{N1}$)—C($R^{N1}$)($R^{N1}$)—C($R^{N1}$)($R^{N1}$), C($R^{N1}$)($R^{N1}$)—O—C($R^{N1}$)($R^{N1}$)—($R^{N1}$)($R^{N1}$)—, —O—C($R^{N1}$)($R^{N1}$)—O—C($R^{N1}$)($R^{N1}$)—, —S—C($R^{N1}$)($R^{N1}$)—C($R^{N1}$)($R^{N1}$)—C($R^{N1}$)($R^{N1}$)—, C($R^{N1}$)—S—C($R^{N1}$)($R^{N1}$)—C($R^{N1}$)($R^{N1}$)—, C($R^{N1}$)—S—($R^{N1}$)($R^{N1}$)—S—C($R^{N1}$)($R^{N1}$)—, —S—C($R^{N1}$)($R^{N1}$)—S—C($R^{N1}$)($R^{N1}$)—, N($R^{N1}$)—C($R^{N1}$)—C($R^{N1}$)($R^{N1}$)—C($R^{N1}$)($R^{N1}$)—, C($R^{N1}$)—N($R^{N1}$)—C($R^{N1}$)($R^{N1}$)—C($R^{N1}$)($R^{N1}$), C($R^{N1}$)—C($R^{N1}$)($R^{N1}$)—N($R^{N1}$), N($R^{N1}$)—C($R^{N1}$)—N($R^{N1}$) or C($R^{N1}$)($R^{N1}$)—C($R^{N1}$)($R^{N1}$)—C($R^{N1}$)($R^{N1}$) when X is 4 atoms in length where $R^{N1}$ is the same as above. Most often, $R^{N1}$ is H.

In embodiments of the present invention X of the [CRBM]/[ASGPRBM] group is OCH$_2$ or CH$_2$O and $R^{N1}$ is preferably H.

In embodiments, the [CRBM]/[ASGPRBM] group is a group according to the chemical structure:

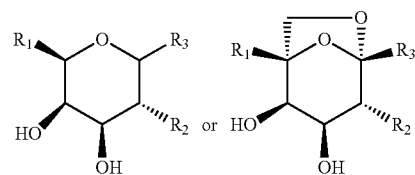

where $R_1$, $R_2$ and $R_3$ are the same as above, or
a pharmaceutically acceptable salt, stereoisomer, solvate or polymorph thereof.

In embodiments, the [CRBM]/[ASGPRBM] group is a group according to the chemical structure:

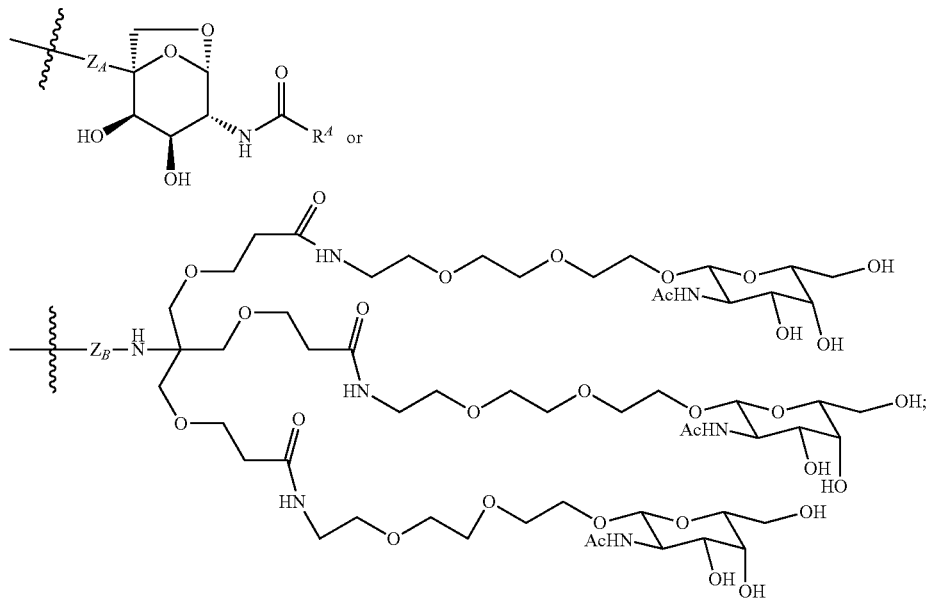

Where $R^A$ is a $C_1$-$C_3$ alkyl group which is optionally (preferably) substituted with 1-5 halo (preferably fluoro) groups (preferably $R^A$ is a methyl or ethyl group which is optionally substituted with from 1-3 fluoro groups);

$Z_A$ is —(CH$_2$)$_{IM}$, —O—(CH$_2$)$_{IM}$, S—(CH$_2$)$_{IM}$, NR$_M$—(CH$_2$)$_{IM}$, C(O)—(CH$_2$)$_{IM}$—, a PEG group containing from 1 to 8 preferably 1-4 ethylene glycol residues or a —C(O) (CH$_2$)$_{IM}$NR$_M$ group (preferably a PEG containing group comprising from 1 to 8 ethylene glycol, preferably 2-4 ethylene glycol residues) where IM and R$_M$ are the same as above; and $Z_B$ is absent, (CH$_2$)$_{IM}$, C(O)—(CH$_2$)$_{IM}$— or C(O) —(CH$_2$)$_{IM}$—NR$_M$, where IM and R$_M$ are the same as above.

In embodiments according to the present invention, R$_1$ and R$_3$ (preferably R$_1$) are each independently often a group according to the chemical structure:

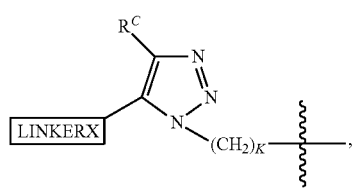

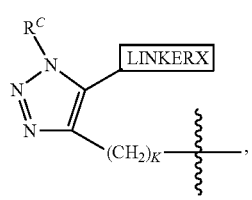

where $R^C$, LINKERX and K are the same as above.

In the above-described compounds,

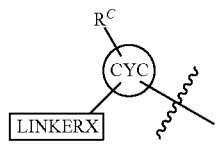

is preferably a group according to the chemical structure:

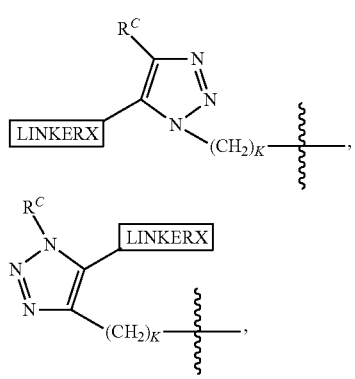

where $R^C$, LINKERX and K are the same as above.

In embodiments, preferred compounds include the compounds which are presented in FIGS. 1, 7 and 13, as well as FIGS. 29-88. In embodiments, additional compounds are presented in FIGS. 16-66 and include final compounds set forth therein and intermediates which are used to make final compounds pursuant to the present invention.

In embodiments, R$_1$ and R$_3$ of the [CRBM]/[ASGPRBM] group include those moieties which are presented in FIG. 68 hereof. In embodiments, R₂ of the [CRBM]/[ASGPRBM] group include those moieties which are presented in FIG. 69 hereof.

In embodiments, the [CPBM]/[IgGBM] group is a peptide moiety according to the chemical structure for FcIII or FcIII-4c:

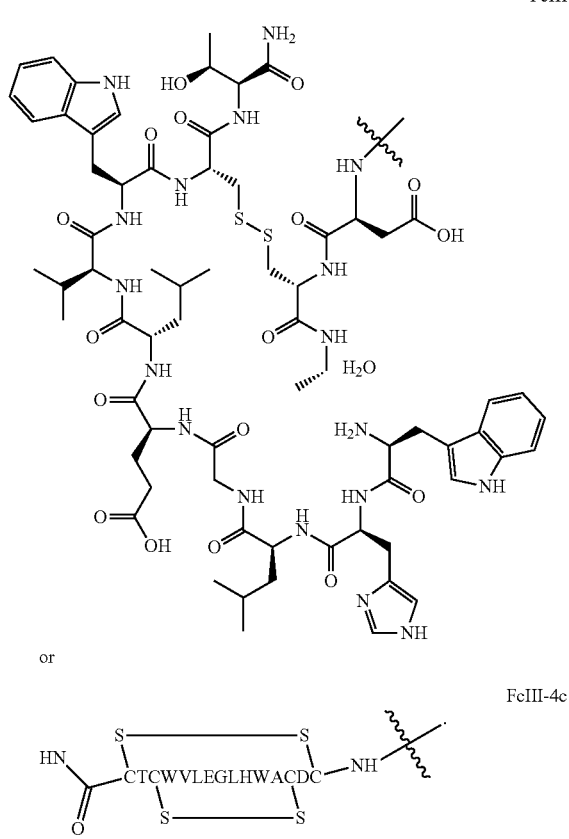

In an additional embodiment, the present invention is directed to a pharmaceutical composition comprising an effective amount of a compound according to the present invention in combination with a pharmaceutically acceptable carrier, additive or excipient, optionally in combination with at least one additional bioactive agent.

In other embodiments, the present invention is directed to a method of treating a disease state or condition where a circulating protein is related to or contributes to a disease state and or condition or the symptomology associated with the disease state or condition. These disease states and/or conditions include, autoimmune diseases and numerous inflammatory diseases for example, rheumatoid arthritis (RA), systemic lupus erythematosus (SLE), Alzheimer's disease, atherosclerosis, heart disease, stroke and cancer (including leukemia), among numerous others as described herein including as set forth in FIG. 89 hereof. The method of treatment according to the present invention comprises administering to a patient or subject in need of therapy an effective amount of at least one compound according to the present invention, optionally in combination with an additional bioactive agent to reduce the likelihood of, inhibit and/or treat the disease state or condition by removing Circulating Protein associated with the disease state and/or condition from the circulation of the patient or subject.

In an additional embodiment, the present invention is directed to a pharmaceutical composition comprising an effective amount of a compound according to the present invention in combination with a pharmaceutically acceptable carrier, additive or excipient, optionally in combination with at least one additional bioactive agent.

In other embodiments, the present invention is directed to a method of treating a disease state or condition where a circulating protein is related to the symptomology associated with the disease state or condition. These disease states and/or conditions include, for example, rheumatoid arthritis (RA), systemic lupus erythematosus (SLE), Alzheimer's disease, atherosclerosis, heart disease, stroke and cancer (including leukemia), among numerous others as described herein. The method comprises administering to a patient or subject in need of therapy an effective amount of at least one compound according to the present invention, optionally in combination with an additional bioactive agent to reduce the likelihood of, inhibit and/or treat the disease state or condition by removing circulating proteins associated with the disease state and/or condition.

DETAILED DESCRIPTION OF THE INVENTION

Figure 1:
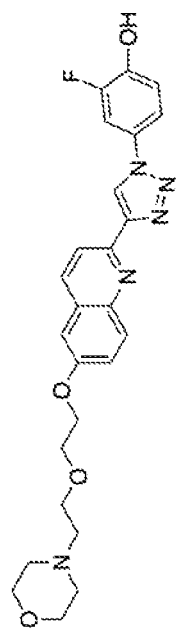
FIG. 1 shows representative compounds according to the present invention. Note that the figure discloses compound 3w (negative control for MIF inhibition), MIF-NVS-PEGnGN3, MIFGN3, MIF-PEGnGN3, MIF-AcF3-1, MIF-AcF3-2 and MIF-AcF3-3. Note that n in the PEG linker preferably ranges from 1-12, 1 to 10, 2 to 8, 2 to 6, 2 to 5 or 1, 2, 3 or 4.
Figure 1:
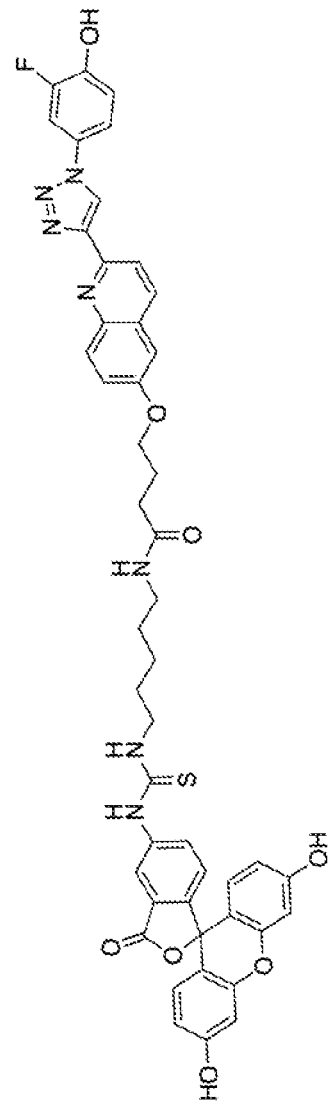
Figure 1:
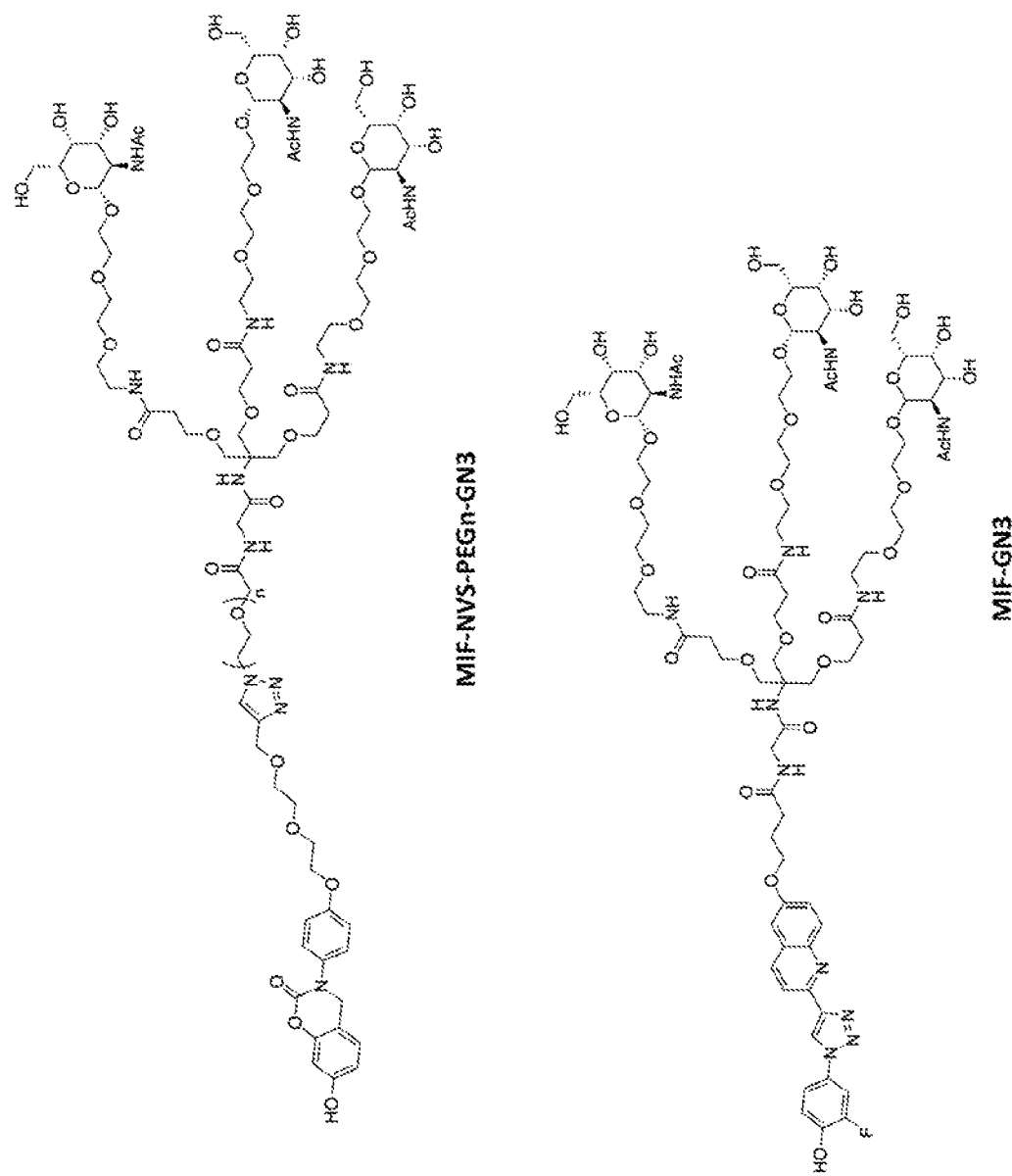
Figure 1:
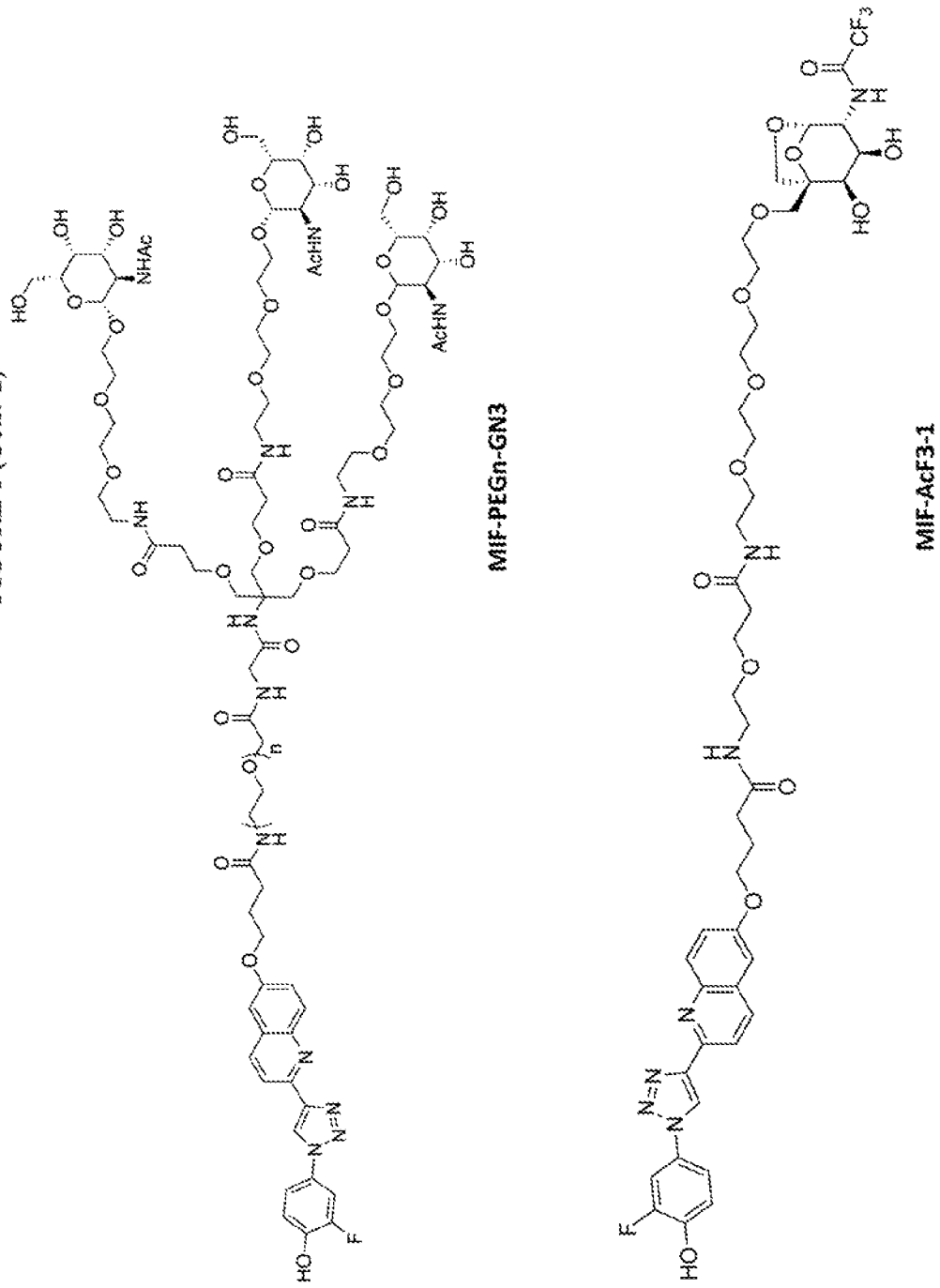
Figure 1:
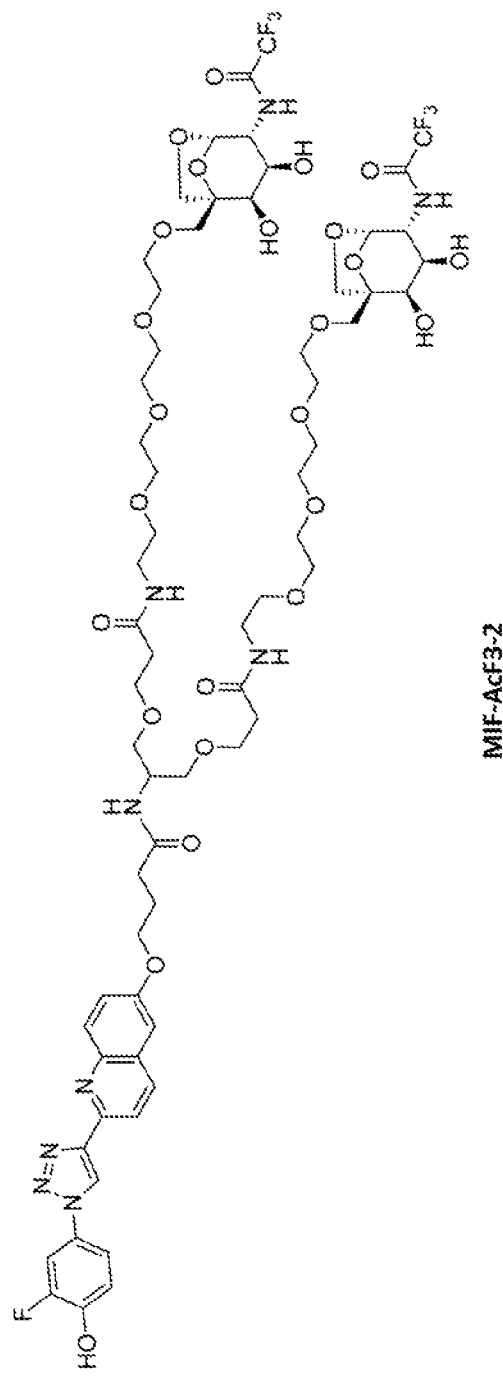
Figure 1:
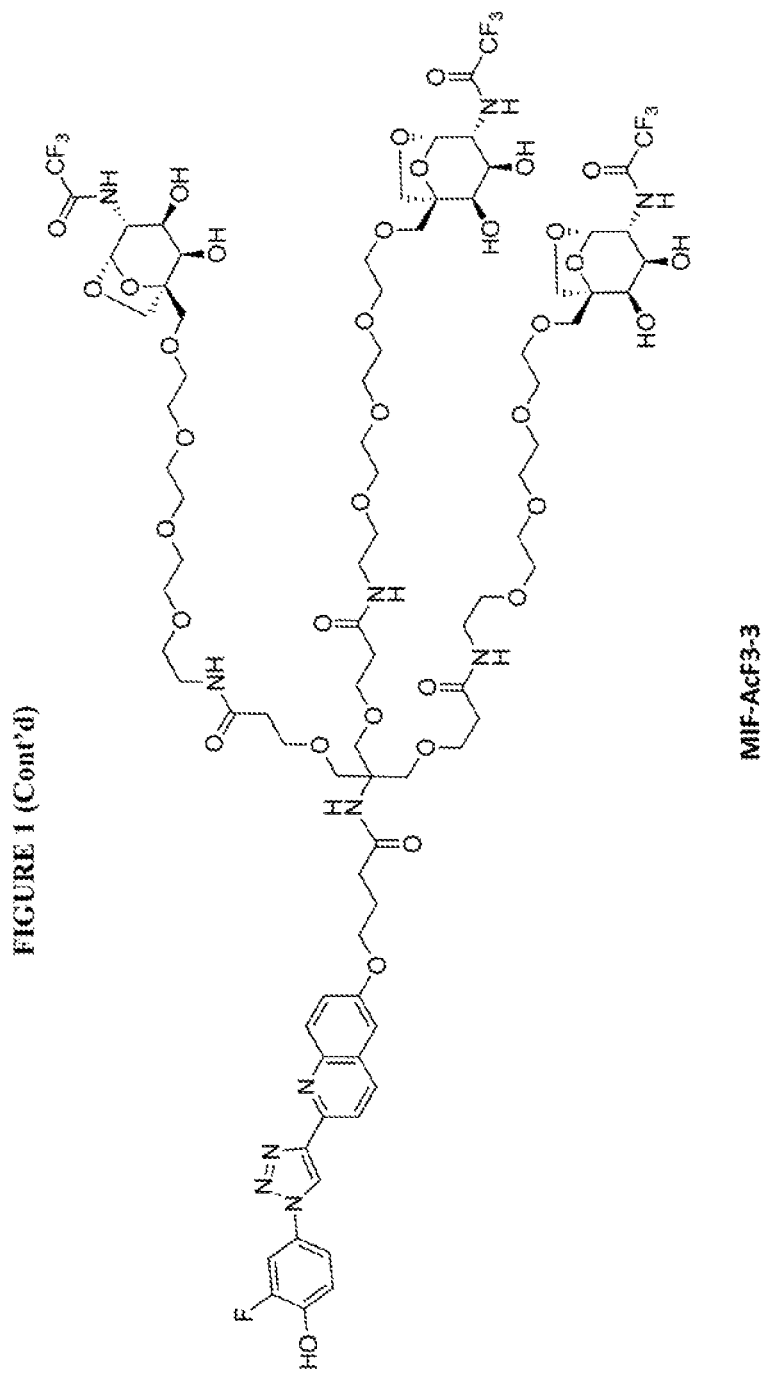

In accordance with the present invention there may be employed conventional chemical synthetic and pharmaceutical formulation methods, as well as pharmacology, molecular biology, microbiology, and recombinant DNA techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "an", "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein and includes tautomers, regioisomers, geometric isomers, stereoisomers and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, within context, to prodrug forms of compounds which have been modified to facilitate the administration and delivery of compounds to a site of activity. It is noted that in describing the present compounds, numerous substituents, linkers and connector molecules and variables associated with same, among others, are described. The use of a bond presented as ----- signifies that a single bond is present or absent, depending on the context of the chemistry described, including the attachment of the bond to another moiety. The use of a bond presented as ≡≡≡≡≡ signifies that a single bond or a double bond is intended depending on the context of the chemistry described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis, including especially as that term is used with respect to reducing the likelihood of metastasis of an existing cancer), with the compositions according to the present invention is provided. For treatment of those infections, conditions or disease states which are specific for a specific animal such as a human patient or a patient of a particular gender, such as a human male or female patient, the term patient refers to that specific animal. Compounds according to the present invention are useful for the treatment of numerous disease states including autoimmune disease states and/or conditions and inflammatory disease states and/or conditions as well as cancer, including especially for use in reducing the likelihood of metastasis or recurrence of a cancer.

The term "effective" is used herein, unless otherwise indicated, to describe an amount of a compound or composition which, in context, is used to produce or effect an intended result, whether that result relates to the inhibition of the effects of a disease state (e.g. an autoimmune disease such as rheumatoid arthritis (RA) or systemic lupus erythematosus (SLE), among others, atherosclerosis, heart disease or stroke, among numerous others or a cancer, including leukemia) on a subject or the treatment or prophylaxis of a subject for secondary conditions, disease states or manifestations of disease states as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for a disease state or condition for which a MIF protein may be removed, such as an autoimmune disease including rheumatoid arthritis (RA) or systemic lupus erythematosus (SLE), among others, atherosclerosis, heart disease, stroke and cancer (including leukemia) including recurrence and/or metastasis of cancer, improvement in the condition through lessening or suppression of at least one symptom of the disease state or condition, inhibition of one or more manifestations of the disease state (e.g., plaque formation, heart disease, cancer growth, reduction in cancer cells or tissue), prevention, reduction in the likelihood or delay in progression of a disease state or condition or manifestation of the disease state or condition, especially including plaque formation in atherosclerosis, deterioration of tissue and inflammation in rheumatoid arthritis, further damage to cardiovascular tissue in heart disease, further damage to central nervous tissue in stroke, cancer, its recurrence or metastasis of the cancer, prevention or delay in the onset of disease states or conditions which occur secondary to the disease state or condition including cancer recurrence or metastasis, among others. Treatment, as used herein, encompasses both prophylactic and therapeutic treatment, depending on the context of the treatment. The term "prophylactic" when used, means to reduce the likelihood of an occurrence or the severity of an occurrence within the context of treatment of disease state or condition, as otherwise described hereinabove.

As used in this application, the terms "about" and "approximately" are used as equivalents. Any numerals used in this application with or without about/approximately are meant to cover any normal fluctuations in a value appreciated by one of ordinary skill in the relevant.

The term "circulating protein binding moiety", which term includes "macrophage migration inhibitory factor binding moiety" or "MIFBM", "immunoglobulin G binding moiety" or "IgGBM" refers to a chemical moiety on one end of the bifunctional compounds according to the present invention which is capable of binding to a circulating protein (such as MIF, IgG, CD40L, TNFalpha, PCSK9, VEGf, TGFbeta, TSP-1, uPAR, PSMA and IL-2 which are associated with or contribute to a disease state or condition as otherwise described herein. In the present invention, the CPBM is capable of binding to the circulating protein, forming a complex with the present compounds, and delivering the bound protein to a hepatocyte or other cell whereupon the other end of the bifunctional molecule which contains a cellular receptor binding moiety (CRBM) such an asialoglycoprotein receptor binding moiety (ASGPRBM) or as otherwise described herein can bind to the surface of a hepatocyte or other cell, respectively. Once attached to the cell, the bifunctional molecule to which is bound circulating protein is internalized by the cell through a phagocytosis/endocytosis mechanism whereupon the cell will destroy the protein via a lysosomal degradation or other degradation pathway. The term "immunoglobulin G binding moiety" or "IgGBM" is used to describe a moiety which binds to circulating IgG immunoglobulin, forming a complex with bifunctional molecules according to the present invention to be ultimately destroyed in hepatocytes. In certain instances in describing the present invention, the terms MIFBM and IgGBM and other cell binding moieties are used synonymously.

Exemplary MIFBMs for inclusion in bifunctional compounds according to the present invention include moieties found in bifunctional chemical structures which appear in FIG. 1, attached hereto. MIFBMs according to the present invention include moieties according to the chemical structures:

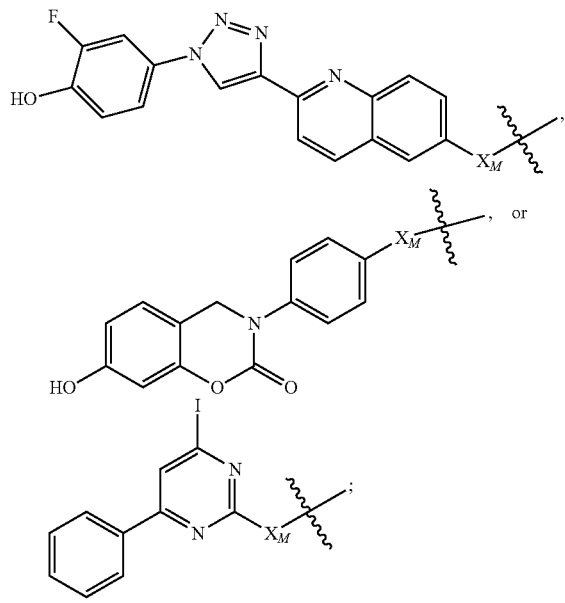

wherein $X_M$ is —$(CH_2)_{IM}$, —O—$(CH_2)_{IM}$, S—$(CH_2)_{IM}$, $NR_M$—$(CH_2)_{IM}$, C(O)—$(CH_2)_{IM}$—, a PEG group containing from 1 to 8, preferably 1-4 ethylene glycol residues or a —C(O)$(CH_2)_{IM}NR_M$ group, $R_M$ is H or a $C_1$-$C_3$ alkyl group which is optionally substituted with one or two hydroxyl groups; and IM is 0-6, preferably 1, 2, 3 or 4, more preferably 1.

Other CPBM groups, such as IgGBM and various previously described moieties which bind to CD40L, TNFalpha, PCSK9, VEGf, TGFbeta, TSP-1, uPAR, PSMA and Il-2 are set forth hereinabove. These bind to the respective circulating proteins, thus forming a complex with the bifunctional compounds according to the present invention and the bifunctional compounds complexed with the bound circulating proteins can be bound to cellular receptors on cells which can take up the complexed compounds using phagocytosis/endocytosis mechanisms of the cell and remove the proteins through a degradation process. It is noted that the CPBM which are peptides which bind to IgGBM, CD40L, TNFalpha, PCSK9, VEGf, TGFbeta, TSP-1, uPAR, PSMA and Il-2 are covalently linked to other portions of the bifunctional molecules according to the present invention through the terminal amine or carboxylic acid group of the peptide. In preferred embodiments, the carboxylic acid is amidated to form a non-reactive amide group, often with a free amine group (substituted with two H's) or an amine group which alkylated with at least one $C_1$-$C_{10}$ alkyl group, more often at least one $C_1$-$C_3$ alkyl group so that the free amine on the other end of the peptide may be used to covalently link to other portions of the bifunctional molecule. In other embodiments, the amine terminus is rendered non-reactive by end-capping the amine group with a $C_2$-$C_{10}$ acyl group, preferably a $C_2$-$C_4$ acyl group, so that the carboxylic acid group may be reacted, often with an amine to form an amide.

The term "cellular receptor binding moiety" refers to a moiety of the bifunctional compounds according to the present invention which is capable of binding to a receptor on a cell capable of degrading circulating proteins pursuant to the present invention herein. These are moieties which bind to asialoglycoprotein receptor, LRPR, LDLR, RcγRI, FcRN, Transferrin Receptor or Macrophage Scavenger Receptor (e.g., membrane receptors of degradation cells) as otherwise described herein. Many of these binding moieties are peptides which are covalently linked to other portions of the bifunctional compounds according to the present invention through a terminal amine or carboxylic acid group. As for the CPBM group described above, in preferred embodiments, the carboxylic acid is amidated to form a non-reactive amide group, often with a free amine group (substituted with two H's) or an amine group which alkylated with at least one $C_1$-$C_{10}$ alkyl group, more often at least one $C_1$-$C_3$ alkyl group so that the free amine on the other end of the peptide may be used to covalently link to other portions of the bifunctional molecule. In other embodiments, the amine terminus is rendered non-reactive by end-capping the amine group with a $C_2$-$C_{10}$ acyl group, preferably a $C_2$-$C_4$ acyl group, so that the carboxylic acid group may be reacted, often with an amine to form an amide.

The term "asialoglycoprotein receptor binding moiety" ("ASGPRBM") refers to a binding moiety which binds to hepatocyte asialoglycoprotein receptor. This binding moiety is also a component of the presently claimed bifunctional compounds as a CRBM group which is covalently bound to the CPBM group moiety through a CON group, a linker or directly. The ASGPRBM group selectively binds to hepatocyte asialoglycoprotein receptor on the surface of hepatocytes. It is through this moiety that bifunctional compounds complexed with circulating protein bind to hepatocytes. Once bound to the hepatocyte, the circulating protein is taken into the hepatocytes or other cells via a phagocytosis mechanism wherein the circulating protein is degraded through lysosomal degradation.

Exemplary ASGPRBM groups for use in compounds according to the present invention, among others, include moieties according to the chemical structures:

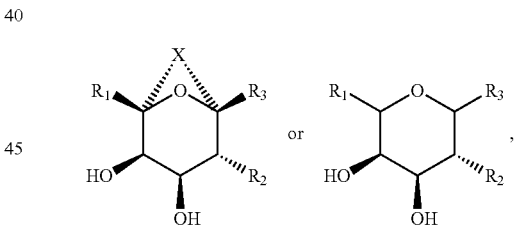

where X is 1-4 atoms in length and comprises O, S, N($R^{N1}$) or C($R^{N1}$)($R^{N1}$) groups such that when X is 1 atom in length, X is O, S, N($R^{N1}$) or C($R^{N1}$)($R^{N1}$), when X is 2 atoms in length, no more than 1 atom of X is O, S or N($R^{N1}$), when X is 3 or 4 atoms in length, no more than 2 atoms of X are O, S or N($R^{N1}$);

where $R^{N1}$ is H or a $C_1$-$C_3$ alkyl group optionally substituted with from 1-3 halo groups, preferably F ($R^{N1}$ is preferably H or methyl, more often H);

$R_1$ and $R_3$ are each independently H, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —$(CH_2)_K$vinyl, O—$(CH_2)_K$vinyl, —$(CH_2)_K$alkynyl, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R_1$ and $R_3$ are each independently a

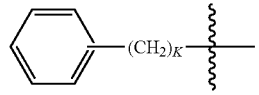

group, which is optionally substituted with up to three (preferably 1) halo groups (preferably F), $C_1$-$C_4$ alkyl groups, each of which is optionally substituted with from one to three halo groups, preferably F, or one or two hydroxyl groups, or O—$C_1$-$C_4$ alkyl groups, each of which alkyl groups is optionally substituted with from one to three halo groups, preferably F, or one or two hydroxyl groups, and K is independently 0-4 (0, 1, 2, 3 or 4), or $R_1$ and $R_3$ are each independently a group according to the chemical structure:

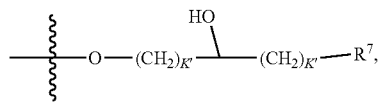

where $R^7$ is O—$C_1$-$C_4$ alkyl, which is optionally substituted with from 1 to 3 halo groups, preferably F and 1 or 2 hydroxy groups, or $R^7$ is a —$NR^{N3}R^{N4}$ group or a

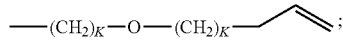

or $R_1$ and $R_3$ are each independently a group according to the structure:

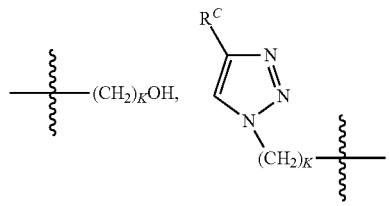

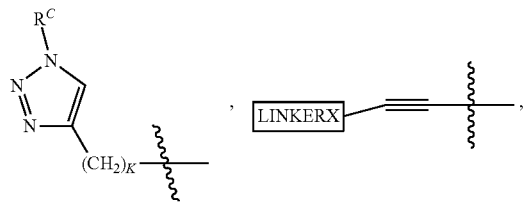

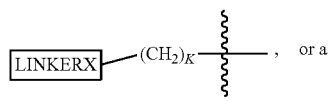, or a

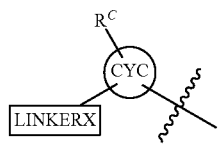

group according to the chemical structure:

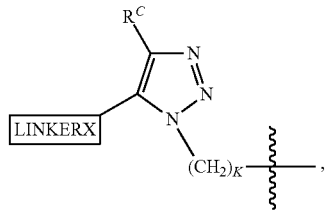

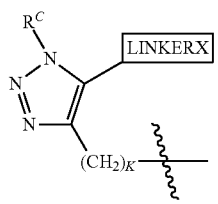

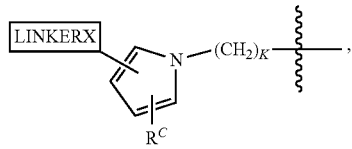

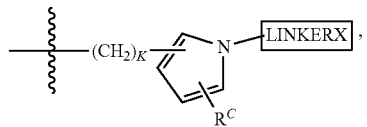

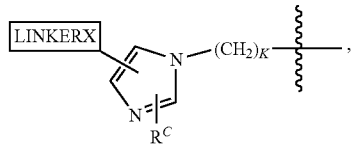

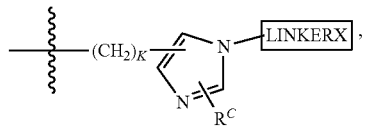

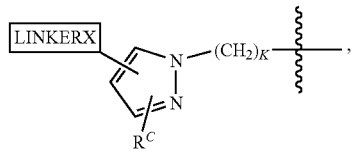

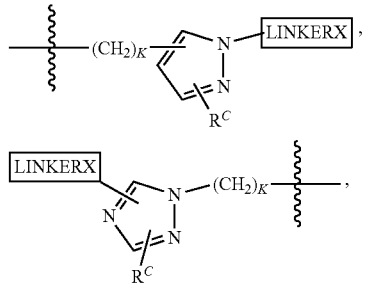

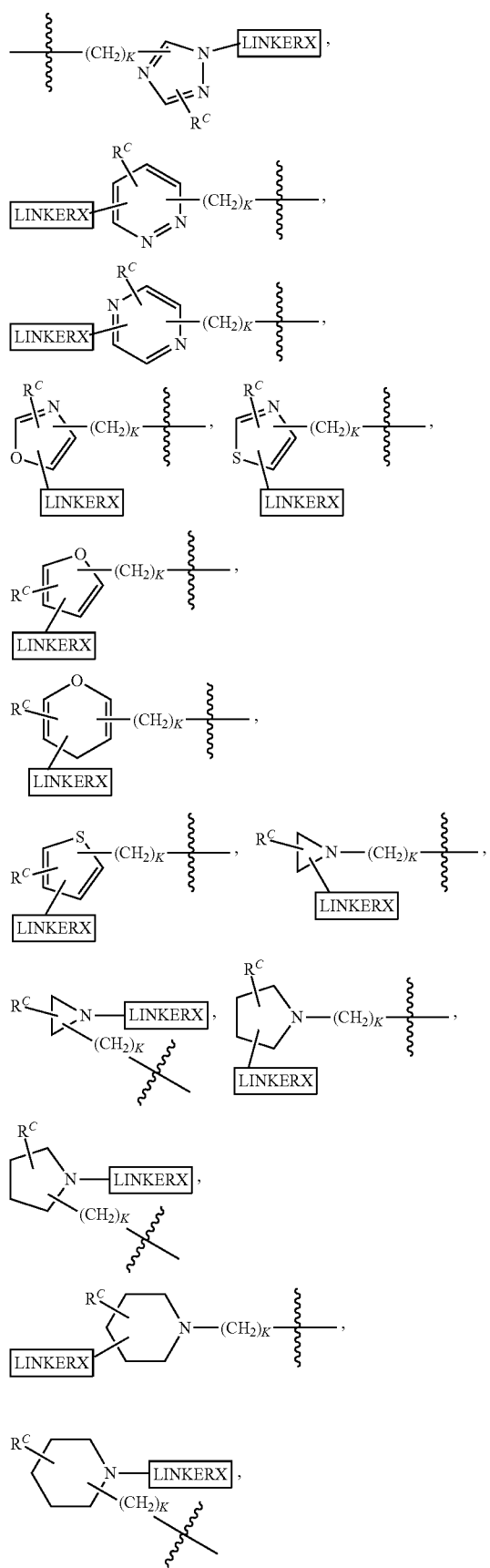
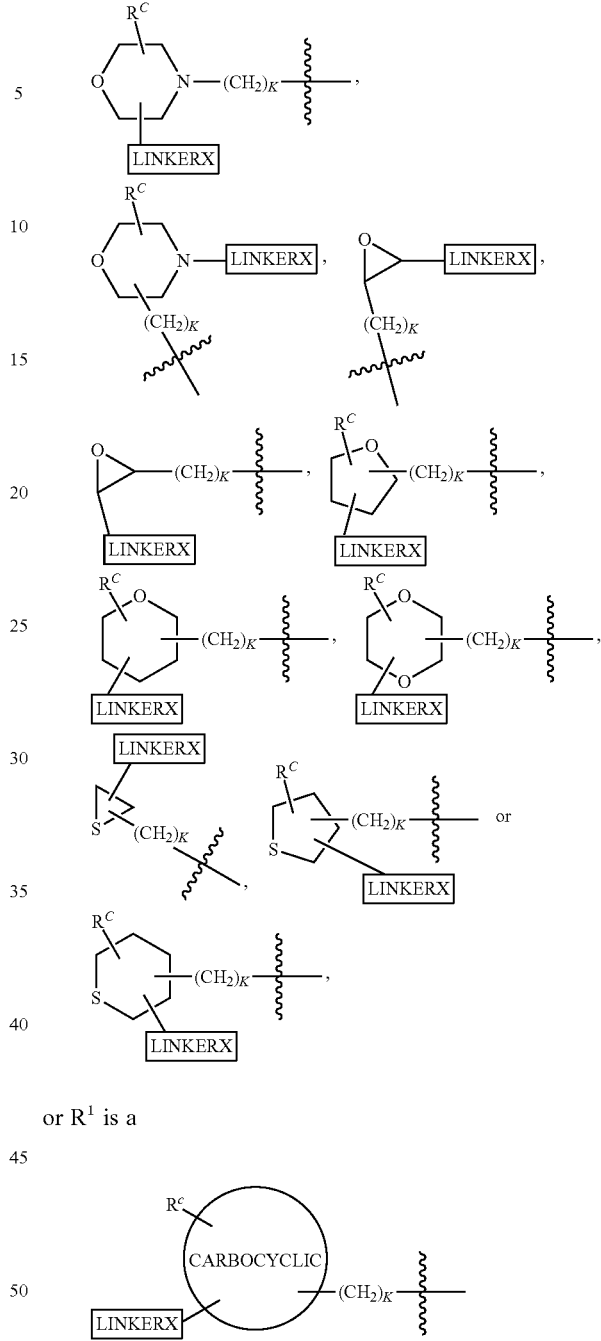
or $R^1$ is a
group, where
is a $C_3$-$C_8$ saturated carbocyclic group;
$R^C$ is absent, H, $C_1$-$C_4$ alkyl which is optionally substituted with from 1-3 halo (preferably fluoro) groups or 1-2 hydroxyl groups, or a group according to the structure:

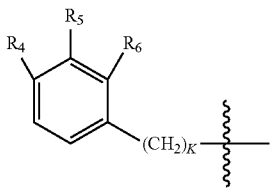

where $R_4$, $R_5$ and $R_6$ are each independently, H, halo (F, Cl, Br, I), CN, $NR^{N1}R^{N2}$, —$(CH_2)_KOH$, —$(CH_2)_KOC_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups, —O—$C_1$-$C_3$-alkyl, which is optionally substituted with from 1-3 halo, preferably F groups, —$(CH_2)_K$COOH, —$(CH_2)_KC(O)O$—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^C$ is a

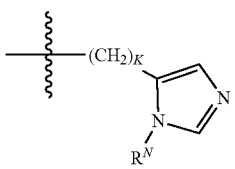

group, a

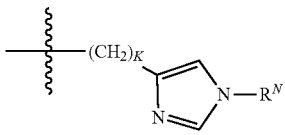

group a

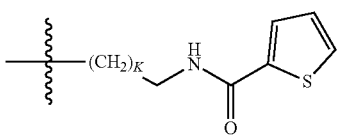

group or a

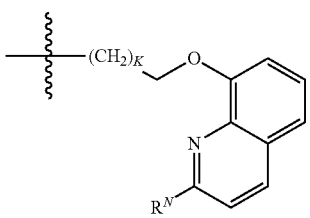

group, where $R^N$, $R^{N1}$ and $R^{N2}$ are each independently H or a $C_1$-$C_3$ alkyl group which is optionally substituted with from one to three halo groups, preferably F, or one or two hydroxyl groups;

K is independently 0-4 (0, 1, 2, 3 or 4), preferably 0 or 1;

K' is 1-4, preferably 1;

$R^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

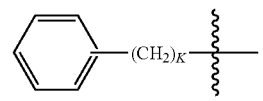

group, where K is preferably 1; [LINKERX] is a linker group which is comprises to at least one [CPBM] group and links the [CPBM] group to the [CRBM]/[ASGPRBM] through one or more optional [CON] groups, or [LINKERX] is a linker group which contains at least one or more functional groups which can be used to covalently bond the linker group to at least one [CRBM][ASGPRBM] group or optional [CON] group;

$R_2$ is a

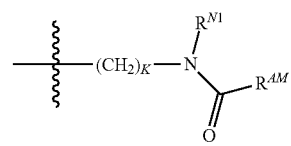

group where $R^{N1}$ and K are the same as above;

$R^{AM}$ is H, a $C_1$-$C_4$ alkyl group optionally substituted with up to 3 halo groups (preferably F) and one or two hydroxyl groups, a —$(CH_2)_K$COOH group, a —$(CH_2)_KC(O)O$—$C_1$-$C_4$ alkyl group which is optionally substituted with from 1-3 halo, preferably F groups, a O—C(O)—$C_1$-$C_4$ alkyl group, which is optionally substituted with from 1-3 halo, preferably F groups, a —C(O)—$C_1$-$C_4$ alkyl group, which is optionally substituted with from 1-3 halo, preferably F groups, a —$(CH_2)_K$—$NR^{N3}R^{N4}$ group where $R^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

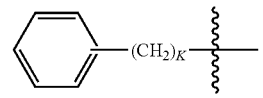

group (K is preferably 1), or
R₂ is a

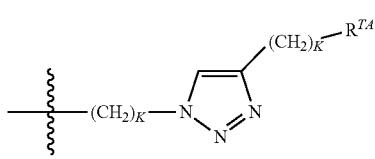

group,
where $R^{TA}$ is H, CN, $NR^{N1}R^{N2}$, —(CH₂)$_K$OH, —(CH₂)$_K$OC₁-C₄ alkyl, which is optionally substituted with from 1-3 halo (F, Cl, Br, I, preferably F) groups, C₁-C₄ alkyl, which is optionally substituted with from 1-3 halo (F, Cl, Br, I, preferably F) groups, —(CH₂)$_K$COOH, —(CH₂)$_K$C(O)O—C₁-C₄ alkyl which is optionally substituted with from 1-3 halo, preferably F groups, O—C(O)—C₁-C₄ alkyl, which is optionally substituted with from 1-3 halo, preferably F groups, —C(O)—C₁-C₄ alkyl, which is optionally substituted with from 1-3 halo, preferably F groups, or $R^{TA}$ is a C₃-C₁₀ aryl or a three- to ten-membered heteroaryl group containing up to 5 heteroaryl atoms, each of said aryl or heteroaryl groups being optionally substituted with up to three (preferably 1) CN, $NR^{N1}R^{N2}$, —(CH₂)$_K$OH, —(CH₂)$_K$OC₁-C₄ alkyl, which is optionally substituted with from 1-3 halo (F, Cl, Br, I, preferably F) groups, C₁-C₃ alkyl, which is optionally substituted with from 1-3 halo (F, Cl, Br, I, preferably F) groups or 1 or 2 hydroxy groups, —O—C₁-C₃-alkyl, which is optionally substituted with from 1-3 halo, preferably F groups, —(CH₂)$_K$COOH, —(CH₂)$_K$C(O)O—C₁-C₄ alkyl which is optionally substituted with from 1-3 halo, preferably F groups, O—C(O)—C₁-C₄ alkyl, which is optionally substituted with from 1-3 halo, preferably F groups or —(CH₂)$_K$C(O)—C₁-C₄ alkyl which is optionally substituted with from 1-3 halo, preferably F groups, or $R^{TA}$ is a

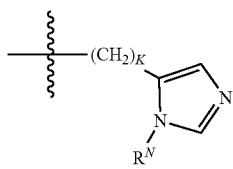

group, a

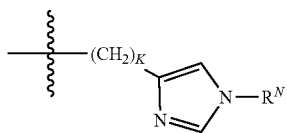

group, a

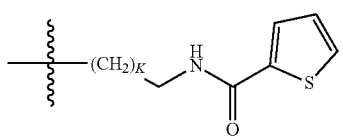

group or a

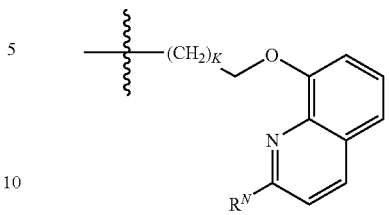

group,
(preferably, $R^{TA}$ is a

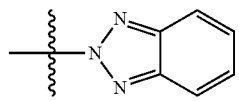 [SMILES: *n1nc2ccccc2n1]

group which is optionally substituted with up to three, preferably 1 C₁-C₃ alkyl groups which are optionally substituted with up to three halo (preferably F) groups, or $R^{TA}$ is a

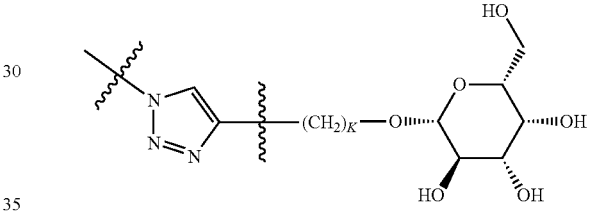

group,
wherein $R^N$, $R^{N1}$ and $R^{N2}$ are each independently H or a C₁-C₃ alkyl group which is optionally substituted with from one to three halo groups, preferably F, or one or two hydroxyl groups and
wherein each —(CH₂)$_K$ group is optionally substituted with 1-4, preferably 1 or 2, C₁-C₃ alkyl groups which are optionally substituted with from 1-3 fluoro groups or 1-2 hydroxyl groups; and K is independently 0-4 (0, 1, 2, 3 or 4), preferably 0 or 1;
[CON] is a connector moiety (including a [MULTICON]) as otherwise described herein; and
[LINKER] is a linking moiety as otherwise described herein which links [CPBM] to the [CRBM] group and optionally contains one or more connector moieties (which optionally connect(s) more than one chemical moiety to provide said linking moiety or which connects said linking moiety to said [CPBM] group or said [CRBM] group, or a pharmaceutically acceptable salt, stereoisomer, solvate or polymorph thereof.

In embodiments of the present invention X is often —O—C($R^{N1}$)($R^{N1}$), C($R^{N1}$)($R^{N1}$)—O—, —S—C($R^{N1}$)($R^{N1}$), C($R^{N1}$)($R^{N1}$)—S—, N($R^{N1}$)—C($R^{N1}$)($R^{N1}$), C($R^{N1}$)($R^{N1}$)—N($R^{N1}$) or C($R^{N1}$)($R^{N1}$)—C($R^{N1}$)($R^{N1}$) when X is 2 atoms in length,
X is —O—C($R^{N1}$)($R^{N1}$)—C($R^{N1}$)($R^{N1}$), C($R^{N1}$)($R^{N1}$)—O—C($R^{N1}$)($R^{N1}$)—, —O—C($R^{N1}$)($R^{N1}$)—O—, —O—C($R^{N1}$)($R^{N1}$)—S—, —O—C($R^{N1}$)($R^{N1}$) N($R^{N1}$)—, —S—C($R^{N1}$)($R^{N1}$)—C($R^{N1}$)($R^{N1}$), C($R^{N1}$)($R^{N1}$)—S—C($R^{N1}$)($R^{N1}$), C($R^{N1}$)($R^{N1}$)—S, —S—C($R^{N1}$)($R^{N1}$)—S—, —S—C($R^{N1}$)($R^{N1}$)—O—, —S—C($R^{N1}$)($R^{N1}$) N($R^{N1}$) N($R^{N1}$)

$C(R^{N1})(R^{N1})C(R^{N1})(R^{N1})$, $C(R^{N1})(R^{N1})$—$N(R^{N1})$—$C(R^{N1})(R^{N1})$, $C(R^{N1})(R^{N1})$—$C(R^{N1})(R^{N1})$—$N(R^{N1})$, $N(R^{N1})$—$C(R^{N1})(R^{N1})$—$N(R^{N1})$ or $C(R^{N1})(R^{N1})$—$C(R^{N1})(R^{N1})$—$C(R^{N1})(R^{N1})$ when X is 3 atoms in length, and X is —O—$C(R^{N1})(R^{N1})$—$C(R^{N1})(R^{N1})$—$C(R^{N1})(R^{N1})$, $C(R^{N1})(R^{N1})$—O—$C(R^{N1})(R^{N1})$—$(R^{N1})(R^{N1})$—, —O—$C(R^{N1})(R^{N1})$—O—$C(R^{N1})(R^{N1})$—, —S—$C(R^{N1})(R^{N1})$—$C(R^{N1})(R^{N1})$—$C(R^{N1})(R^{N1})$—, $C(R^{N1})(R^{N1})$—S—$C(R^{N1})(R^{N1})$—$C(R^{N1})(R^{N1})$—, $C(R^{N1})(R^{N1})$—$(R^{N1})(R^{N1})$—S—$C(R^{N1})(R^{N1})$—, —S—$C(R^{N1})(R^{N1})$—S—$C(R^{N1})(R^{N1})$—, $N(R^{N1})$—$C(R^{N1})(R^{N1})$—$C(R^{N1})(R^{N1})$—$C(R^{N1})(R^{N1})$—, $C(R^{N1})(R^{N1})$—$N(R^{N1})$—$C(R^{N1})(R^{N1})$—$C(R^{N1})(R^{N1})$, $C(R^{N1})(R^{N1})$—$C(R^{N1})(R^{N1})$—$N(R^{N1})$, $N(R^{N1})$—$C(R^{N1})(R^{N1})$—$N(R^{N1})$ or $C(R^{N1})(R^{N1})$—$C(R^{N1})(R^{N1})$—$C(R^{N1})(R^{N1})$ when X is 4 atoms in length where $R^{N1}$ is the same as above. Most often, $R^{N1}$ is H.

In embodiments of the present invention X is $OCH_2$ or $CH_2O$ and $R^{N1}$ is preferably H.

In embodiments, the [CRBM]/[ASGPRBM] group is a group according to the chemical structure:

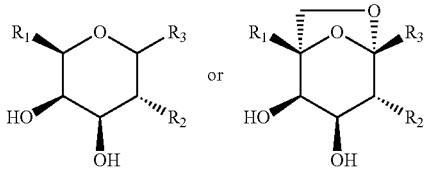

where $R_1$, $R_2$ and $R_3$ are the same as above, or a pharmaceutically acceptable salt, stereoisomer, solvate or polymorph thereof.

In embodiments, the [CRBM]/[ASGPRBM] group is a group according to the chemical structure:

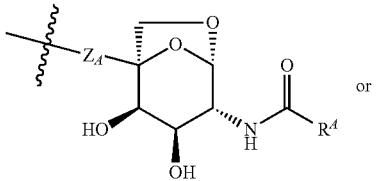

Where $R^A$ is a $C_1$-$C_3$ alkyl group which is optionally (preferably) substituted with 1-5 halo (preferably fluoro) groups (preferably $R^A$ is a methyl or ethyl group which is optionally substituted with from 1-3 fluoro groups);

$Z_A$ is —$(CH_2)_{IM}$-, —O—$(CH_2)_{IM}$-, S—$(CH_2)_{IM}$-, $NR_M$—$(CH_2)_{IM}$-, $C(O)$—$(CH_2)_{IM}$—, a PEG group containing from 1 to 8 preferably 1-4 ethylene glycol residues or a —$C(O)$—$(CH_2)_{IM}NR_M$ group (preferably a PEG containing group comprising from 1 to 8 ethylene glycol, preferably 2-4 ethylene glycol residues) where IM and $R_M$ are the same as above; and $Z_B$ is absent, $(CH_2)_{IM}$-, $C(O)$—$(CH_2)_{IM}$— or $C(O)$—$(CH_2)_{IM}$—$NR_M$, where IM and $R_M$ are the same as above.

Note that the [CRBM][ASPGRM] group set forth above may also be represented as follows:

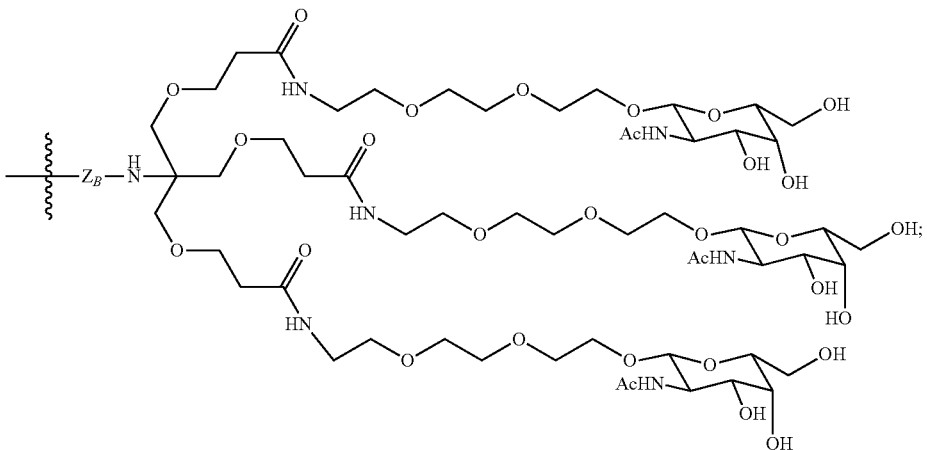

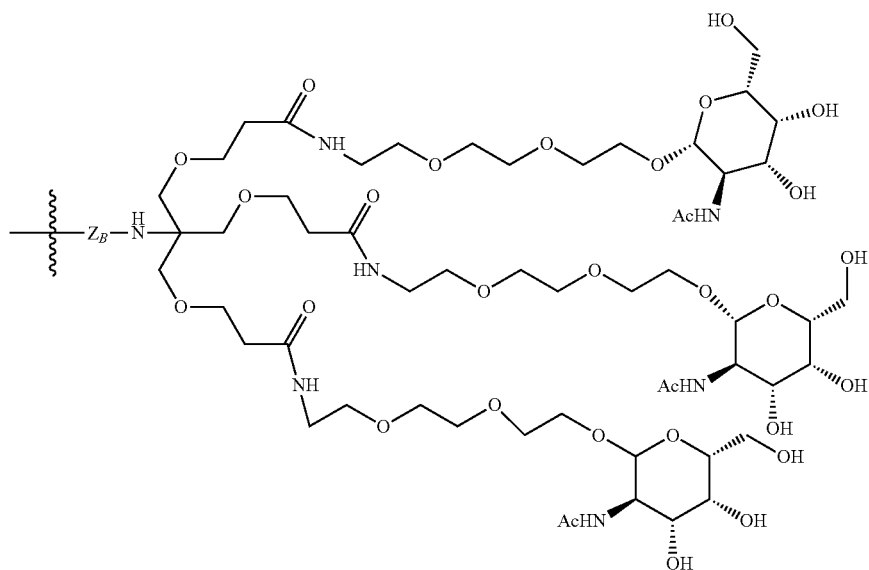

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a multiple drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor).

Thus, the present invention is generally applicable and may be used to treat any cancer in any tissue, regardless of etiology.

The term "tumor" is used to describe a malignant or benign growth or tumefacent.

The term "autoimmune disease" refers to a disease or illness that occurs when the body tissues are attacked by its own immune system. The immune system is a complex organization within the body that is designed normally to "seek and destroy" invaders of the body, including infectious agents. In diseases which are described as autoimmune diseases, MIF levels are often elevated. The present invention seeks to inhibit or lower elevated MIF levels in patients with autoimmune disease (as well as inflammatory diseases and conditions and cancer) and by decreasing MIF levels, ameliorate many of the symptoms and secondary effects of these disease states and conditions. Examples of autoimmune diseases which often exhibit high expressed levels of MIF including, for example, systemic lupus erythematosus, Sjogren syndrome, Hashimoto thyroiditis, rheumatoid arthritis, juvenile (type 1) diabetes, polymyositis, scleroderma, Addison's disease, vtiligo, pernicious anemia, glomerulonephritis, and pulmonary fibrosis, among numerous others.

A more complete list of autoimmune diseases which may be treated by compounds and pharmaceutical compositions according to the present invention includes Addison's Disease, Autoimmune polyendodrine syndrome (APS) types 1, 2 and 3, autoimmune pancreatitis (AIP), diabetes mellitus type 1, autoimmune thyroiditis, Ord's thyroiditis, Grave's disease, autoimmune oophoritis, endometriosis, autoimmune orchitis, Sjogren's syndrome, autoimmune enteropathy, coeliac disease, Crohns' disease, microscopic colitis, ulcerative colitis, autophospholipid syndrome (APlS), aplastic anemia, autoimmune hemolytica anemia, autoimmune lymphoproliferative syndrome, autoimmune neutropenia, autoimmune thrombocytopenic purpura, cold agglutinin disease, essential mixed cryoglulinemia, Evans syndrome, pernicious anemia, pure red cell aplasia, thrombocytopenia, adiposis dolorosa, adult-onset Still's disease, anklyosing spondylitis, CREST syndrome, drug-induced lupus, enthesitis-related arthritis, esosiniphilic fasciitis, Felty syndrome, AgG4-related disease, juvenile arthritis, Lyme disease (chronic), mixed connective tissue dease (MCTD), palindromic rheurmatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus, undifferentiated connective tissue disease (UCTD), dematomyositis, fibromyalgia, myositis, inclusion body myositis, myasthenia gravis, neuromyotonia, paraneoplastic cerebellar degeneration, polymysositis, acute disseminated encephalomyelitis (ADEM), acute motor axonic neuropathy, anti-NMDA receptor encephalitis, Balo concentric sclerosis, Bickerstaffs encephalitis, chronic inflamatory demyelinating polyneuropathy, Guillain-Barré syndrome, Hashimoto's encephalopathy, idiopathic inflammatory demyelinating diseases, Lambert-Eaton myasthenic syndrome, multiple sclerosis, pattern II, Oshtoran Syndrome, Pendiatric Autoimmune Neuropsychiatric Disorder Associated with Streptococcus (PANDAS), progressive inflammatory neuropathy, restless leg syndrome, stiff person syndrome, Syndenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease (AIED), Meniere's disease, Behçet's disease, Eosiniphilic granulomatosis with polyangiitis (EGPA), giant cell arteritis, granulomatosis with polyangiitis (GPA), IgA vasculitis (IgAV), Kawasaki's disease, leukocytoclastic vasculitis, lupus vasculitis, rheumatoid vasculitis, microscopic polyangiitis (VIPA), polyarteritis nodosa (PAN), polymyalgia rheumatica, urticarial vasculitis, vasculitis, primary immune deficiency, chronic fatigue syndrome, complex regional pain syndrome, eosiniphilic esopagitis, gastritis, interstitial lung disease, POEMS syndrome, Raynaud's syndrome, primary immunodeficiency and pyoderma gangrenosum, among others.

The term "inflammatory disease" is used to describe a disease or illness with acute, but more often chronic inflammation as a principal manifestation of the disease or illness. Inflammatory diseases include diseases of neurodegeneration (including, for example, Alzheimer's disease, Parkinson's disease, Huntington's disease; other ataxias), diseases of compromised immune response causing inflammation (e.g., dysregulation of T cell maturation, B cell and T cell homeostasis, counters damaging inflammation), chronic inflammatory diseases including, for example, inflammatory bowel disease, including Crohn's disease, rheumatoid arthritis, lupus, multiple sclerosis, chronic obstructive pulmony disease/COPD, pulmonary fibrosis, cystic fibrosis, Sjogren's disease; hyperglycemic disorders, diabetes (I and II), affecting lipid metabolism islet function and/or structure, pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), elevated triglycerides and metabolic syndrome, liver disease, renal disease (apoptosis in plaques, glomerular disease), cardiovascular disease (especially including infarction, ischemia, stroke, pressure overload and complications during reperfusion), muscle degeneration and atrophy, low grade inflammation, gout, silicosis, atherosclerosis and associated conditions such as cardiac and neurological (both central and peripheral) manifestations including stroke, age-associated dementia and sporadic form of Alzheimer's disease, and psychiatric conditions including depression), stroke and spinal cord injury, arteriosclerosis, among others. In these diseases, elevated MIF is very often observed, making these disease states and/or conditions response to therapy using compounds and/or pharmaceutical compositions according to the present invention. It is noted that there is some overlap between certain autoimmune diseases and inflammatory diseases as described herein.

The term "linker", refers to a chemical entity including a complex linker connecting a circulating protein binding moiety (CPBM) to the cellular receptor binding moiety (CRBM) including an asialoglycoprotein receptor binding moiety (ASGPRBM), optionally through at least one (preferably one or two) connector moiety [CON] through covalent bonds in compounds according to the present invention. The linker between the two active portions of the molecule, that is the CPBM group and the CRBM/ASGPRBM group ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 2 and 15 glycol units, 1 and 8 glycol units, 1, 2, 3, 4, 5, and 6 glycol units in length may be preferred, although the length of certain linkers may be far greater. By having a linker with a length as otherwise disclosed herein, the CPBM group and the CRBM/ASGPRBM group may be situated to advantageously take advantage of the biological activity of compounds according to the present invention which bind to receptors, including asialoglycoprotein receptors on hepatocytes and other cells resulting in the selective and targeted degradation of circulating proteins within the lysosomal degradation mechanism or other degradation mechanism of the hepatocytes. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, 1 to 3, 1 to 4, 2 to 6, 1 to 5, etc.) may be favored as a linker because of the chemical and biological characteristics of these molecules. The use of polyethylene (PEG) linkages of between 2 and 15 ethylene glycol units is preferred. When describing linkers according to the present invention, including polyethylene glycol linkers or other linkers, one or more additional groups (e.g., methylene groups, amide groups, keto groups, amine groups, etc., with methylene groups or amide groups being preferred) may be covalently attached at either end of the linker group to attach to a CRBM/ASGPRBM group, a [CON] group, another linker group or a CPBM group.

Alternative linkers may include, for example, polyamino acid linkers of up to 100 amino acids (of any type, preferably D- or L-amino acids, preferably naturally occurring L-amino acids) in length (about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc. in length), optionally including one or more connecting groups (preferably 1 or 2 connecting groups at one or both ends of the polyamino acid linker).

Preferred linkers include those according to the chemical structures:

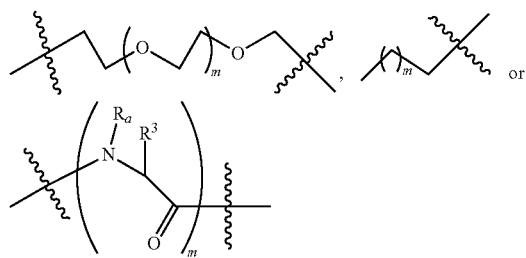

Or a polypropylene glycol or polypropylene-co-polyethylene glycol linker having between 1 and 100 alkylene glycol units, preferably about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3; Where $R_a$ is H, $C_1$-$C_3$ alkyl or alkanol or forms a cyclic ring with $R^3$ (proline) and $R^3$ is a side chain derived from a D- or L amino acid (preferably a naturally occurring L-amino acid) preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline hydroxyproline ($R^3$ forms a cyclic ring with $R_a$ and the adjacent nitrogen group to form a pyrrolidine or hydroxypyrrolidine group), serine (methanol), threonine (ethanol, 1-hydroxyethane), tryptophan (methyleneindole), tyrosine (methylene phenol) or valine (isopropyl);

m (within the context of this use) is an integer from 1 to 100, 1 to 75, 1 to 60, 1 to 55, 1 to 50, 1 to 45, 1 to 40, 2 to 35, 3 to 30, 1 to 15, 1 to 12, 1 to 10, 1 to 8, 1 to 6, 1, 2, 3, 4 or 5.

Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units, to which is bonded a lysine group or other amino acid moiety at one or both ends of the linker (which can consist of between 1 and 10 amino acids which can bind the CPBM and/or the CRBM/ASGPRBM group. Still other linkers comprise amino acid residues (D or L) which are bonded to CPBM and/or CRBM/ASGPRBM moieties as otherwise described herein. In another embodiment, as otherwise described herein, the amino acid has anywhere from 1-15 methylene groups separating the amino group from the acid (acyl) group in providing a linker to the MIFBM and/or the ASGPRBM group, wherein the linker contains from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 amino acid groups linked together through peptide linkages to form the linker. This linker is represented by the chemical structure:

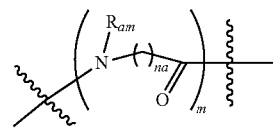

where $R_{am}$ is H or a $C_1$-$C_3$ alkyl optionally substituted with one or two hydroxyl groups;

na is 1-15, 1-12, 1-10, 1-8, 1, 2, 3, 4, 5, 6, 7, 8, 9, 10 or 11;

m is an integer from 1 to 100, 1 to 75, 1 to 60, 1 to 55, 1 to 50, 1 to 45, 1 to 40, 2 to 35, 3 to 30, 1 to 15, 1 to 12, 1 to 10, 1 to 8, 1 to 6, 1, 2, 3, 4 or 51 to 50, 1 to 45, 1 to 40, 2 to 35, 3 to 30, 1 to 15, 1 to 10, 1 to 8, 1 to 6, 1, 2, 3, 4 or 5.

Or another linker is according to the chemical formula:

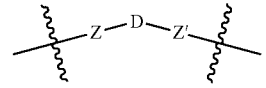

Where Z and Z' are each independently a bond, —(CH$_2$)$_i$—O, —(CH$_2$)$_i$—S, —(CH$_2$)$_i$—N—R,

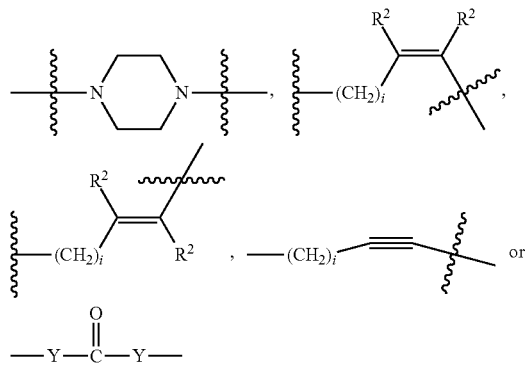

wherein said —(CH$_2$), group, if present in Z or Z', is bonded to a connector (CON), CPBM or CRBM/ASGPRBM;
Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 0 to 100, 0 to 75, 1 to 60, 1 to 55, 1 to 50, 1 to 45, 1 to 40, 2 to 35, 3 to 30, 1 to 15, 1 to 10, 1 to 8, 1 to 6, 0, 1, 2, 3, 4 or 5;
D is

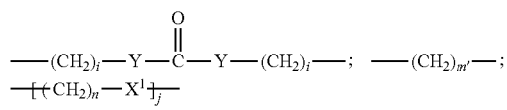

or
a bond, with the proviso that Z, Z' and D are not each simultaneously bonds;
j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 (n is preferably 2);
X$^1$ is O, S or N—R; and
R is H, or a C$_1$-C$_3$ alkyl or alkanol group, or a pharmaceutical salt thereof.

Other linkers which are included herein include preferred linkers according to the chemical structure:

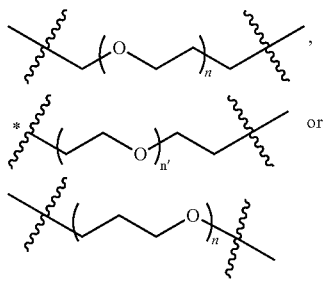

where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and
each n" is independently 0 to 8, often 1 to 7, or 1, 2, 3, 4, 5 or 6 (preferably 2, 3, 4 or 5).

Linkers also can comprise two or more linker segments (based upon the linkers described above) which are attached directly to each other or through [CON] groups forming a complex linker. Certain linkers which include a [CON] group (especially a diamide [CON] group as otherwise described herein) connecting a first and second (PEG) linker group include the following structures:

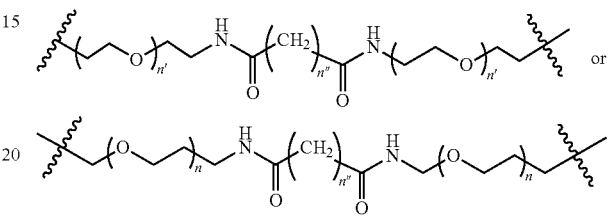

where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and
each n" is independently 0 to 8, often 1 to 7, or 1, 2, 3, 4, 5 or 6 (preferably 3). Noted is that each of these linkers may also contain alkylene groups containing from 1 to 4 methylene groups at the distal ends of each linker group in order to facilitate connection of the linker group.

Other linkers which include a connector group [CON] include groups which are represented by the chemical formula

PEG-[CON]-PEG

Wherein each PEG linker is independently a polyethylene glycol group containing from 1-12 ethylene glycol residues and [CON] is a connector group as otherwise set forth herein, preferably a triazole group

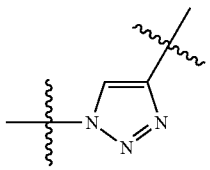

The term "connector", symbolized in the generic formulas by "CON" or [CON], is used to describe a chemical moiety which is optionally included in bifunctional compounds according to the present invention which forms from the reaction product of an activated linker with a CPBM moiety (which also is preferably activated for covalently bonding the linker with the moiety) or a CRBM/ASGPRBM group with an activated linker. The connector group is often the resulting moiety which forms from the facile condensation of two or more separate chemical fragments which contain reactive groups which can provide connector groups as otherwise described to produce bifunctional or multifunctional compounds according to the present invention. It is noted that a connector may be distinguishable from a linker in that the connector is the result of a specific chemistry which is used to provide bifunctional compounds according to the present invention wherein the reaction product of these groups results in an identifiable connector group or part of a connector group which is distinguishable from the linker group, although in certain instances, the connector group is incorporated into and integral with the linker group as otherwise described herein. It is noted also that a connector group may be linked to a number of linkers to provide multifunctionality (i.e., more than one CPBM moiety and/or more than one CRBM/ASGPRBM moiety) within the same molecule. It is noted that there may be some overlap between the description of the connector group and the linker group such that the connector group is actually incorporated or forms part of the linker, especially with respect to more common connector groups such as amide groups, oxygen (ether), sulfur (thioether) or amine linkages, urea or carbonate —OC(O)O— groups or as otherwise described herein. It is further noted that a connector (or linker) may be connected to CPBM, CRBM/ASGPRBM or a linker at positions which are represented as being linked to another group using the symbol

Where two or more such groups are present in a linker or connector, any of an CRBM/ASGPRBM, a linker or a CPBM group may be bonded to such a group. Where that symbol is not used, the linker may be at one or more positions of a moiety.

Common connector groups which are used in the present invention include the following chemical groups:

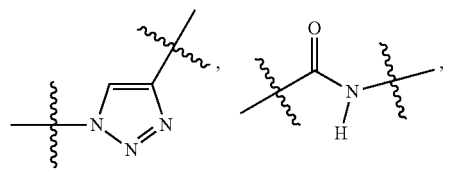

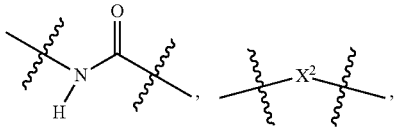

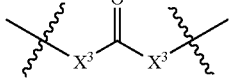

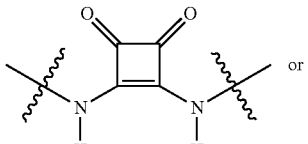 or

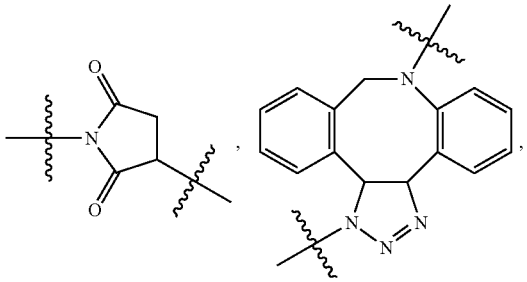

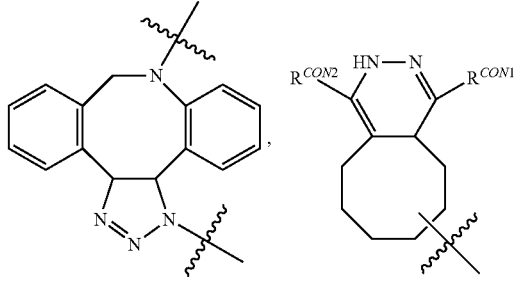

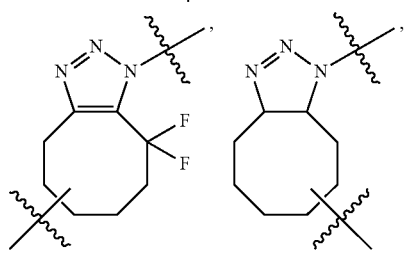

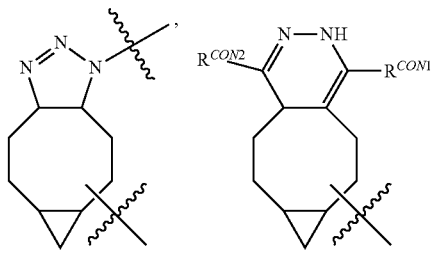

where $R^{CON1}$ and $R^{CON2}$ are each independently H, methyl or a bond (for attachment to another moiety); or a diamide group according to the structure:

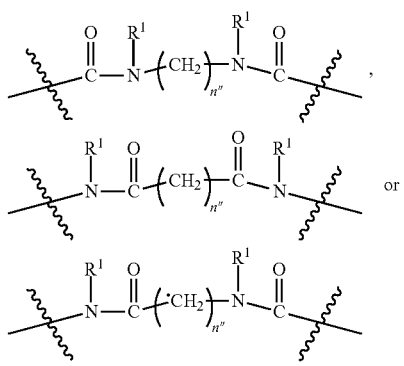

Where $X^2$ is $CH_2$, O, S, $NR^4$, C(O), S(O), $S(O)_2$, —$S(O)_2O$, —$OS(O)_2$, or $OS(O)_2O$;

$X^3$ is O, S, $NR^4$;

$R^4$ is H, a $C_1$-$C_3$ alkyl or alkanol group, or a —C(O)($C_1$-$C_3$) group;

$R^1$ is H or a $C_1$-$C_3$ alkyl group (preferably H); and n" is independently 0 to 8, often 1 to 7, or 1, 2, 3, 4, 5 or 6 (preferably 3);

or the connector group [CON] is a group according to the chemical structure:

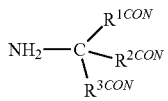

Where $R^{1CON}$, $R^{2CON}$ and $R^{3CON}$ are each independently H, —$(CH_2)_{MC1}$, —$(CH_2)_{MC1a}C(O)_{XA}(NR^4)_{XA}$—$(CH_2)_{MC1a}$, —$(CH_2)_{MC1a}(NR^4)_{XA}C(O)_{XA}$—$(CH_2)_{MC1a}$ or —$(CH_2)_{MC1a}O$—$(CH_2)_{MC1}$—$C(O)NR^4$—, with the proviso that $R^{1CON}$, $R^{2CON}$ and $R^{3CON}$ are not simultaneously H;

Each MC1 is independently 1-4 (preferably 1 or 2);

Each MC1a is independently 0-4 (preferably 0, 1 or 2); and $R^4$ is H, a $C_1$-$C_3$ alkyl or alkanol group, or a —$C(O)(C_1$-$C_3)$ group.

The triazole group, indicated above, may be a preferred connector group. An additional preferred connector group is

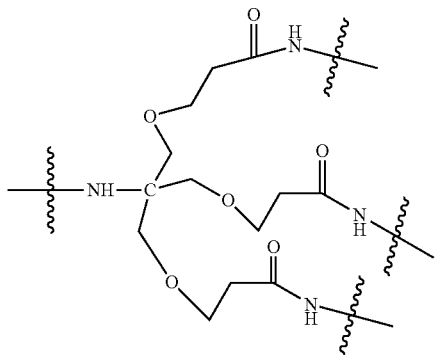 [SMILES: *NC(=O)CCOCC(COCCC(=O)N*)(COCCC(=O)N*)N*]

which is linked to at least one CPBM and/or at least one CRBM/ASPRGBM (preferably 3 CRBM/ASPRGBM moieties). This connector group may be used to form GN3 as otherwise described herein.

It is noted that each connector may be extended with one or more methylene groups to facilitate connection to a linker group, another CON group, a CPBM group or a CRBM/ASGPRBM group. It is noted that in certain instances, within context the diamide group may also function independently as a linker group.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer.

The term "anticancer agent" or "additional anticancer agent" refers to a compound other than the chimeric compounds according to the present invention which may be used in combination with a compound according to the present invention for the treatment of cancer.

Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol), among others. Exemplary anticancer compounds for use in the present invention may include everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258), 3-[5-(methylsulfonylpiperadinemethyl)-indolyl]-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-NH 2 acetate [$C_{59}H_{84}N_{18}Oi_4$-$(C_2H_4O_2)$x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714: TAK-165, HKI-272, erlotinib, lapatanib, canertinib. ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, S16668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, vemurafenib among others, including immunotherapy agents such as IDO inhibitors (an inhibitor of indoleamine 2,3-dioxygenase (IDO) pathway) such as Indoximod (NLG-8187), Navoximod (GDC-0919) and NLG802, PDL1 inhibitors (an inhibitor of programmed death-ligand 1) including, for example, nivolumab, durvalumab and atezolizumab, PD1 inhibitors such as pembrolizumab (Merck) and CTLA-4 inhibitors (an inhibitor of cytotoxic T-lymphocyte associated protein 4/cluster of differentiation 152), including ipilimumab and tremelimumab, among others.

In addition to anticancer agents, a number of other agents may be coadministered with chimeric compounds according to the present invention in the treatment of cancer. These include active agents, minerals, vitamins and nutritional supplements which have shown some efficacy in inhibiting cancer tissue or its growth or are otherwise useful in the treatment of cancer. For example, one or more of dietary selenium, vitamin E, lycopene, soy foods, curcumin (turmeric), vitamin D, green tea, omega-3 fatty acids and phytoestrogens, including beta-sitosterol, may be utilized in combination with the present compounds to treat cancer.

Without not being limited by way of theory, compounds according to the present invention which contain a CPBM binding moiety (CPBM) and CRBM/ASGPR binding moiety selectively bind to circulating proteins and through that binding, facilitate the introduction of the cellular protein into hepatocytes or other cells (degrading cells) which bind the CRBM/ASGPRBM selectively, where, the circulating protein, inside the hepatocyte or other degrading cell is degraded and removed from circulation. Thus, compounds according to the present invention both bind to MIF proteins and remove the MIF proteins from circulation resulting in a dual action which is particularly effective for treating disease states and conditions.

Pharmaceutical compositions comprising combinations of an effective amount of at least one compound disclosed herein, often a bi-functional chimeric compound (containing at least one MIFBM group or antibody binding moiety and at least one ASGPRBM) according to the present invention, and one or more of the compounds as otherwise described herein, all in effective amounts, in combination with a pharmaceutically effective amount of a carrier, additive or excipient, represents a further aspect of the present invention. These may be used in combination with at least one additional, optional anticancer agent as otherwise disclosed herein.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir, among others. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally (including via intubation through the mouth or nose into the stomach), intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 1.5 grams, from 0.1 milligram to 1 gram, 0.5 milligram to 750 milligrams, more often about 1 milligram to about 600 milligrams, and even more often about 10 milligrams to about 500 milligrams of active ingredient, alone or in combination with at least one additional compound which may be used to treat cancer, prostate cancer or metastatic prostate cancer or a secondary effect or condition thereof.

Methods of treating patients or subjects in need for a particular disease state or condition as otherwise described herein, especially cancer, comprise administration of an effective amount of a pharmaceutical composition comprising therapeutic amounts of one or more of the novel compounds described herein and optionally at least one additional bioactive (e.g. anti-cancer, anti-inflammatory) agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dose of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a human) suffering from an autoimmune disease, an inflammatory disease or cancer can be treated by administering to the patient (subject) an effective amount of a chimeric/bi-functional compound according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating autoimmune and/or inflammatory diseases or cancer, including metastatic cancer or recurrent cancer or ameliorating the secondary effects and/or symptoms associated with these disease states and/or conditions. This treatment can also be administered in conjunction with other conventional therapies, such as radiation treatment or surgery for cancer.

The present compounds, alone or in combination with other agents as described herein, can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from about 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-500 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, anti-inflammatory agents, immunosuppressants, antibiotics, antifungals, or antiviral compounds. In certain preferred aspects of the invention, one or more chimeric/bifunctional CPBM binding compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled and/or sustained release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions or cholestosomes may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Chemical Synthesis

Figure 7:
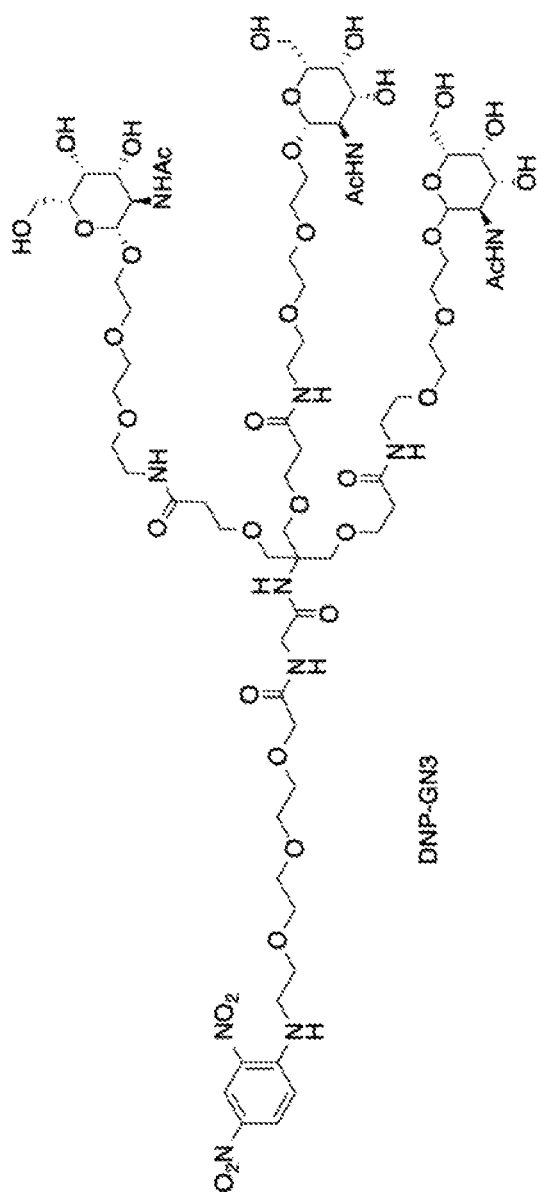
FIG. 7 shows molecules DNP-GN3 and DNP-AcF3-3, which are bifunctional molecules that bind to anti-DNP IgG and ASGPR.
Figure 7:
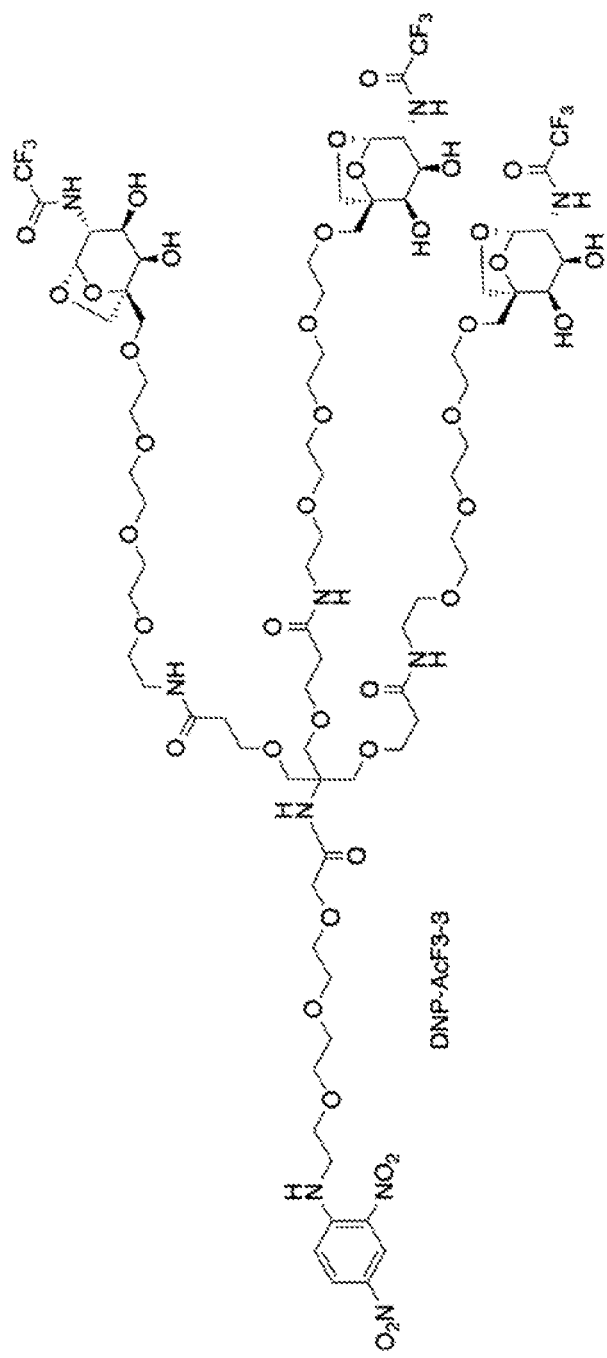
Figure 13:
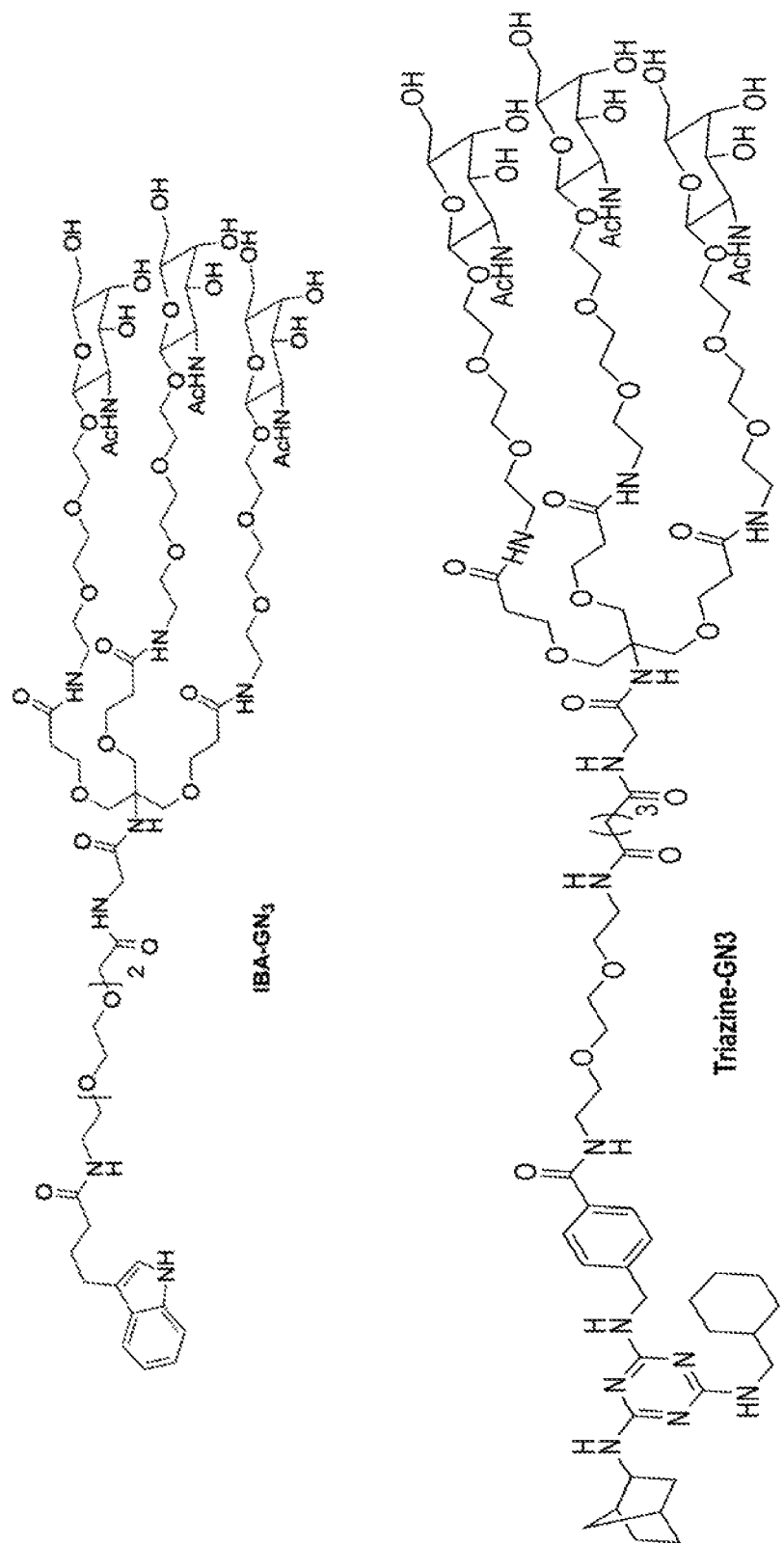
FIG. 13 shows the structures of IgG-degrading molecules IBA-GN3, Triazine-GN3, FcIII-GN3, and FcIII-4c-GN3.
Figure 13:
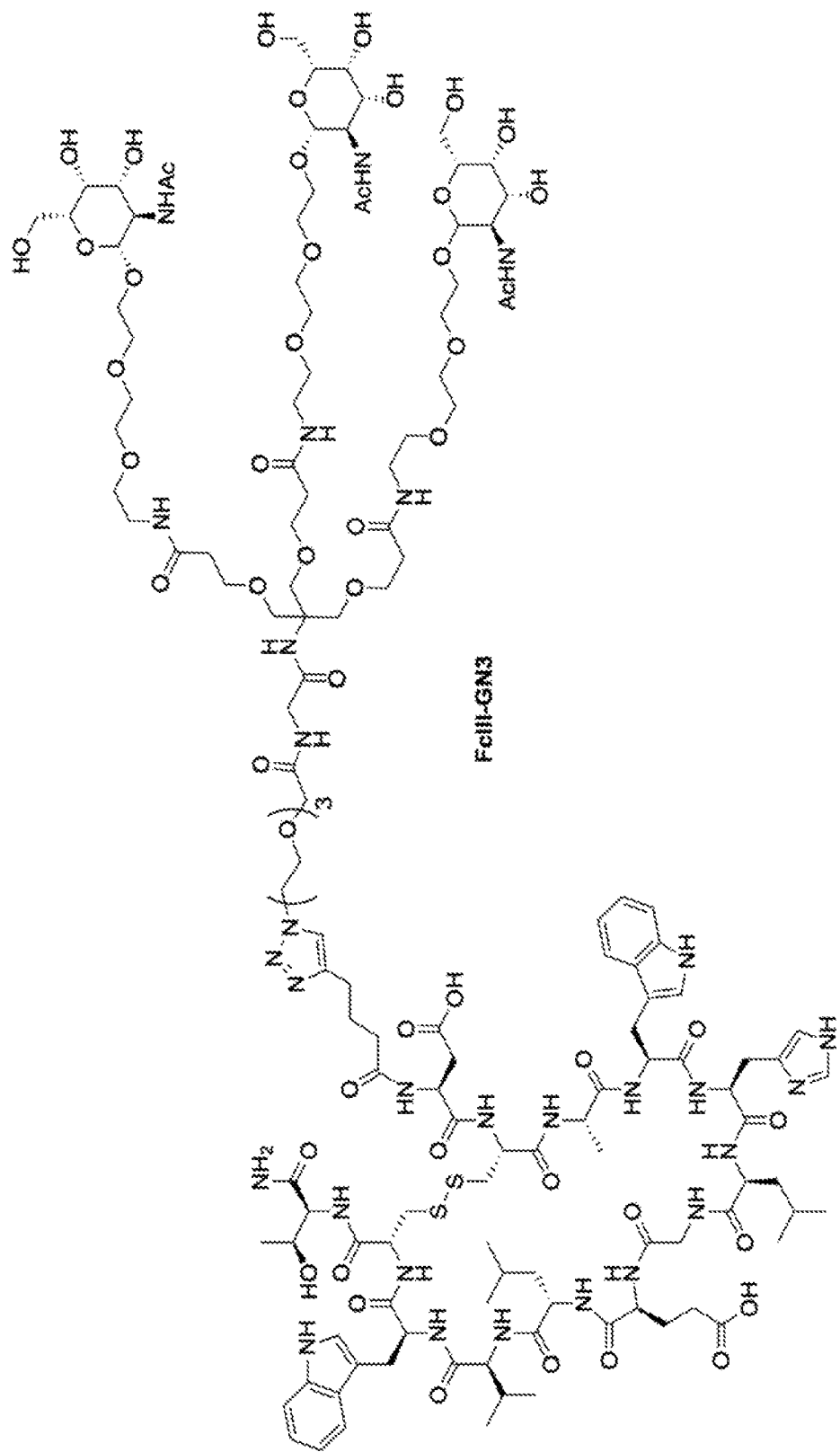
Figure 13:
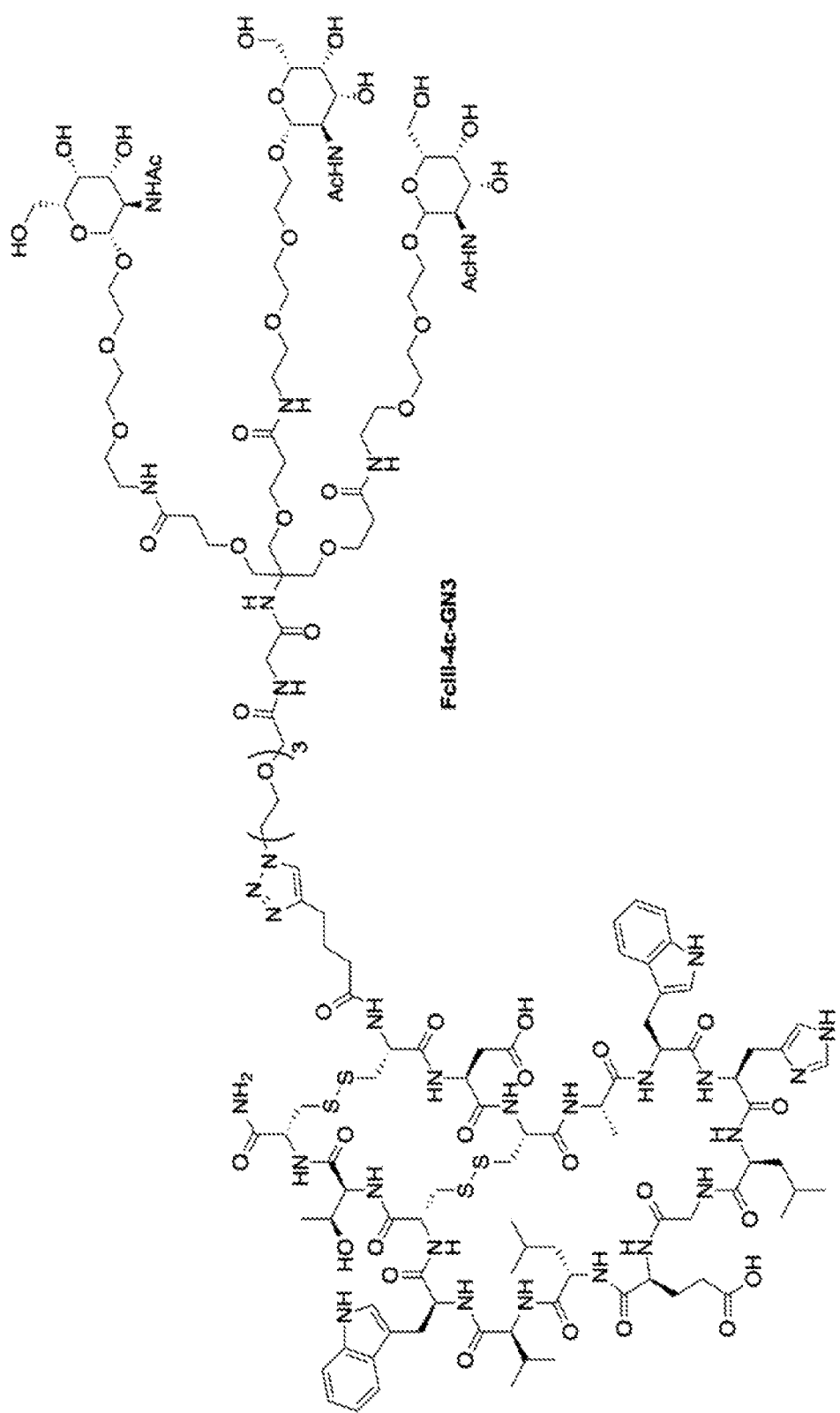

FIGS. 1, 7, and 13 attached hereto identify particular compounds according to the present invention which exhibit activity in binding to and reducing and/or eliminating unwanted circulating proteins for therapeutic and/or diagnostic purposes. These compounds are based upon an MIF, anti-DNP IgG, or IgG binding moiety to which is covalently attached an ASPGR group such as $GN_3$ or AcF3-3 group through a linker which contains from 1 to 100 ethylene glycol groups, more often from 1 to 15 ethylene glycol groups, from 1 to 10 ethylene glycol groups, often from 2 to 10 ethylene glycol groups which are optionally attached through a [CON] group, such as a 1,2,3-triazole or other [CON] group as described herein.

Figure 16:
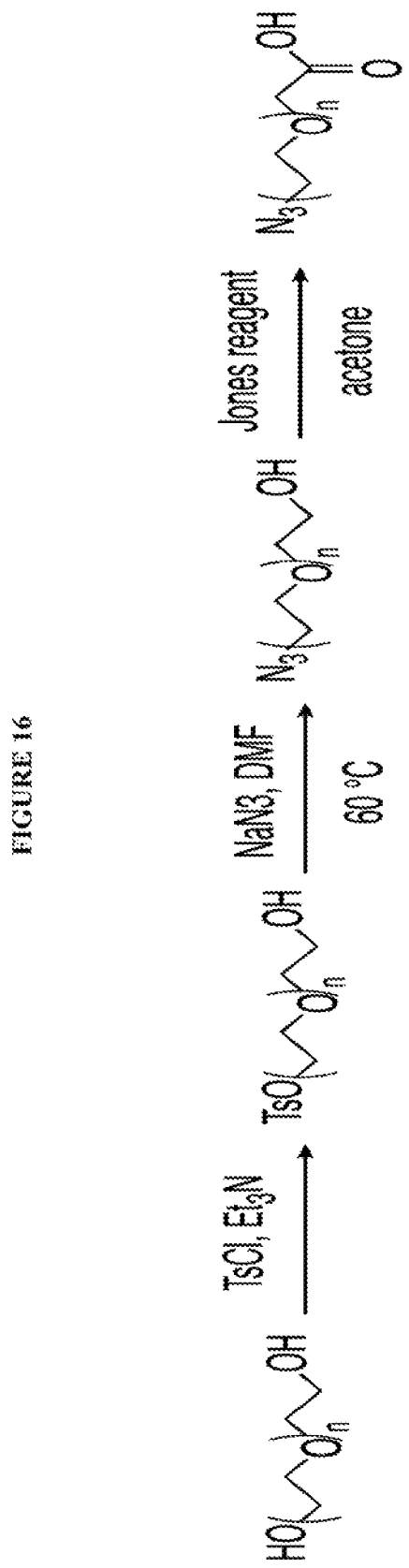
FIGS. 16-18 show the synthesis of PEG linkers used in several molecules outlined in this invention.

FIG. 16 shows the synthesis of azide/amide carboxylic end capped PEG linker intermediates which may be condensed onto an alkynyl precursor (e.g. NVS alkyne precursor of FIG. 5) to provide carboxylic acid capped intermediate which can be used to provide bifunctional molecules.

Figure 17:
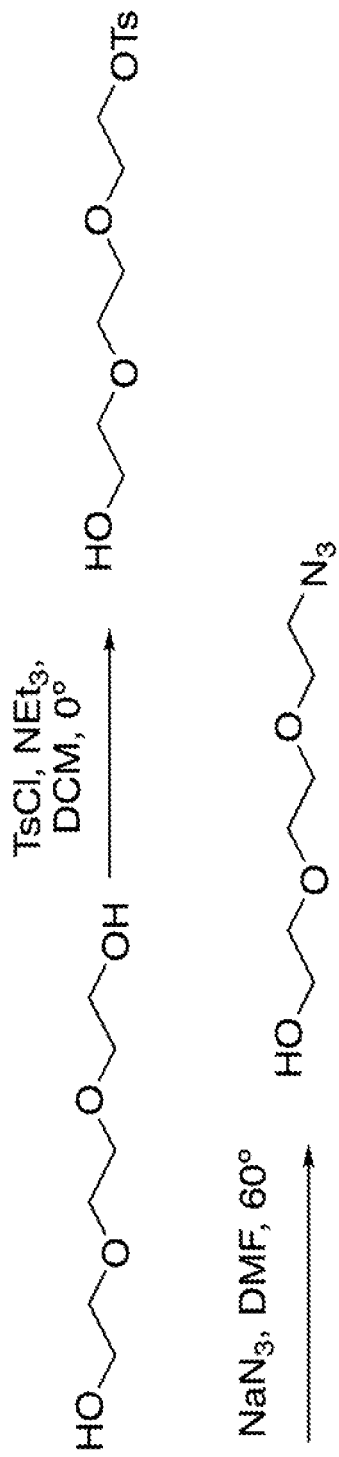

FIG. 17 describes a general method for conversion of PEG molecules into hydroxyl azides. The PEG compound is tosylated (TsCl, DCM, in the presence of base) at reduced temperature and further reacted with sodium azide at elevated temperature in a non-nucleophilic solvent. The final azidoalcohol is used in subsequent figures.

Figure 18:
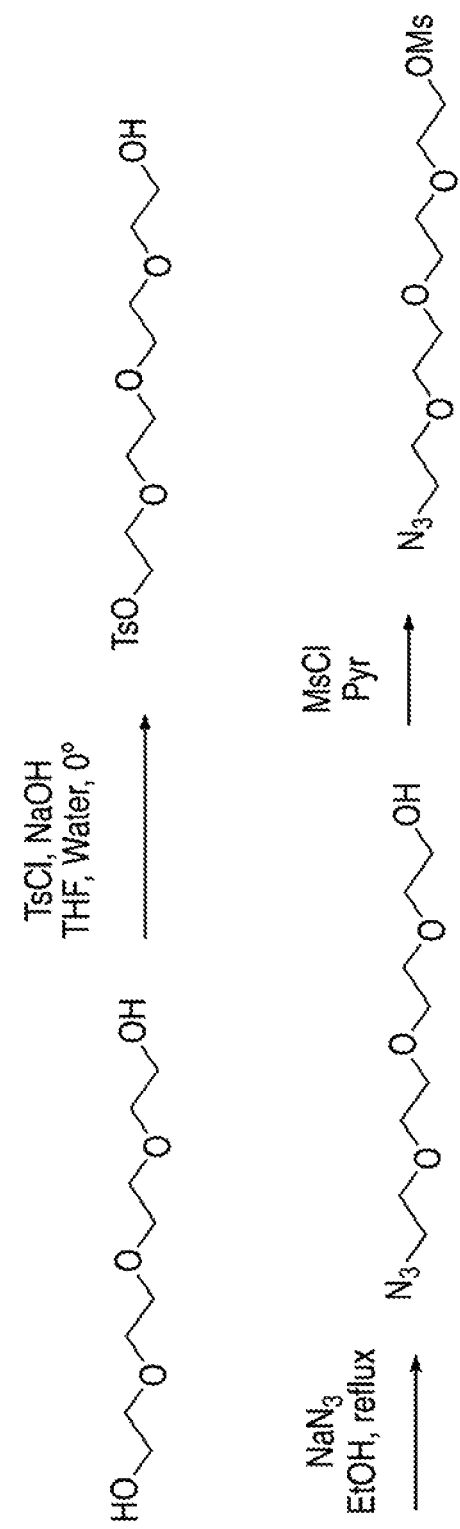

FIG. 18 describes the synthesis of a mesylated azide from a starting PEG molecule employing the same synthetic steps to reach the intermediate azido alcohol. This is then treated with MSCl in pyridine to afford the final compound.

Figure 19:
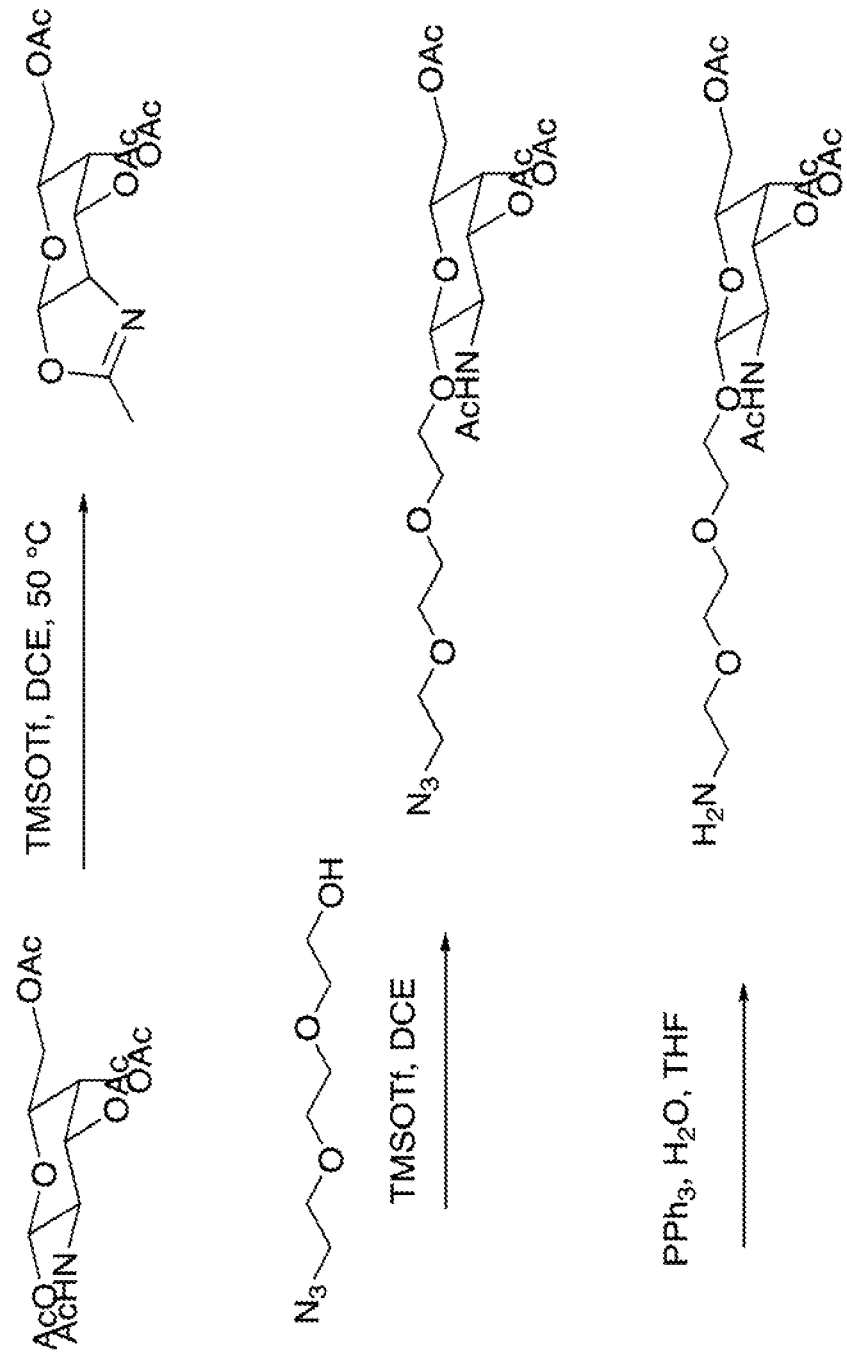
FIGS. 19-21 show the synthesis of ASGPR-binding precursors and ligands used in several molecules in this invention.

FIG. 19 shows the synthesis of the GalNAc ASGPR ligand linked through PEG to a terminating amine. Pentaacetyl galactosamine is reacted with TMSOTf at elevated temperature in DCE to produce a bicyclic intermediate, which is then reacted with an azido alcohol to give an azide intermediate (TMSOTf, DCE). This molecule is then subjected to a Staudinger reduction to give an amine which is used in subsequent figures.

Figure 20:
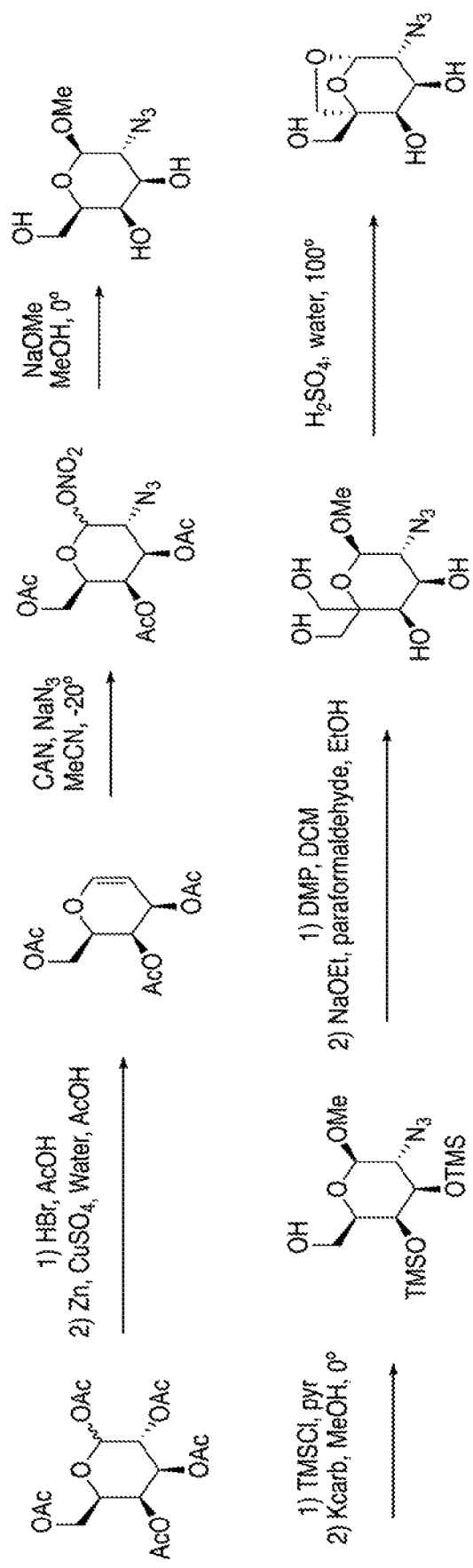

FIG. 20 shows the synthesis of a higher affinity bicyclic ASGPR ligand. Galactose pentaacetate is treated with HBr/AcOH to give the brominated intermediate, which is treated with Zn and CuSO4 (water/AcOH) to give the galactal. This is treated with ammonium cerium nitrate and sodium azide at reduced temperature (MeCN) to give the disubstituted intermediate compound. This is then treated with strong base (NaOMe/MeOH) to give the triol azide intermediate. This compound is silylated completely (TMSCl/pyr) then the primary alcohol is deprotected (potassium carbonate, MeOH, lowered temperature) and oxidized (Dess-Martin Periodinane, DCM). Treatment with strong base (NaOEt/HOEt) and paraformaldehyde gives the tetraol intermediate, which is cyclized in strong acid (H2SO4/water) to give the bicyclic azide ligand.

Figure 21:
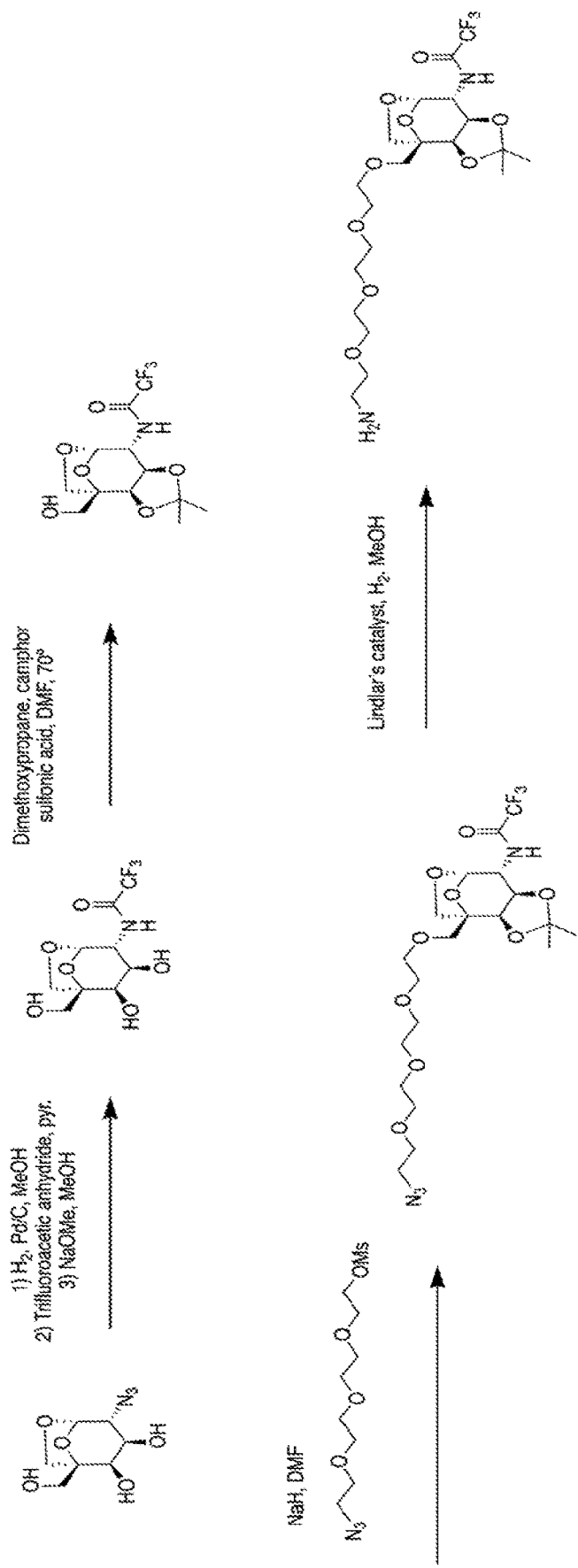

FIG. 21 shows the synthesis of a trifluoro-acetate derivative of the bicyclic ASGPR ligand. The triol azide is reduced (Pd/C, MeOH) to give the intermediate amine, which is then peracylated with trifuloroacetic anhydride. The esters are hydrolyzed with strong base (NaOMe/HOMe) to give the intermediate amide, which is protected using dimethoxypropane in the presence of camphorsulfonic acid in DMF at elevated temperature. This is then reacted a mesylated azdio alcohol in the presence of strong base (NaH/DMF) to give an intermediate azide that is reduced (Lindlar's catalyst, MeOH) to give the final amine.

Figure 22:
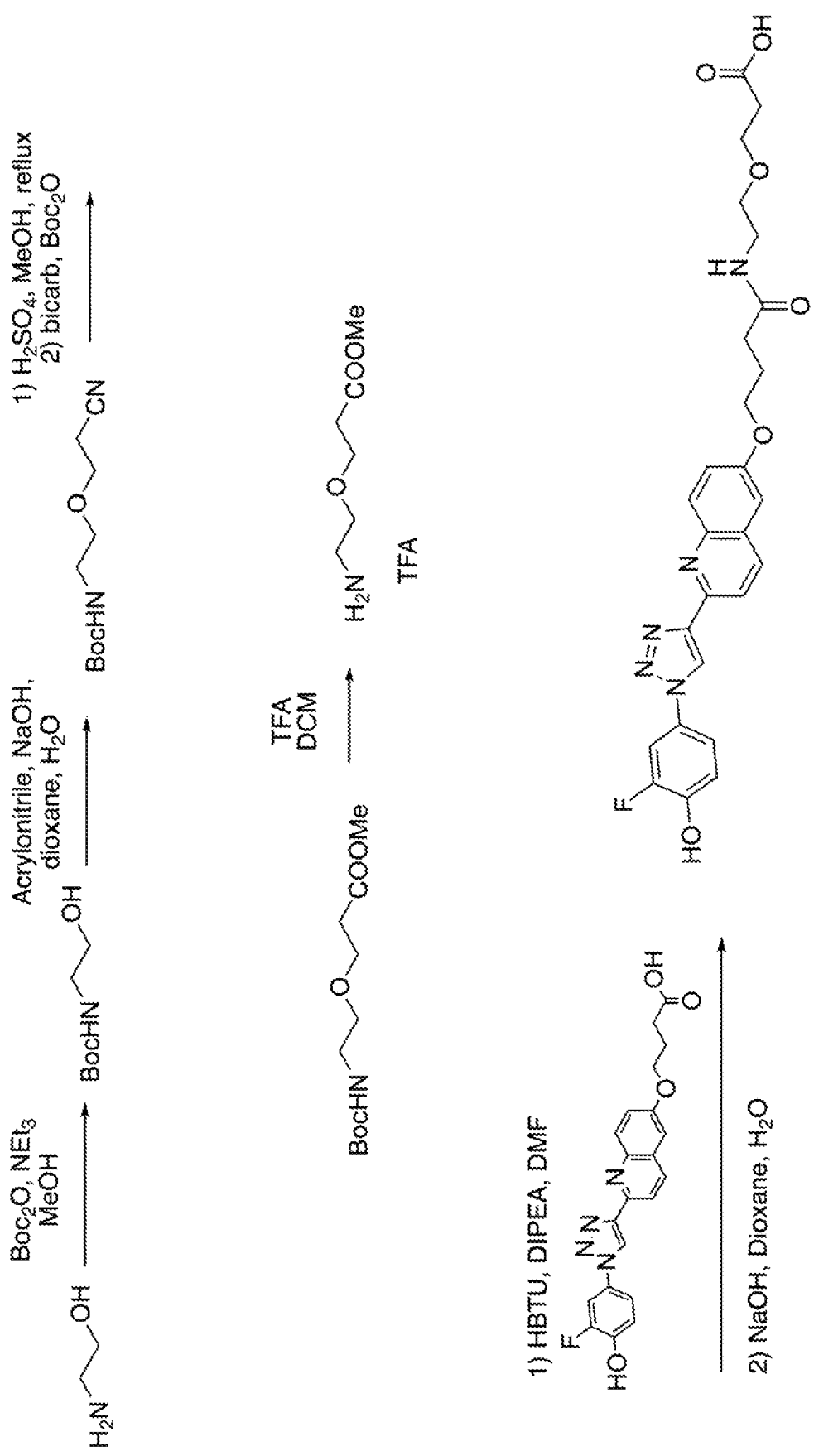
FIGS. 22-26 show the synthesis of valency linkers used in several molecules in this invention.

FIG. 22 shows the synthesis of the MIF-targeting linker to a monovalent linker, which is synthesized through analagous methods as described in a previous figure. The boc-protected methyl ester is deprotected with TFA in DCM, then coupled to the MIF-targeting carboxylic acid (HBTU, DIPEA, DMF). Subsequent hydrolysis with strong base (NaOH/dioxane/H2O) gives the MIF-targeting carboxylic acid.

Figure 23:
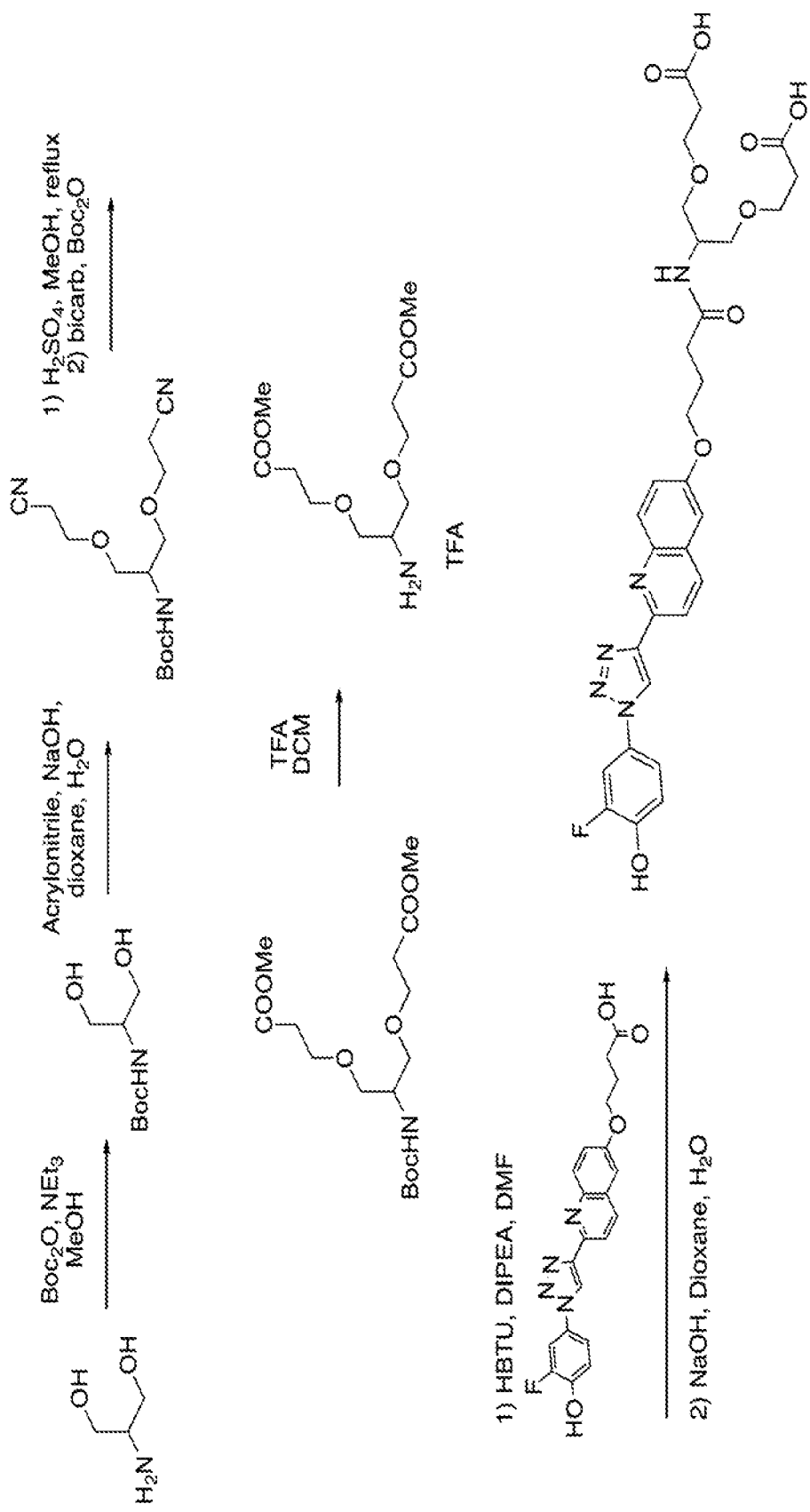

FIG. 23 shows the synthesis of the di-carboxylic acid MIF targeting motif, which is synthesized as described in previous figures.

Figure 24:
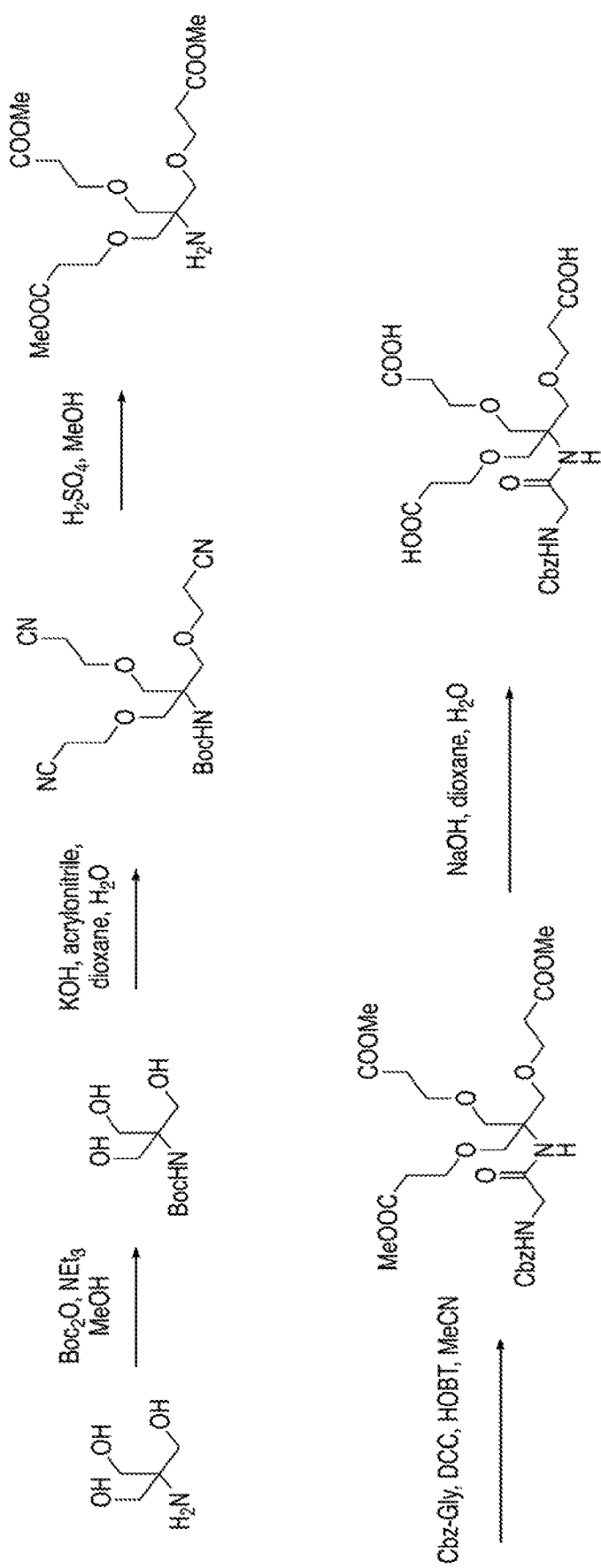

FIG. 24 shows the synthesis of a tris base-derived trivalent linker. Tris base is treated with di-t-butyl dicarbonate in the presence of base to give the boc protected triol, which is then reacted with acrylonitrile in the presence of base (dioxane/H20) to give a trinitrile intermediate. This is then converted to the methyl ester through treatment with strong acid in methanol. The amine is then reacted with Cbz-glycine through a DCC-mediated amide formation, and deprotected to give a tricarboxylic acid that is used in subsequent figures.

Figure 25:
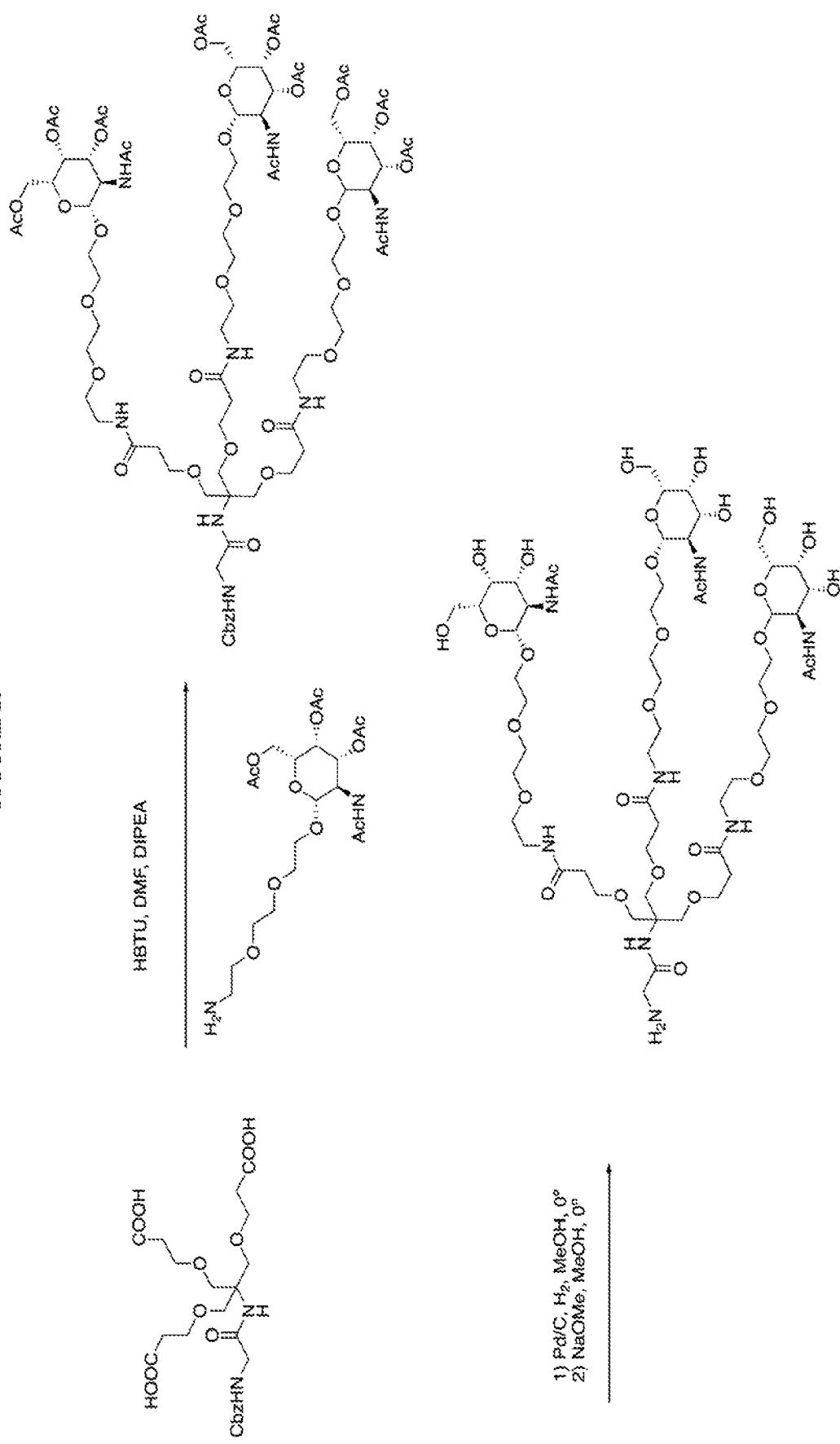

FIG. 25 describes the synthesis of an ASGPR-targeting moiety employing three GalNAc ASGPR ligands. The tri-carboxylic acid is reacted with amine-terminated protected GalNAc (amide bond formation in the presence of HBTU and DIPEA), then deprotected by reduction (Pd/C, solvent) and treatment with strong base (NaOMe/MeOH).

Figure 26:
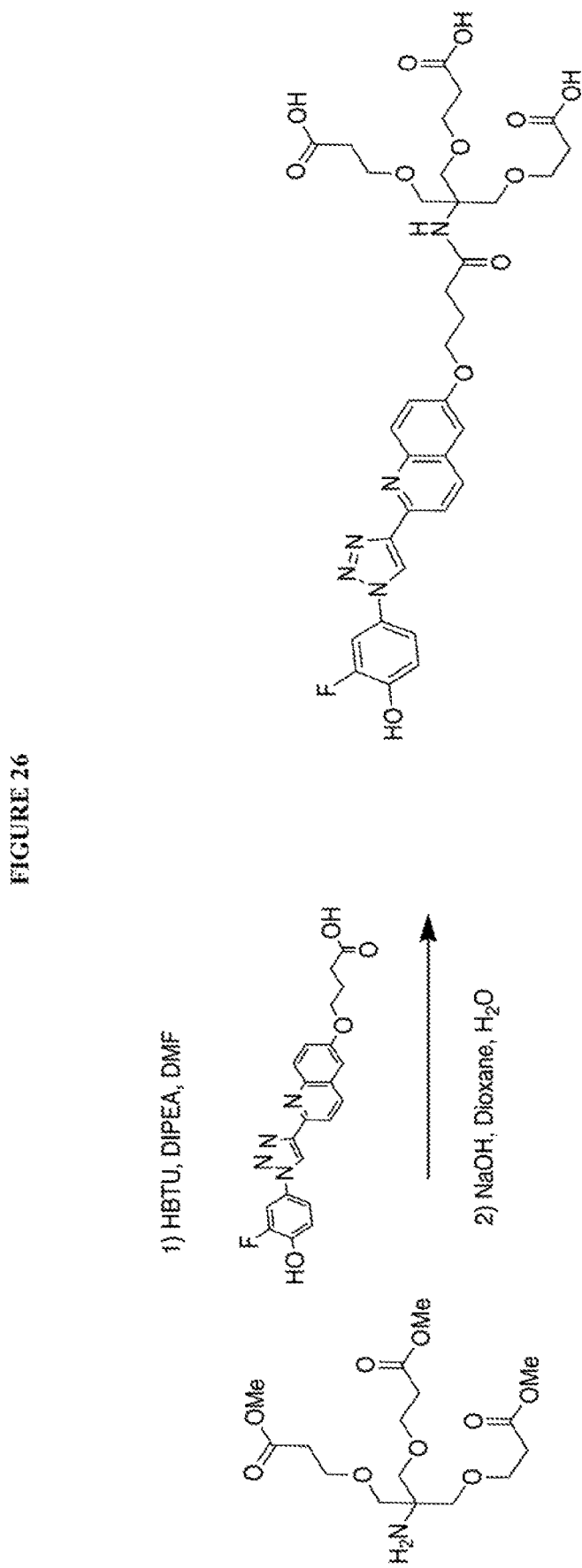

FIG. 26 shows the synthesis of the tri-carboxylic acid MIF targeting motif, which is synthesized as described in previous figures.

Figure 27:
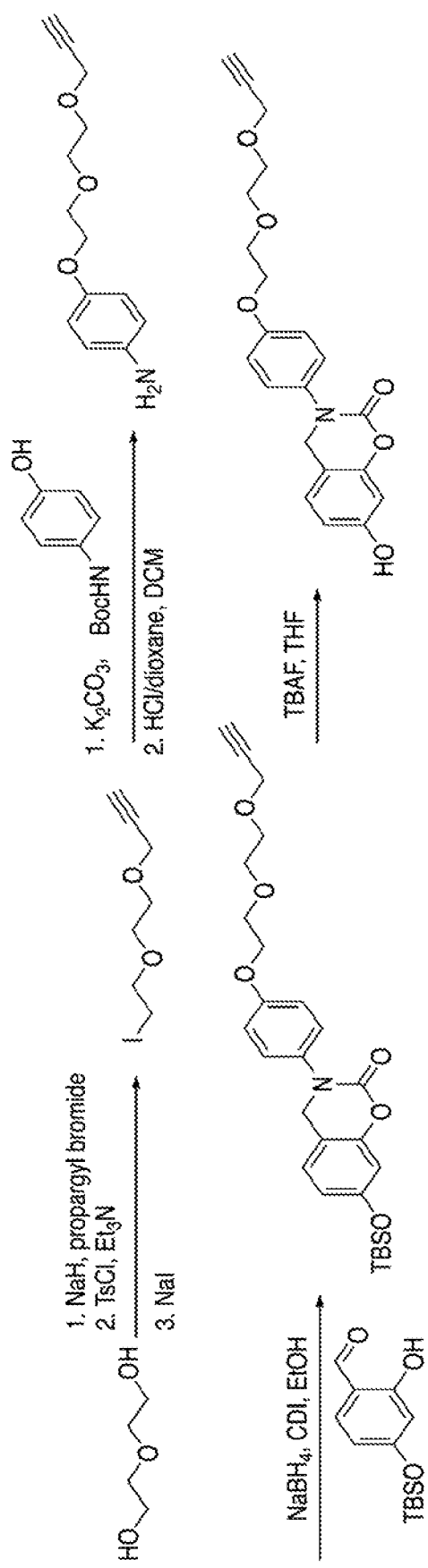
FIGS. 27-28 show the synthesis of MIF ligands used in several bifunctional molecules.

FIG. 27 shows the synthesis of the MIF NVS alkyne precursor which can be reacted with an azido reactant containing a carboxylic acid (as set forth in subsequent figures) to provide MIF-NVS-carboxylic acid capped reactants to produce bifunctional compounds according to the present invention.

Figure 28:
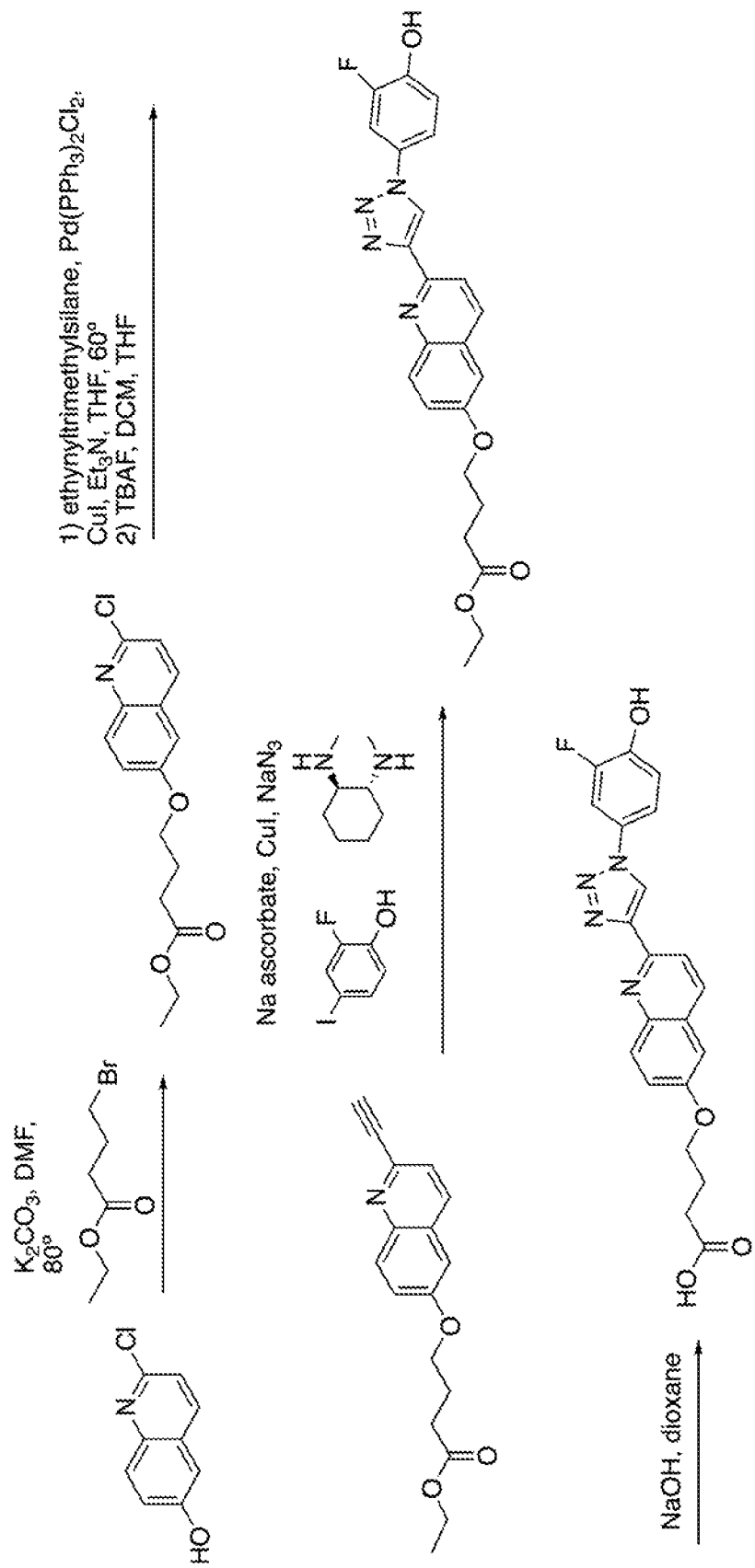

FIG. 28 shows the synthesis of the MIF-targeting moiety terminating in a carboxylic acid. 2-chloroquinolin-6-ol is reacted with ethyl 4-bromobutanoate in the presence of base (DMF, elevated temperature) to give an aryl chloride that then undergoes Sonogashira coupling at elevated temperature with ethynyltrimethylsilane. The intermediate silylated compound is deprotected with TBAF (DCM/THF). A click reaction then forms a triazole between the alkyne intermediate and in situ synthesized 4-azido-2-fluorophenol to give an ethyl ester intermediate that is hydrolyzed with strong base (NaOH/dioxane) to give the carboxylic acid that is used in subsequent figures.

Figure 29:
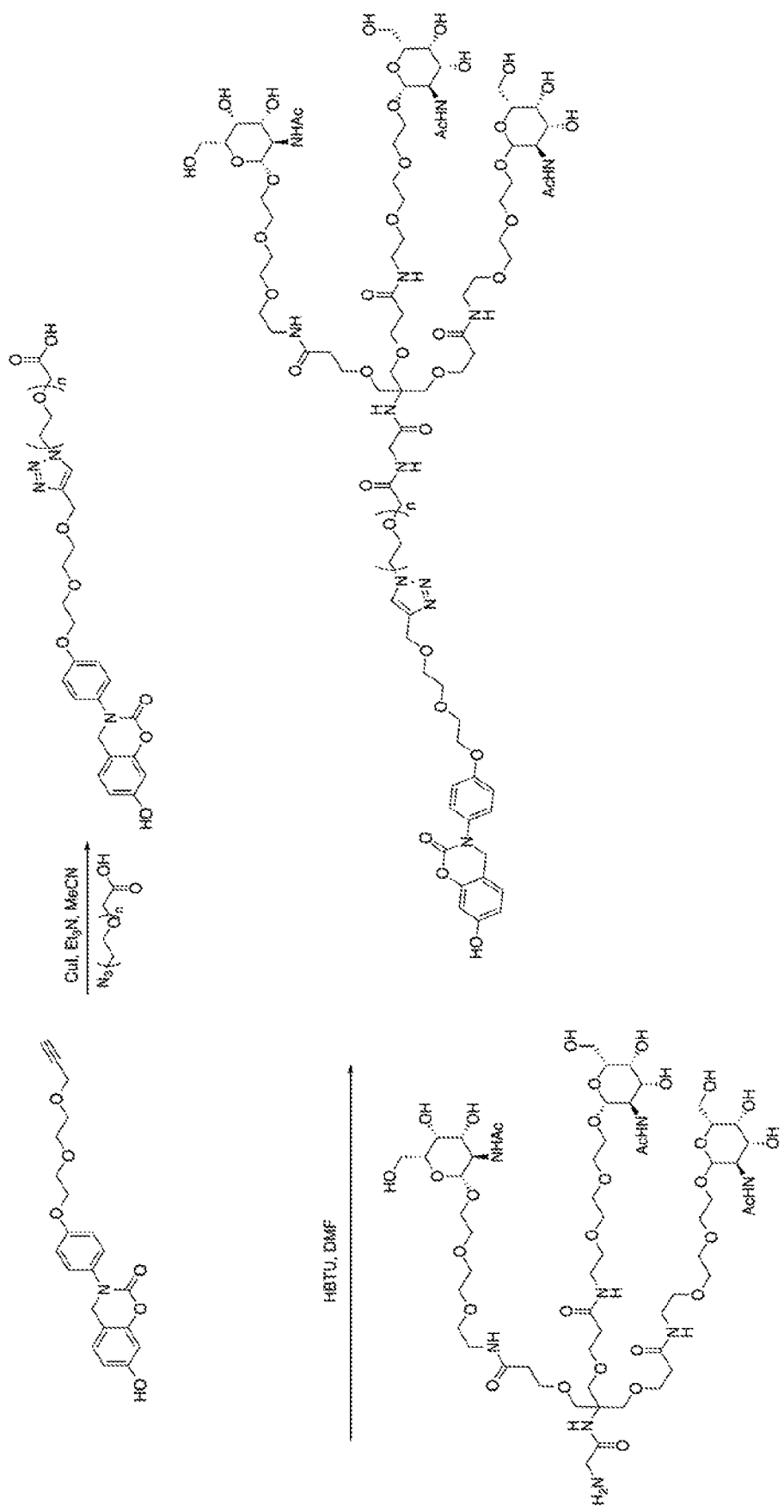
FIG. 29 describes the synthesis of the bifunctional molecule MIF-NVS-PEGn-GN3.

FIG. 29 describes the synthesis of the bifunctional molecule MIF-NVS-PEGn-GN3 through HBTU-mediated coupling in DMF of the ASPGR-targeting amine and the MIF targeting carboxylic acid prepared by first forming the MIF-targeting carboxylic acid by condensing the reactant azido PEG-carboxylic acid onto the MIF moiety containing a alkyne terminated PEG group.

Figure 30:
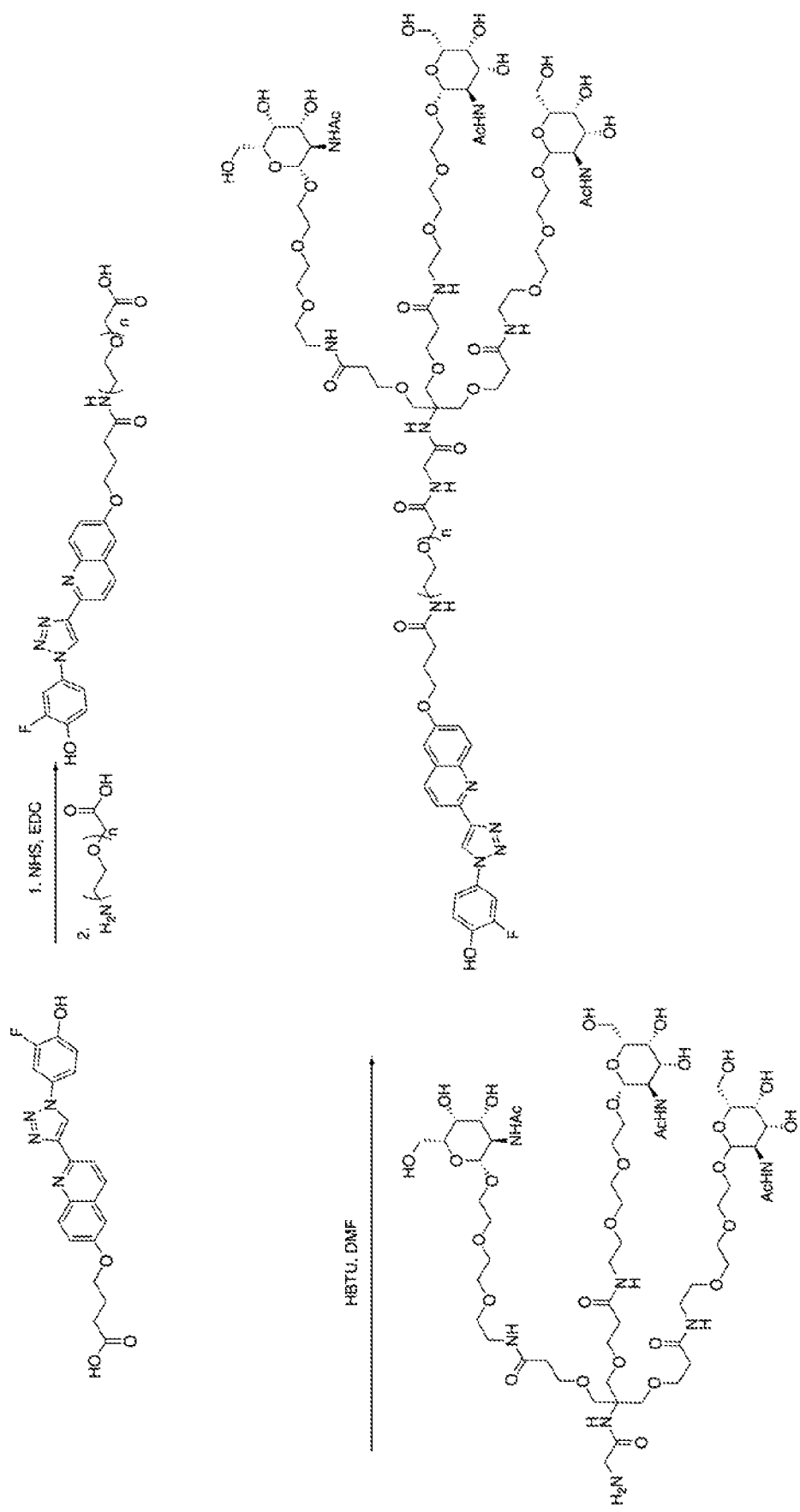
FIG. 30 describes the synthesis of bifunctional molecules MIF-GN3 and MIF-PEGn-GN3.

FIG. 30 describes the synthesis of bifunctional molecules MIF-GN3 and MIF-PEGn-GN3 through HATU-mediated coupling (DMF, DIPEA) of ASGPR-targeting amine and MIF-targeting carboxylic acid.

Figure 31:
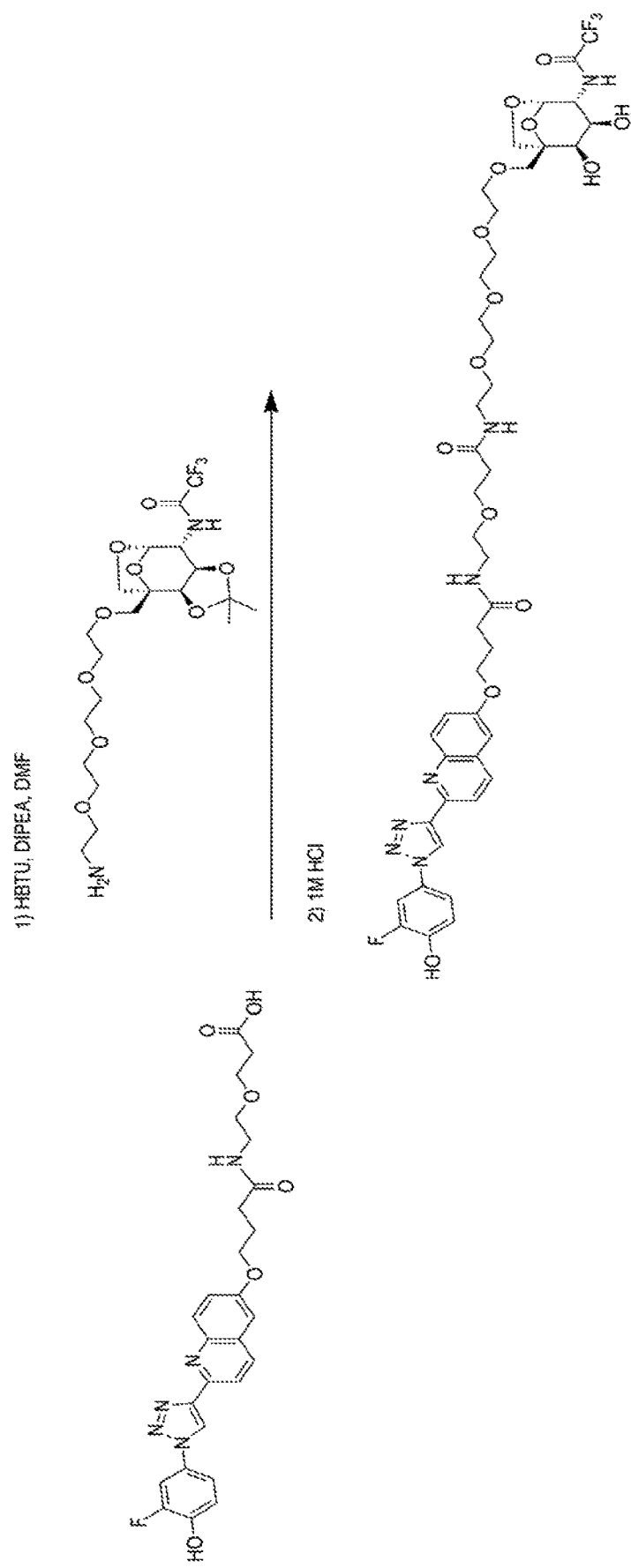
FIG. 31 describes the synthesis of the bifunctional molecule targeting MIF and ASGPR, containing one bicyclic ASGPR AcF3 ligands.

FIG. 31 describes the synthesis of the bifunctional molecule targeting MIF and ASGPR, containing one bicyclic ASGPR AcF3 ligands. MIF-binding mono-carboxylic acid is treated with HBTU, DIPEA, the amine terminated ligand, and DMF to give the amide, which is then deprotected with 1M HCl to give the final compound.

Figure 32:
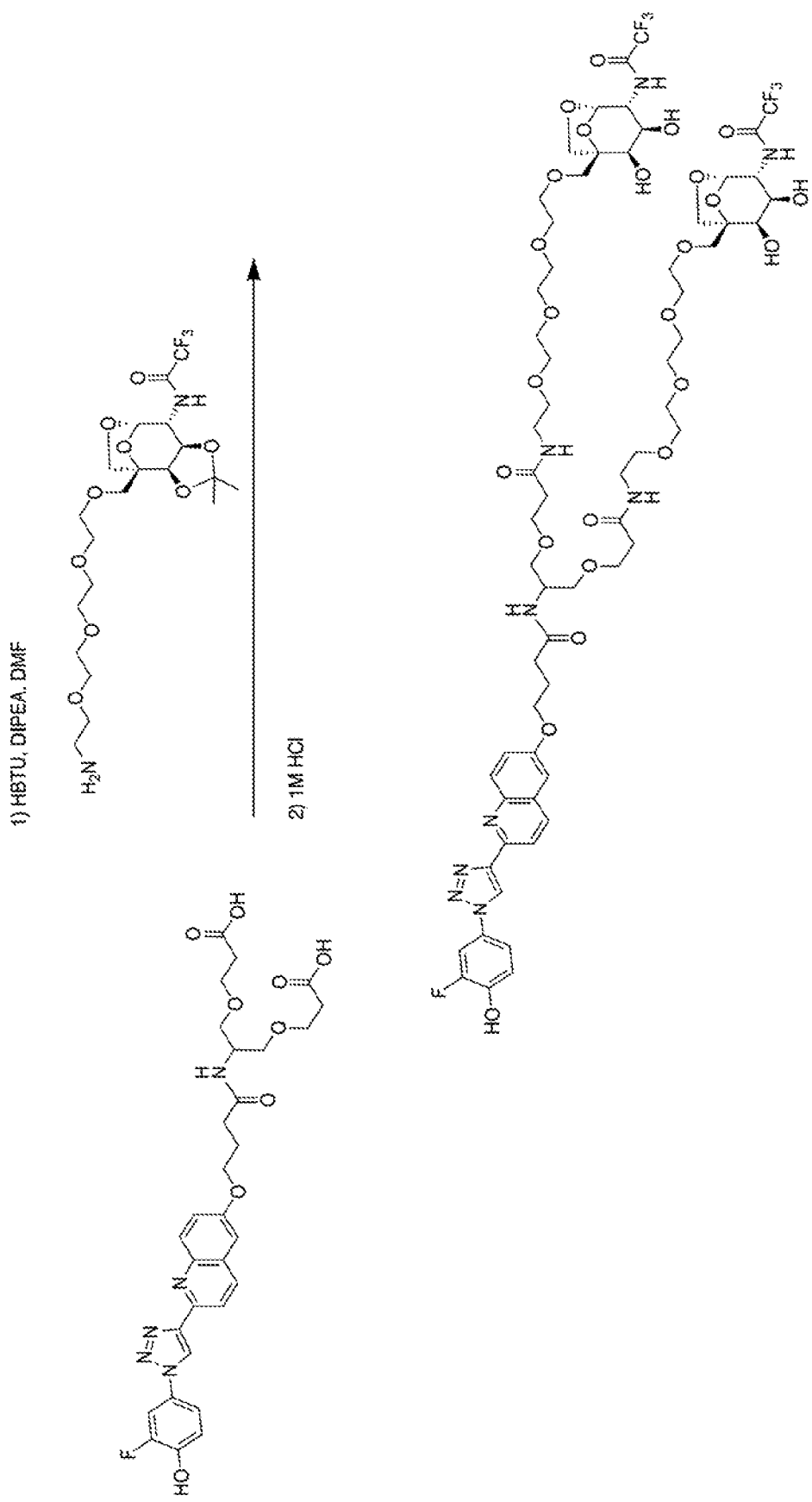
FIG. 32 describes the synthesis of the bifunctional molecule targeting MIF and ASGPR, containing two bicyclic ASGPr AcF3 ligands.

FIG. 32 describes the synthesis of the bifunctional molecule targeting MIF and ASGPR, containing two bicyclic ASGPr ligands. It is synthesized as described above.

Figure 33:
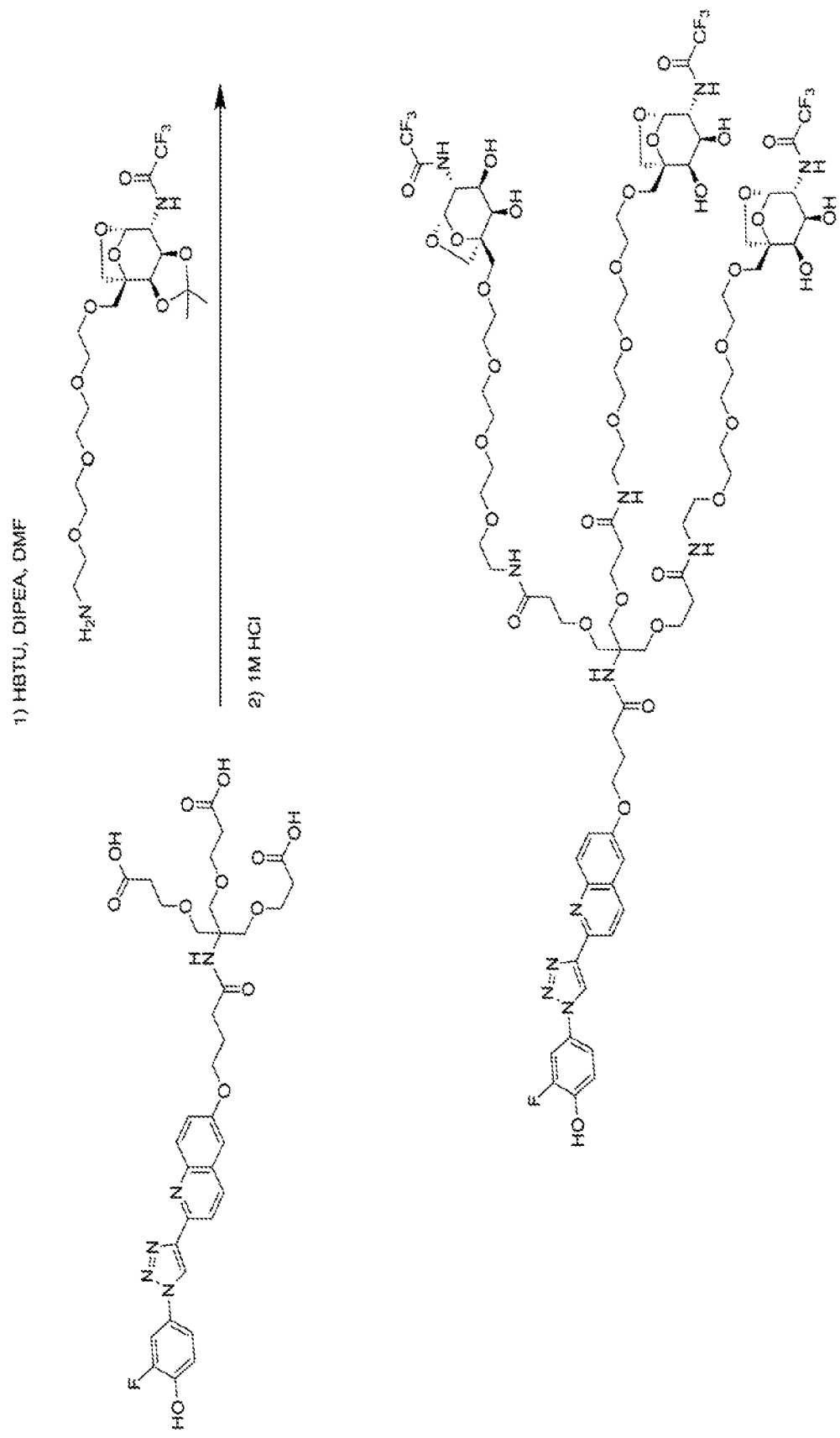
FIG. 33 describes the synthesis of the bifunctional molecule targeting MIF and ASGPR, containing three bicyclic ASGPr ligands.

FIG. 33 describes the synthesis of the bifunctional molecule targeting MIF and ASGPR, containing three bicyclic ASGPr ligands. It is synthesized as described above.

Figure 34:
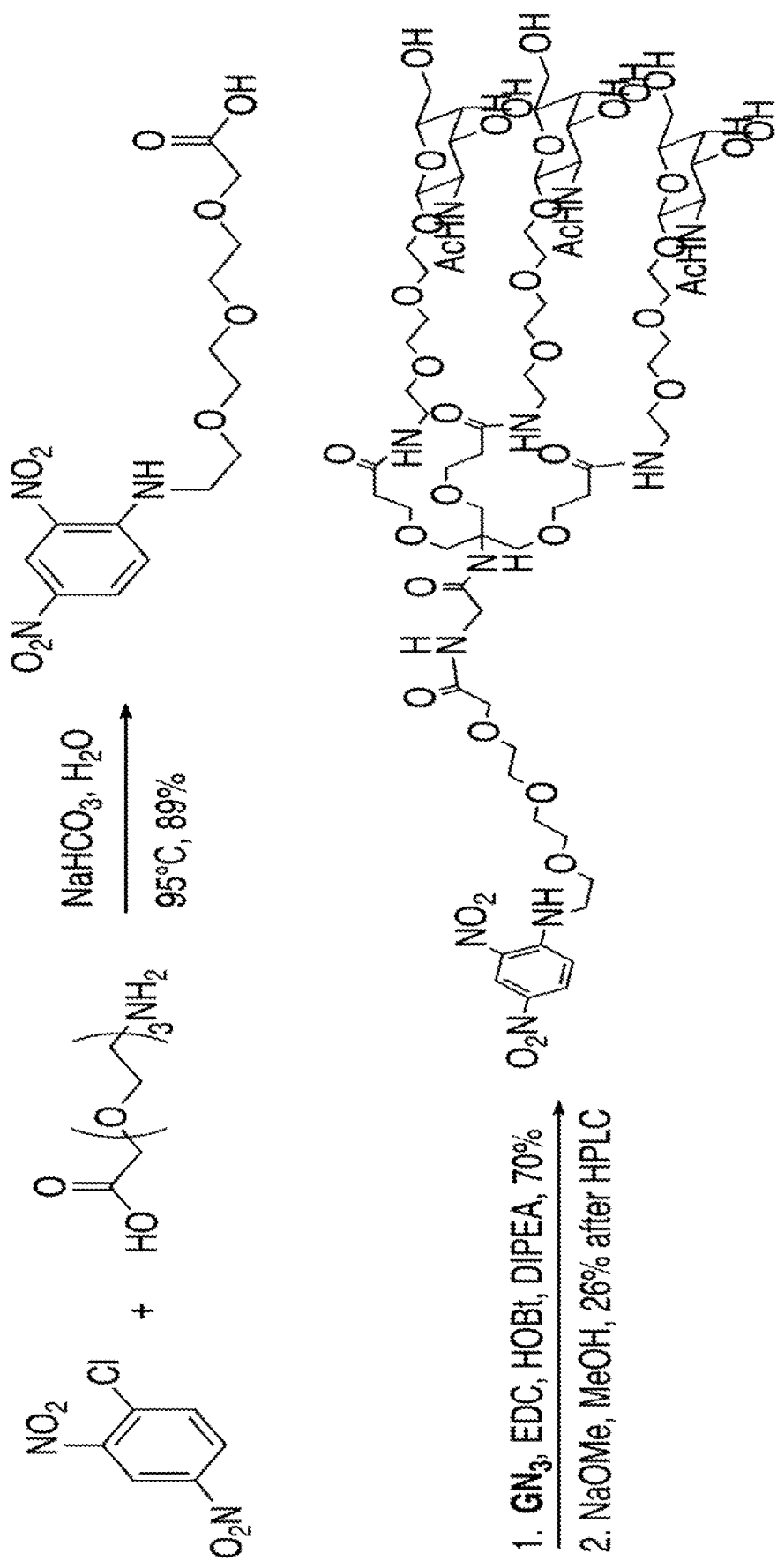
FIG. 34 shows the synthesis of DNP-GN3.

FIG. 34 shows the synthesis of DNP-GN3. 2,4-dinitro chlorobenzene was treated with an amino carboxylic acid in the presence of weak base to give the di-nitro analine carboxylic acid intermediate. Further steps were carried out as described for previous molecules.

Figure 35:
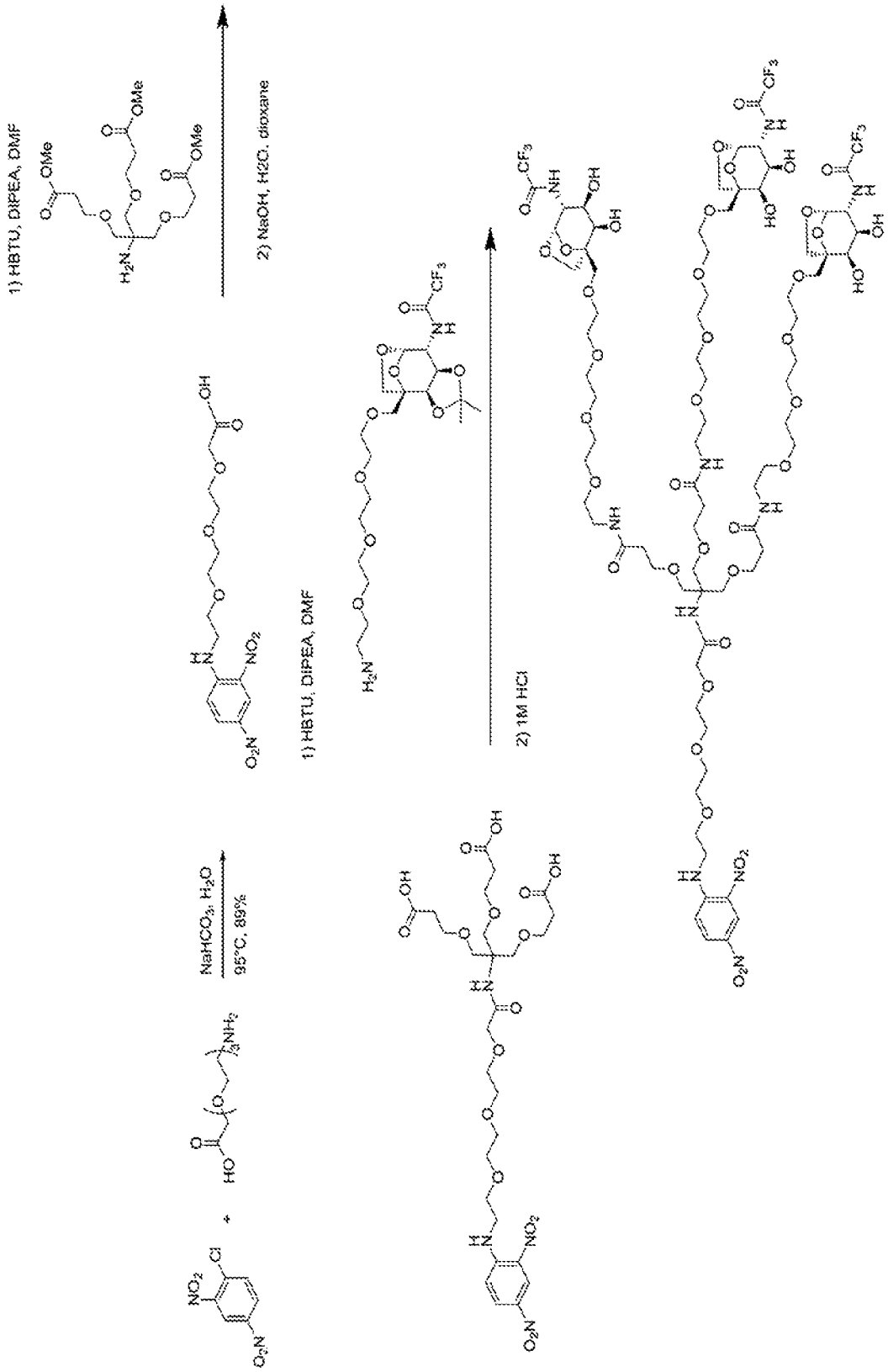
FIG. 35 shows the synthesis of DNP-AcF3-3.

FIG. 35 shows the synthesis of DNP-AcF3-3, which was carried out with methods analogous previous compounds.

Figure 36:
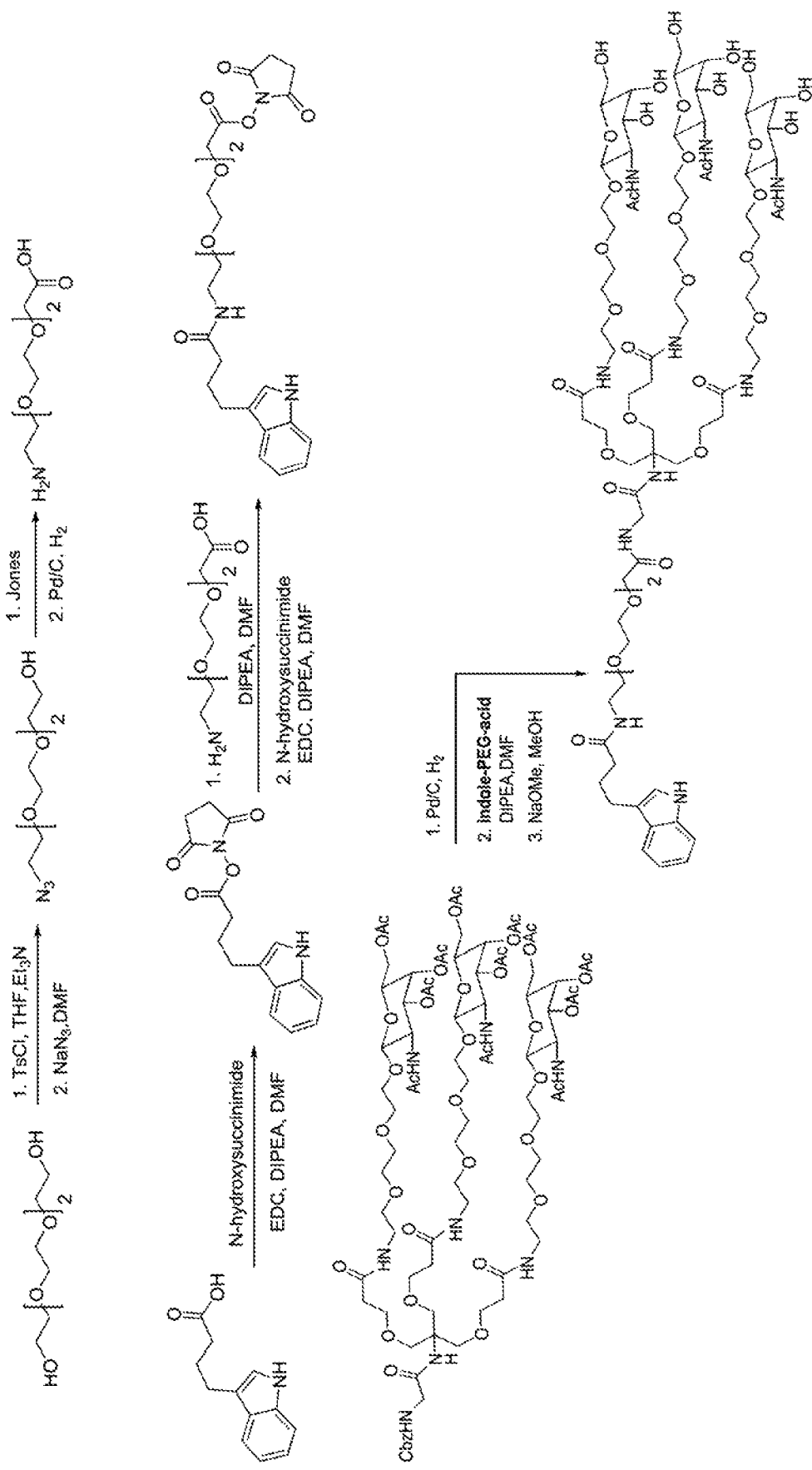
FIG. 36 shows the synthetic scheme used to obtain IBA-GN3.

FIG. 36 shows the synthetic scheme used to obtain IBA-GN3. Pentaethylene glycol was treated with tosyl chloride in the presence of base to give the mono-tosylated alcohol, which was then treated with sodium azide at elevated temperature to give the azidoalcohol. This compound was then oxidized using Jones reagent, then reduced with Palladium on carbon under hydrogen atmosphere to give a carboxylic acid-amine. Separately, indole butyric acid was treated with N-hydroxysuccinimide, EDC, and DIPEA to give the NETS-ester indole, which was then reacted with the above carboxylic acid-amine. The product was again reacted with N-hydroxysuccinimide, EDC, and DIPEA to give a NETS ester. This NETS ester was reacted with NH2-GN3, which was prepared as described previously. The subsequent amide was deprotected with NaOMe in MeOH to give compound IBA-GN3.

Figure 37:
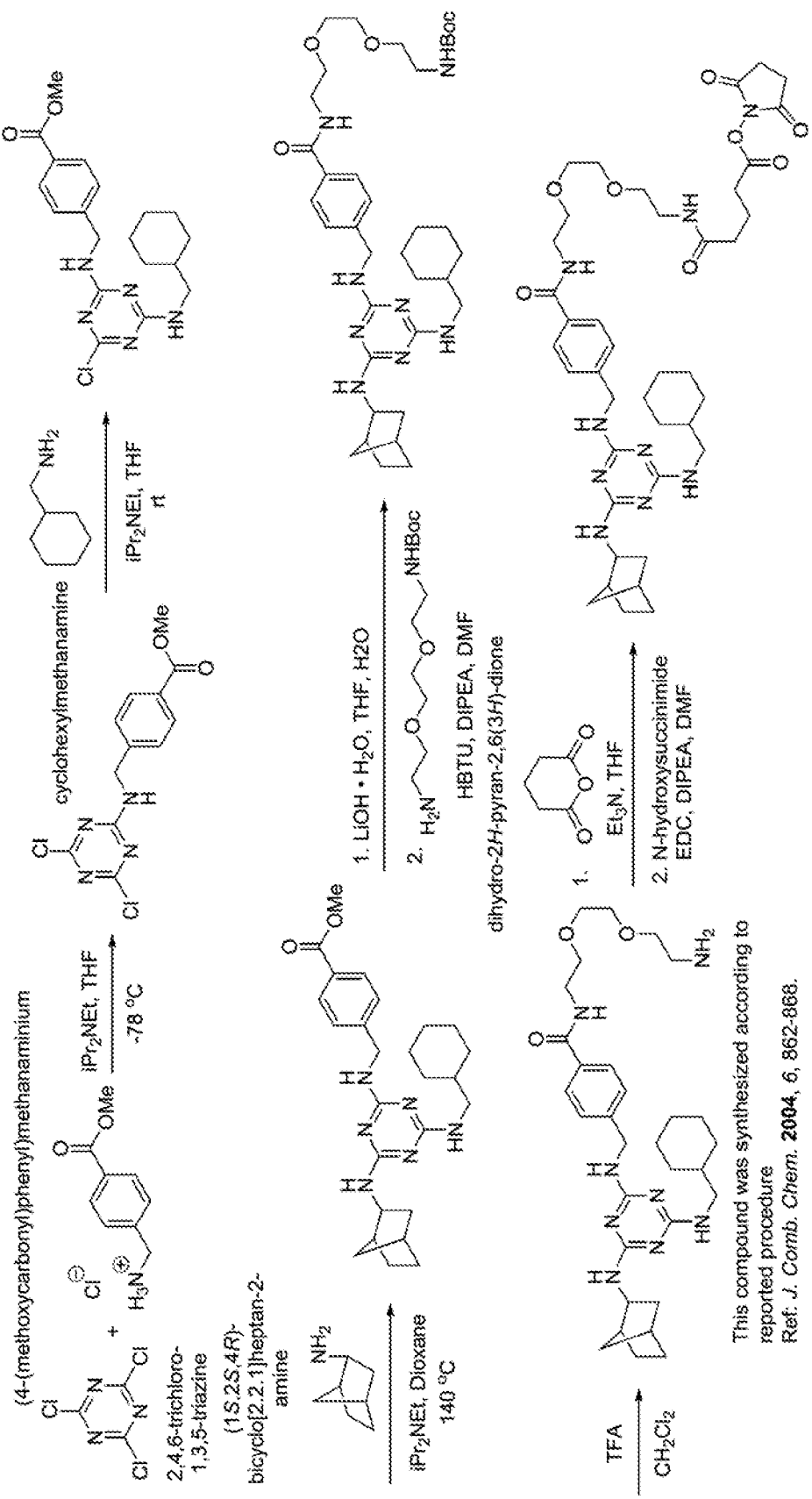
FIG. 37 shows the synthesis of triazine-GN3.
Figure 37:
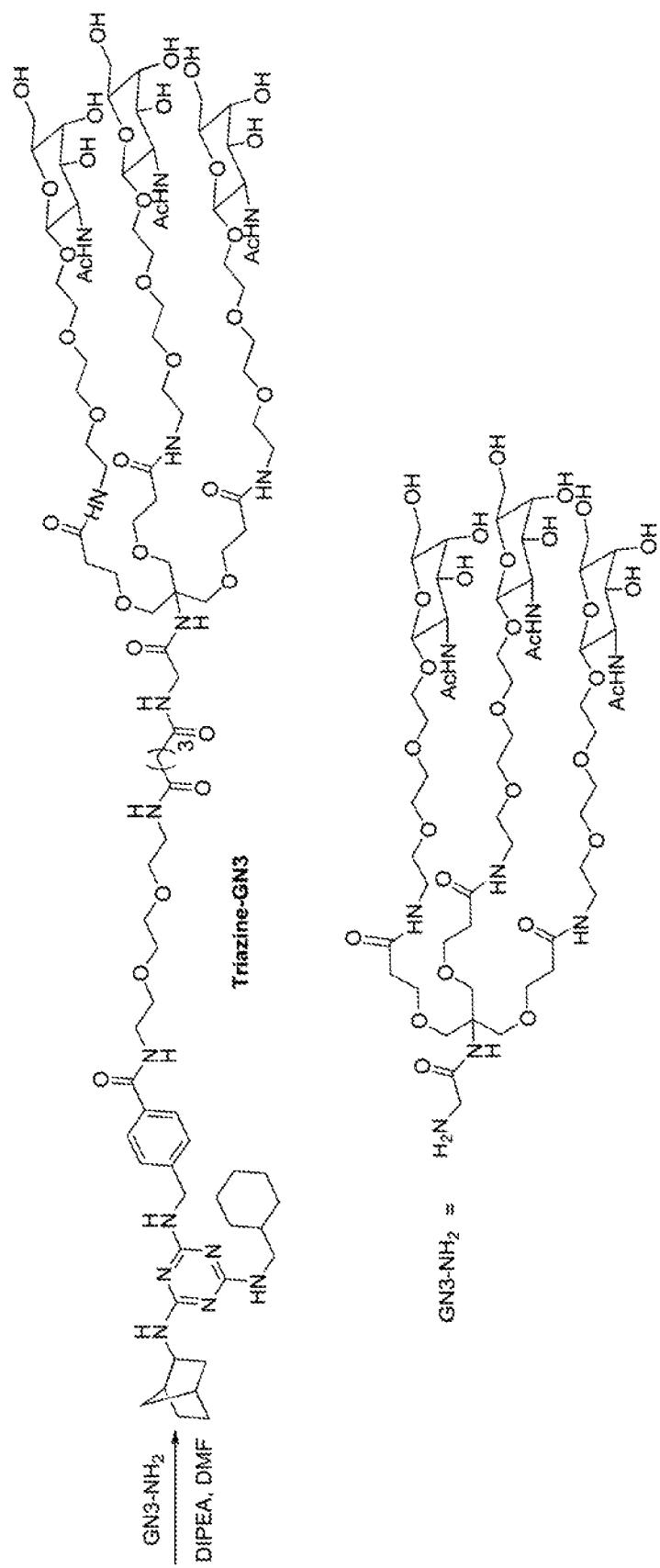

FIG. 37 shows the synthesis of triazine-GN3. Cyanuric chloride was treated with (4-(methoxycarbonyl)phenyl) methanaminium in THF and diisopropylethlamine at −78° C. to give the mono-substituted product. This was then treated with cyclohexylmethanamine at room temperature to afford the second substitution. The final substitution was accomplished under elevated temperature with (1S,2S,4R)-bicyclo[2.2.1]heptan-2-amine to give the trisubstituted triazine. Deprotection with lithium hydroxide followed by amide coupling with a monoprotected diamine gave the Boc-protected derivative, which was deprotected and reacted with glutaric anhydride to give a carboxylic acid that was converted to an NETS ester using standard coupling conditions. This was reacted with NH2-GN3 to give the final product.

Figure 38:
FIG. 38 shows the synthetic scheme used to access FcIII-GN3.
Figure 38:
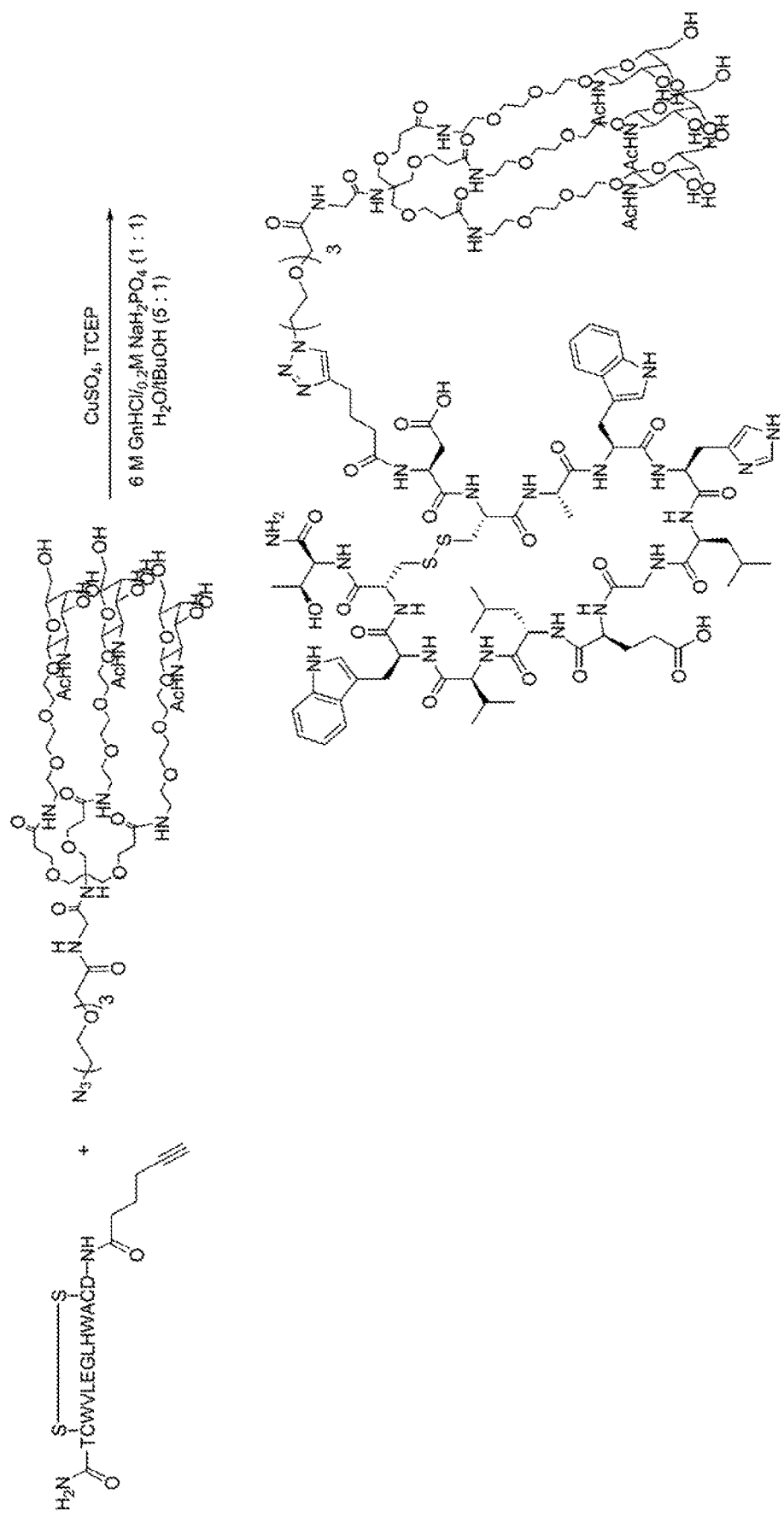

FIG. 38 shows the synthetic scheme used to access FcIII-GN3. The hexynyl peptide was prepared using standard solid phase peptide synthesis techniques. The peptide was removed from Rink resin using Reagent L, then oxidized using ammonium bicarbonate buffer (pH8-9) in MeOH under air to give the cyclic peptide. The peptide was reacted with GN3-azide, which was described previously, to give the product triazole FcIII-GN3.

Figure 39:
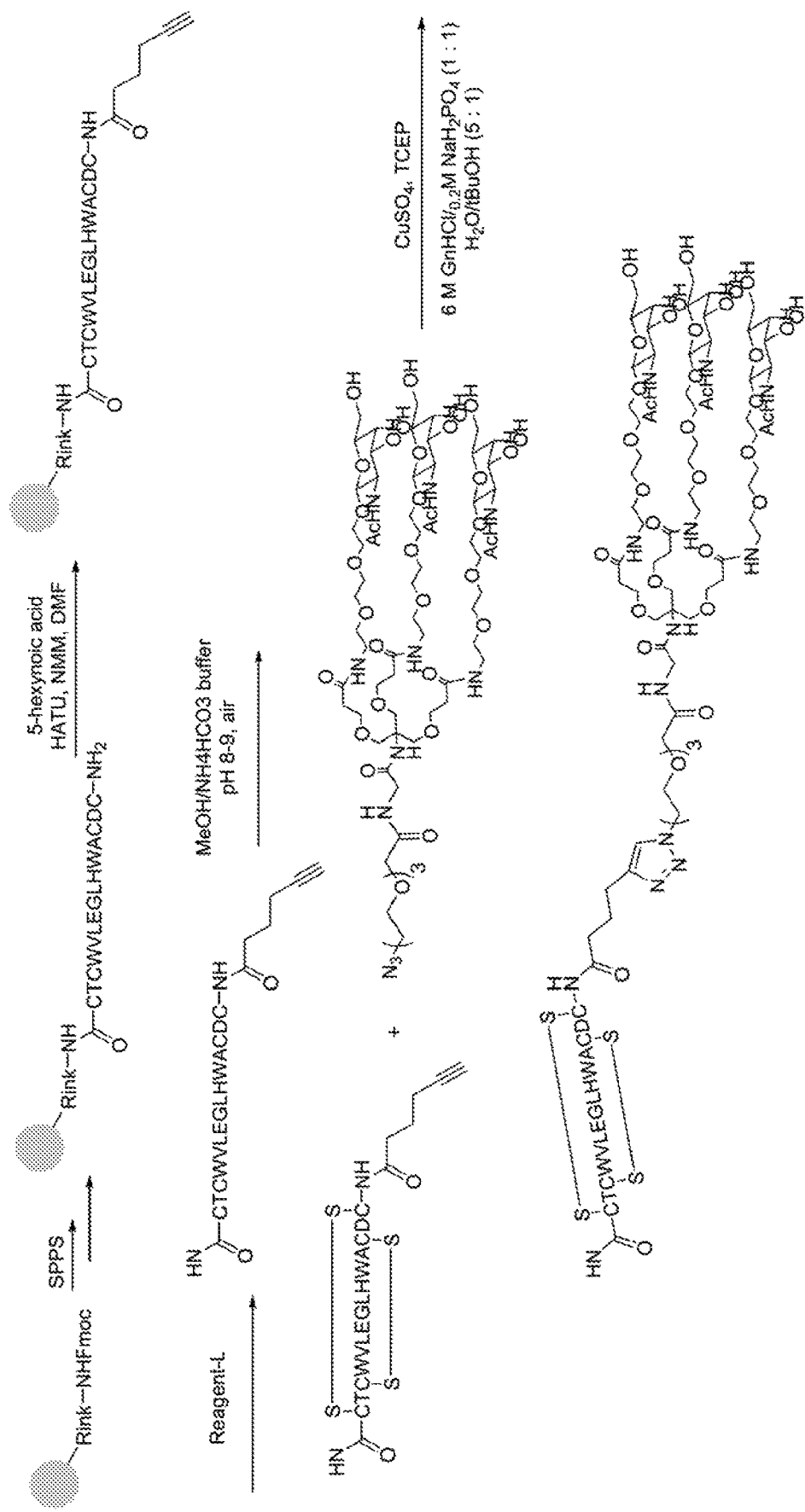
FIG. 39 shows the synthetic scheme used to access FcIII-4c-GN3.
Figure 40:
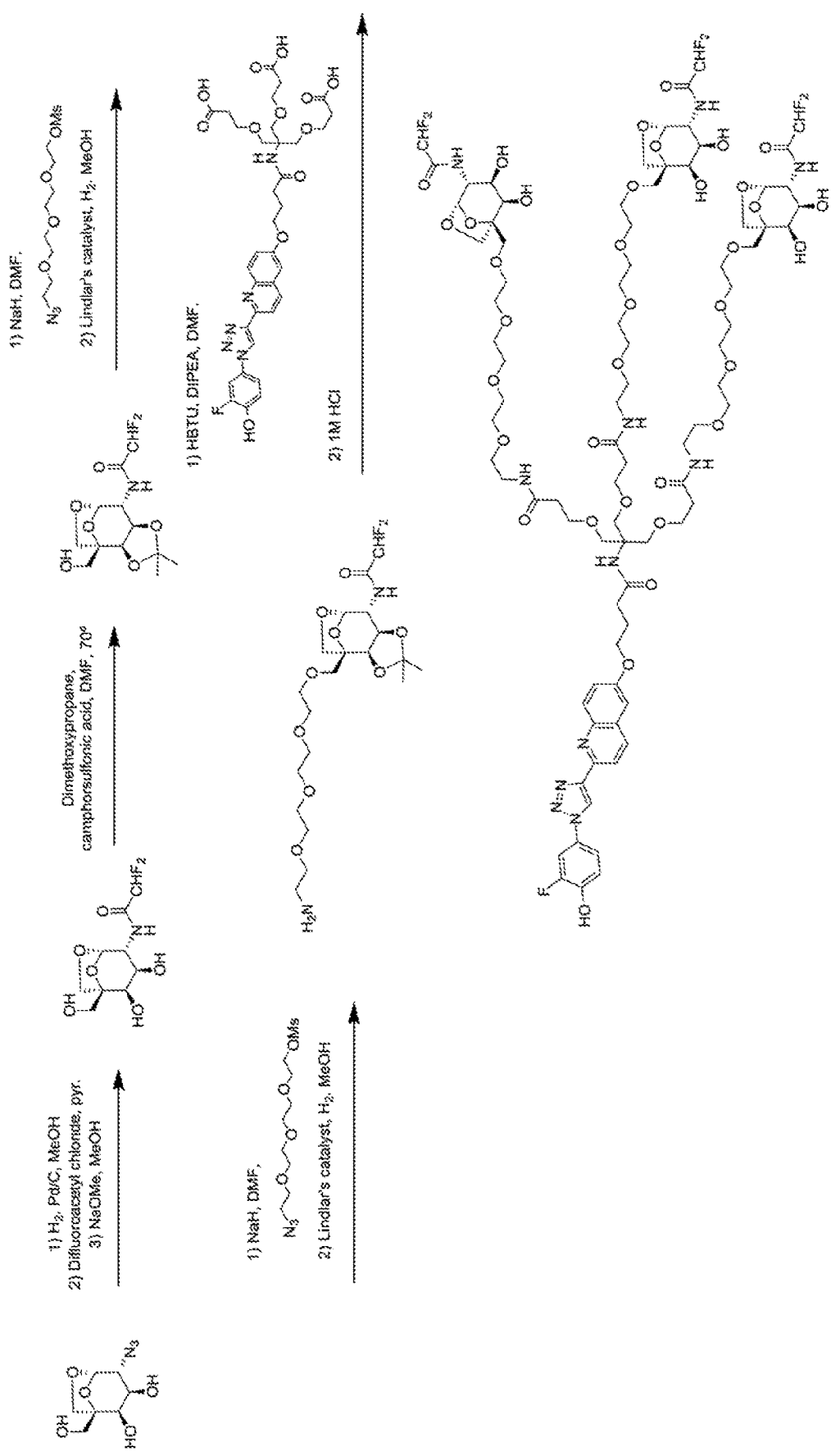
FIGS. 40-43 describe the synthesis of bifunctional molecules targeting MIF and ASGPr, containing three bicyclic ASGPR ligands with different substitutions on the 2-amine of the sugar.
Figure 41:
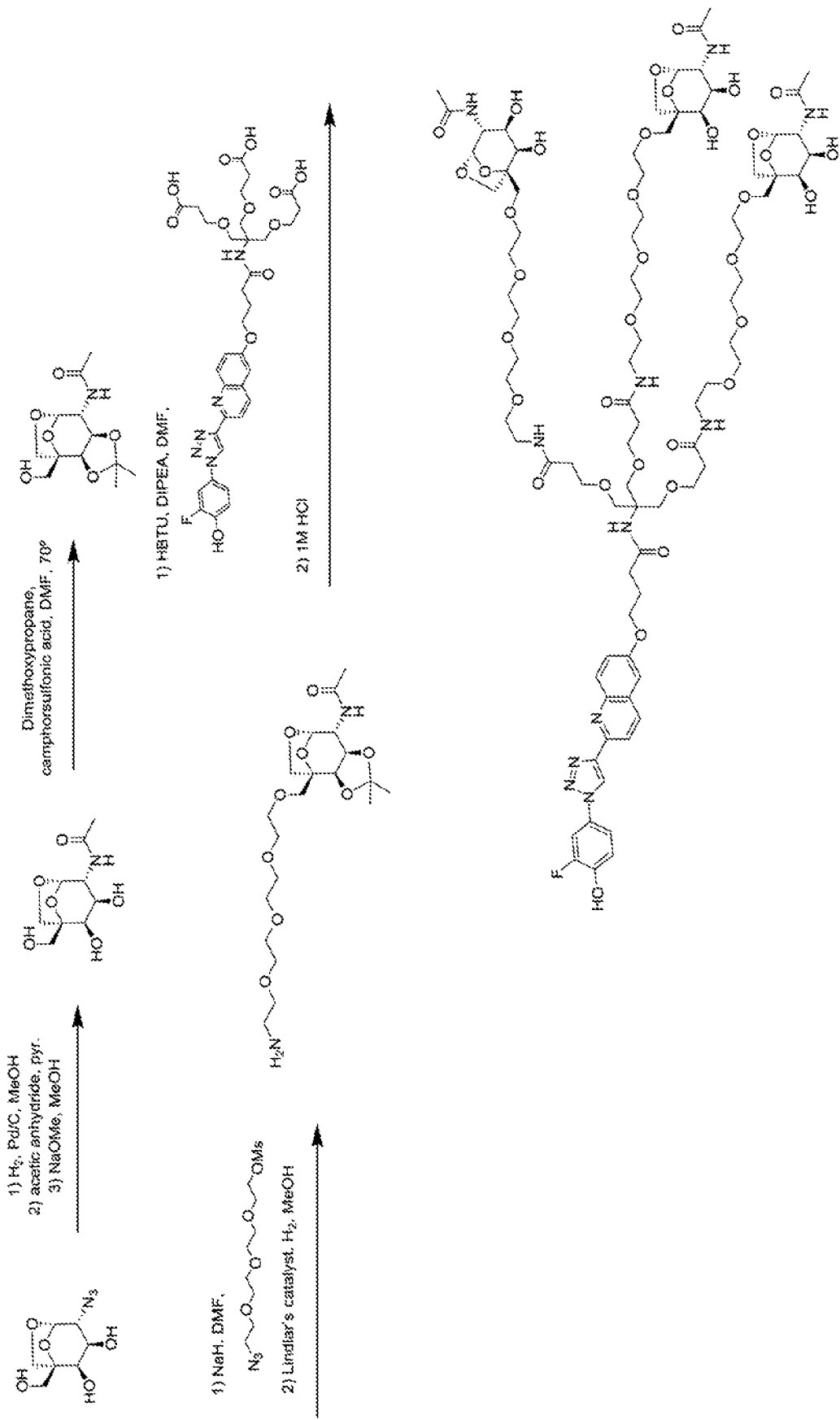
Figure 42:
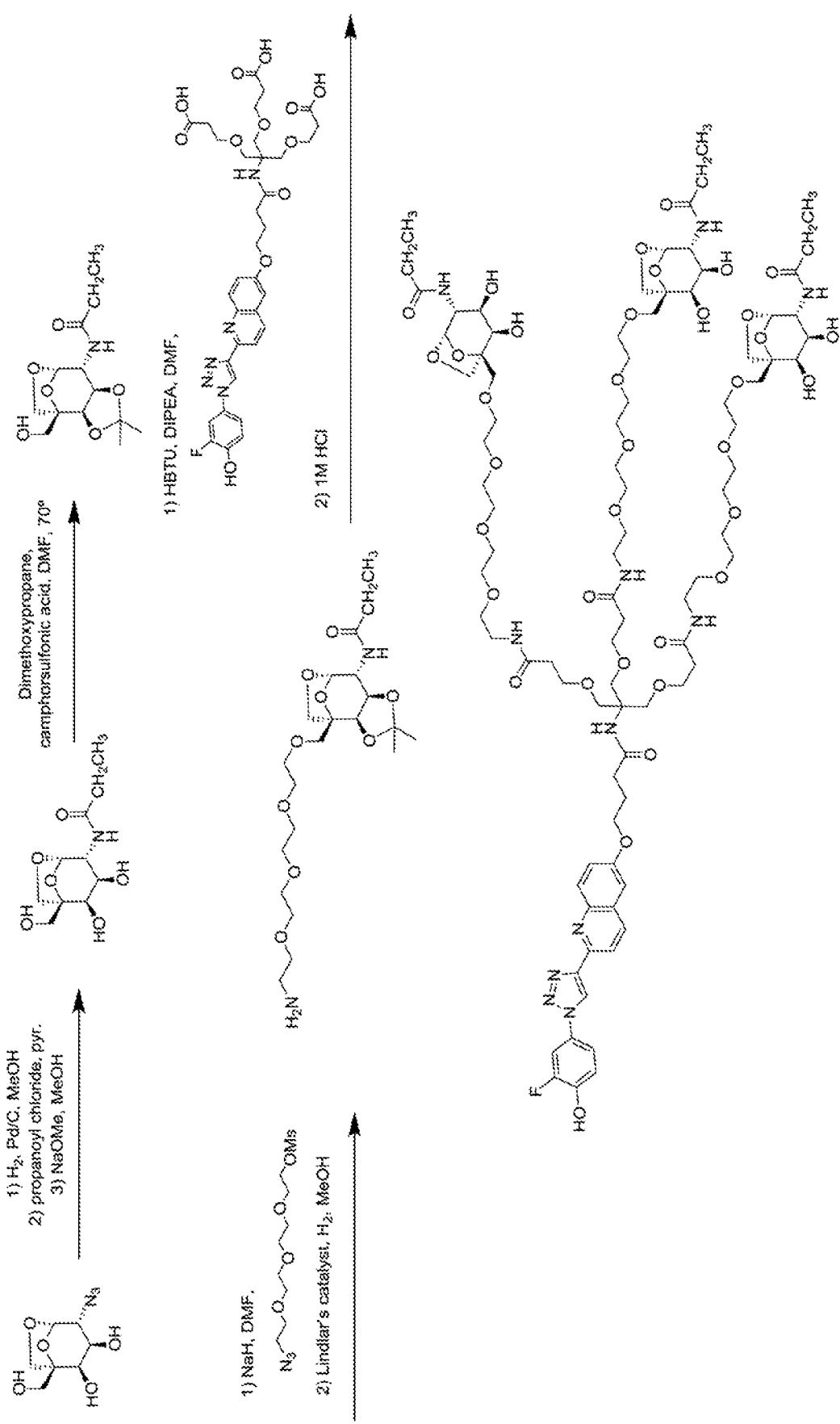
Figure 43:
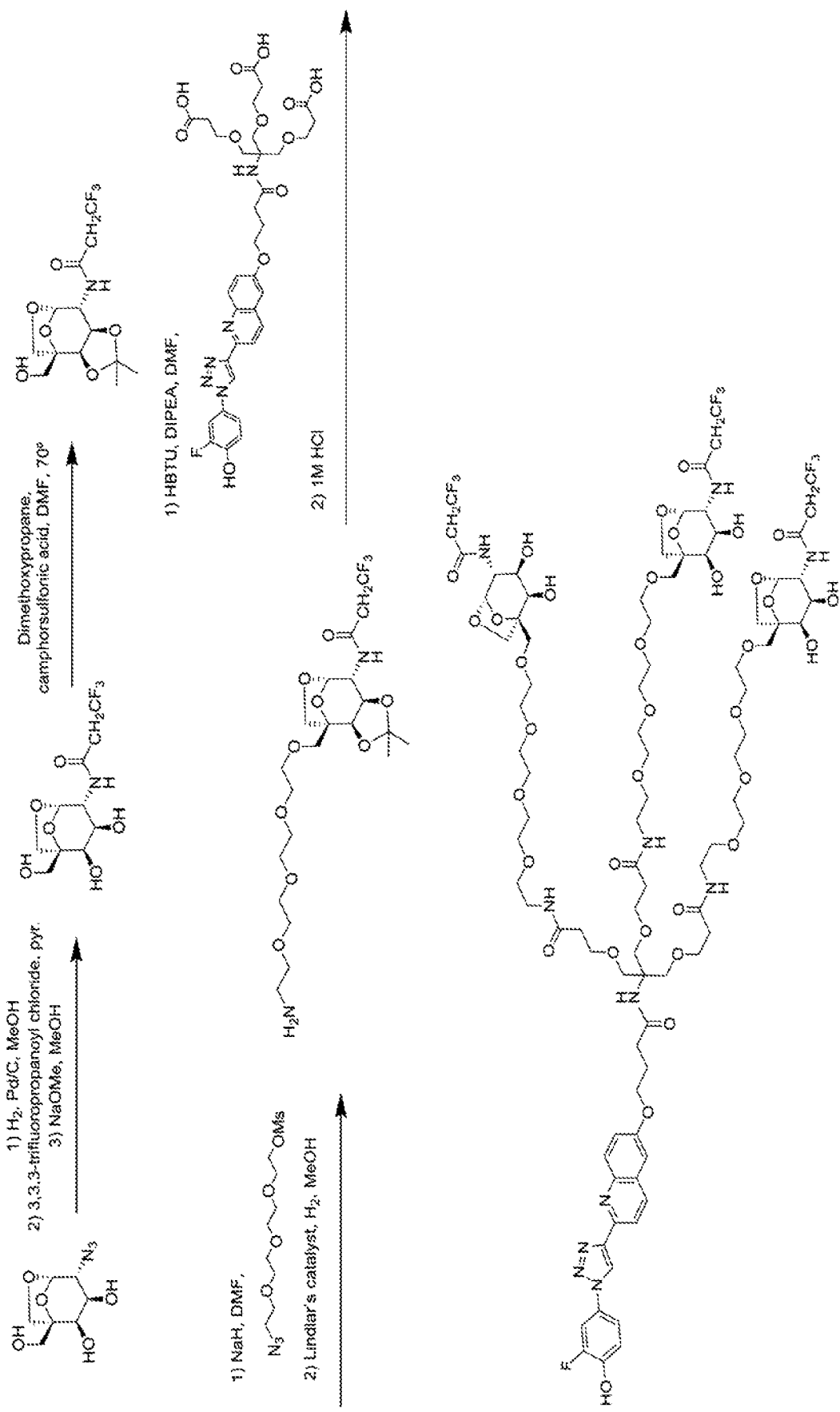

FIG. 39 shows the synthetic scheme used to access FcIII-4c-GN$_3$, which was accomplished using methods described above.

FIGS. 40-43 describe the synthesis of bifunctional molecules targeting MIF and ASGPr, containing three bicyclic ASGPR ligands with different substitutions on the 2-amine of the sugar. They are synthesized through analagous methods described above as set forth in the attached figures.

Figure 44:
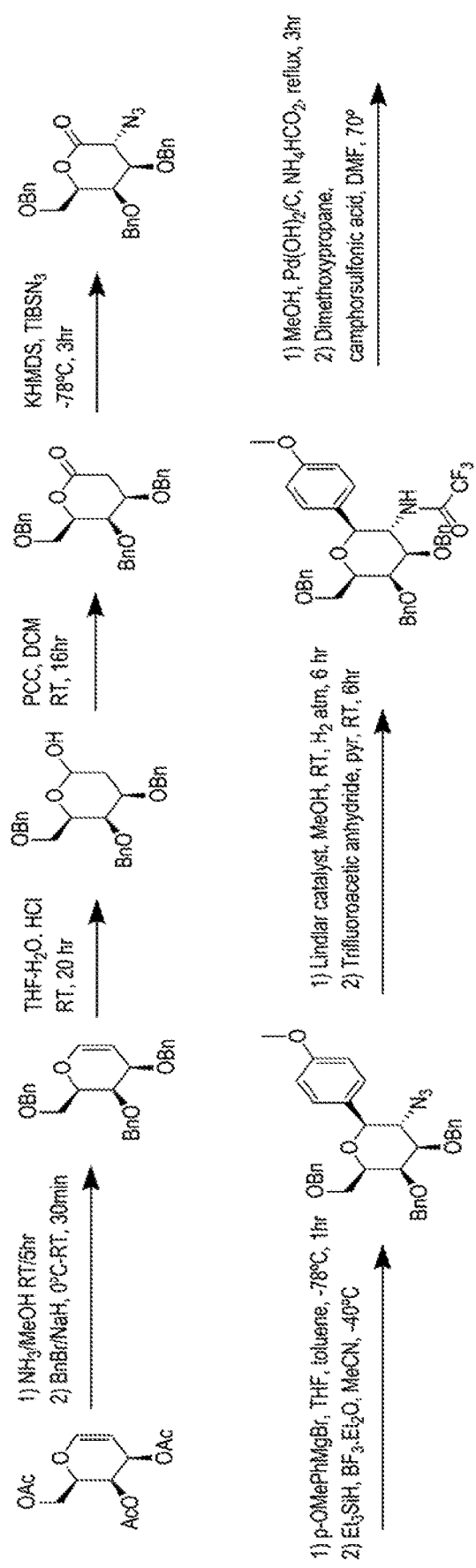
FIG. 44 shows the synthesis of compound MIF-18-3.
Figure 44:
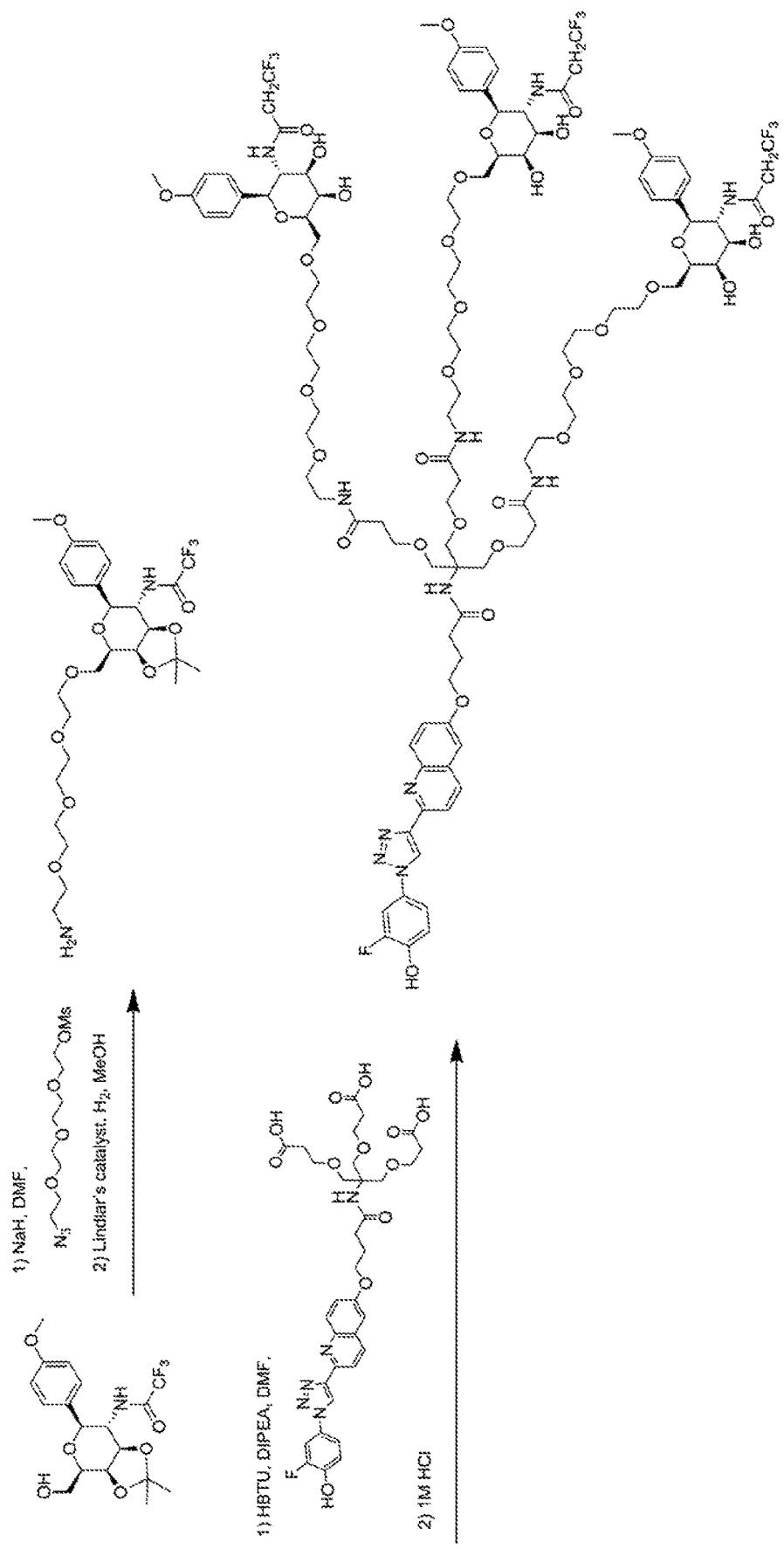

FIG. 44 shows the synthesis of compound MIF-18-3. Tri-acyl galactal was deprotected with ammonia in methanol, then tri-benzyl protected with benzylbromide in the presence of base. The alkene was hydrolyzed overnight with HCl in THF/H20, then oxidized with PCC to give an aldehyde. Sodium azide was then added alpha to the carbonyl with KHMDS and TIBSN3 at lowered temperature. The intermediated was then treated with p-OMePhMgBr in THF and toluene to give an intermediate alcohol, which was then reduced using Et3SiH in the presence of BF3-Et2O at reduced temperature. The resulting azide was then reduced with Lindlar's catalyst under a hydrogen atmosphere to give the corresponding amine, which was acylated with trifluoroacetic acid in pyridine. The benzyl groups were then removed with Pd(OH2) on carbon in MeOH at reflux, and the resulting tri-ol protected as an acetal with dimethoxypropane and camphorsulfonic acid at elevated temperature. The remainder of the synthesis was carried out as described for previous molecules.

Figure 45:
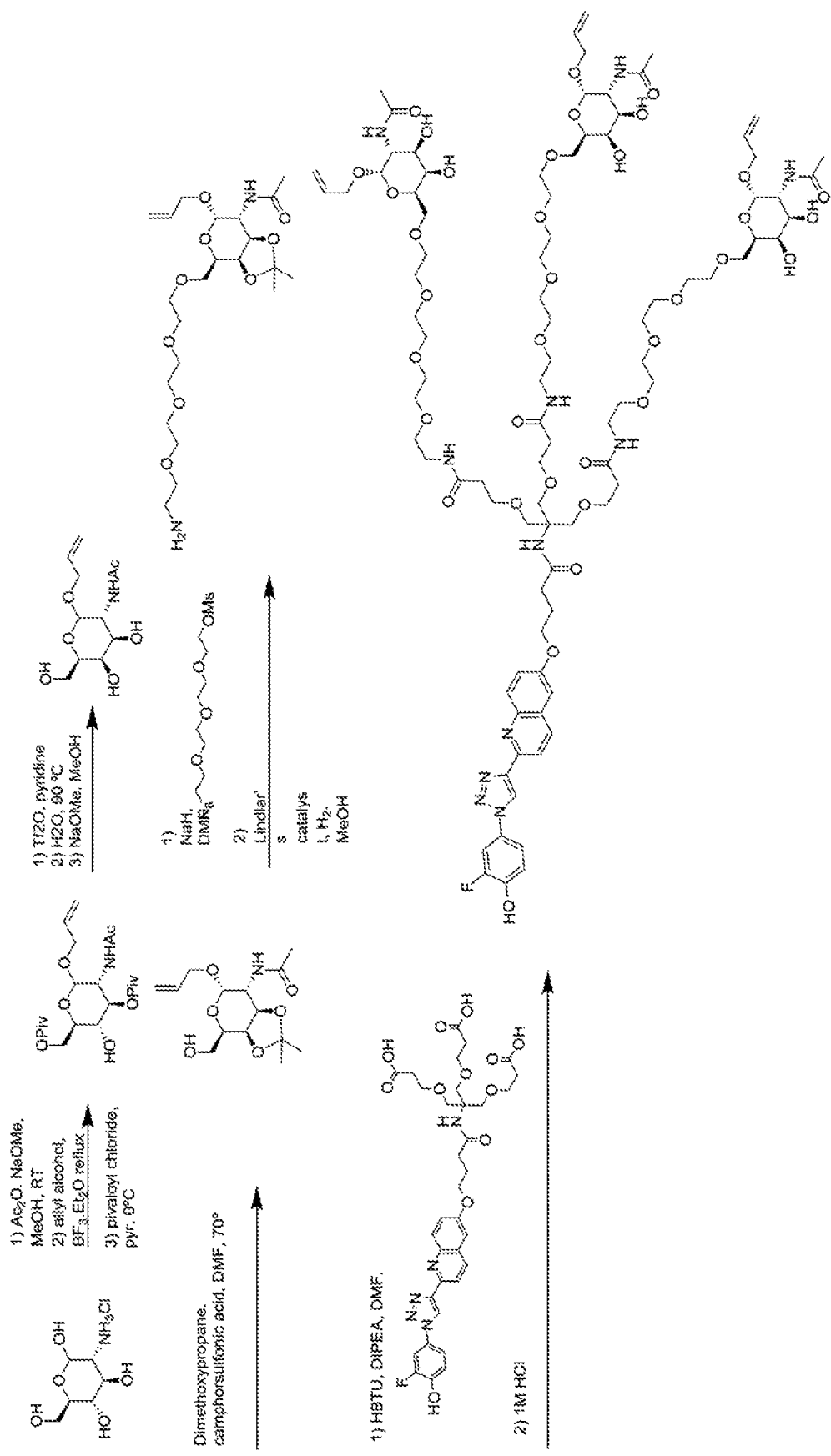
FIG. 45 shows the synthesis of compound MIF-31-3.

FIG. 45 shows the synthesis of compound MIF-31-3. Galactosamine hydrochloride was fully protected with acetic anhydride, then treated with allyl alcohol in the presence of BF3 etherate to give the allyl intermediate. Treatment with pivaloyl chloride in pyridine gave a di-Piv protected intermediate, which was treated with triflic anhydride and subsequently subjected to hydrolysis in water at elevated temperature. The pivaloyl groups were removed by treatment with NaOMe in MeOH to give the allyl triol intermediate. Subsequent steps were performed as described for previous molecules.

Figure 46:
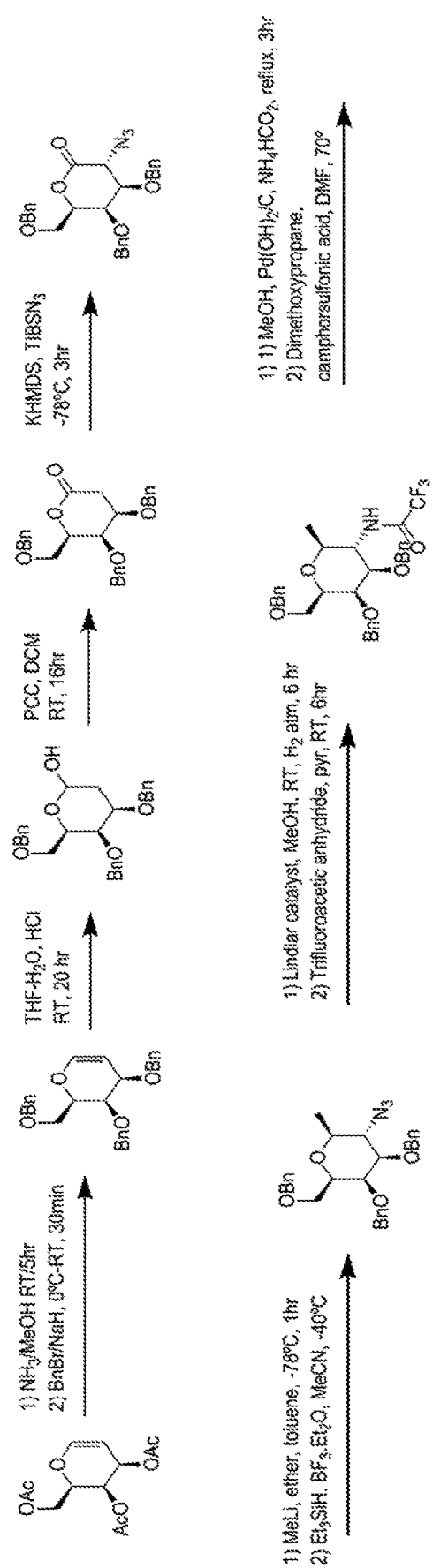
FIG. 46 shows the synthesis of compound MIF-15-3.
Figure 46:
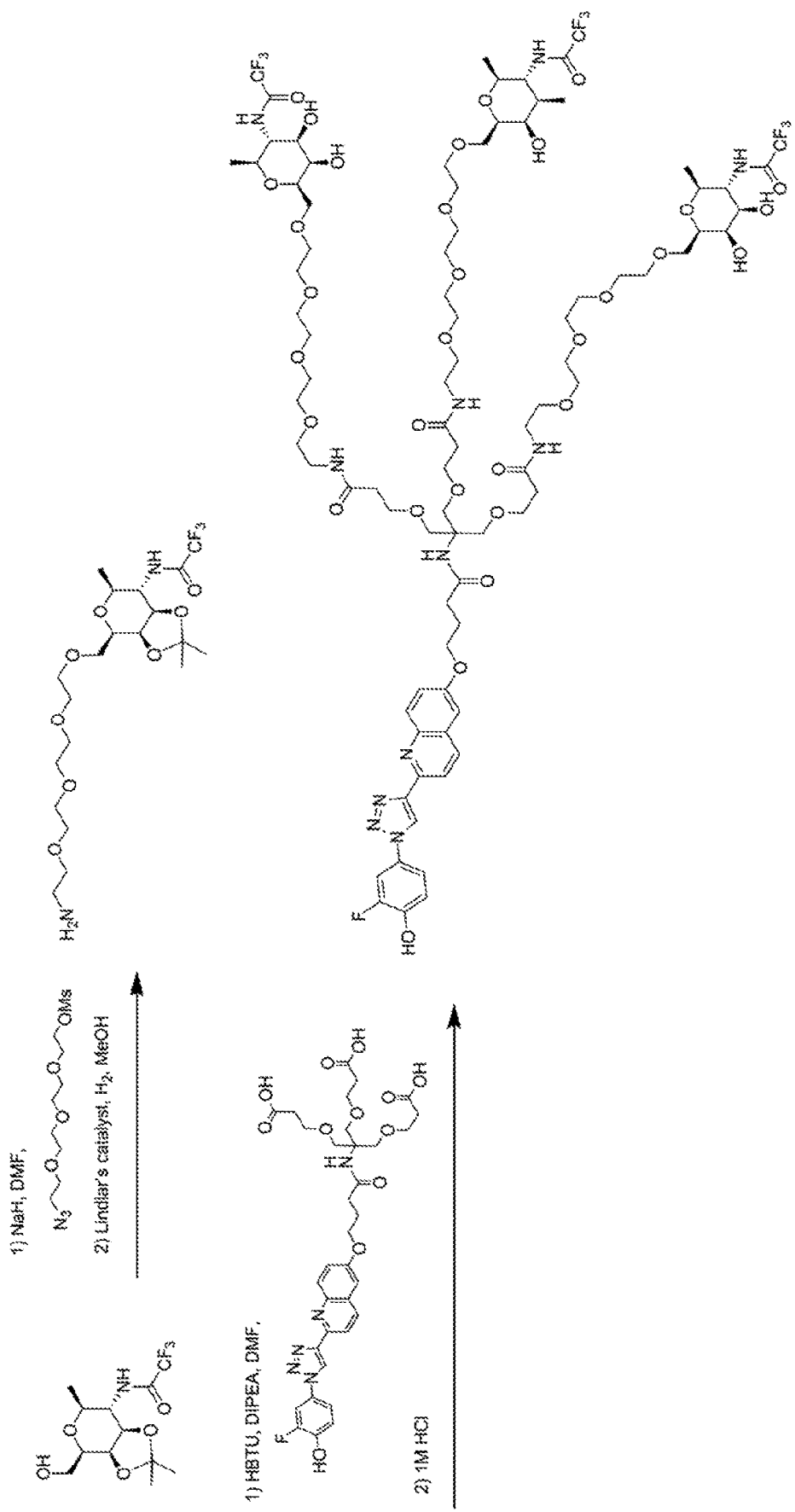

FIG. 46 shows the synthesis of compound MIF-15-3, which was synthesized using procedures analogous to compounds described above.

Figure 47:
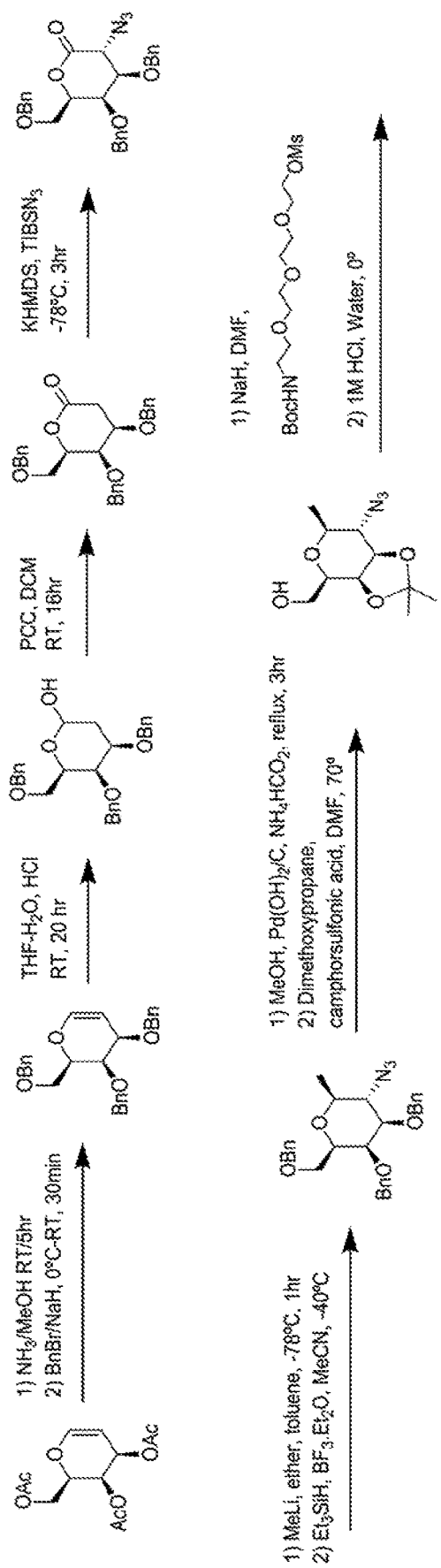
FIG. 47 shows the synthesis of compound MIF-19-3.
Figure 47:
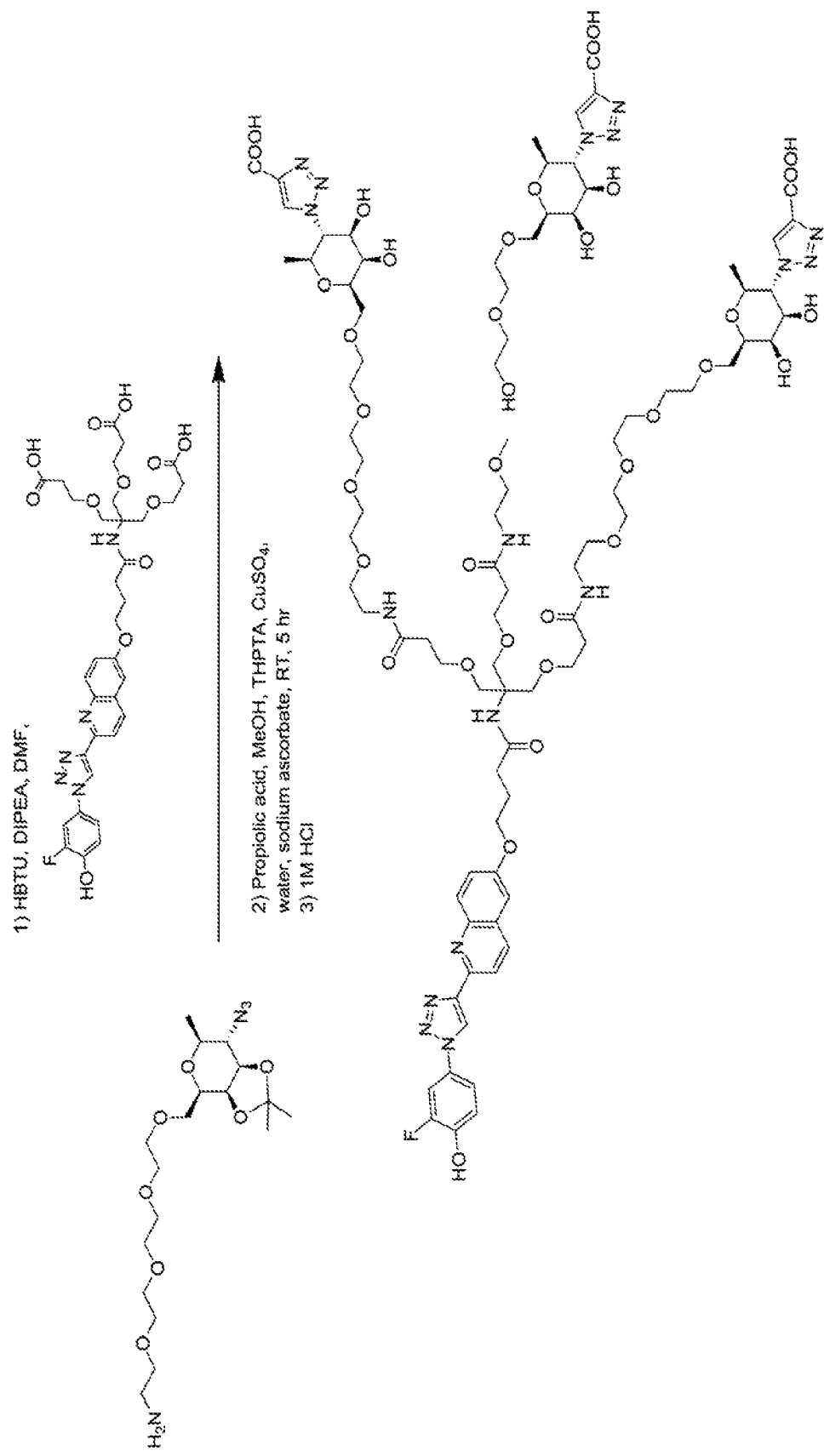

FIG. 47 shows the synthesis of compound MIF-19-3. The molecule is synthesized through a late stage triazole-forming click reaction between the triazide and propiolic acid in methanol in the presence of THPTA, copper sulfate, water, and sodium ascorbate. All other reactions are performed as described above.

Figure 48:
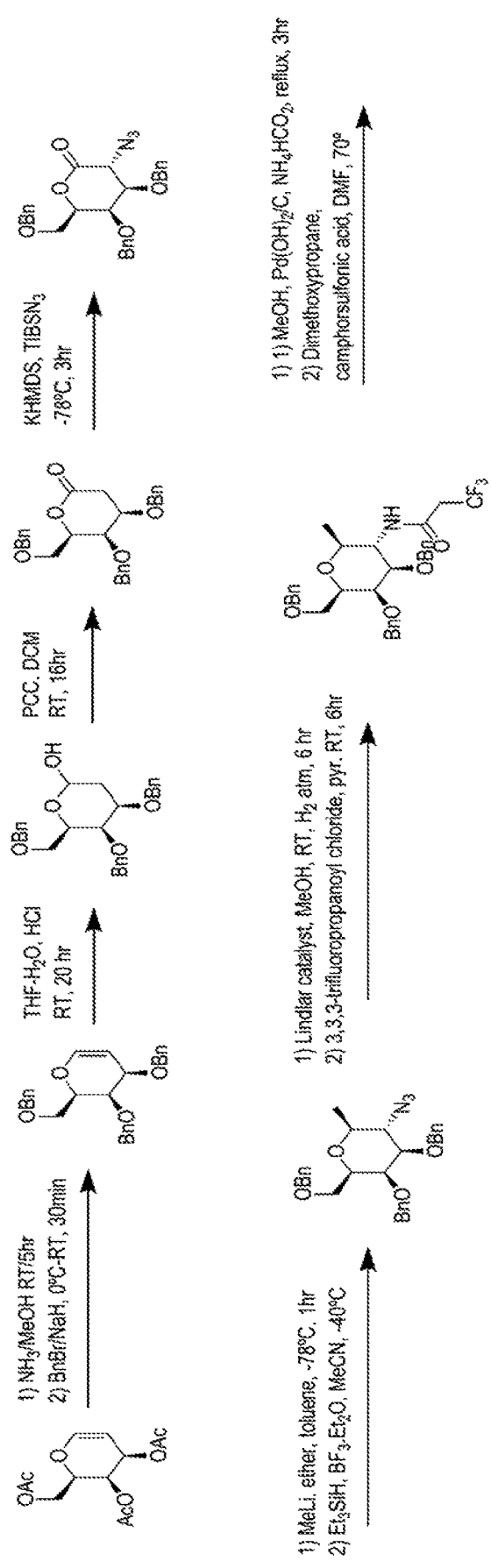
FIG. 48 shows the synthesis of compound MIF-16-3
Figure 48:
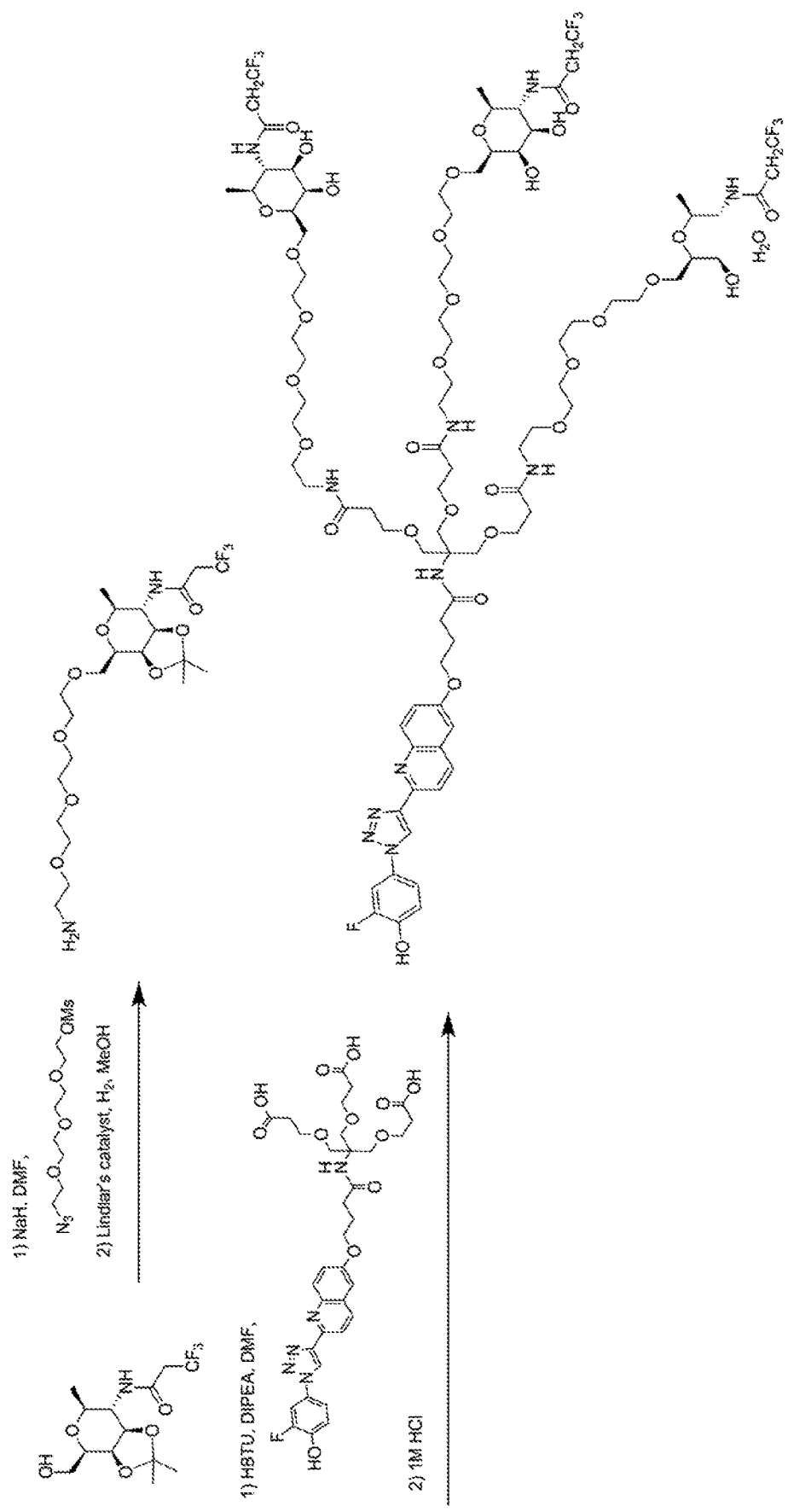

FIG. 48 shows the synthesis of compound MIF-16-3, which was synthesized using procedures analogous to compounds described above.

Figure 49:
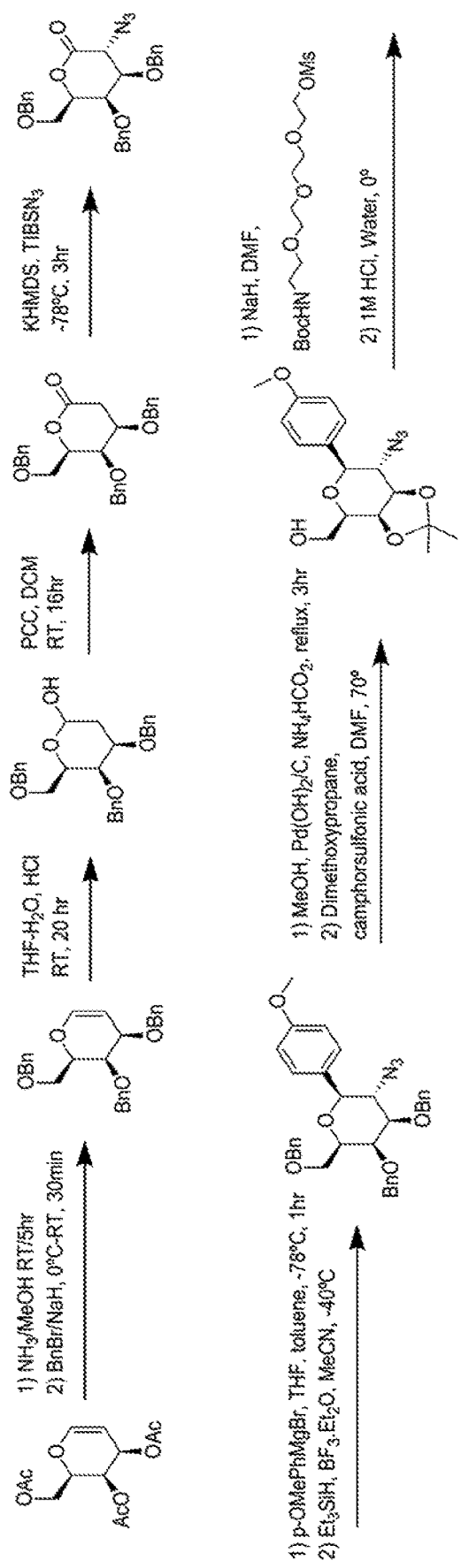
FIG. 49 shows the synthesis of compound MIF-20-3
Figure 49:
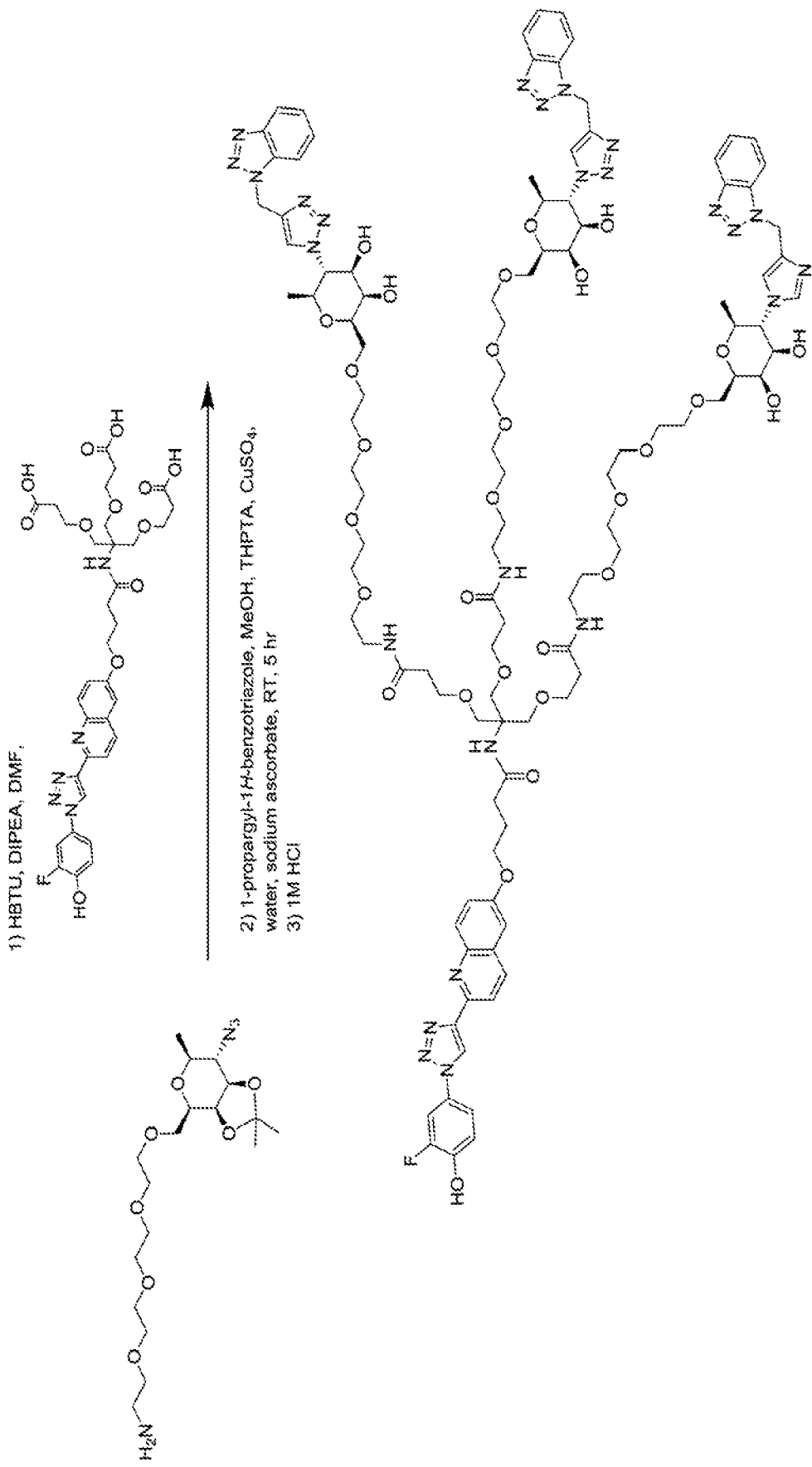

FIG. 49 shows the synthesis of compound MIF-20-3, which was synthesized using procedures analogous to compounds described above.

Figure 50:
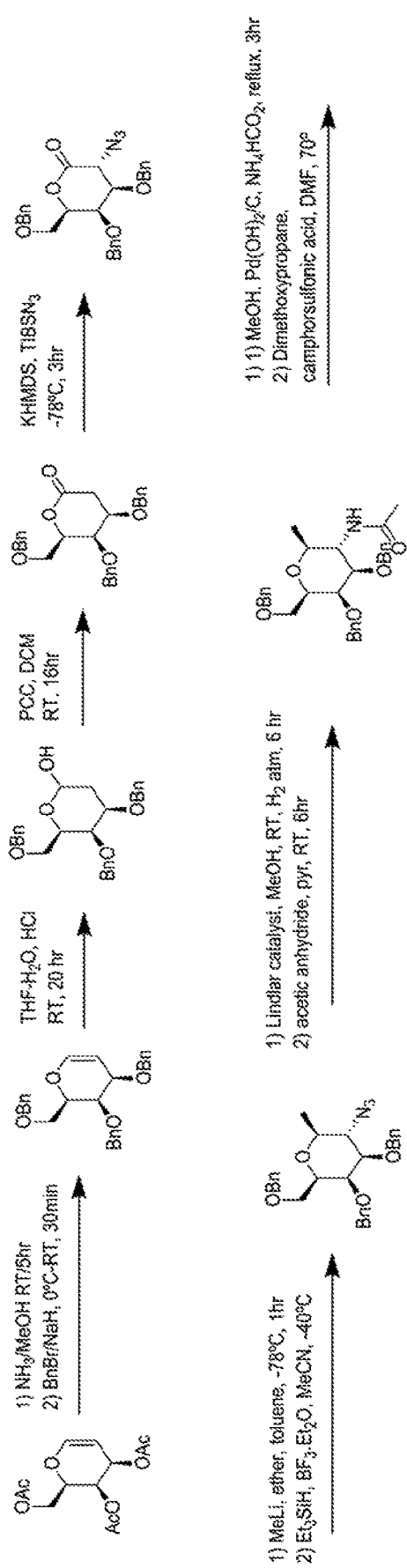
FIG. 50 shows the synthesis of compound MIF-14-3
Figure 50:
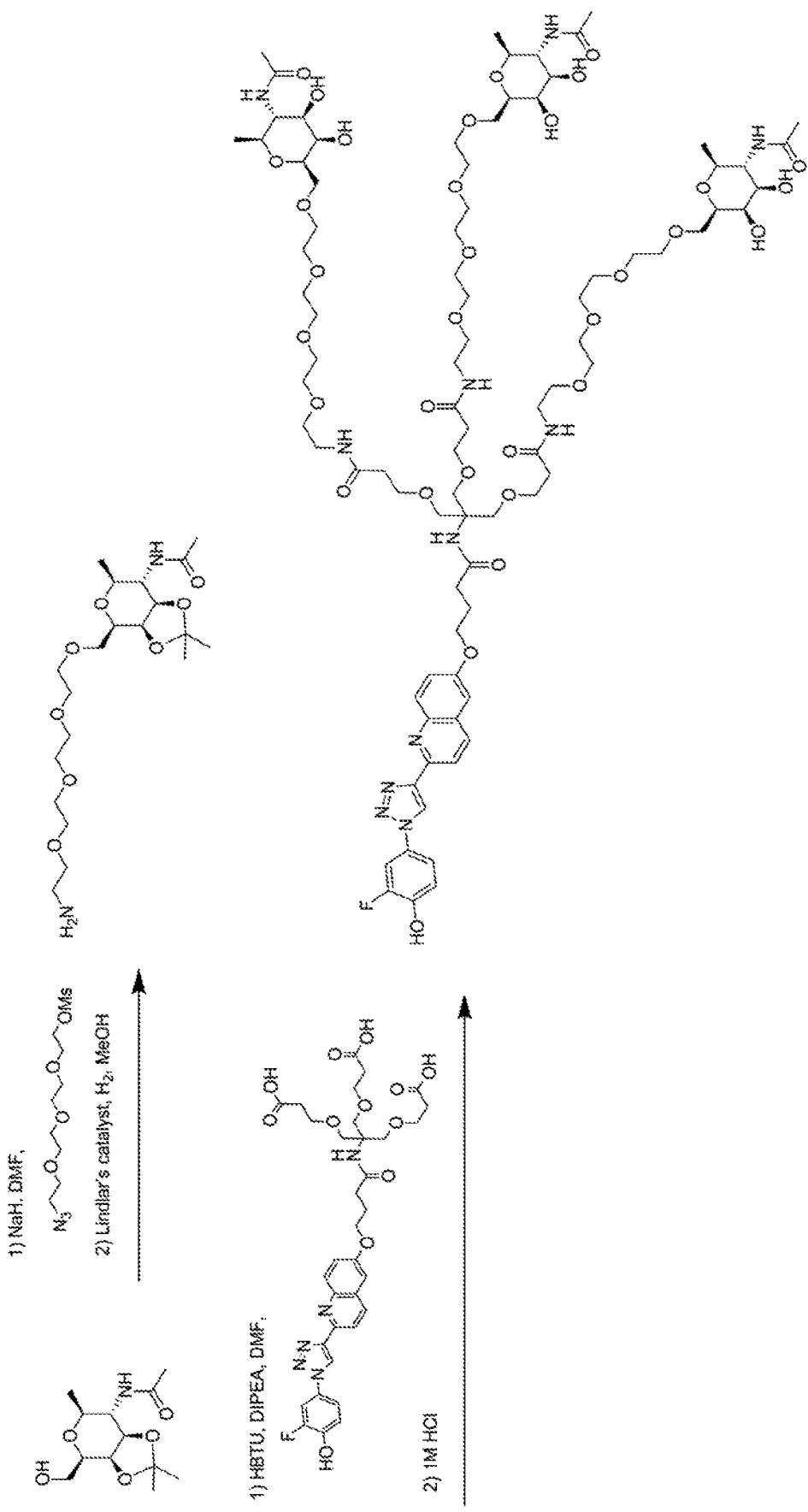

FIG. 50 shows the synthesis of compound MIF-14-3, which was synthesized using procedures analogous to compounds described above.

Figure 51:
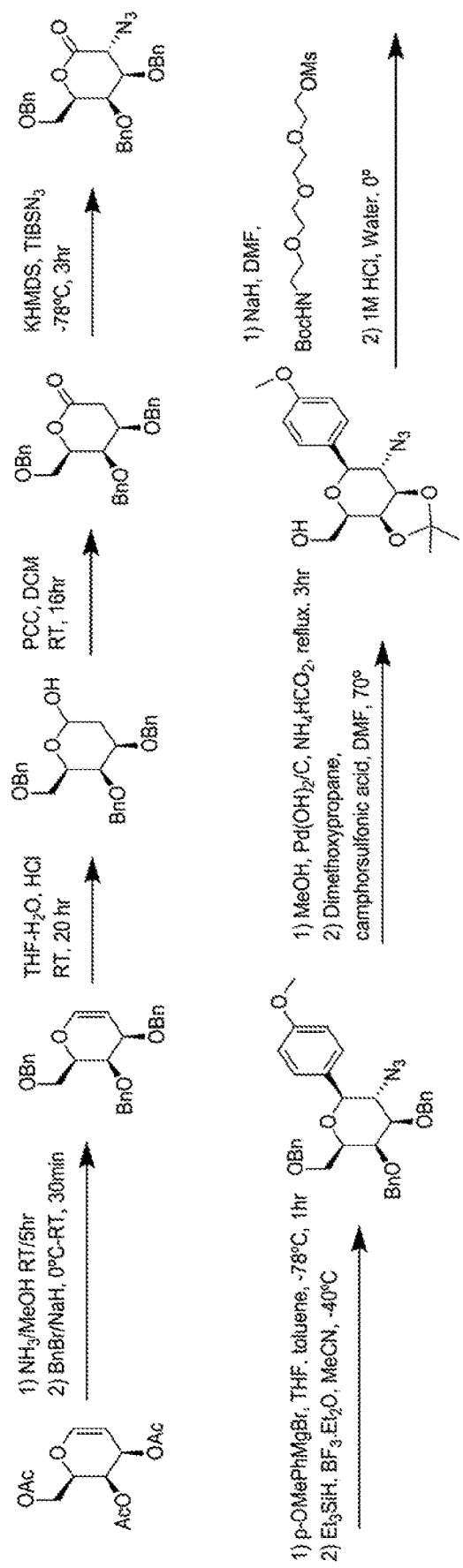
FIG. 51 shows the synthesis of compound MIF-21-3
Figure 51:
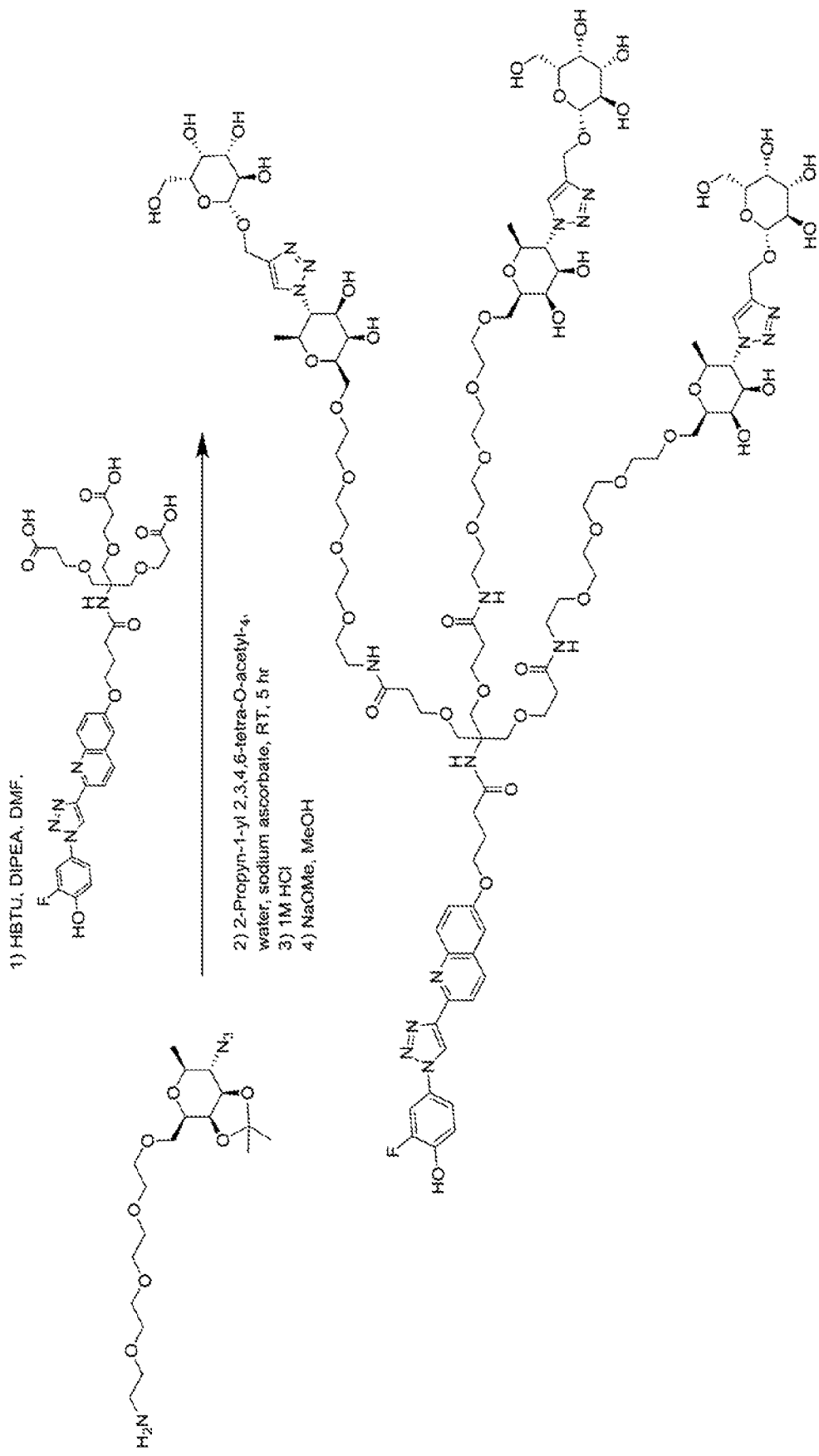

FIG. 51 shows the synthesis of compound MIF-21-3, which was synthesized using procedures analogous to compounds described above.

Figure 52:
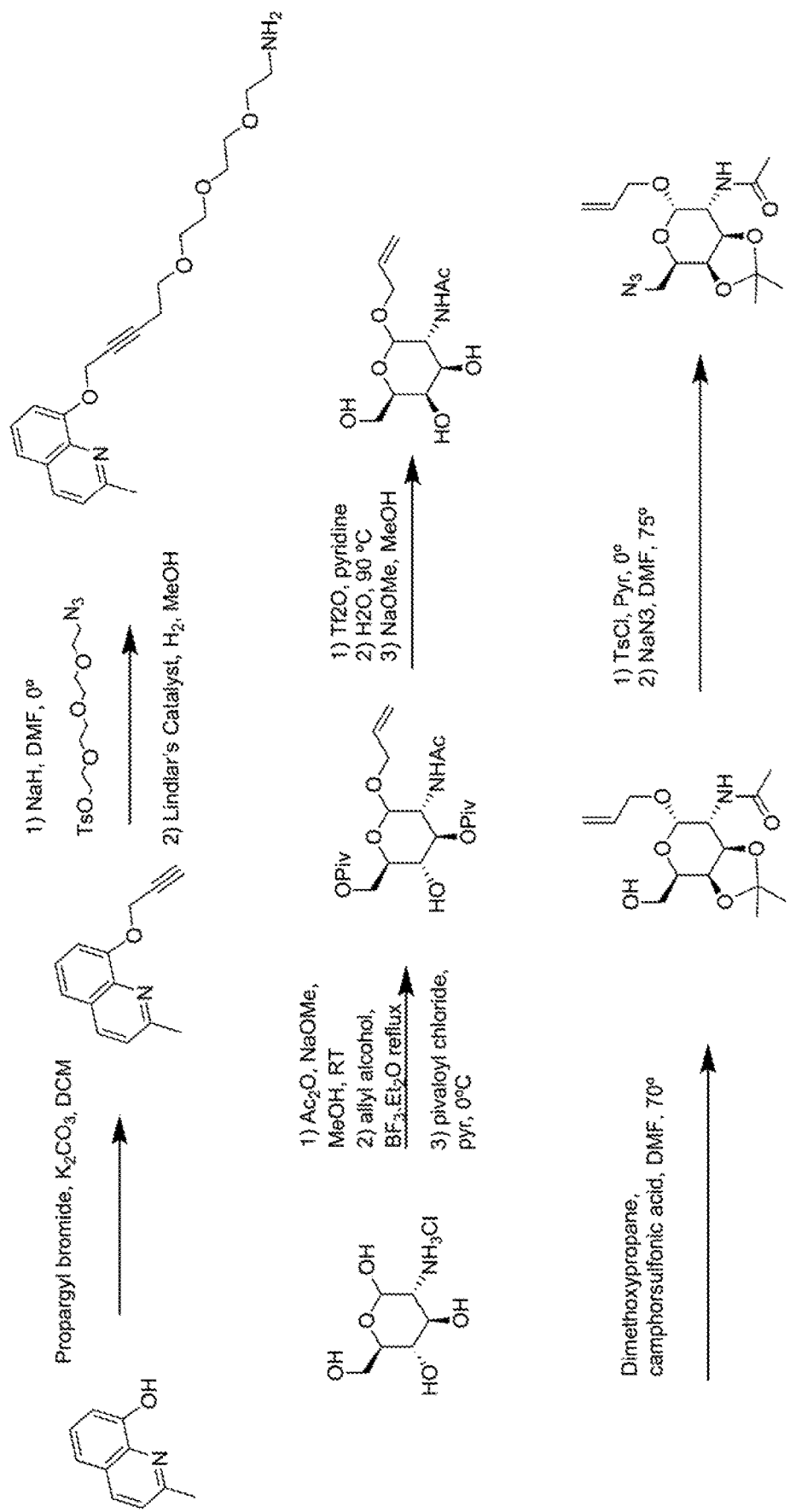
FIGS. 52-66 show the synthesis of a number of MIF-binding compounds with various ASGPRBM moieties.
Figure 52:
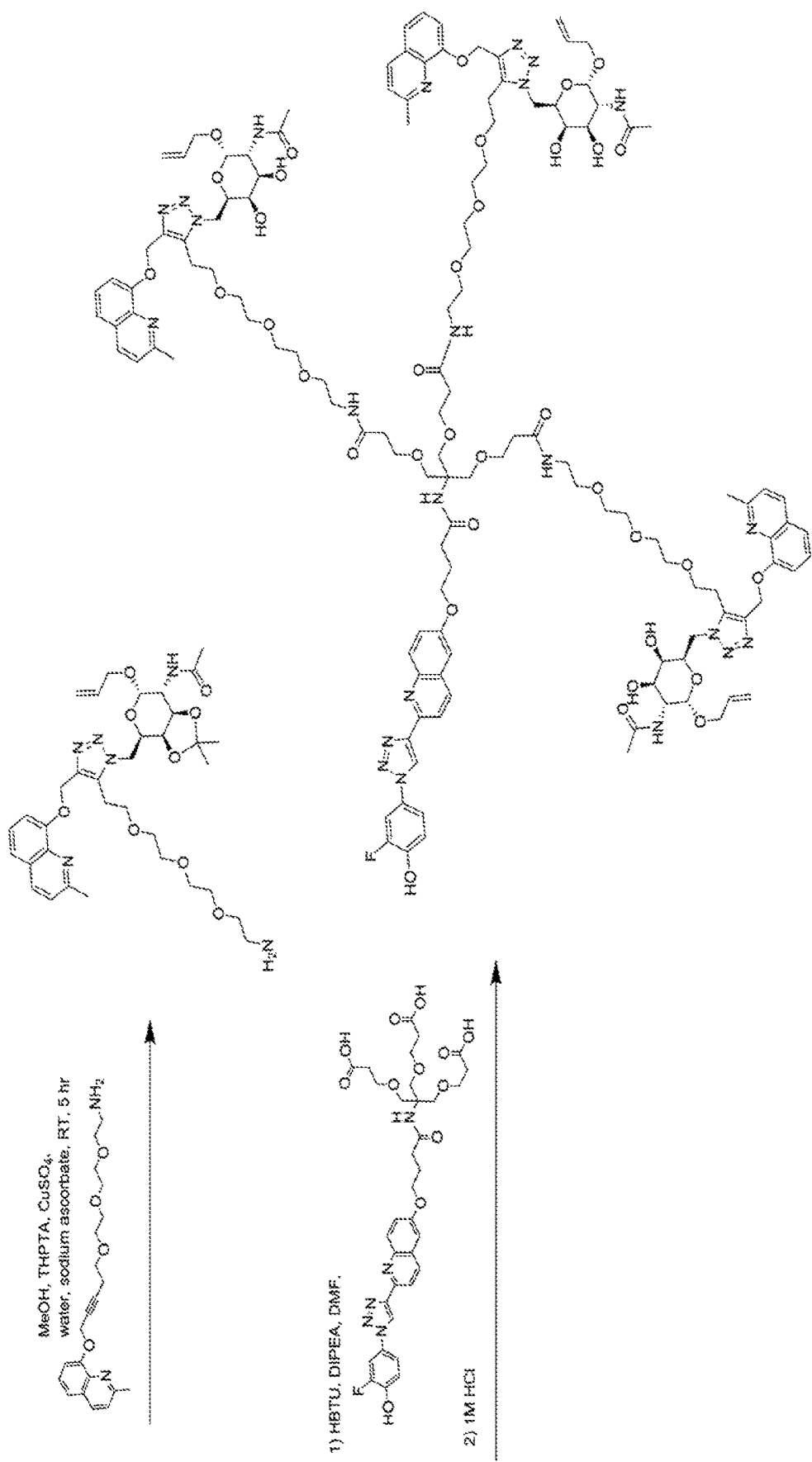
Figure 53:
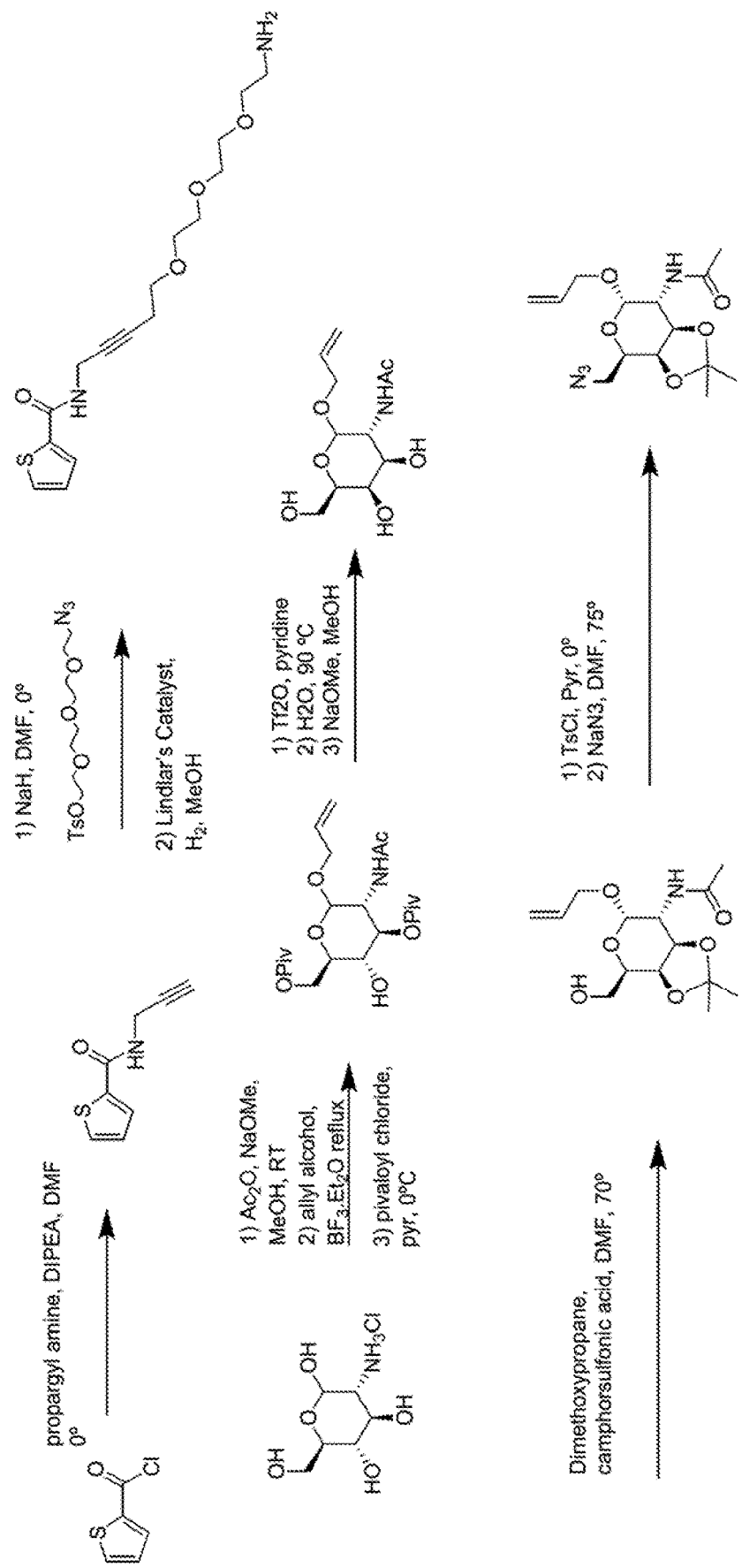
Figure 53:
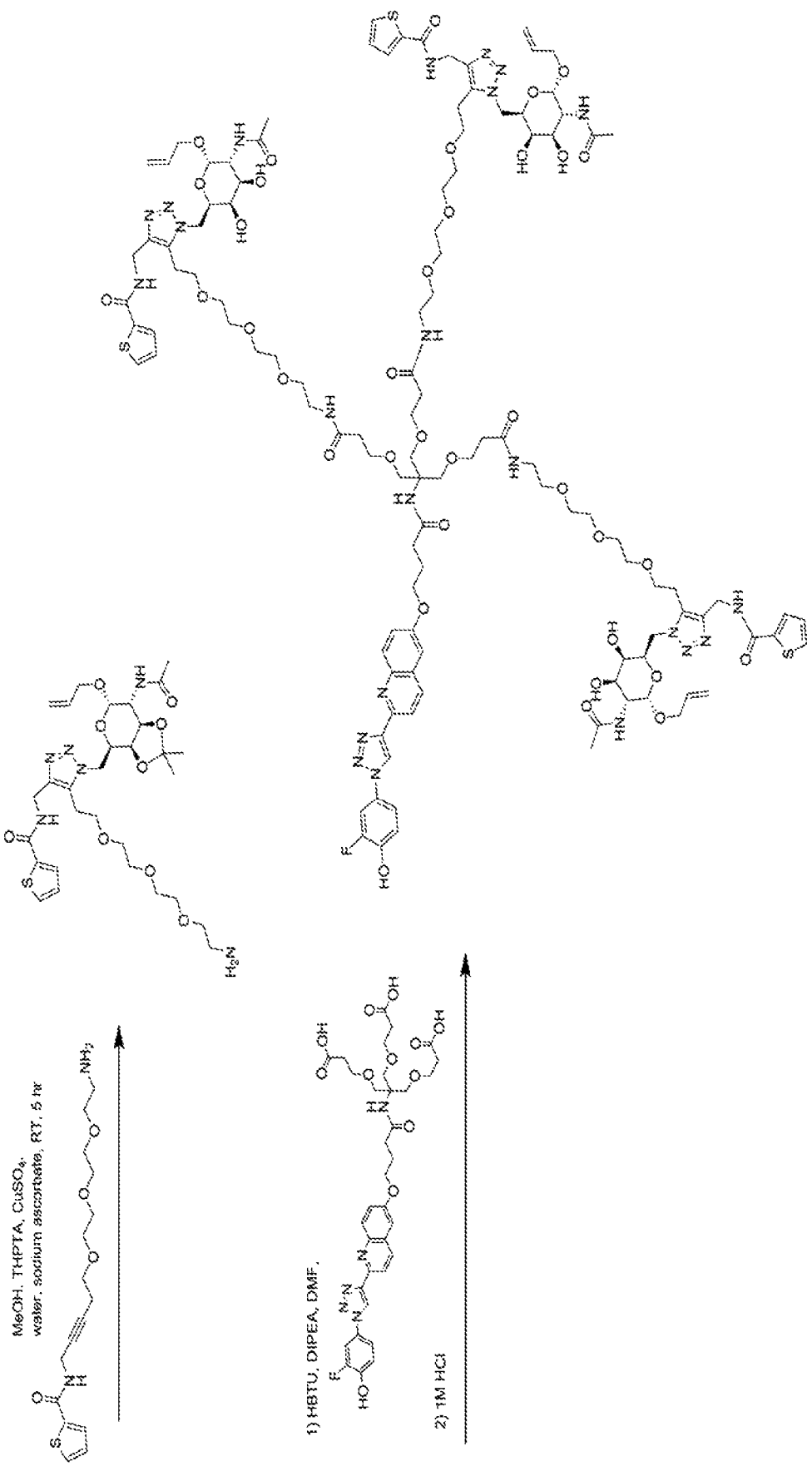
Figure 54:
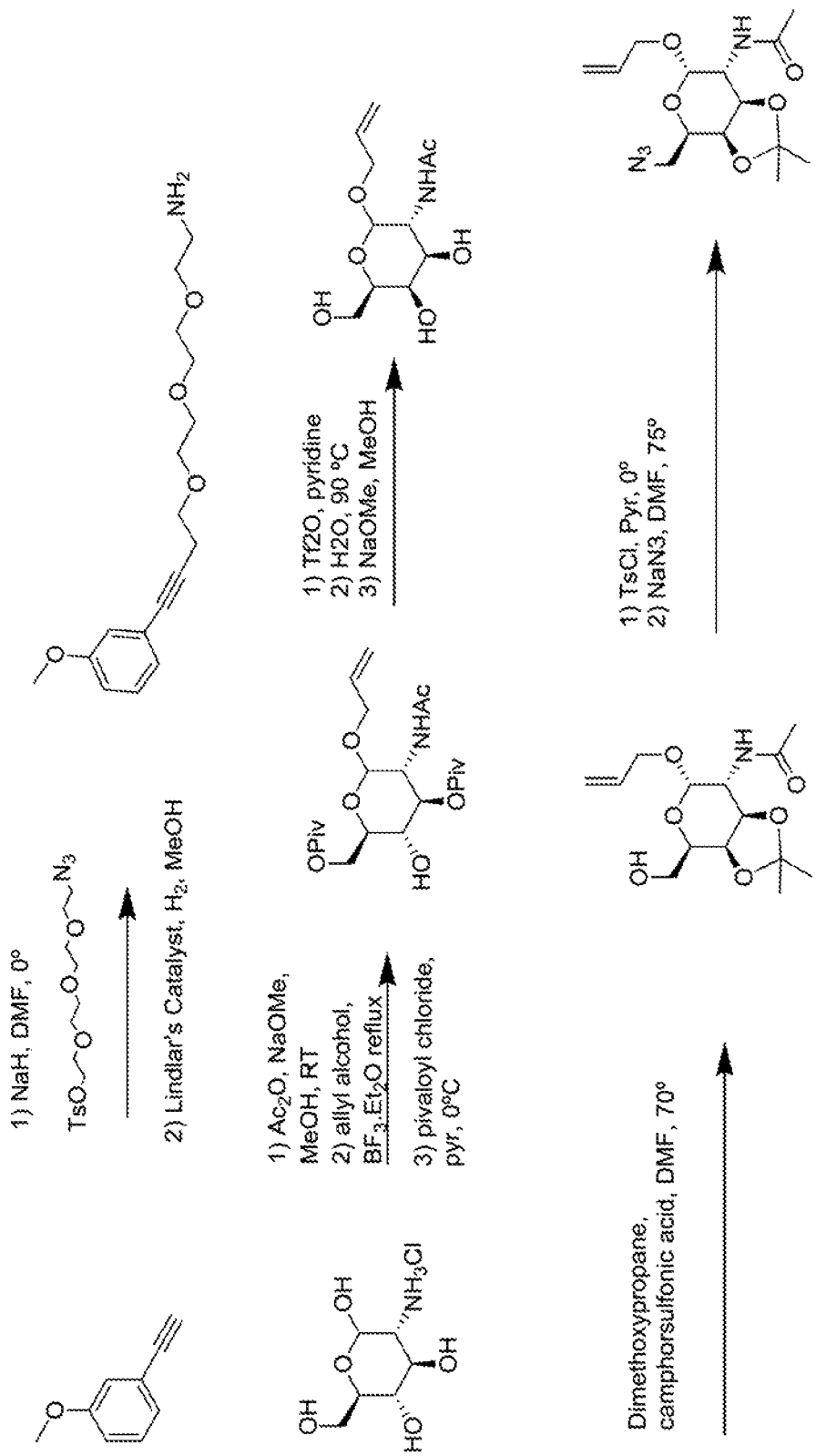
Figure 54:
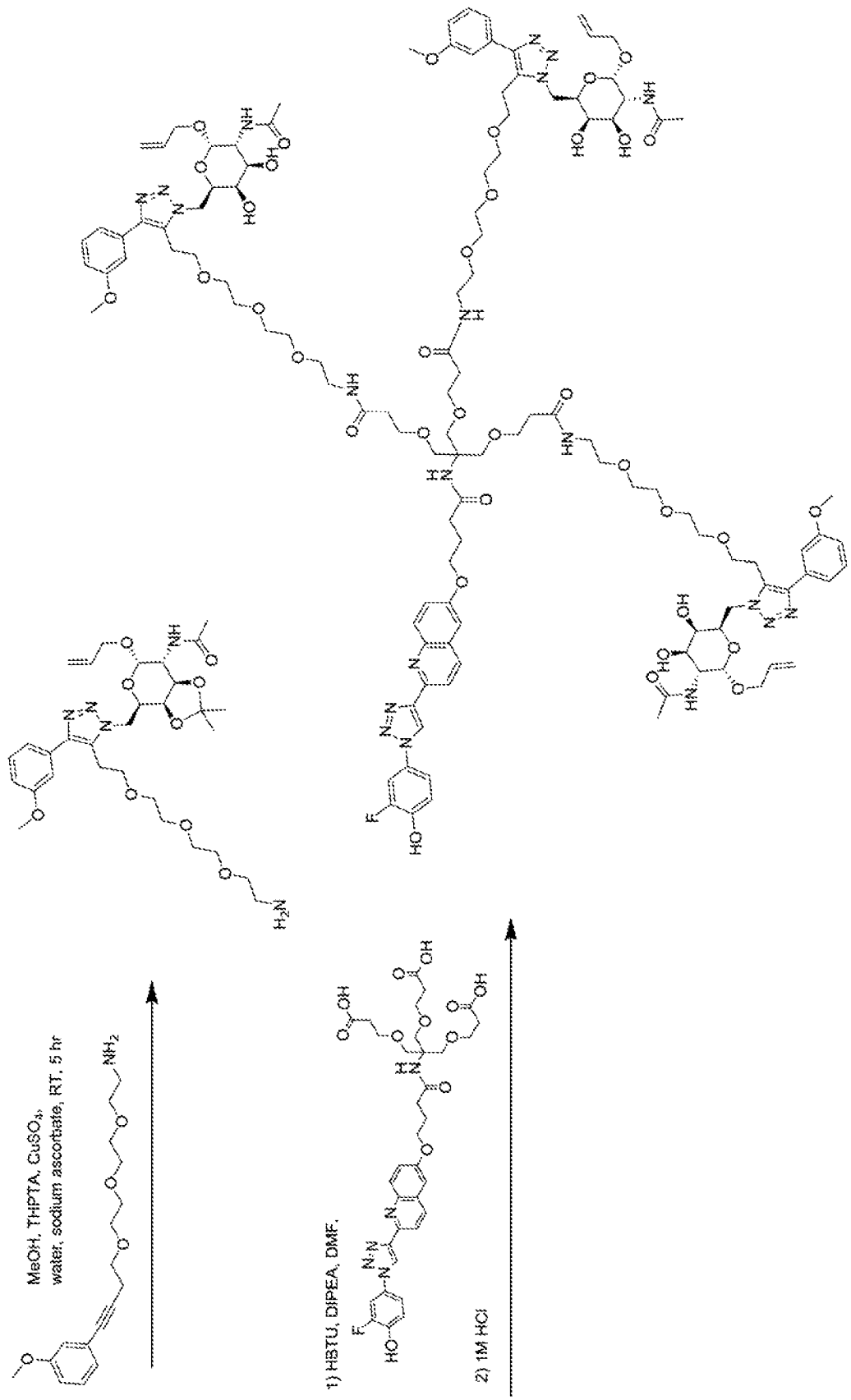
Figure 55:
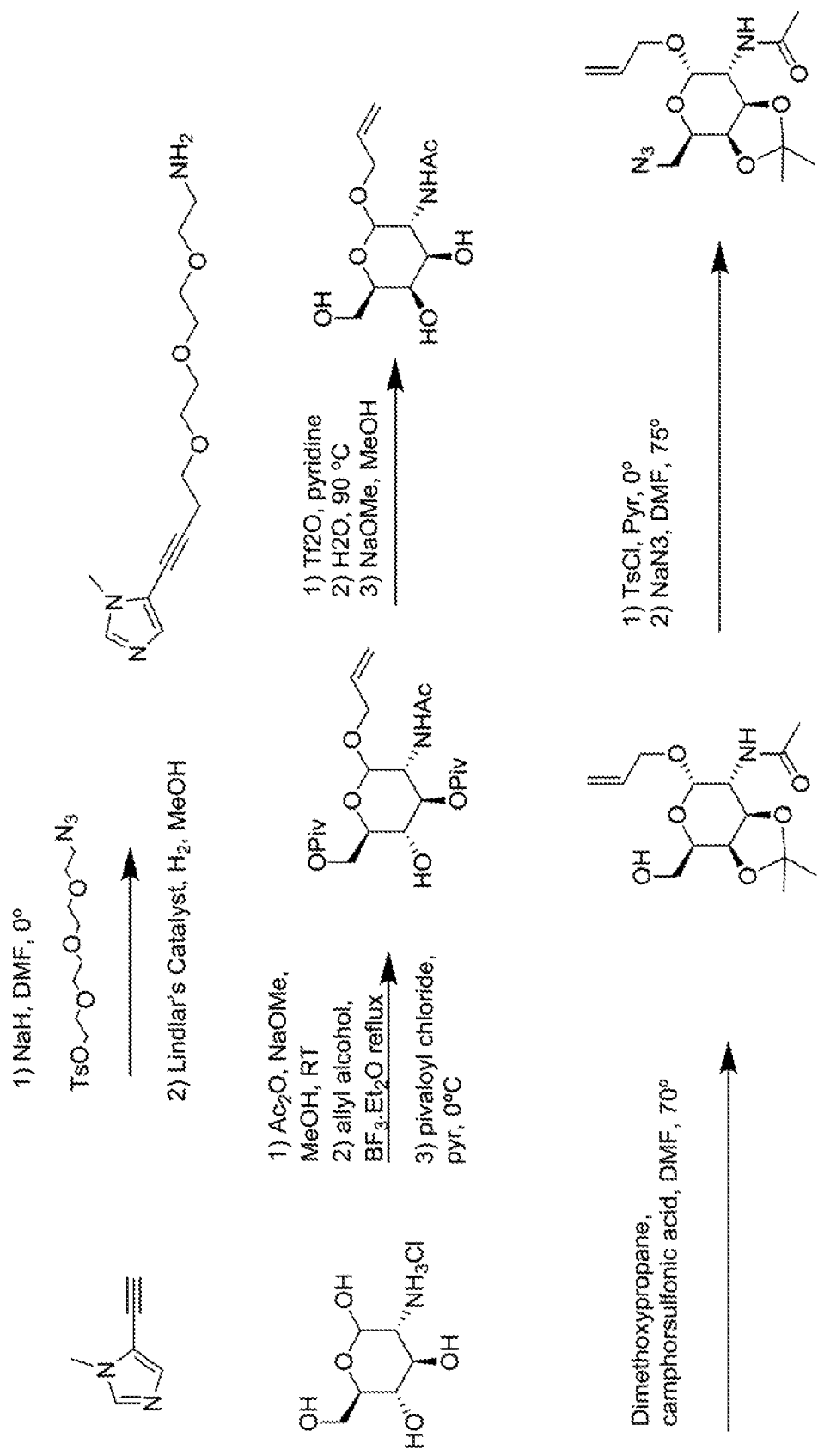
Figure 55:
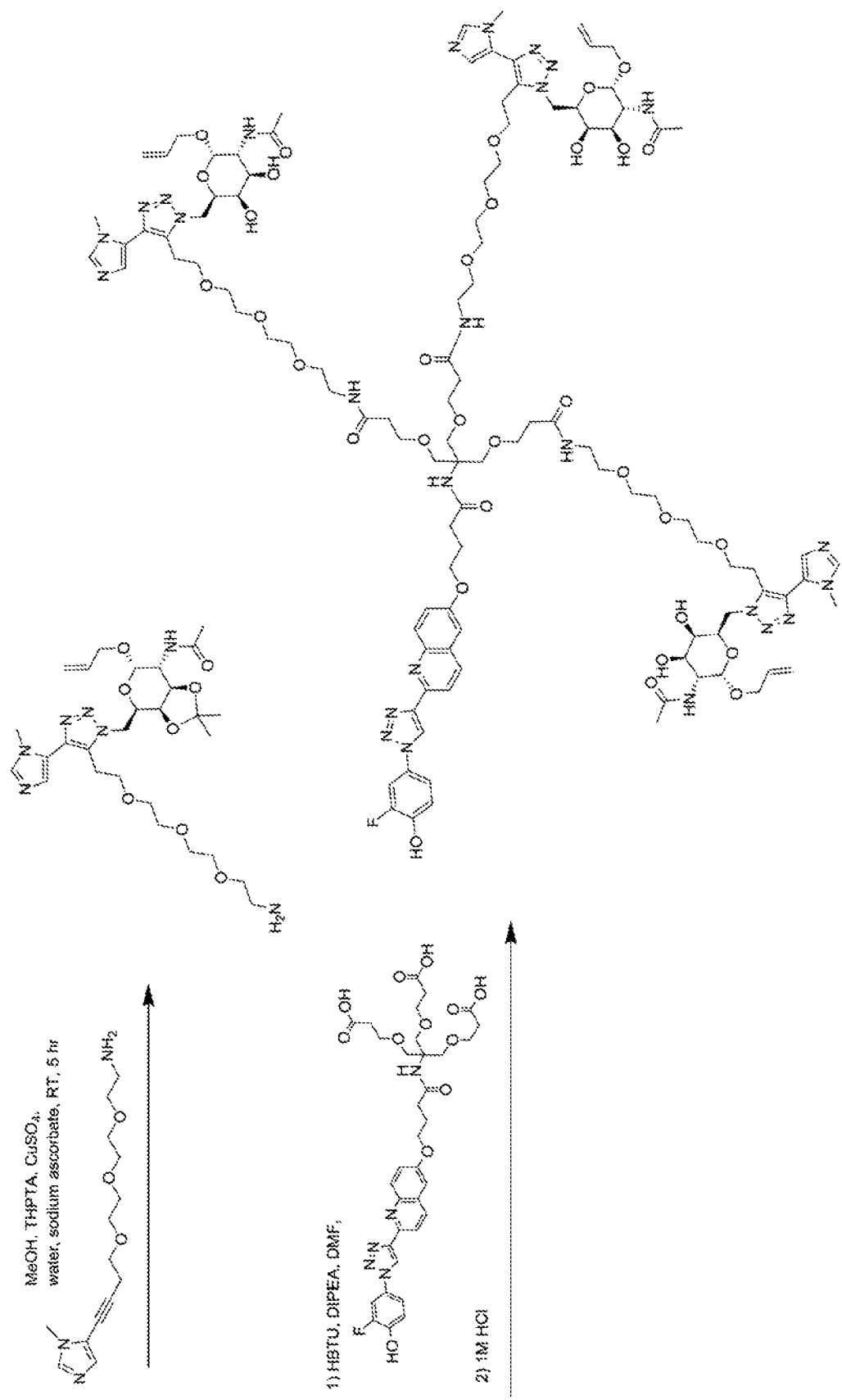
Figure 56:
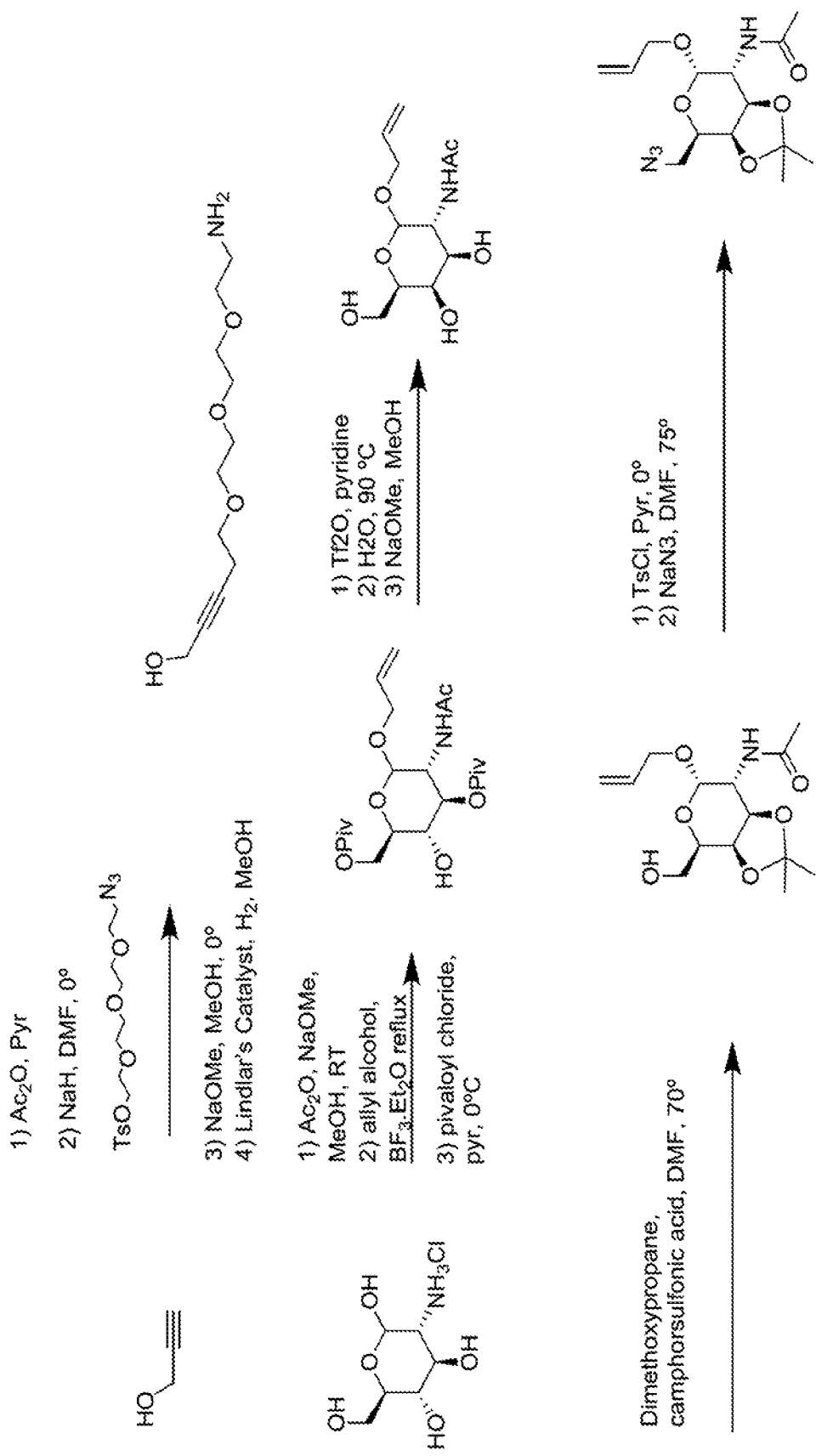
Figure 56:
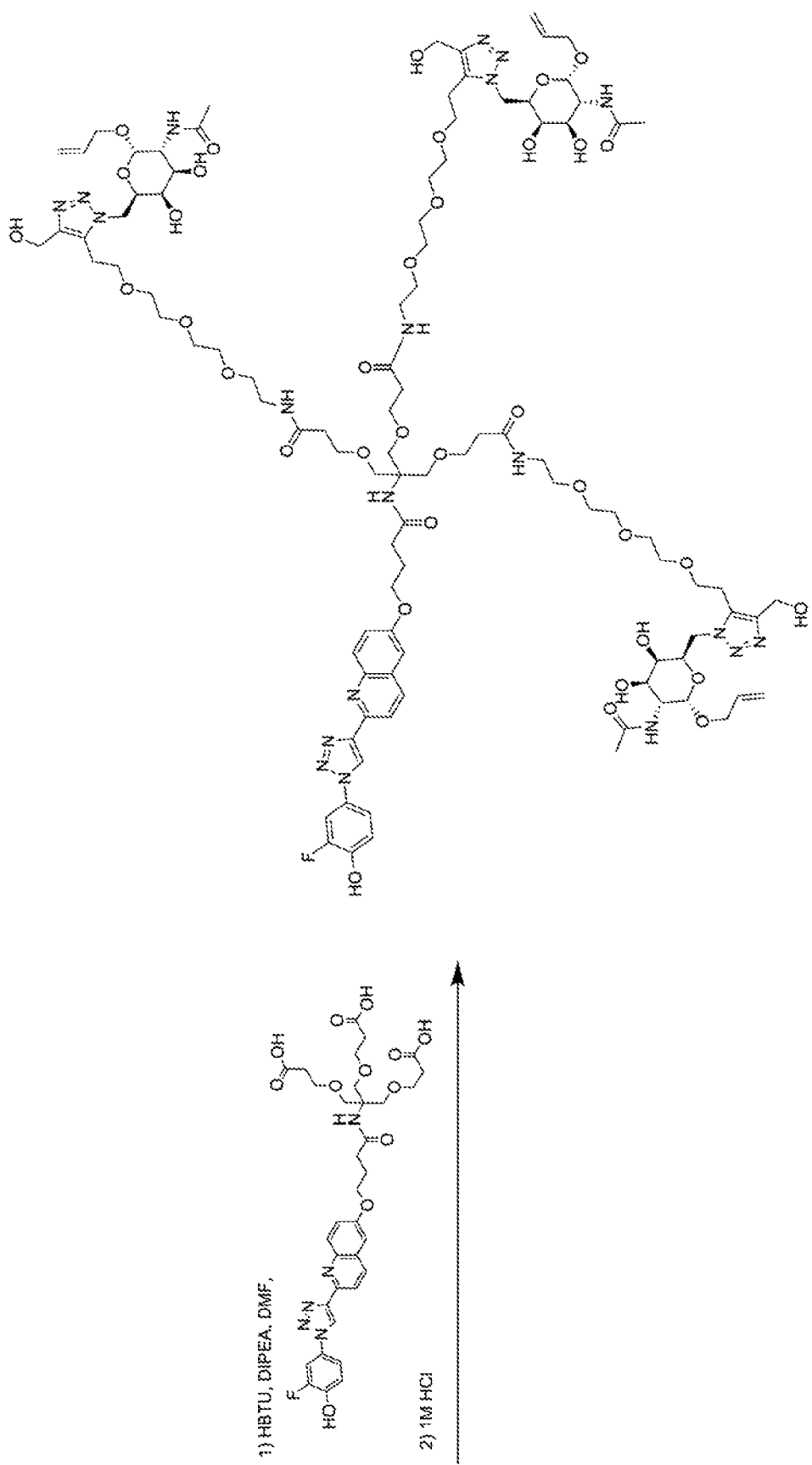
Figure 57:
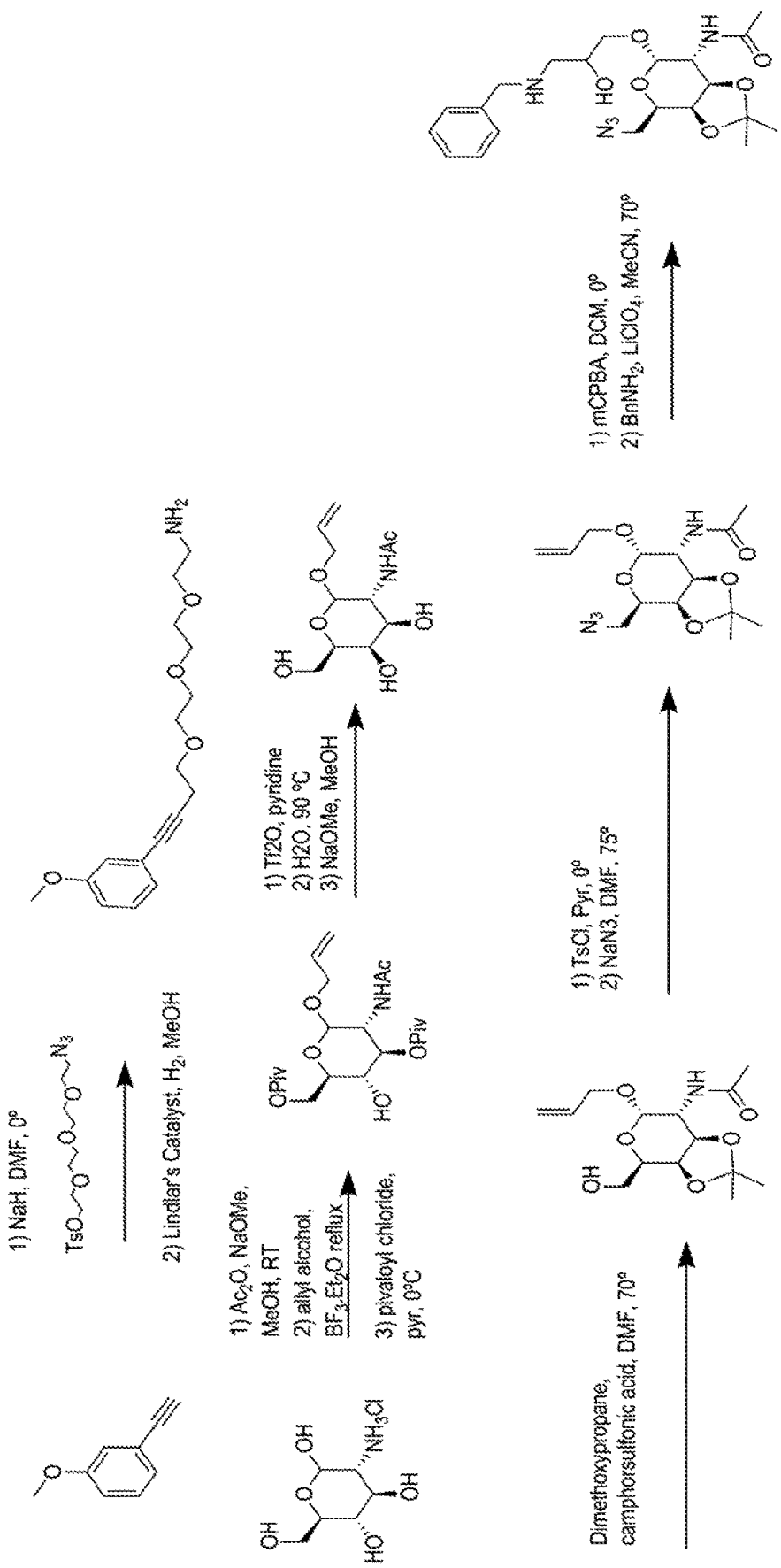
Figure 57:
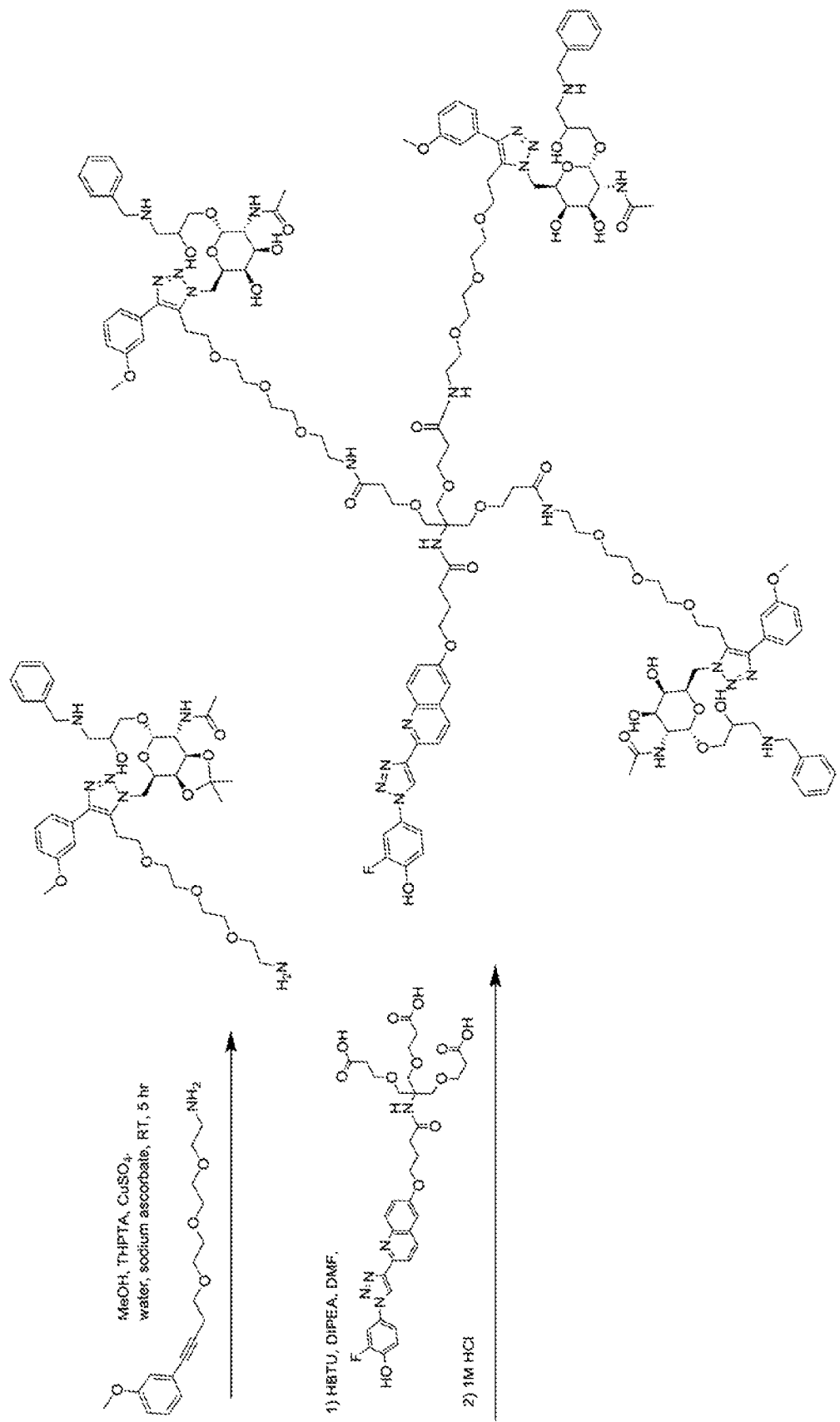
Figure 58:
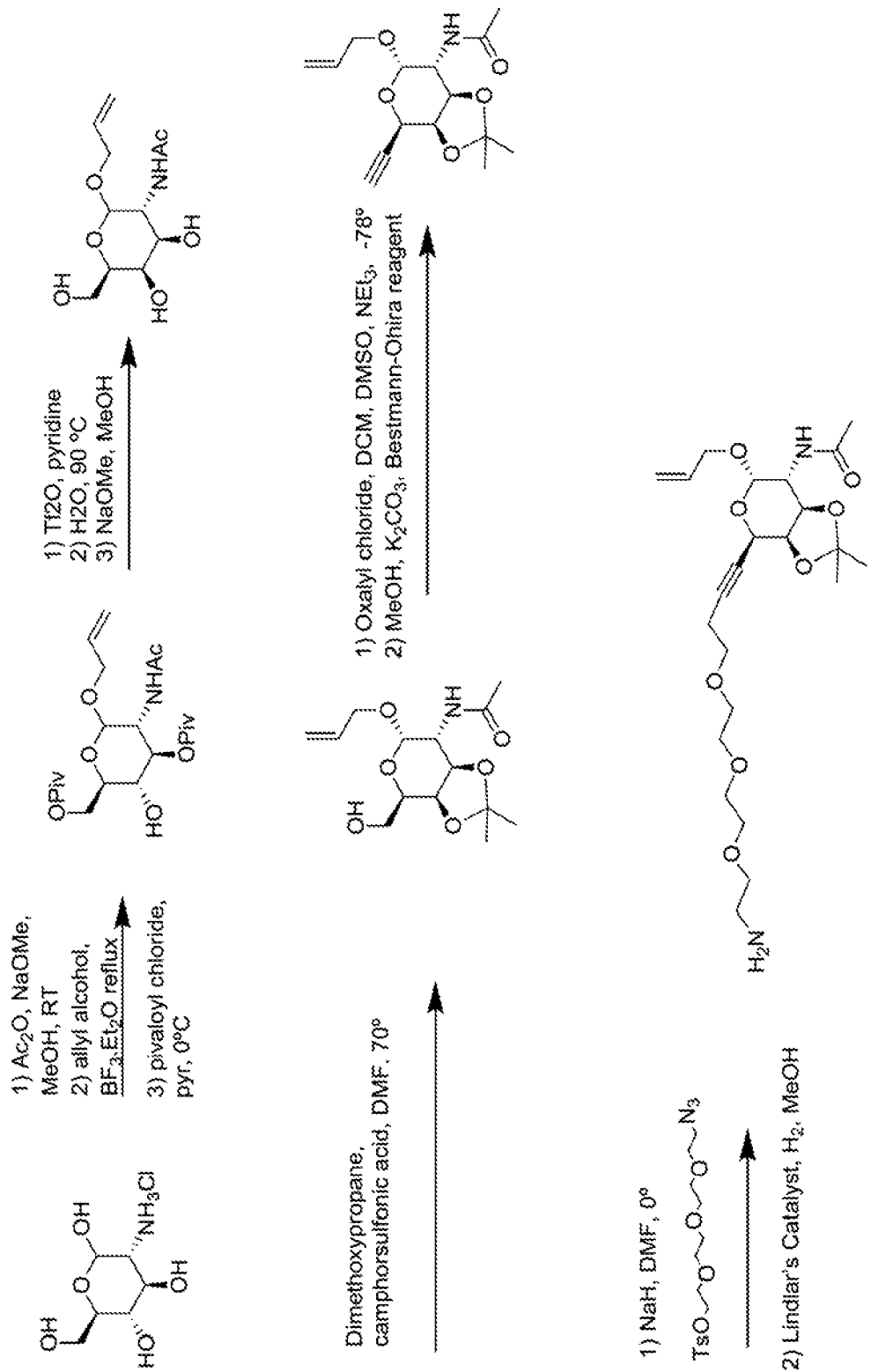
Figure 58:
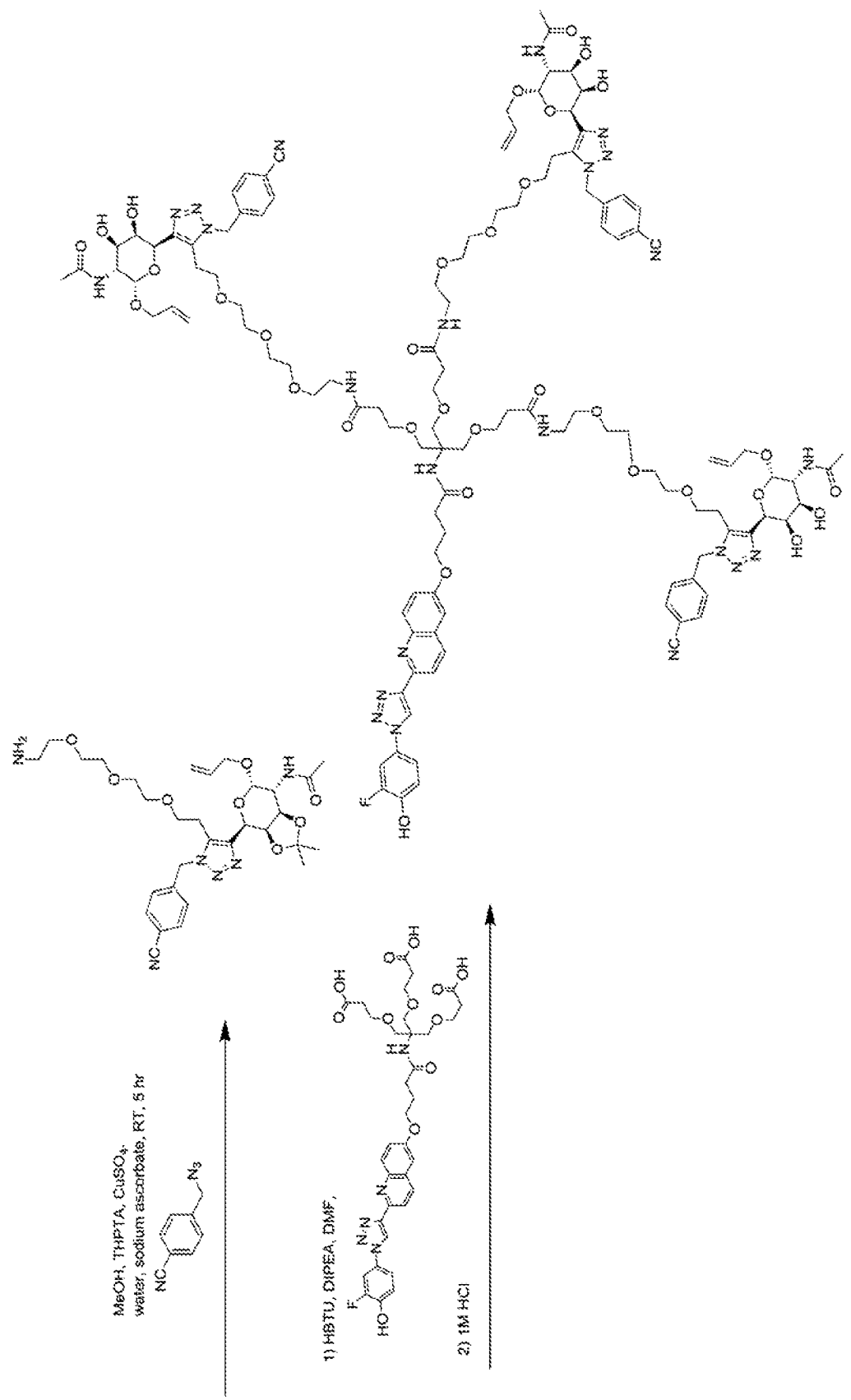
Figure 59:
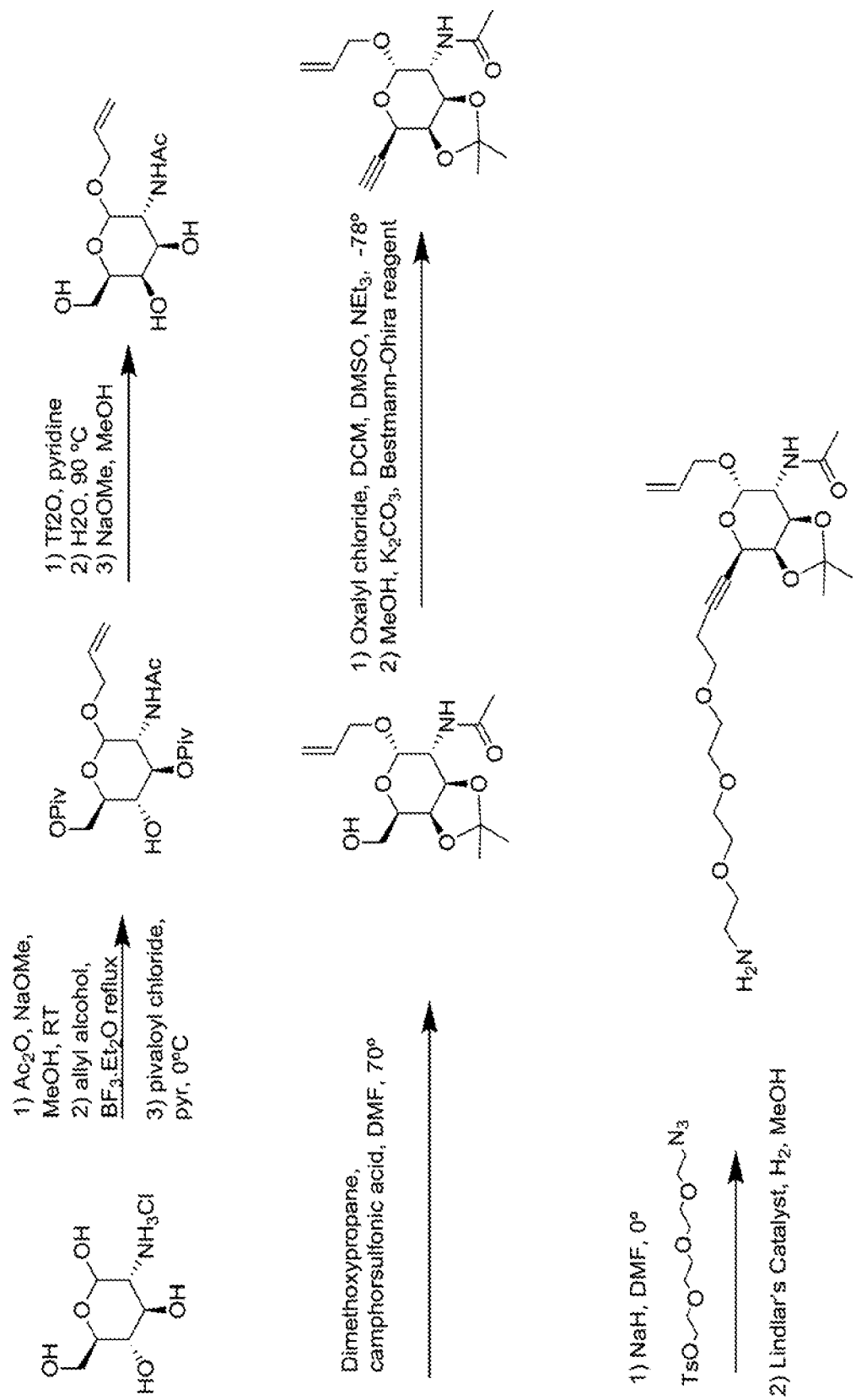
Figure 59:
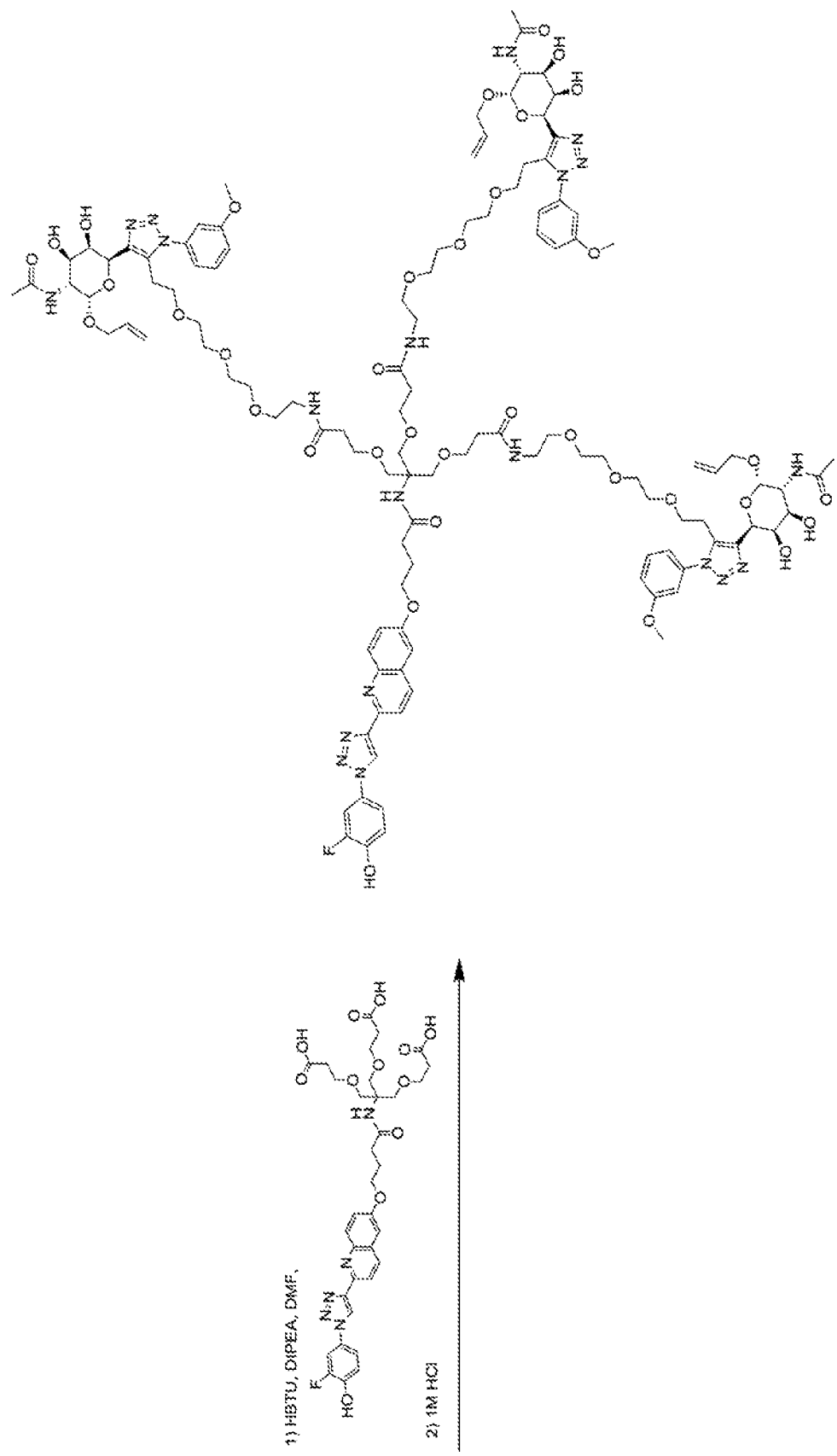
Figure 60:
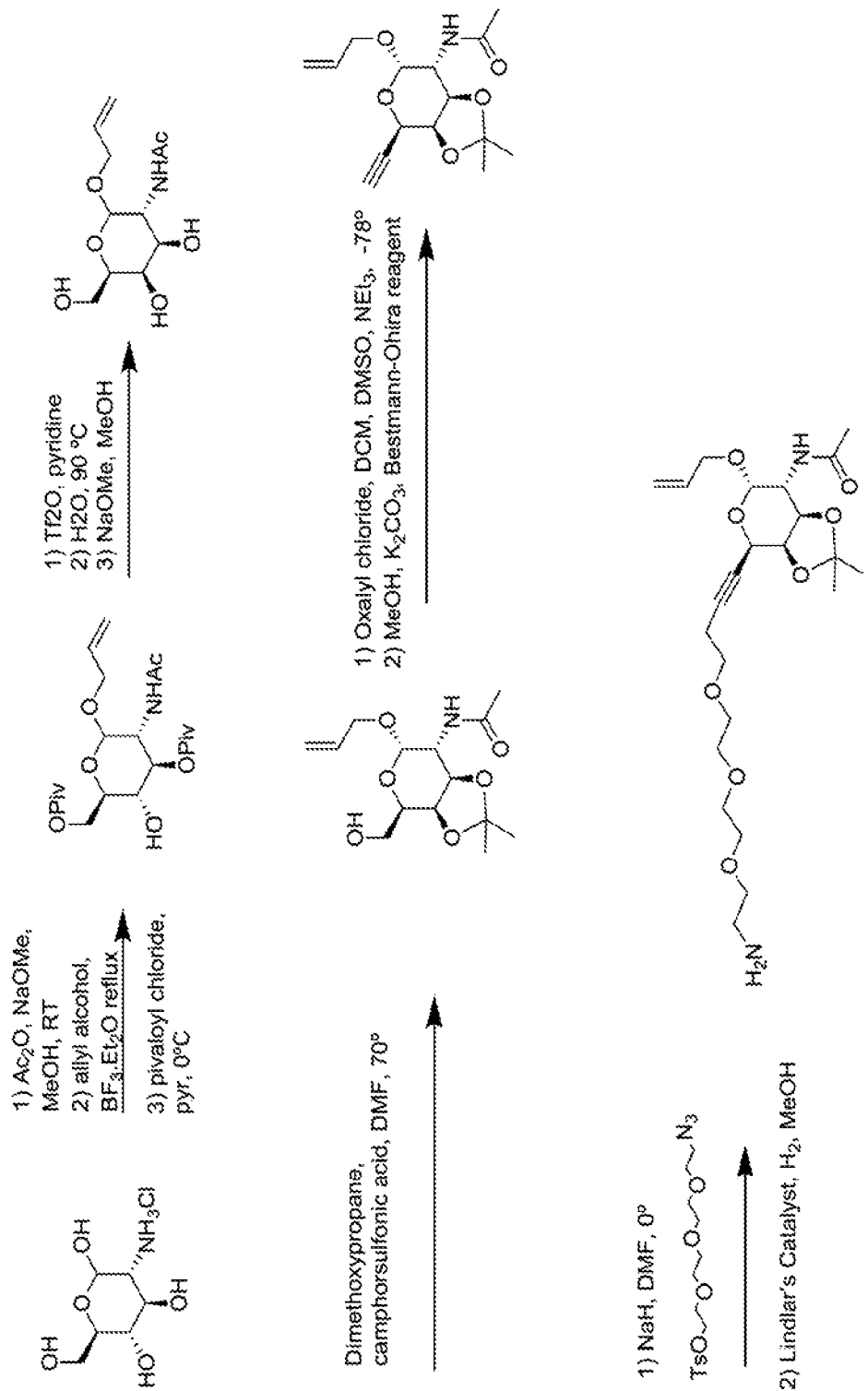
Figure 60:
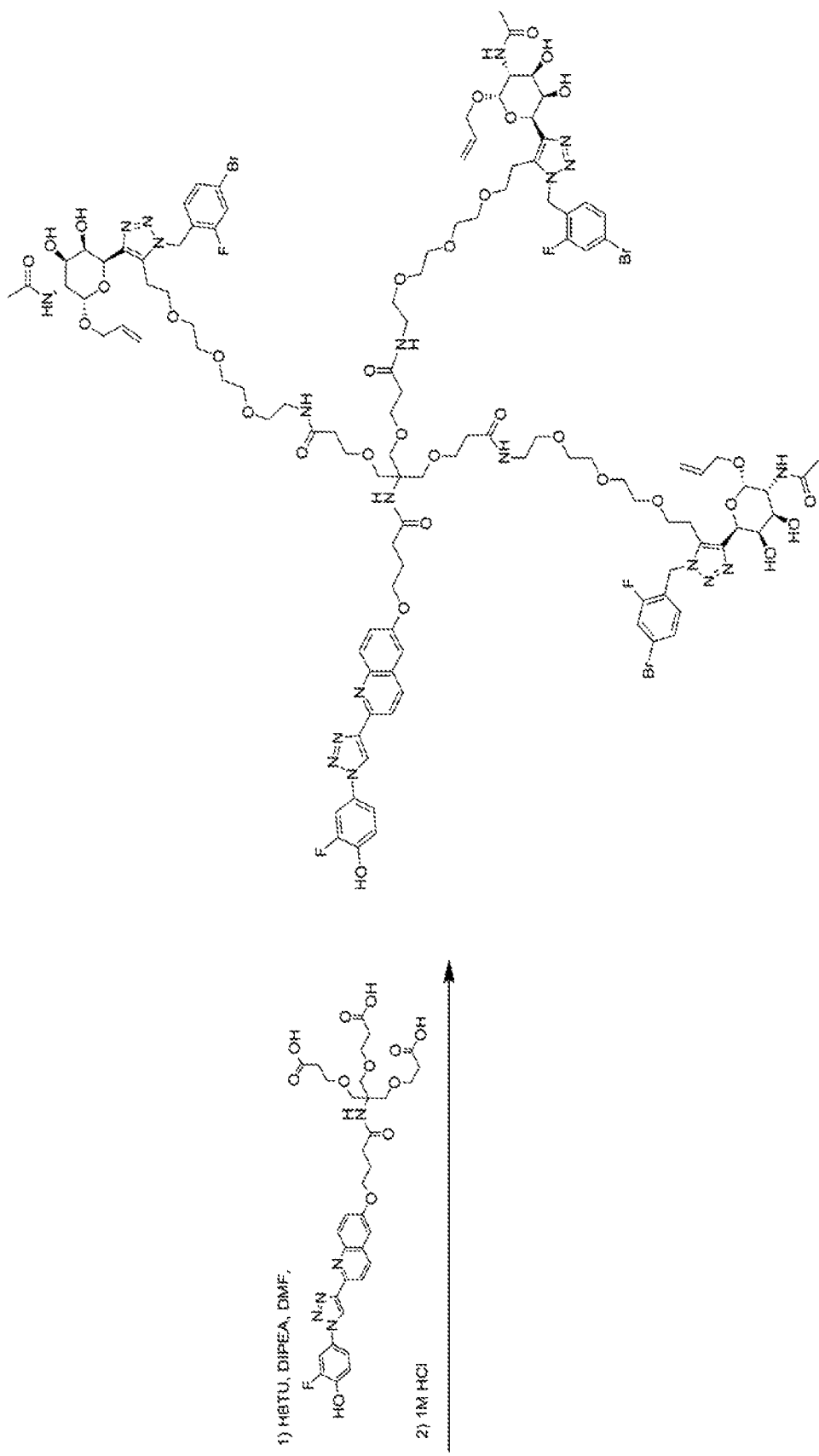
Figure 61:
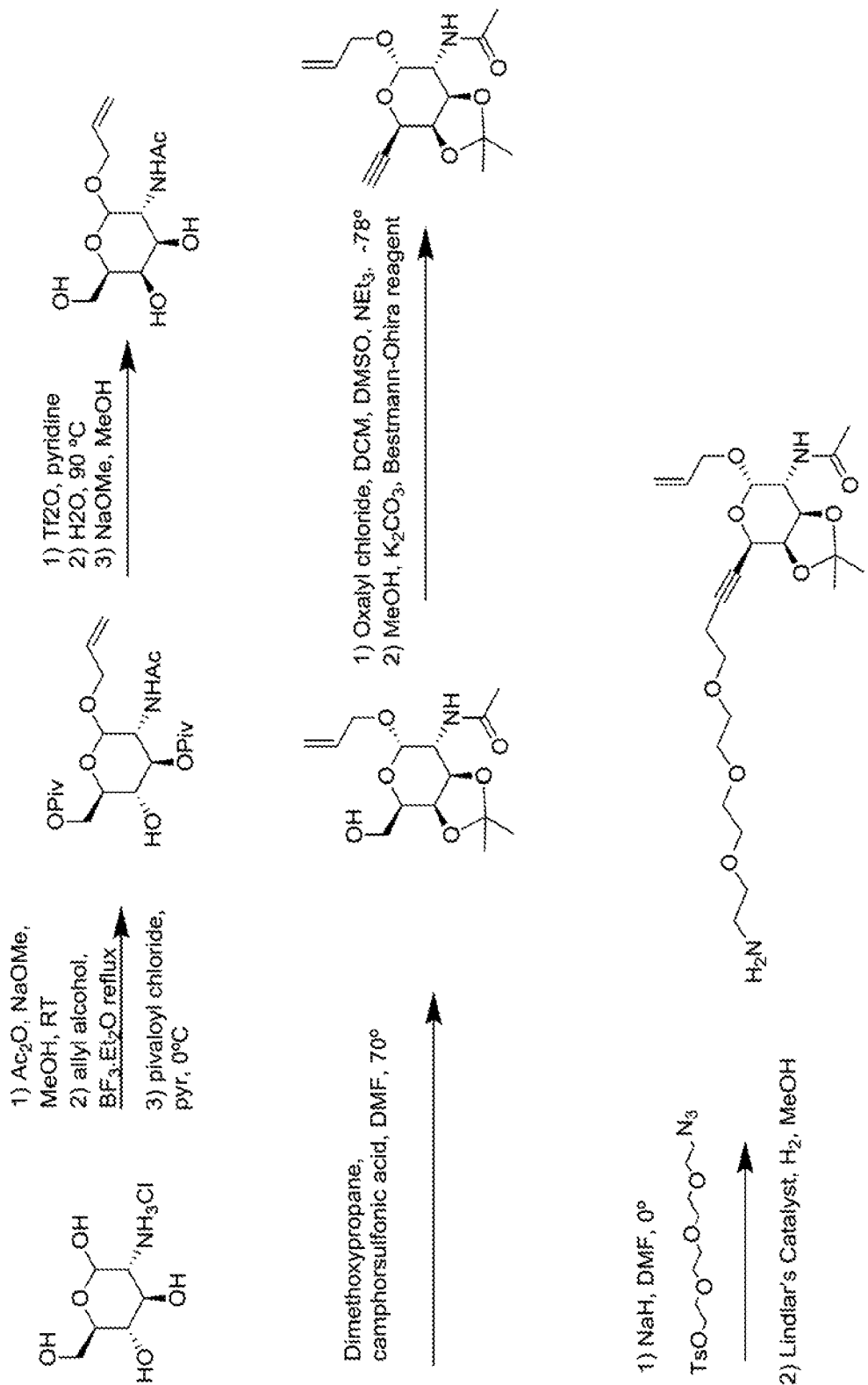
Figure 61:
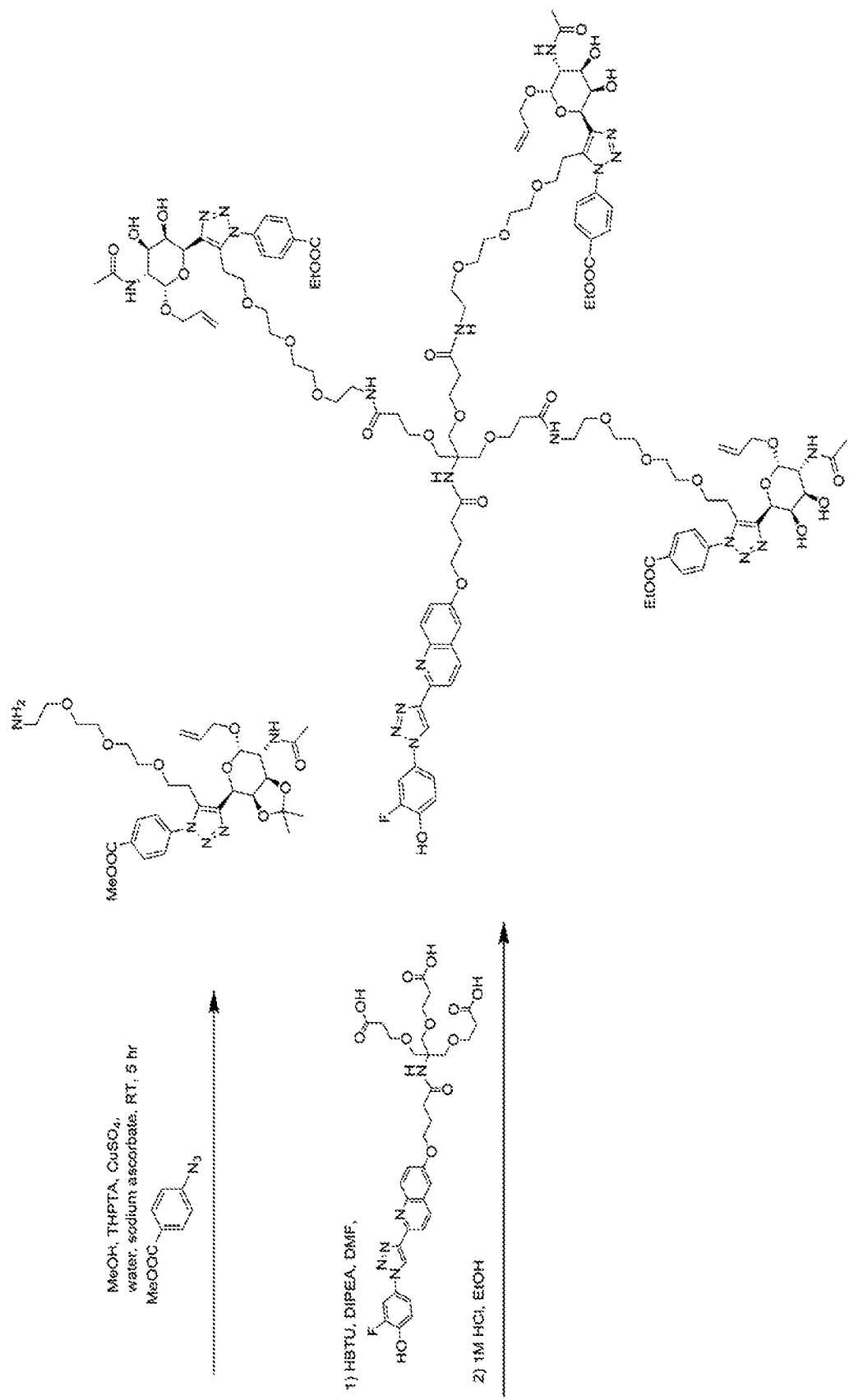
Figure 62:
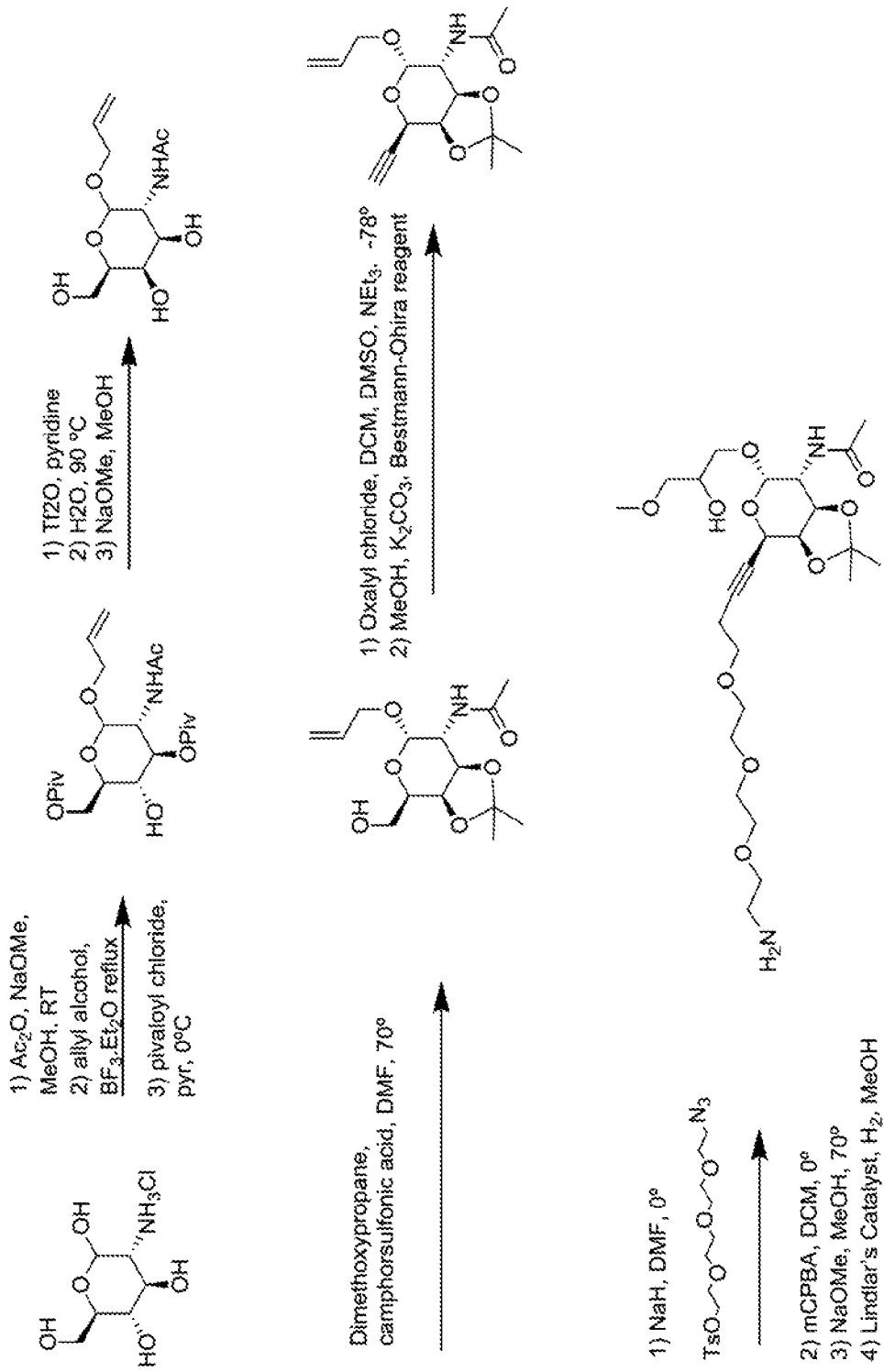
Figure 62:
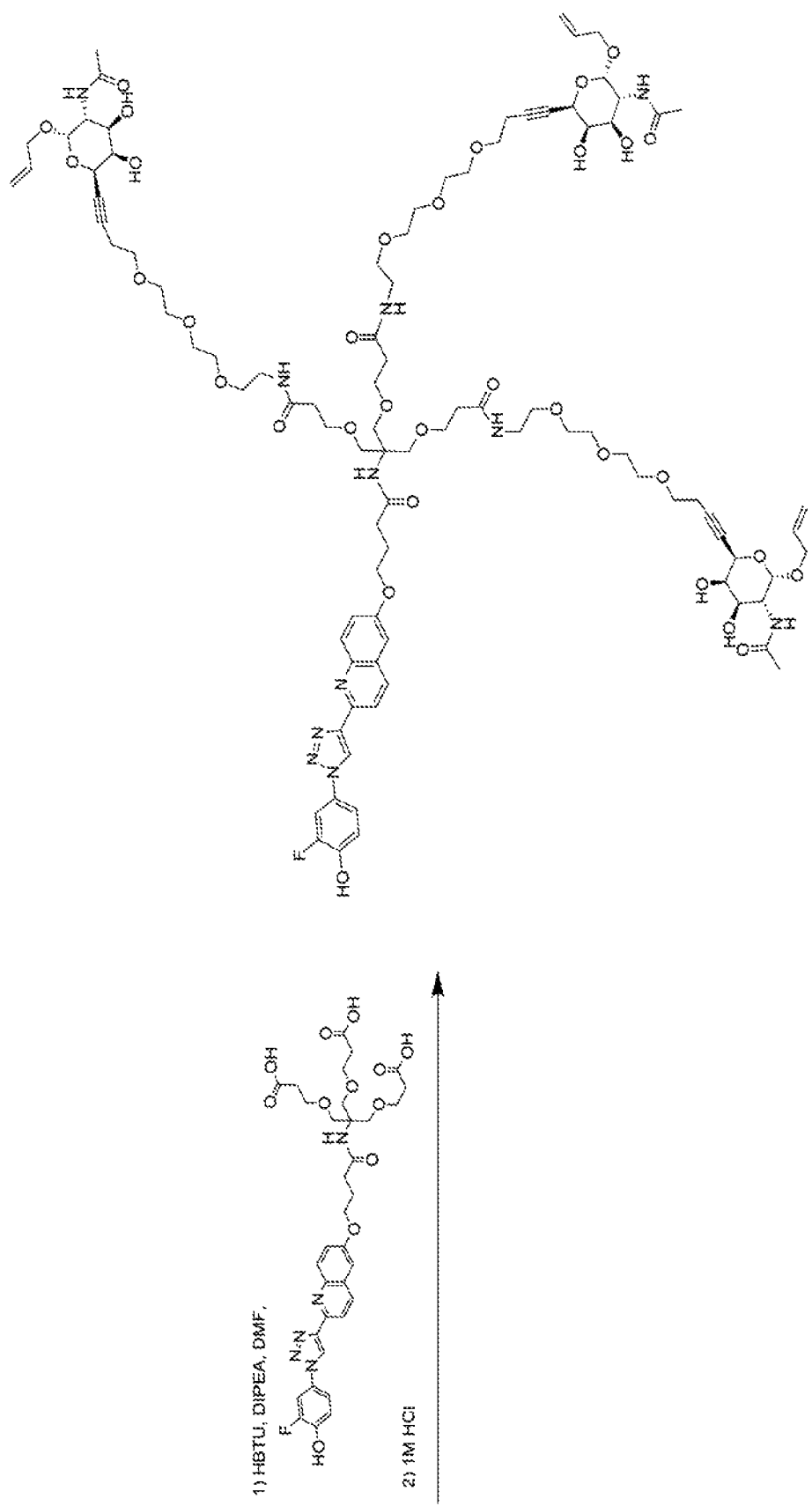
Figure 63:
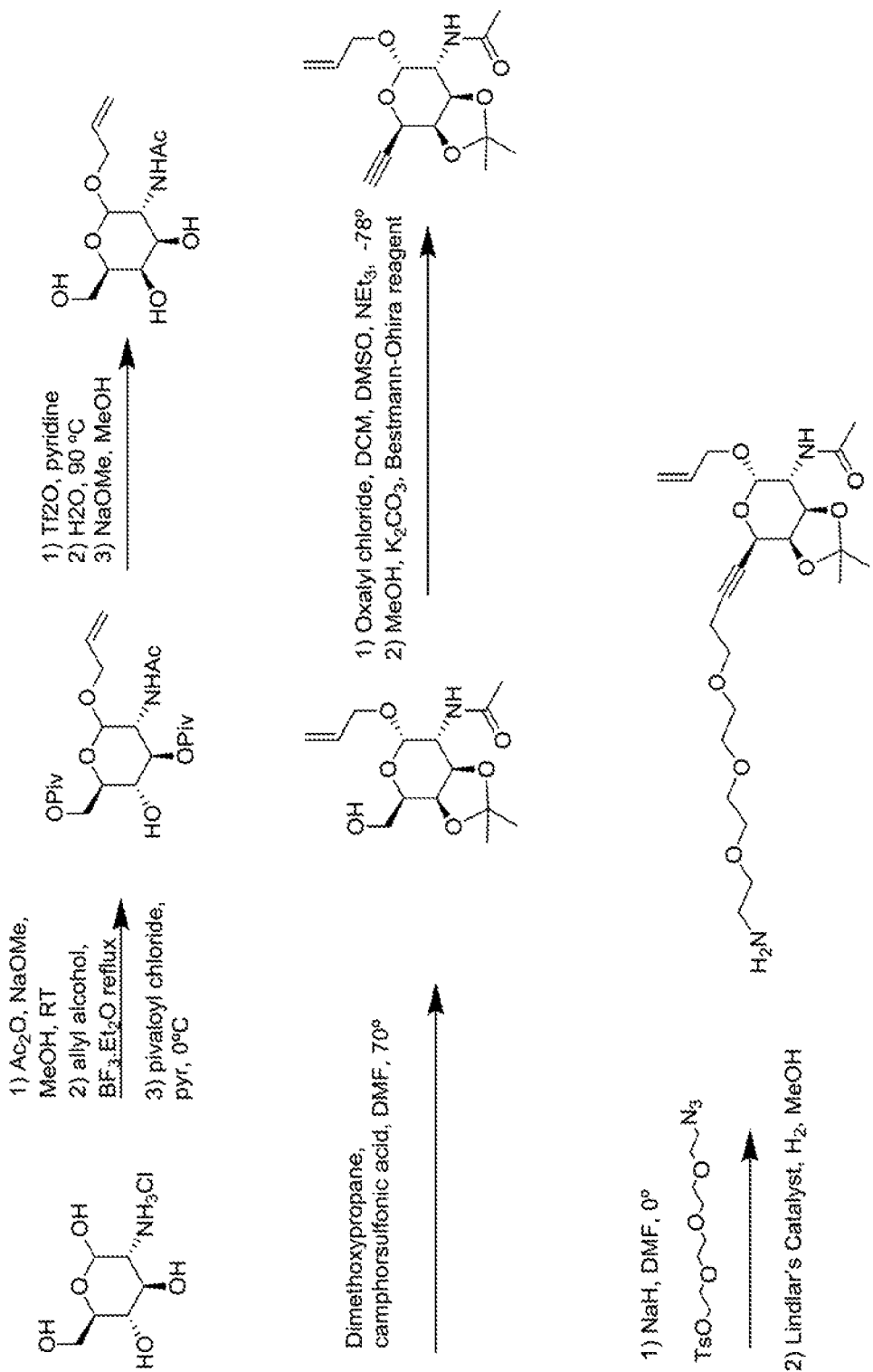
Figure 63:
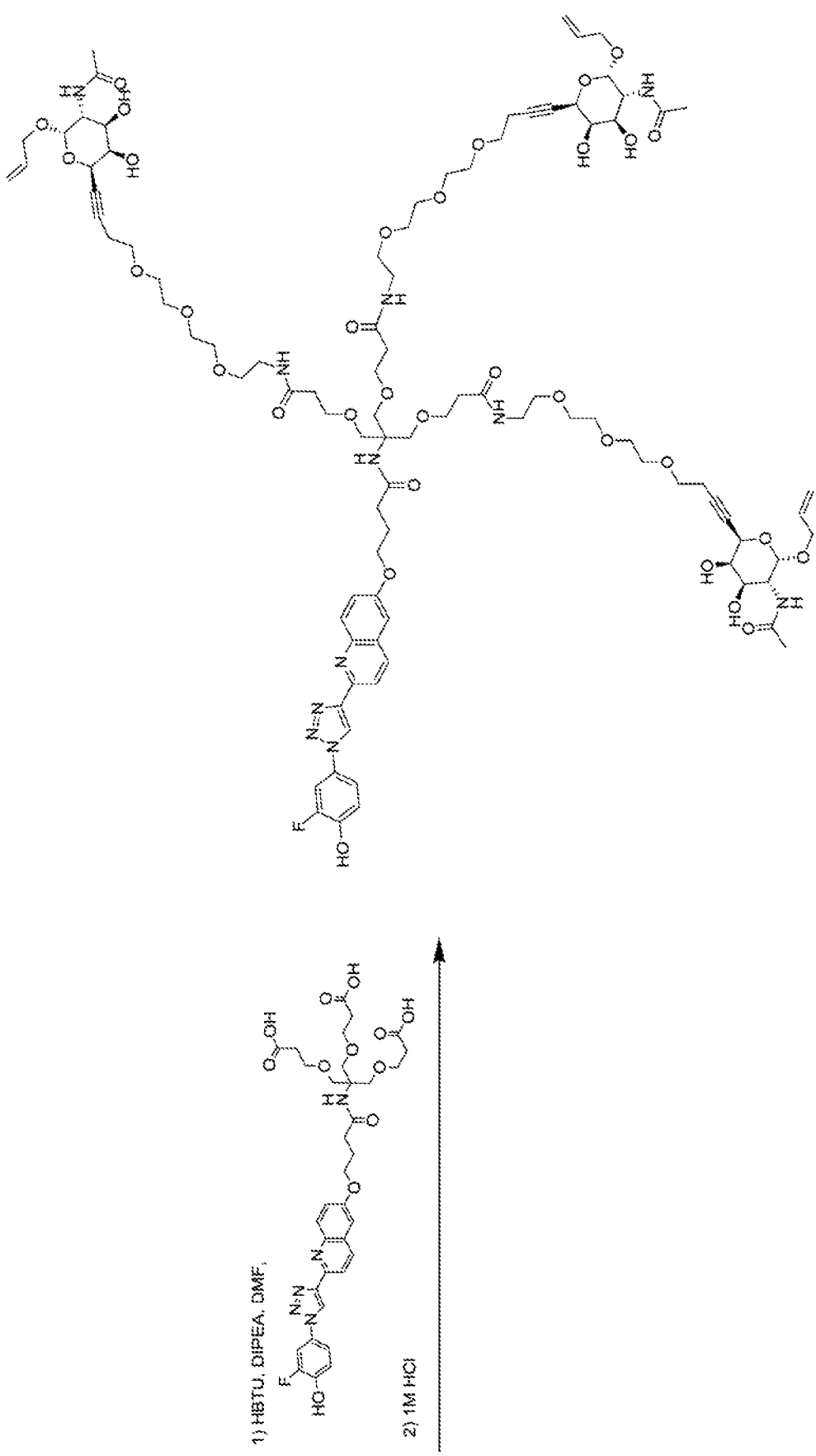
Figure 64:
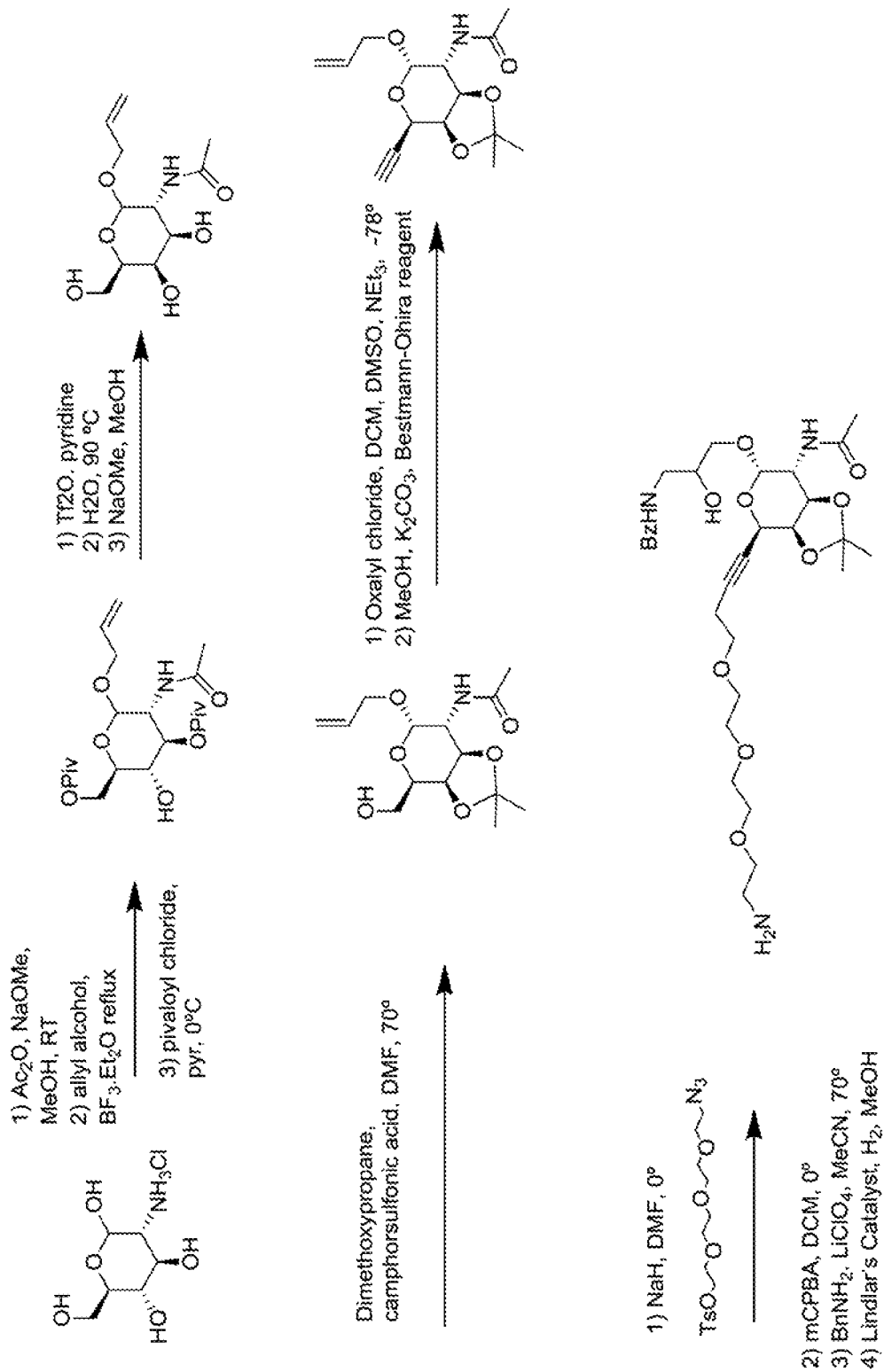
Figure 64:
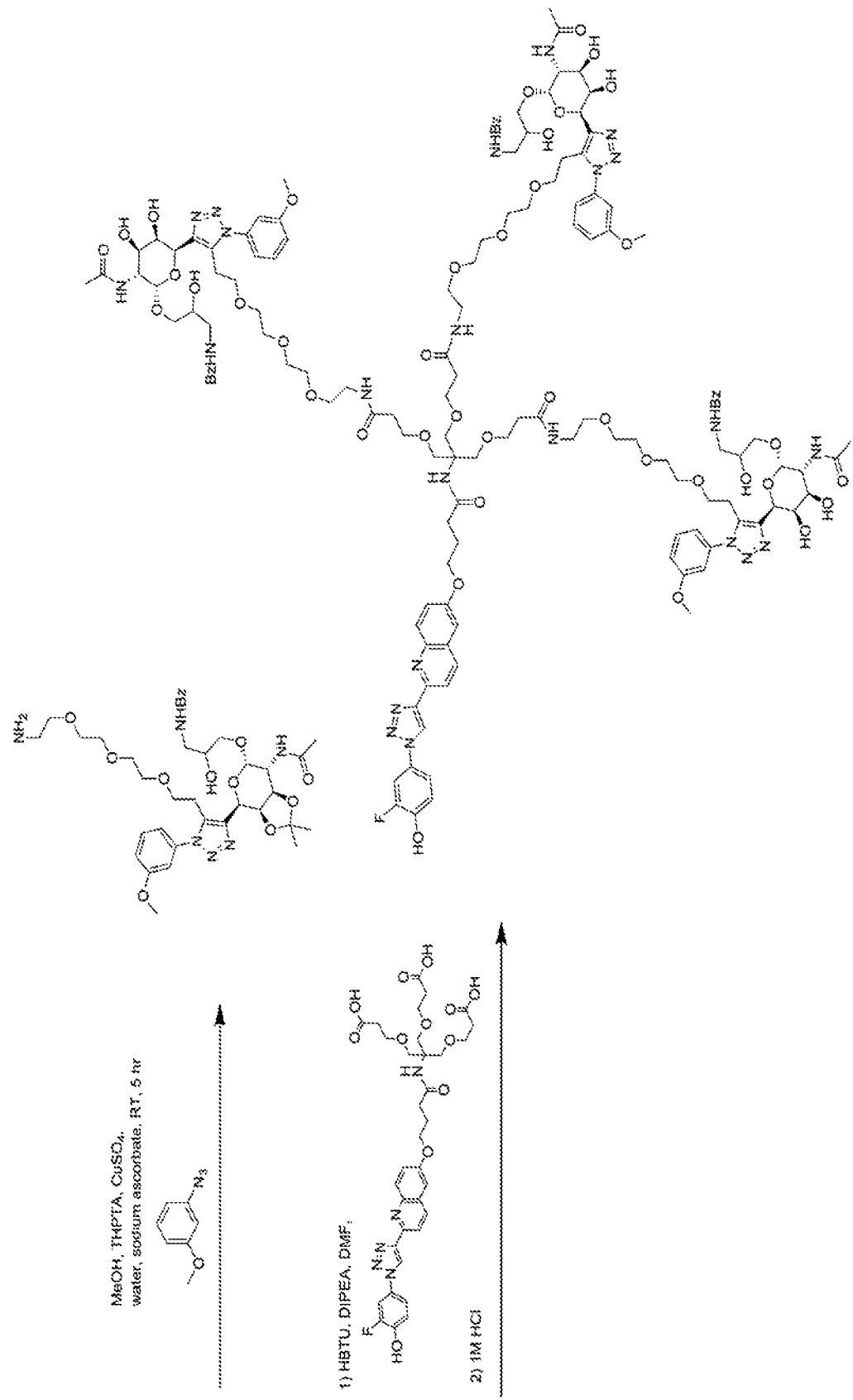
Figure 65:
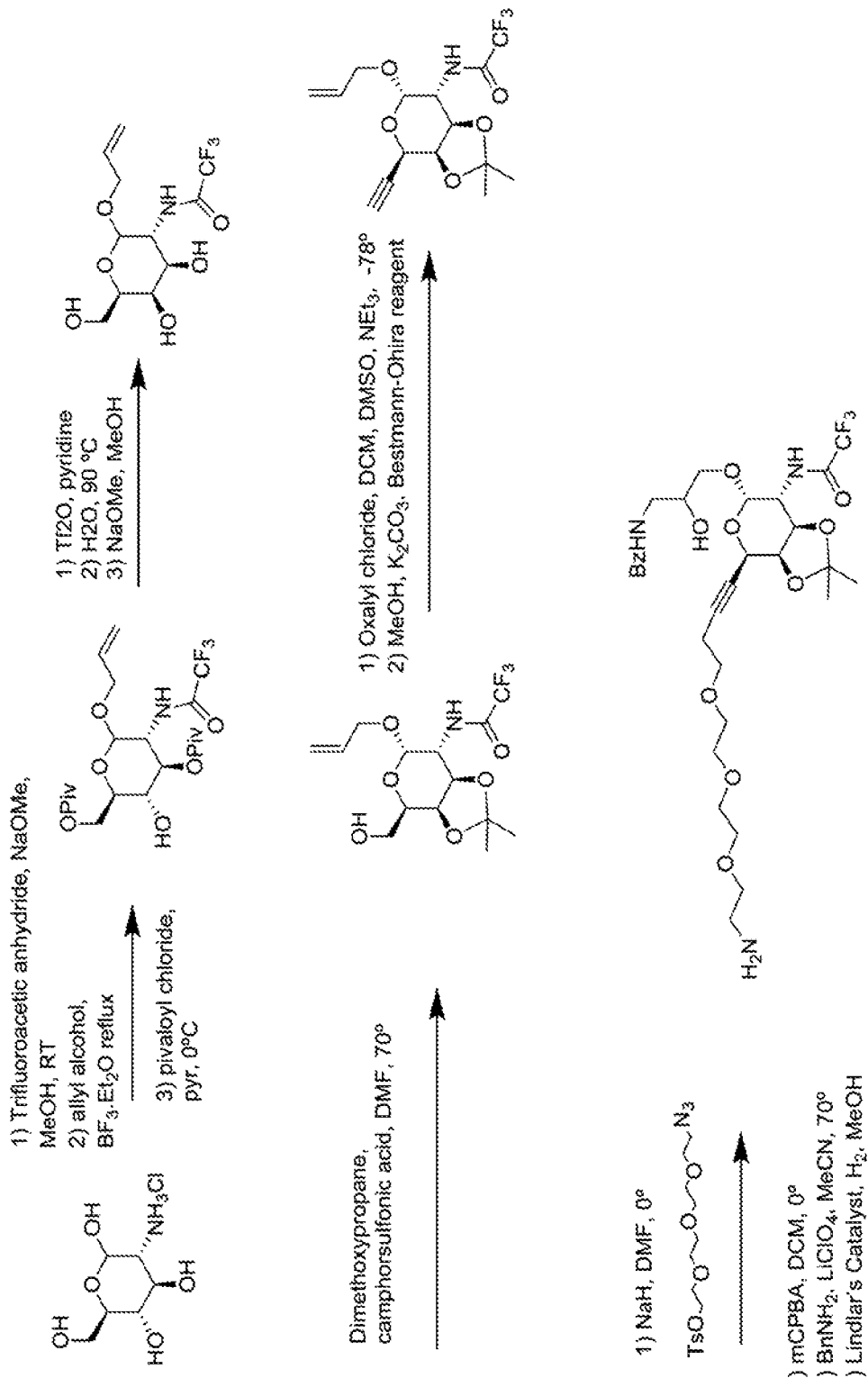
Figure 65:
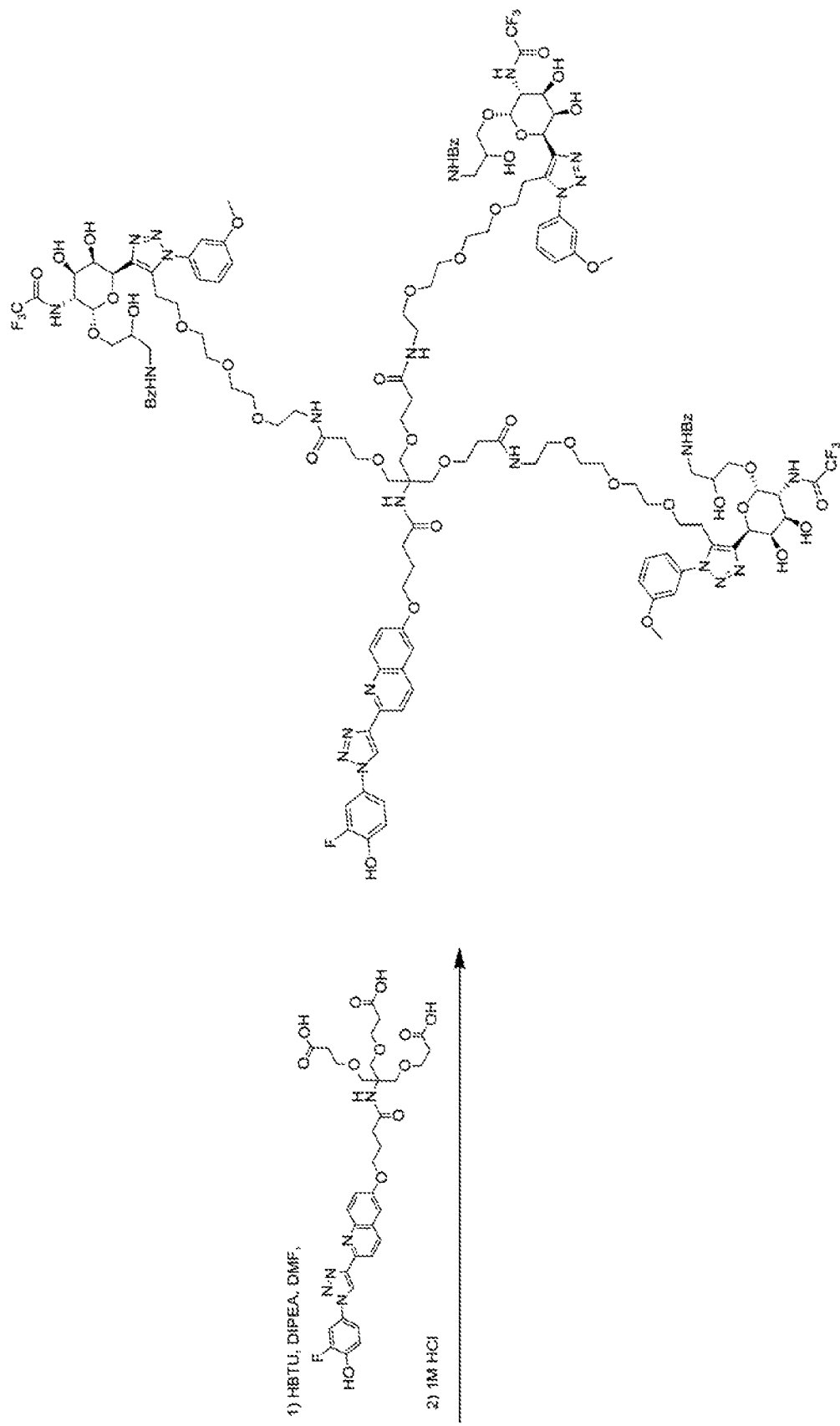
Figure 66:
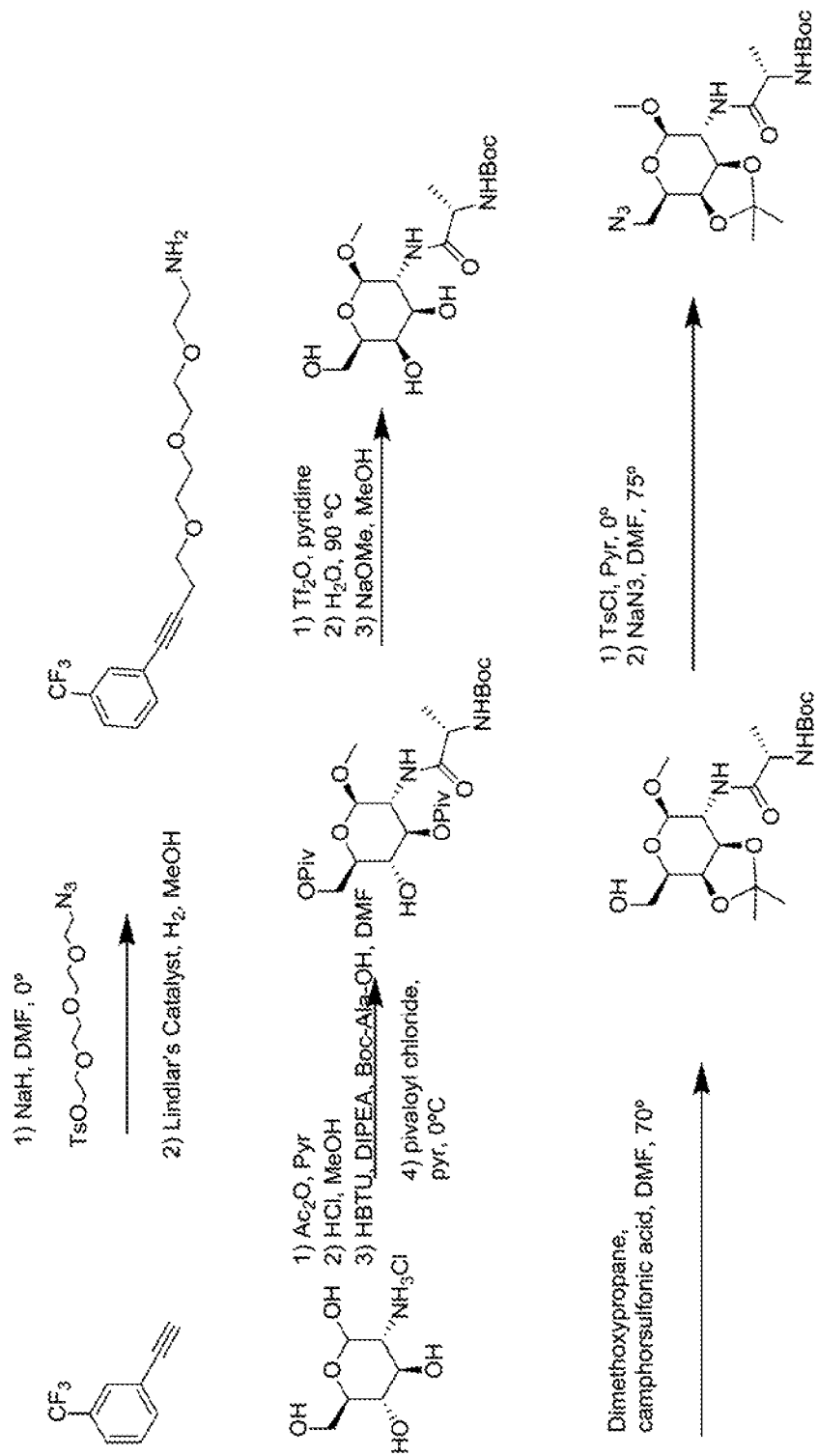
Figure 66:
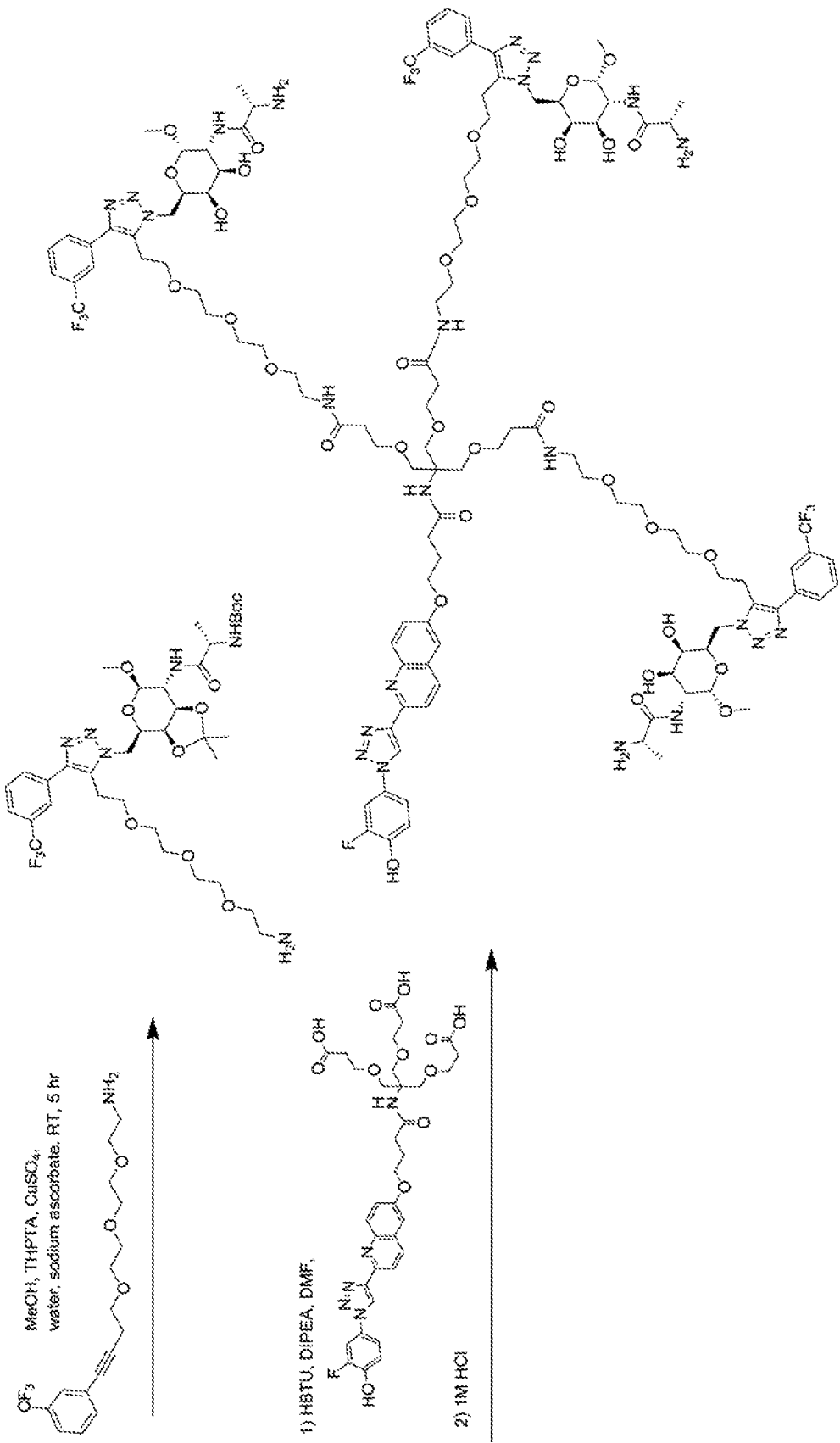
Figure 67:
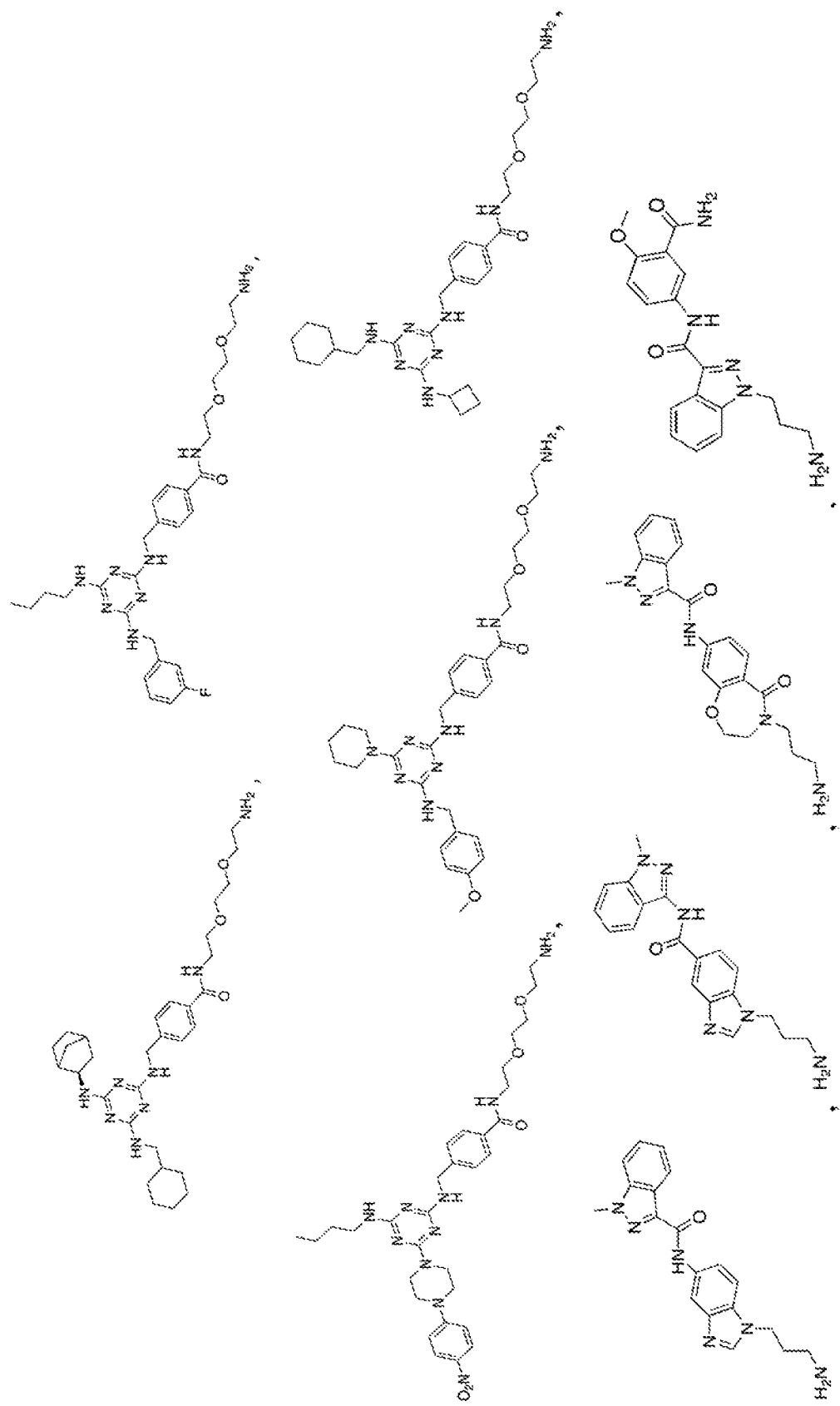
FIG. 67 shows exemplary IgGBM groups each of which is covalently attached to a [CON] group, a [LINKER] group or a [ASGPRBM] group through an amine group, preferably a primary or secondary alkyl amine group which is optionally substituted on the amine group with a $C_1$-$C_3$ alkyl group.
Figure 67:
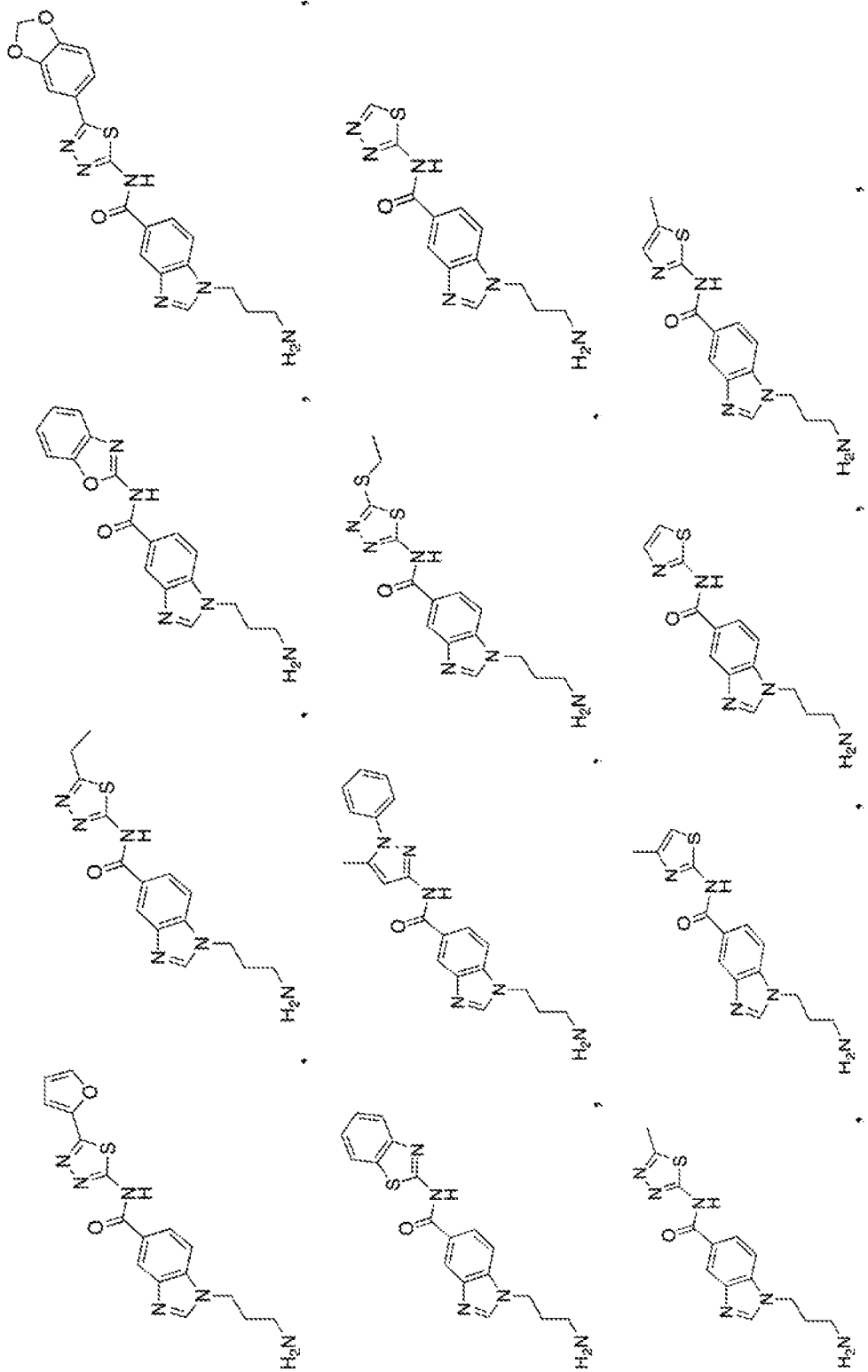
Figure 67:
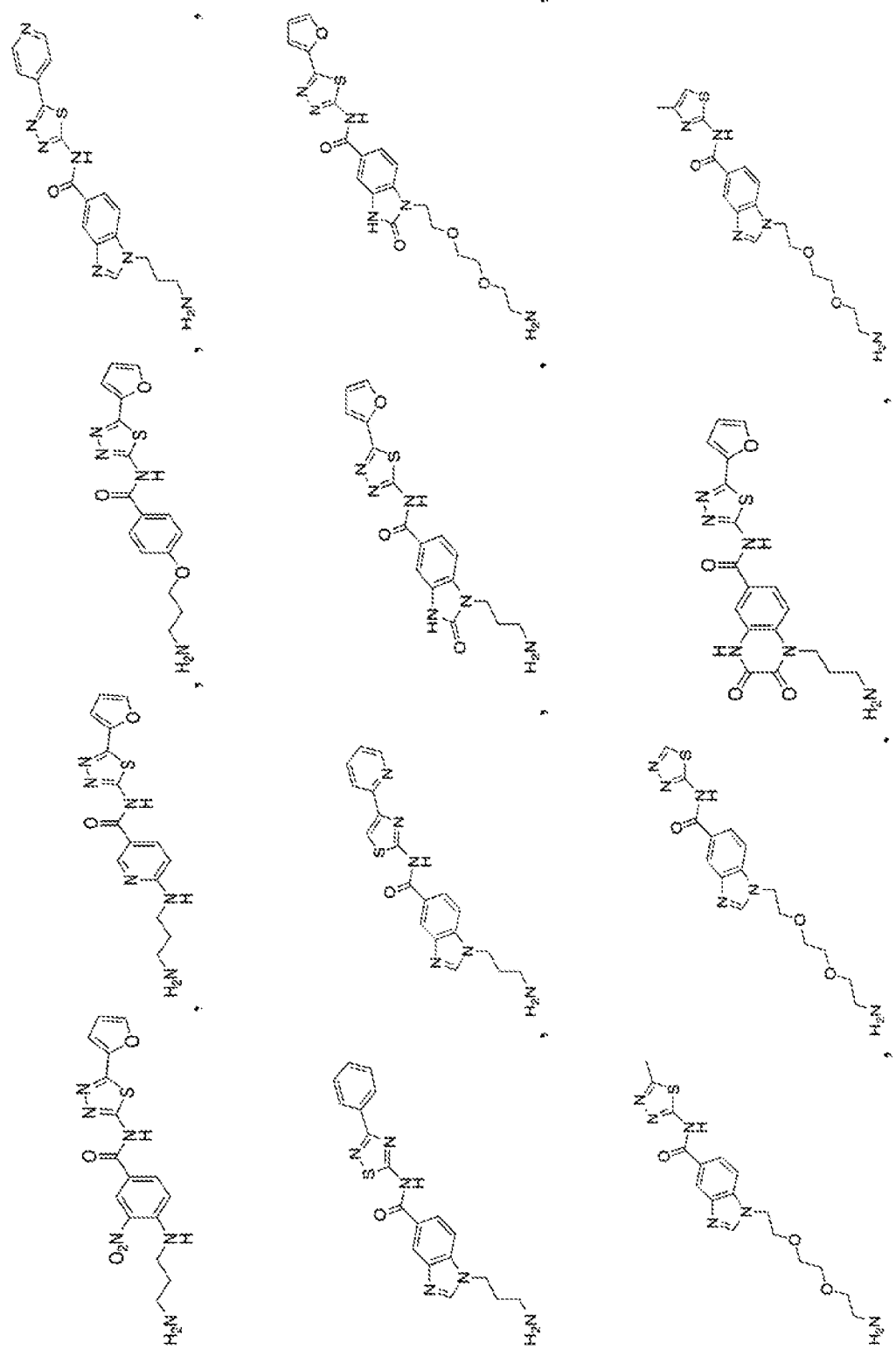
Figure 67:
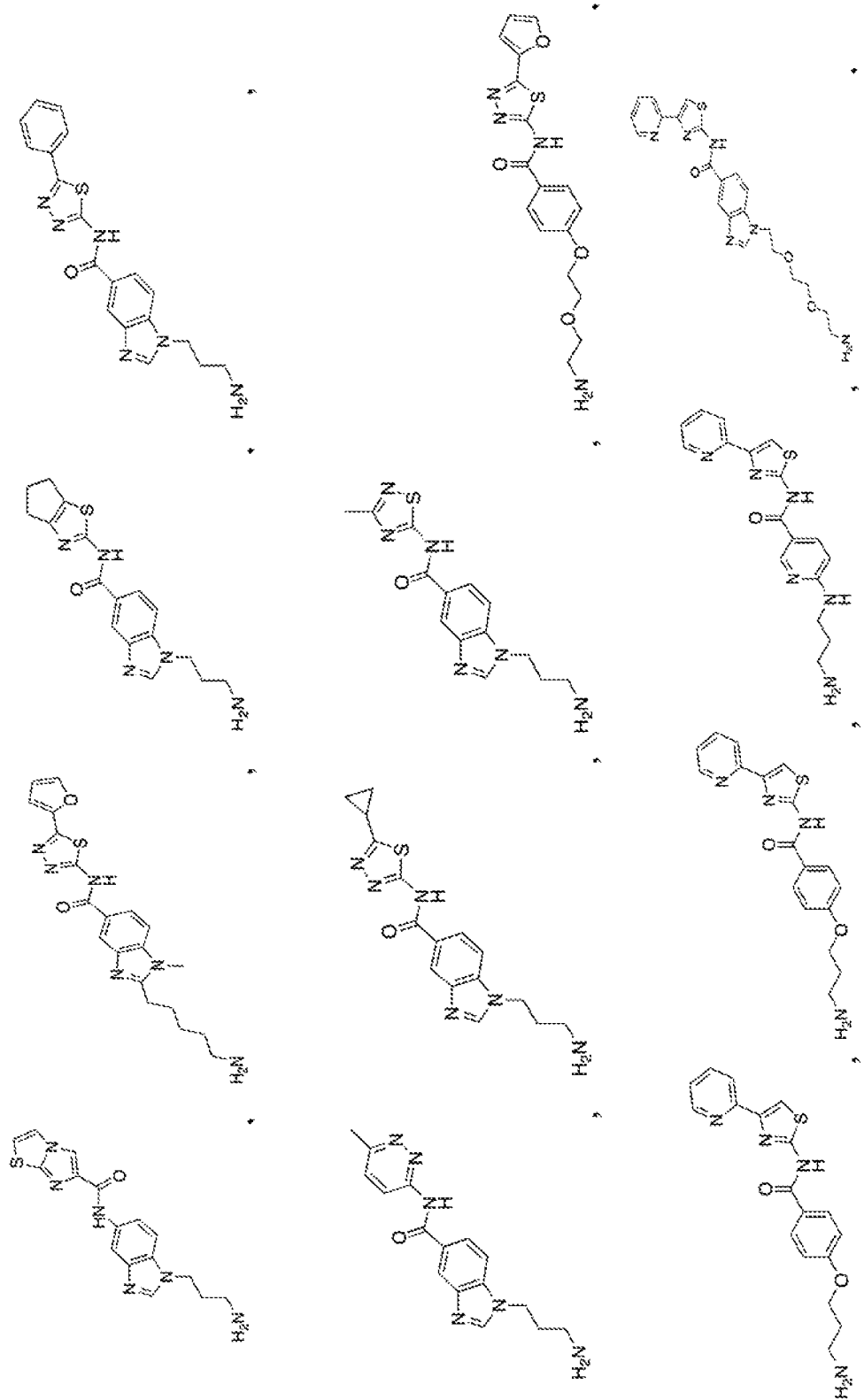
Figure 67:
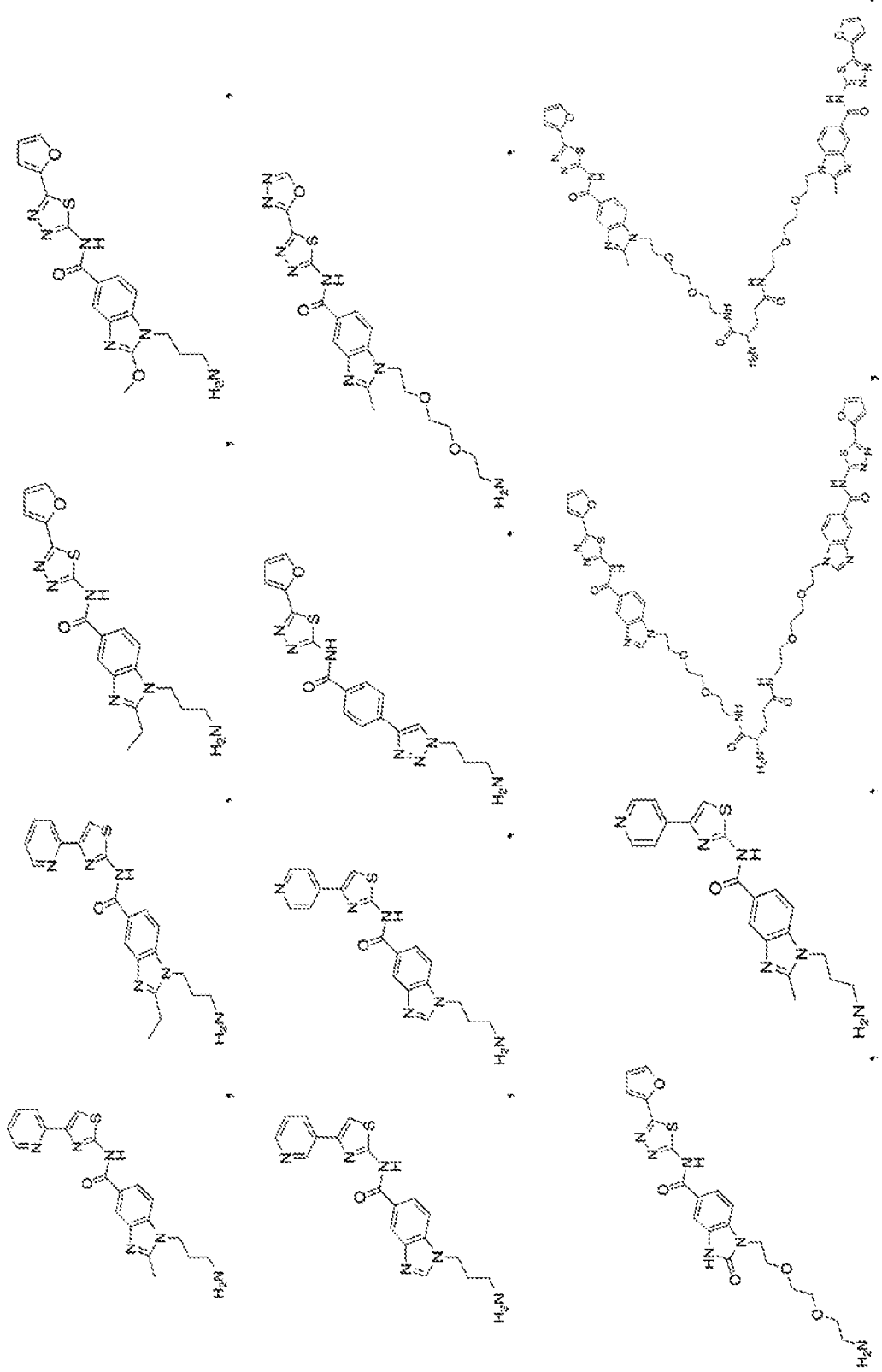
Figure 67:
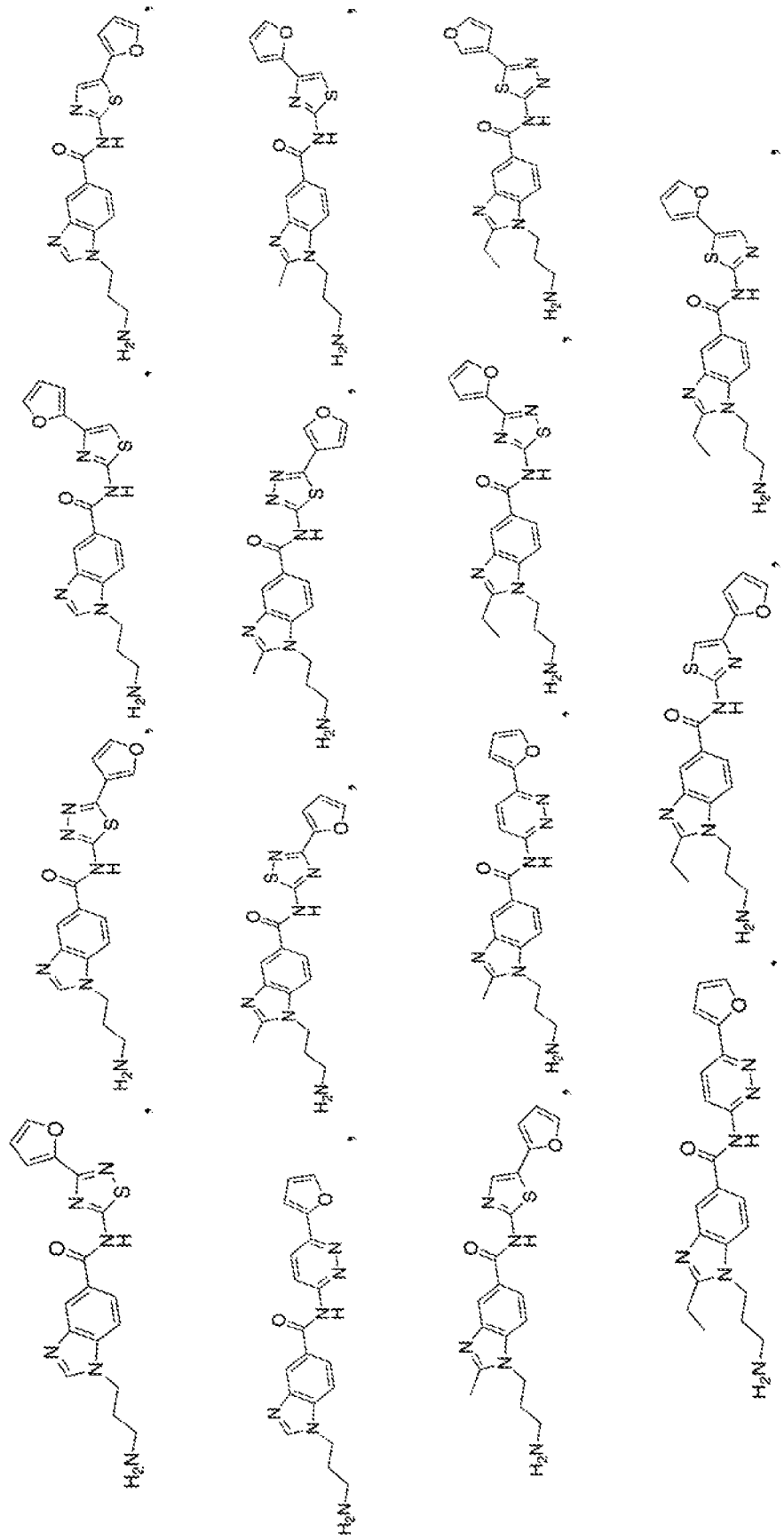
Figure 67:
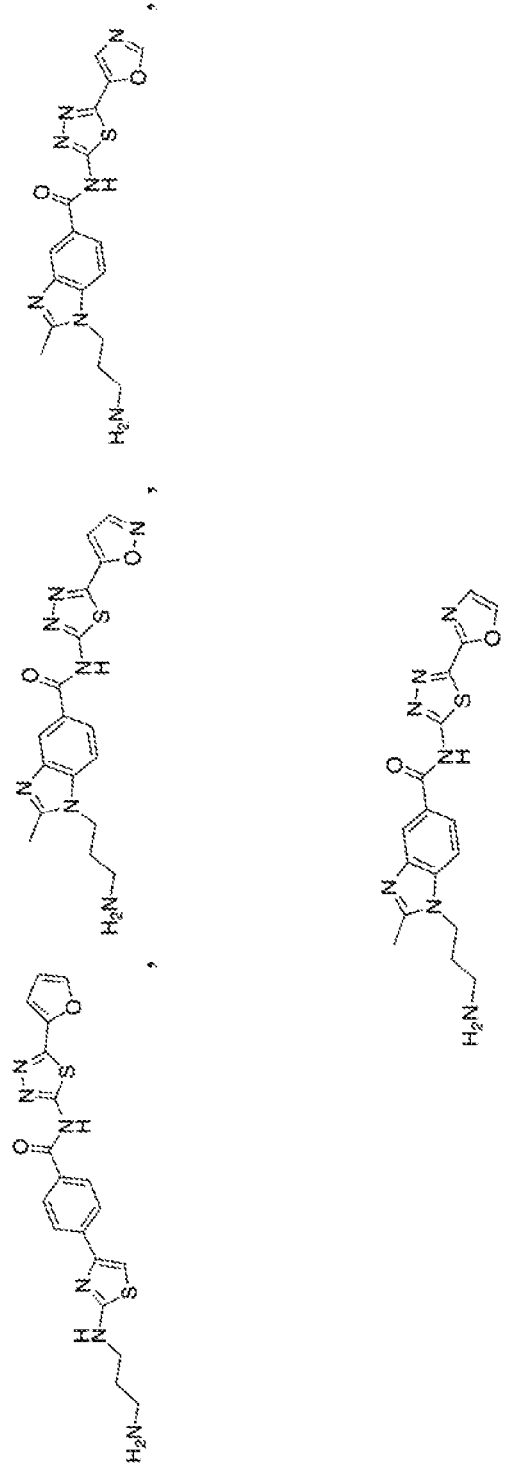
Figure 68:
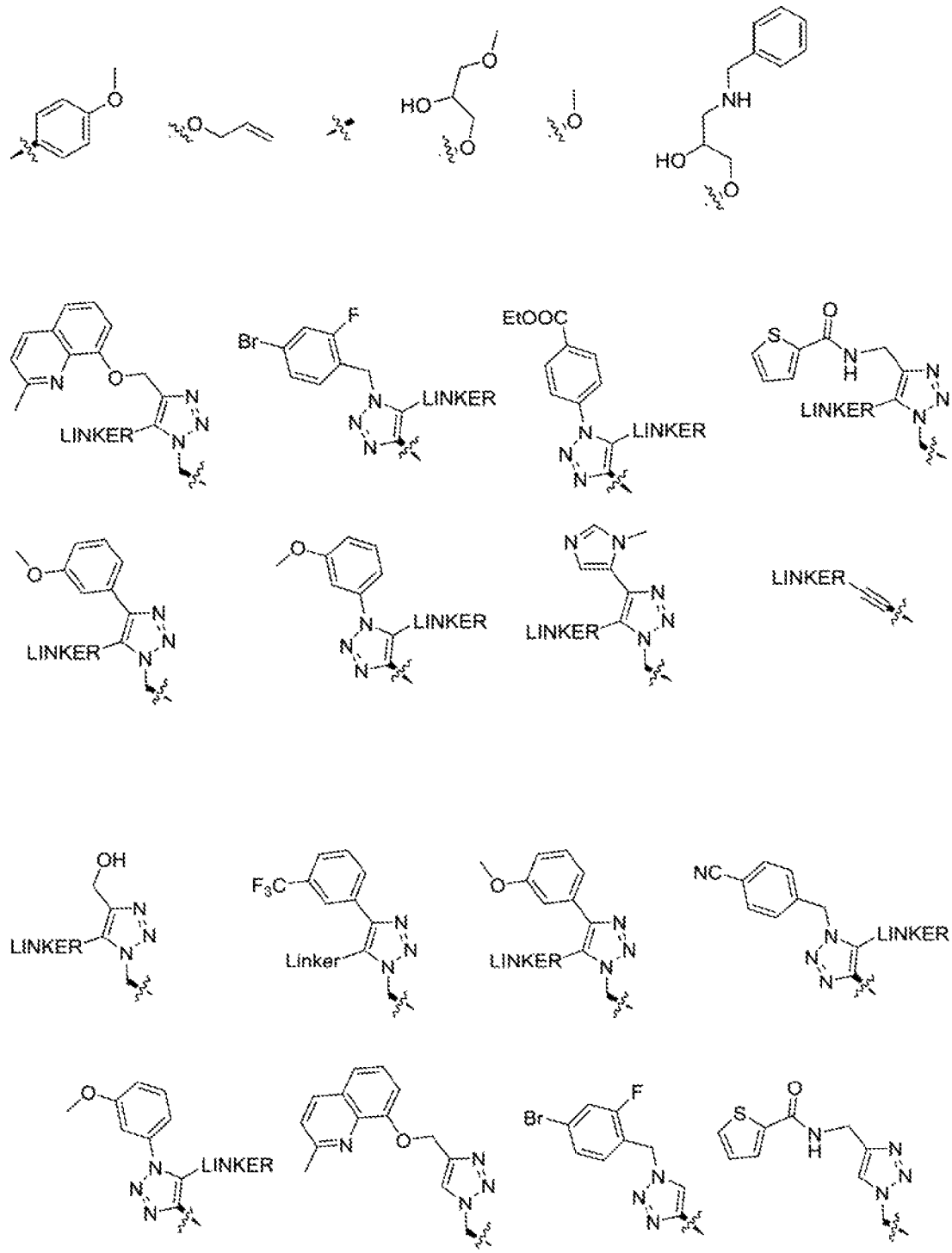
FIG. 68 shows exemplary $R_1$ and $R_3$ substituents on ASGPRBM groups as otherwise described herein.
Figure 68:
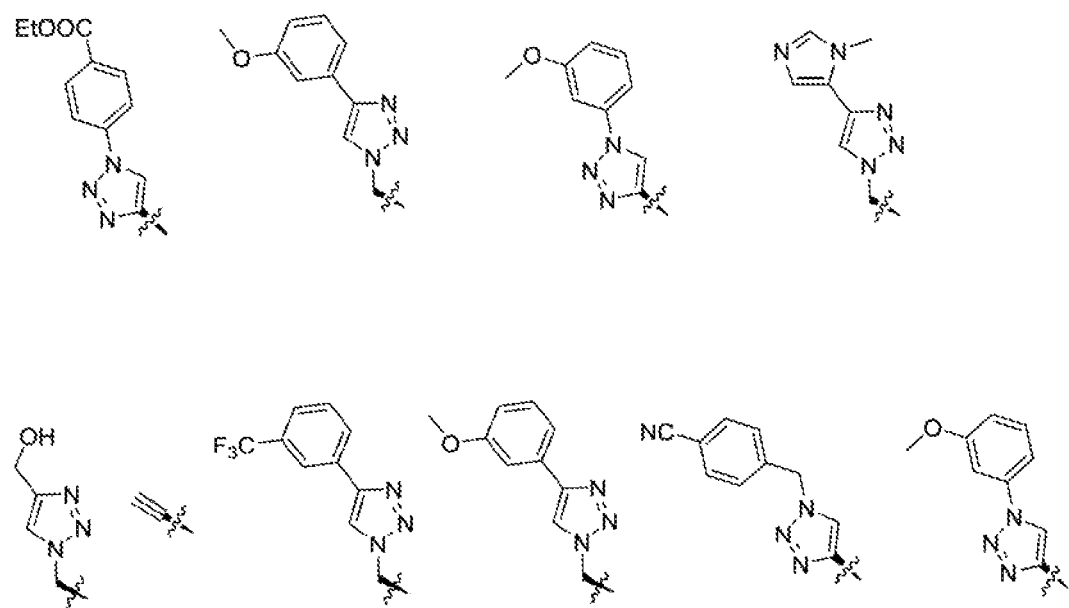
Figure 69:
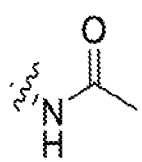
FIG. 69 shows exemplary $R_2$ substituents on ASGPRBM groups as otherwise described herein.
Figure 69:
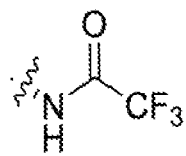
Figure 69:
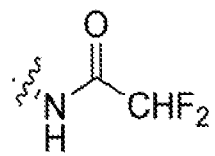
Figure 69:
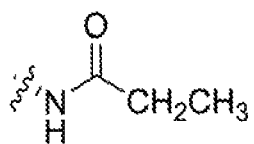
Figure 69:
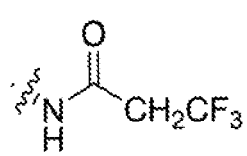
Figure 69:
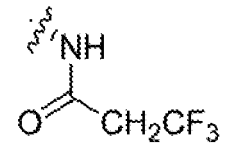
Figure 69:
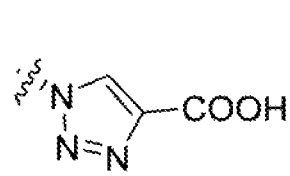
Figure 69:
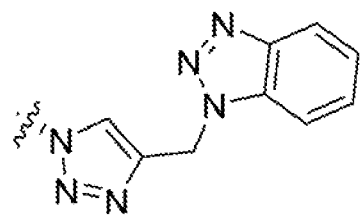
Figure 69:
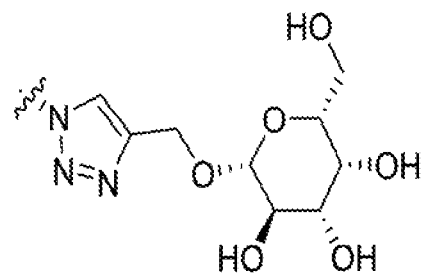
Figure 69:
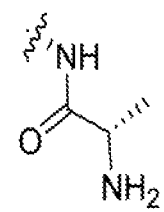
Figure 70:
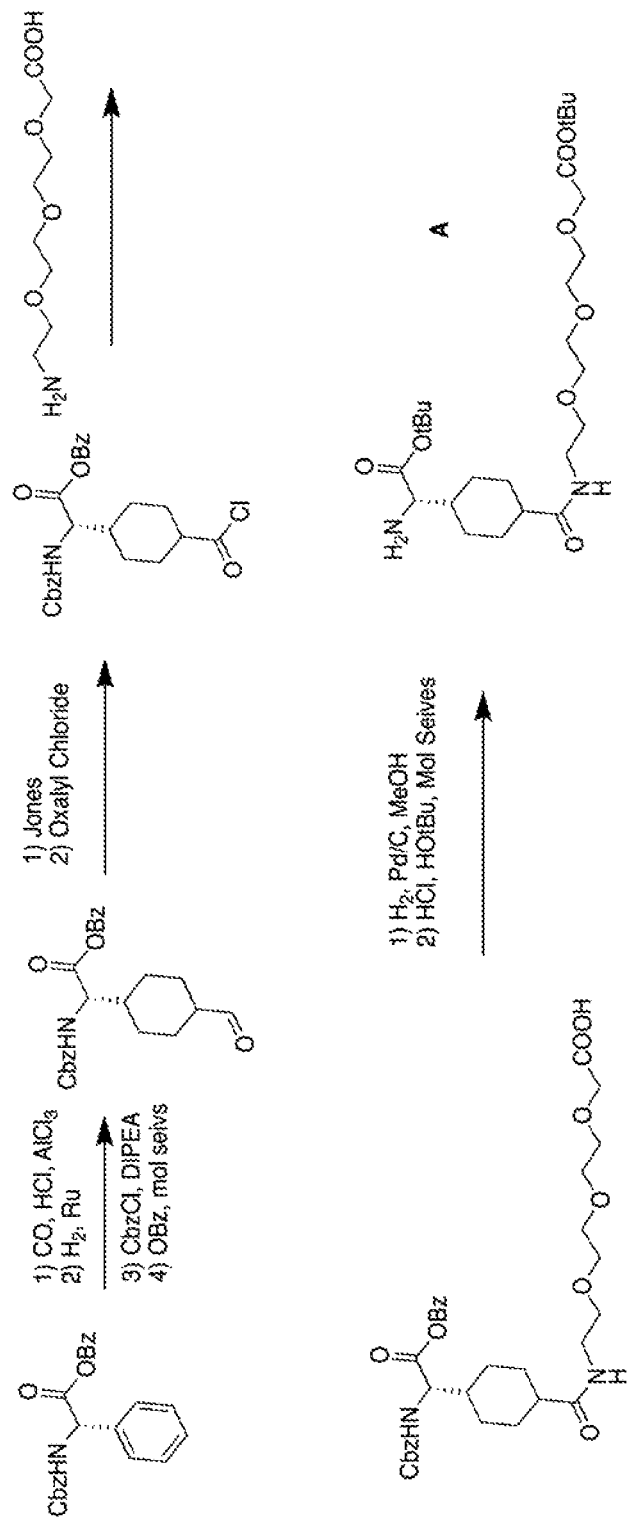
FIG. 70 shows the synthesis of CD40L-binding bifunctional molecule BIO8898-GN3.
Figure 70:
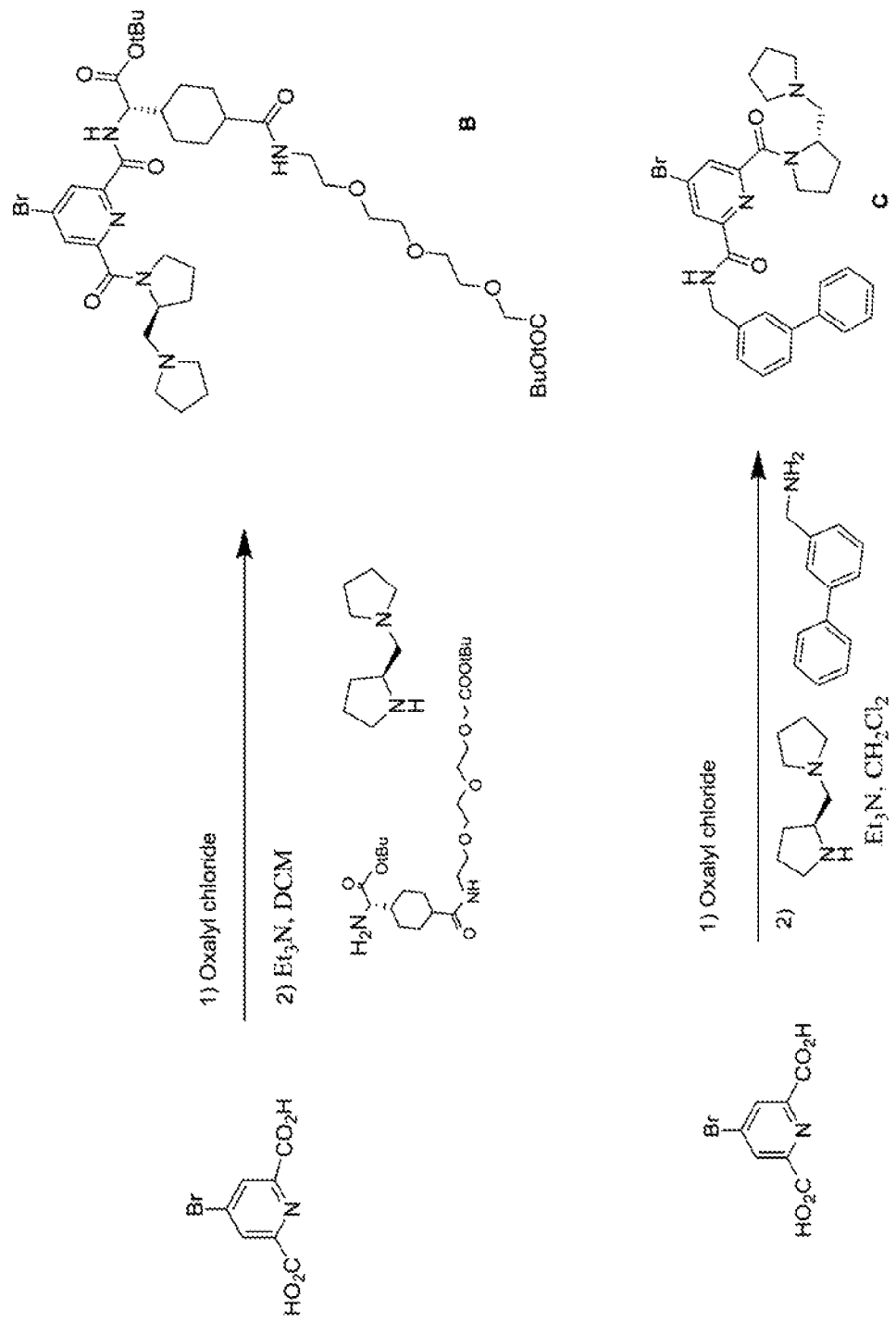
Figure 70:
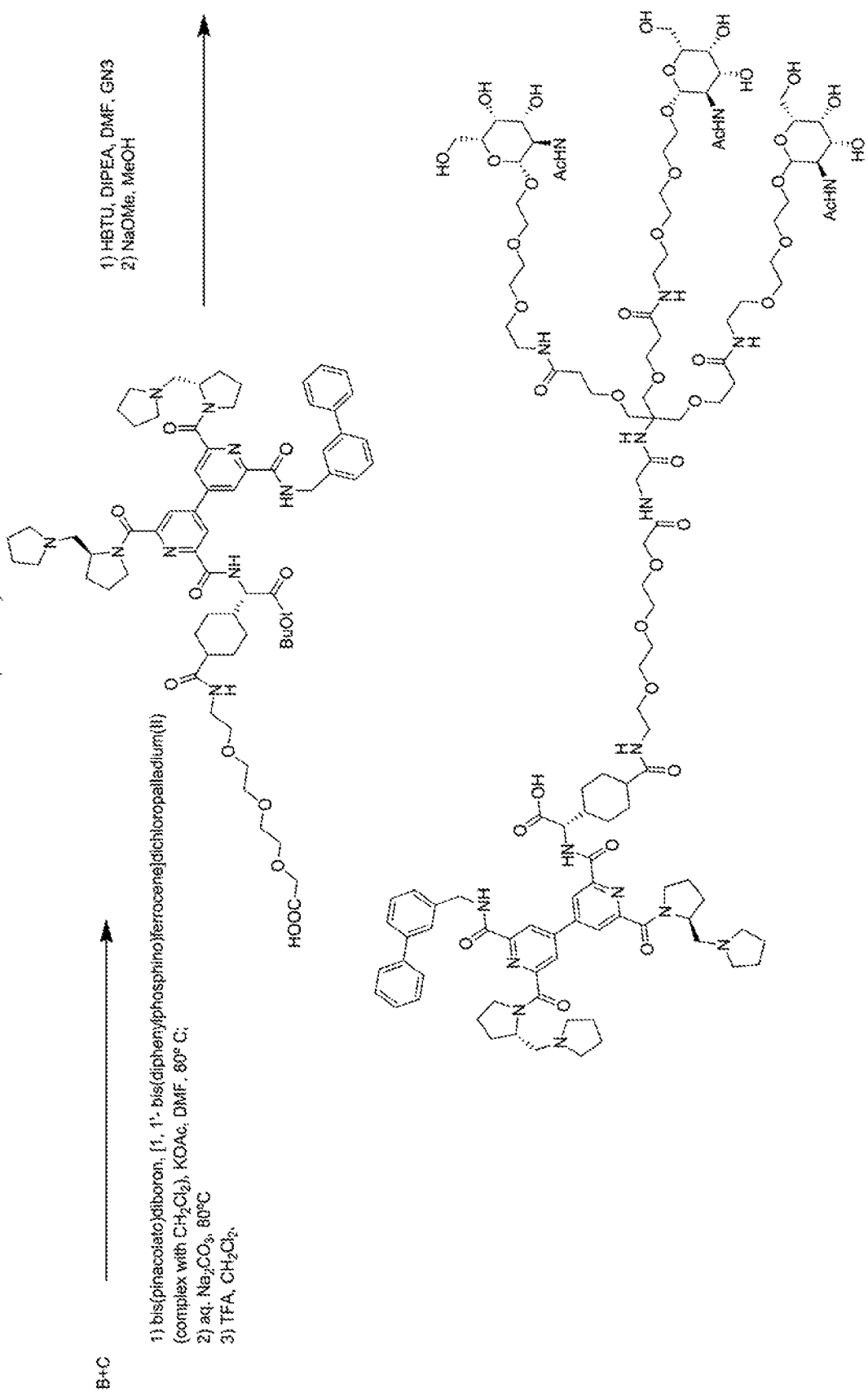
Figure 71:
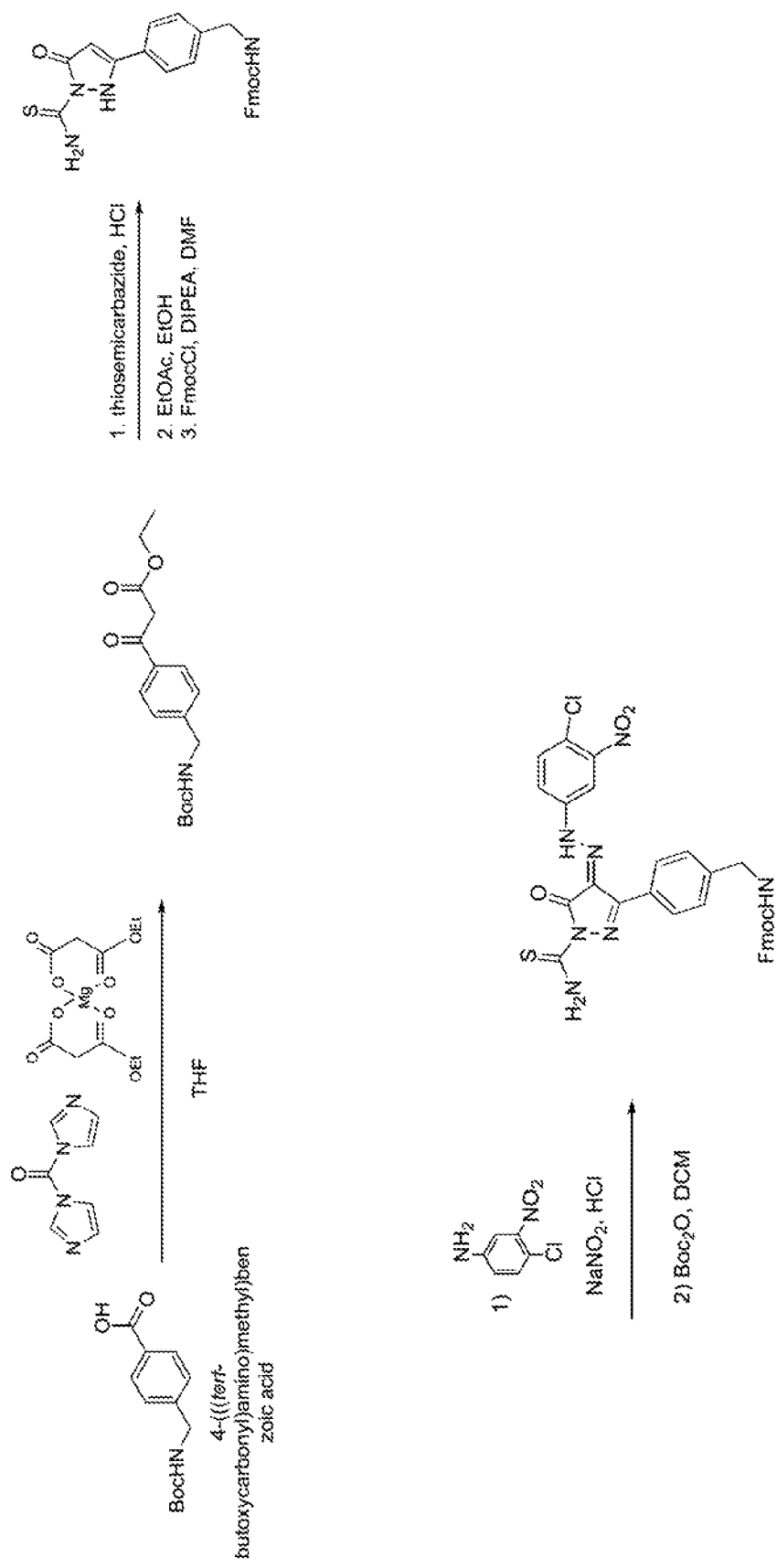
FIG. 71 shows the synthesis of TNF-alpha binding bifunctional molecule c87-GN3.
Figure 71:
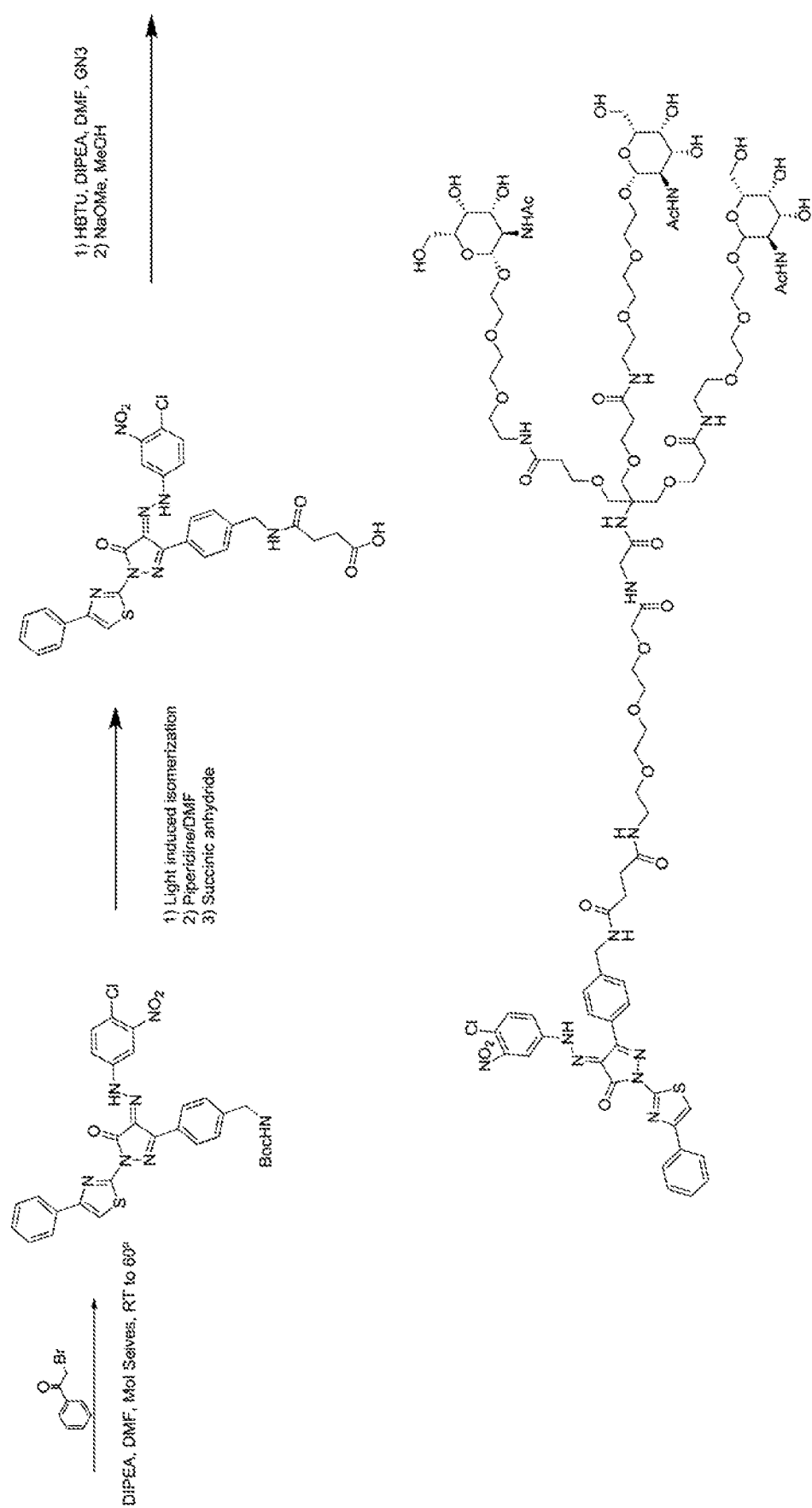
Figure 72:
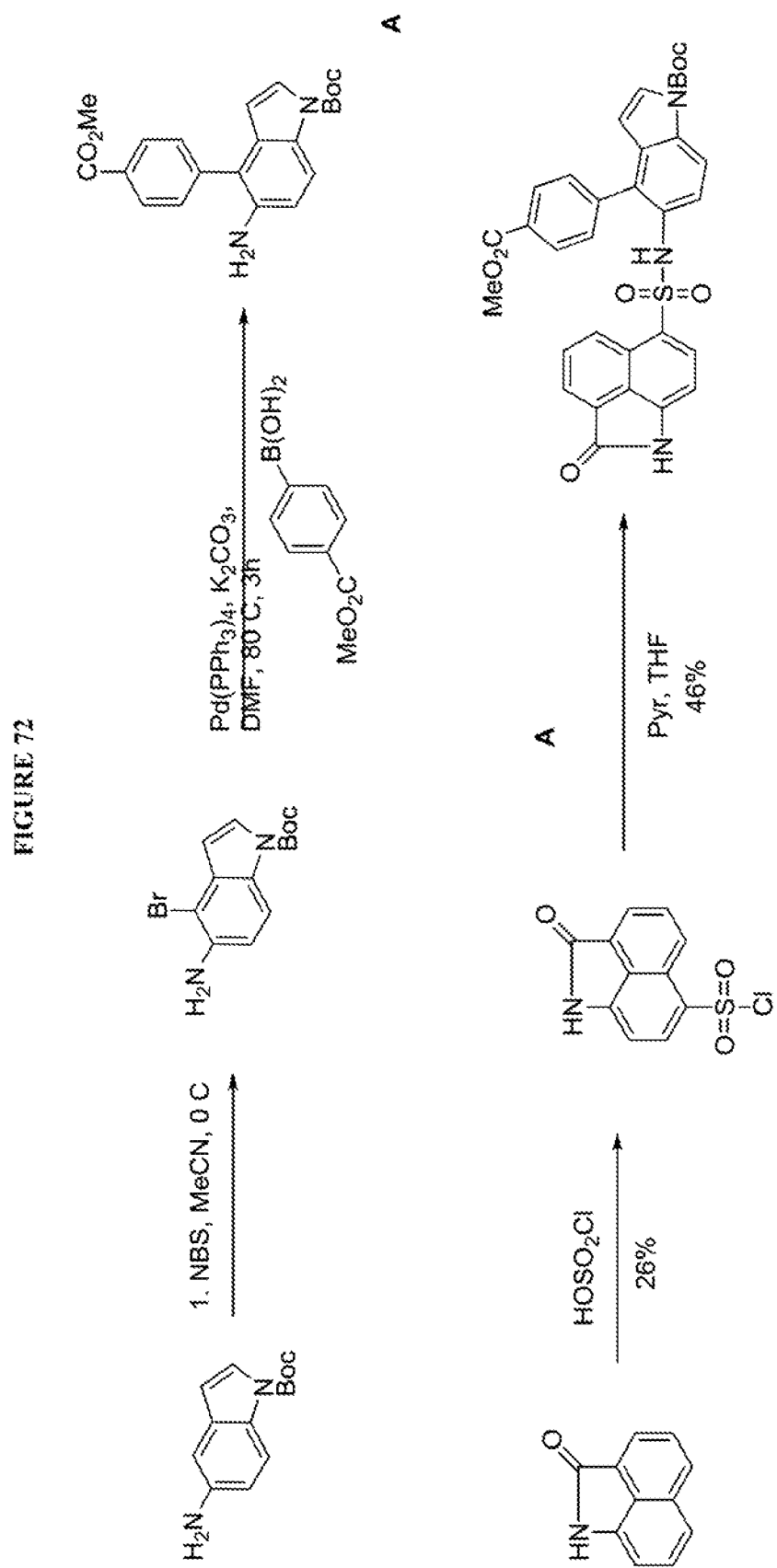
FIG. 72 shows the synthesis of TNF-alpha binding bifunctional molecule 4e-GN3.
Figure 72:
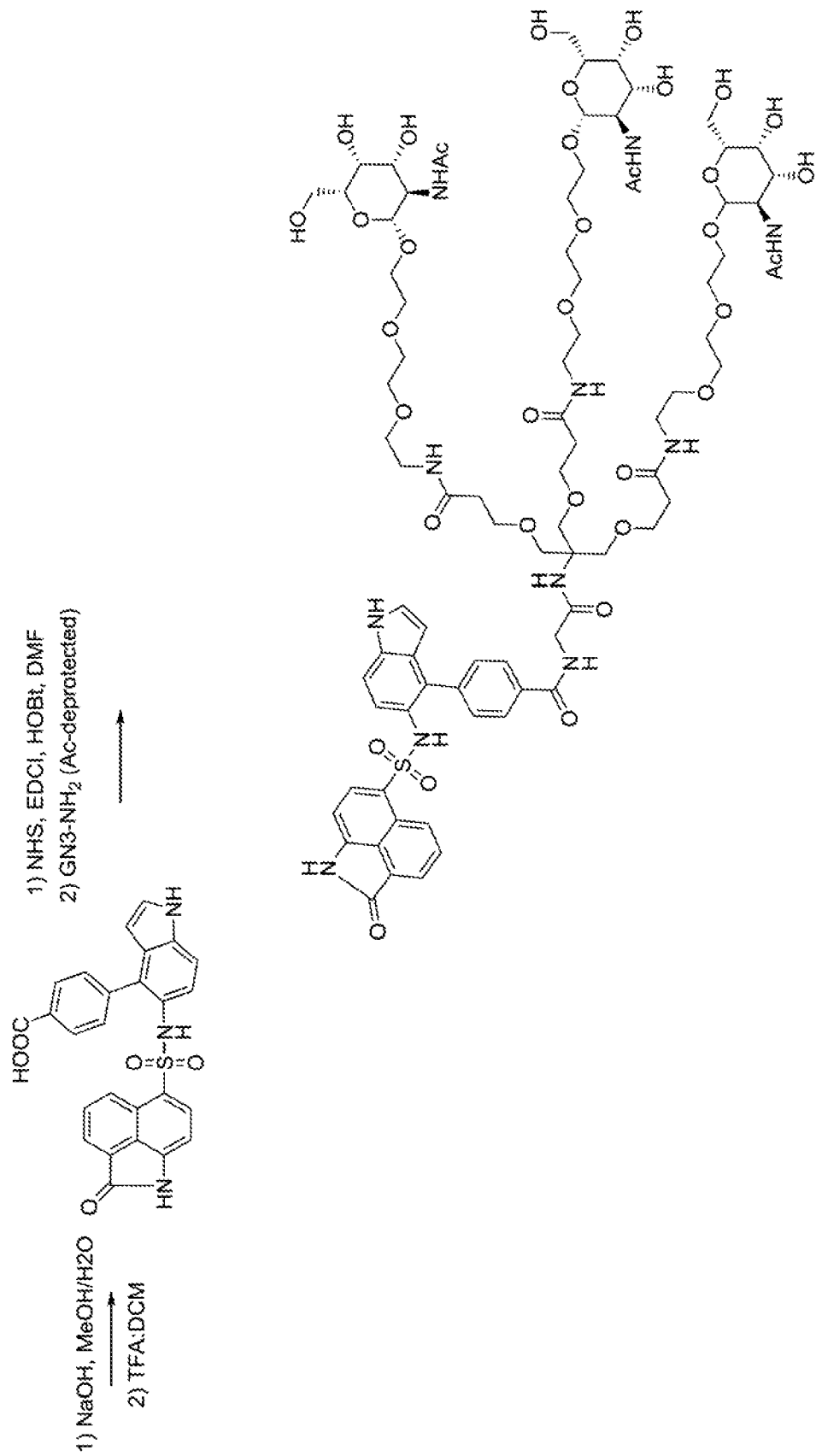
Figure 73:
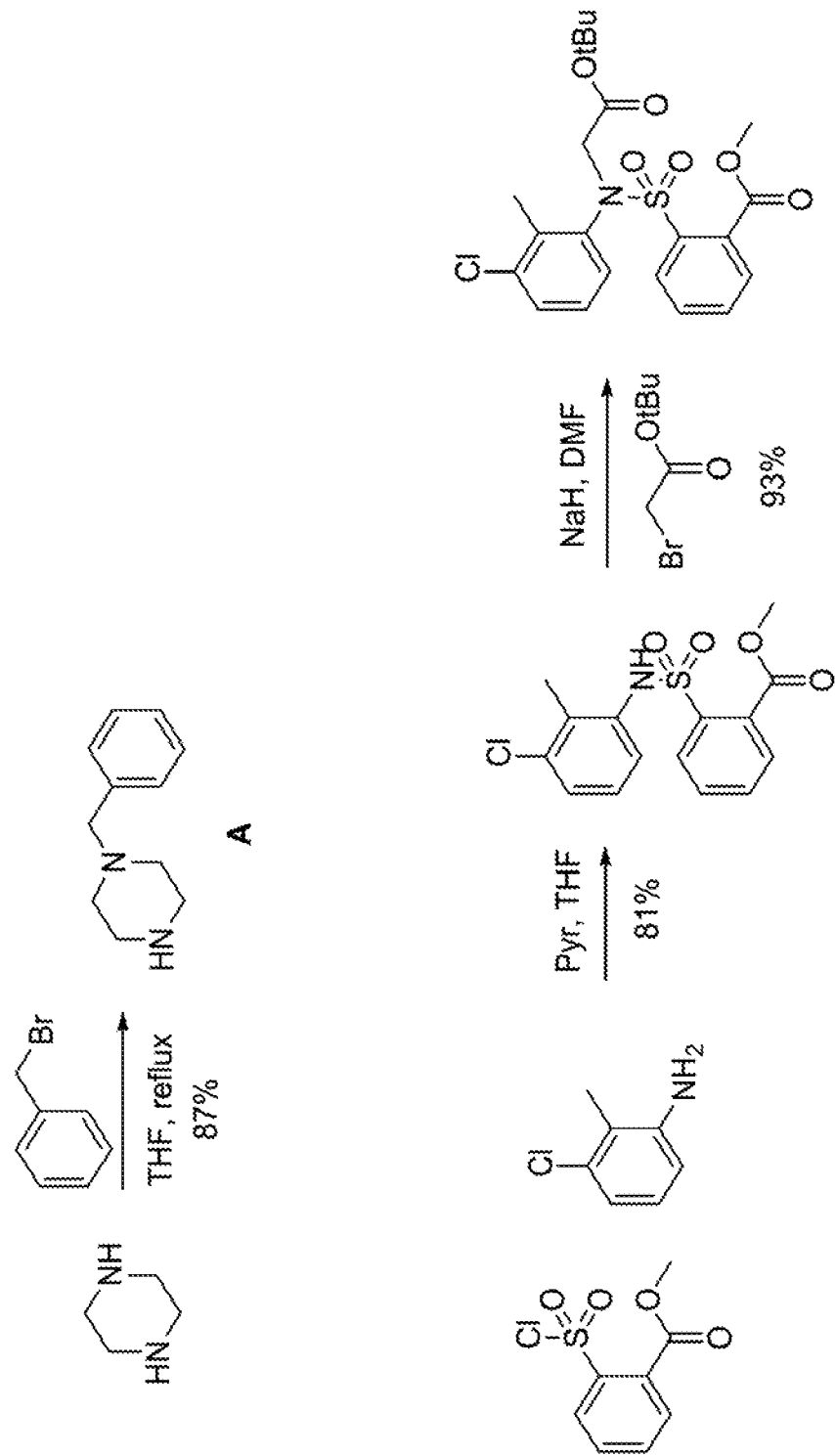
FIG. 73 shows the synthesis of TNF-alpha binding bifunctional molecule Cpd1-GN3.
Figure 73:
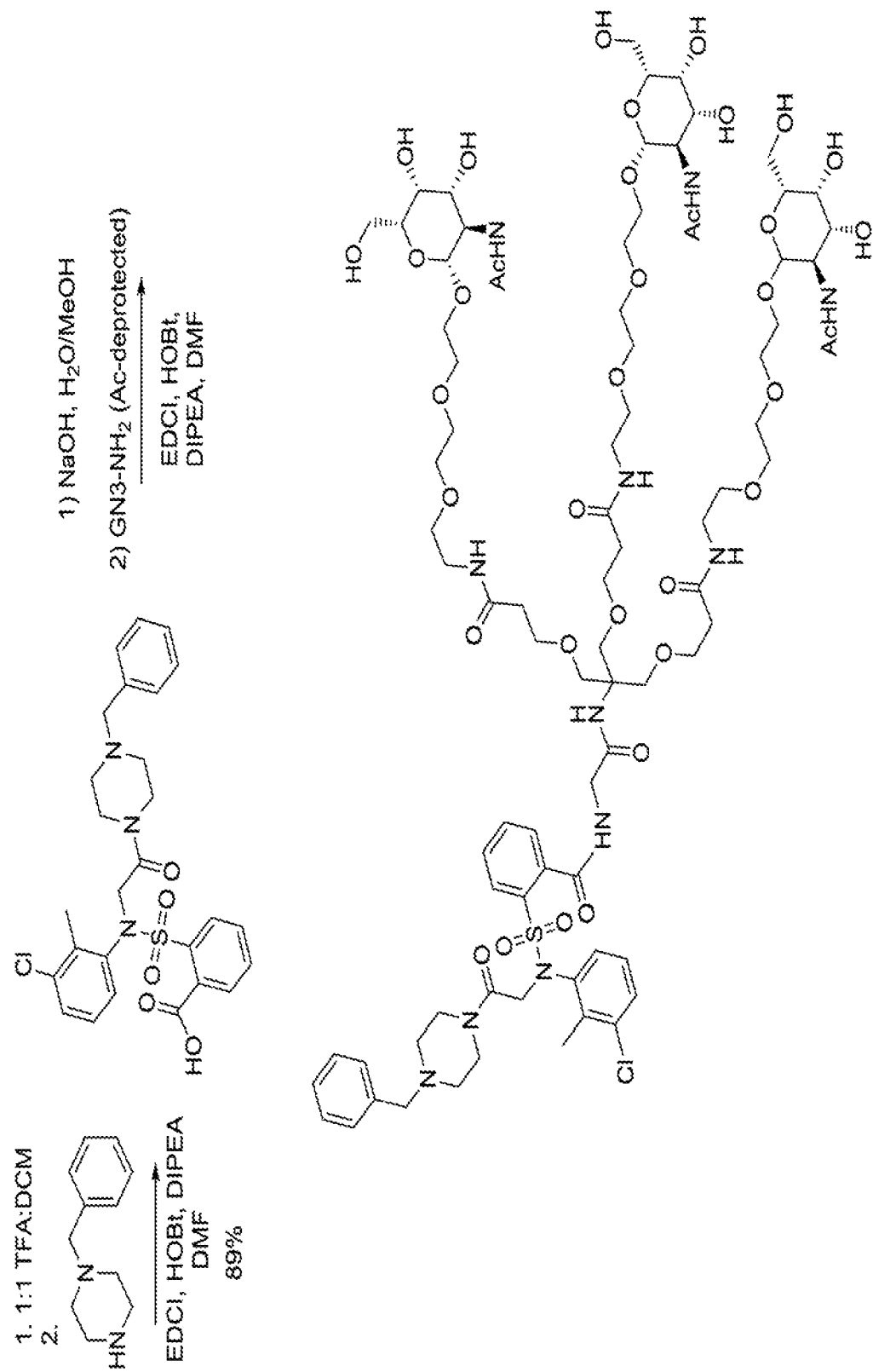
Figure 74:
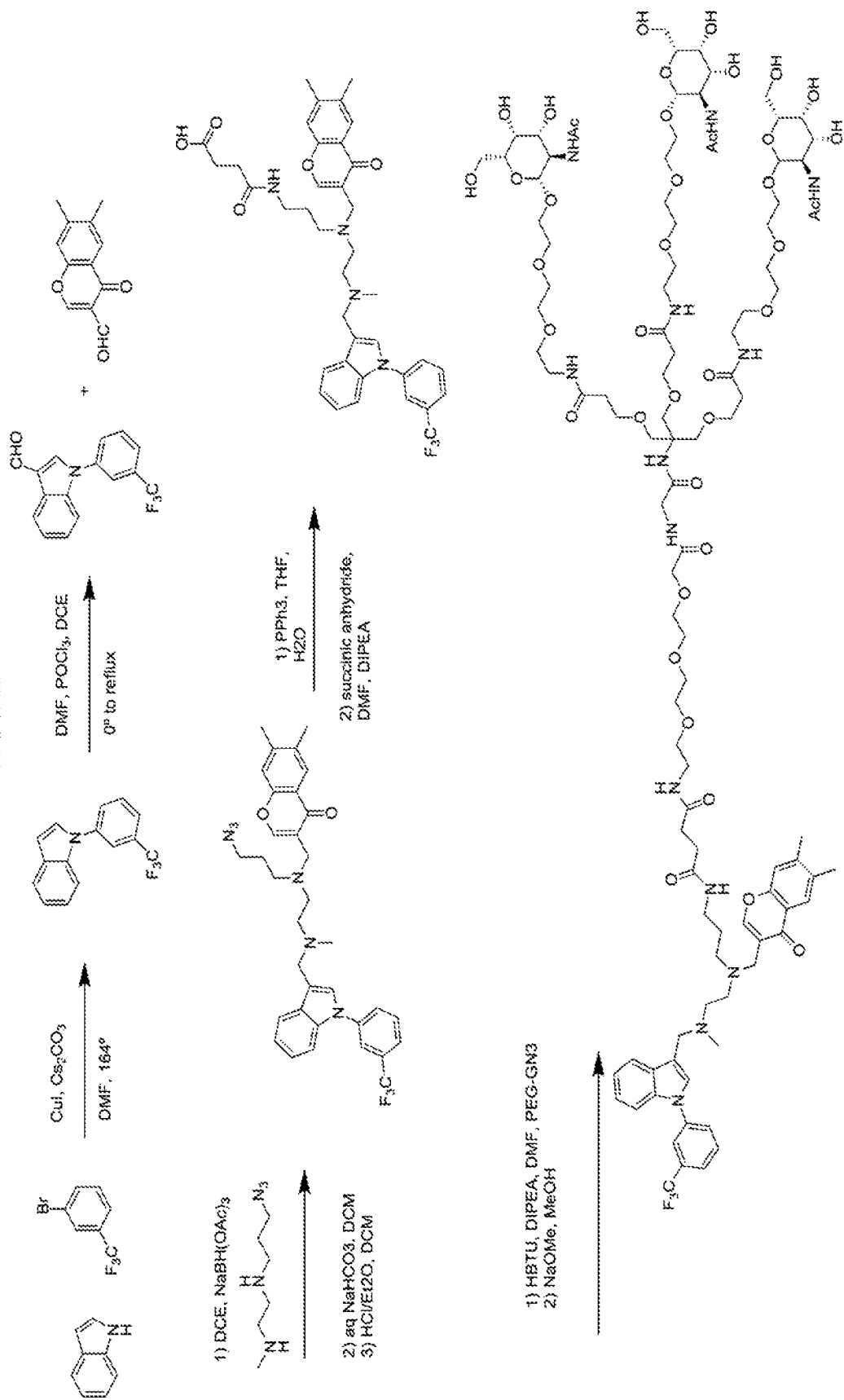
FIG. 74 shows the synthesis of TNF-alpha binding bifunctional molecule SP307-GN3.
Figure 75:
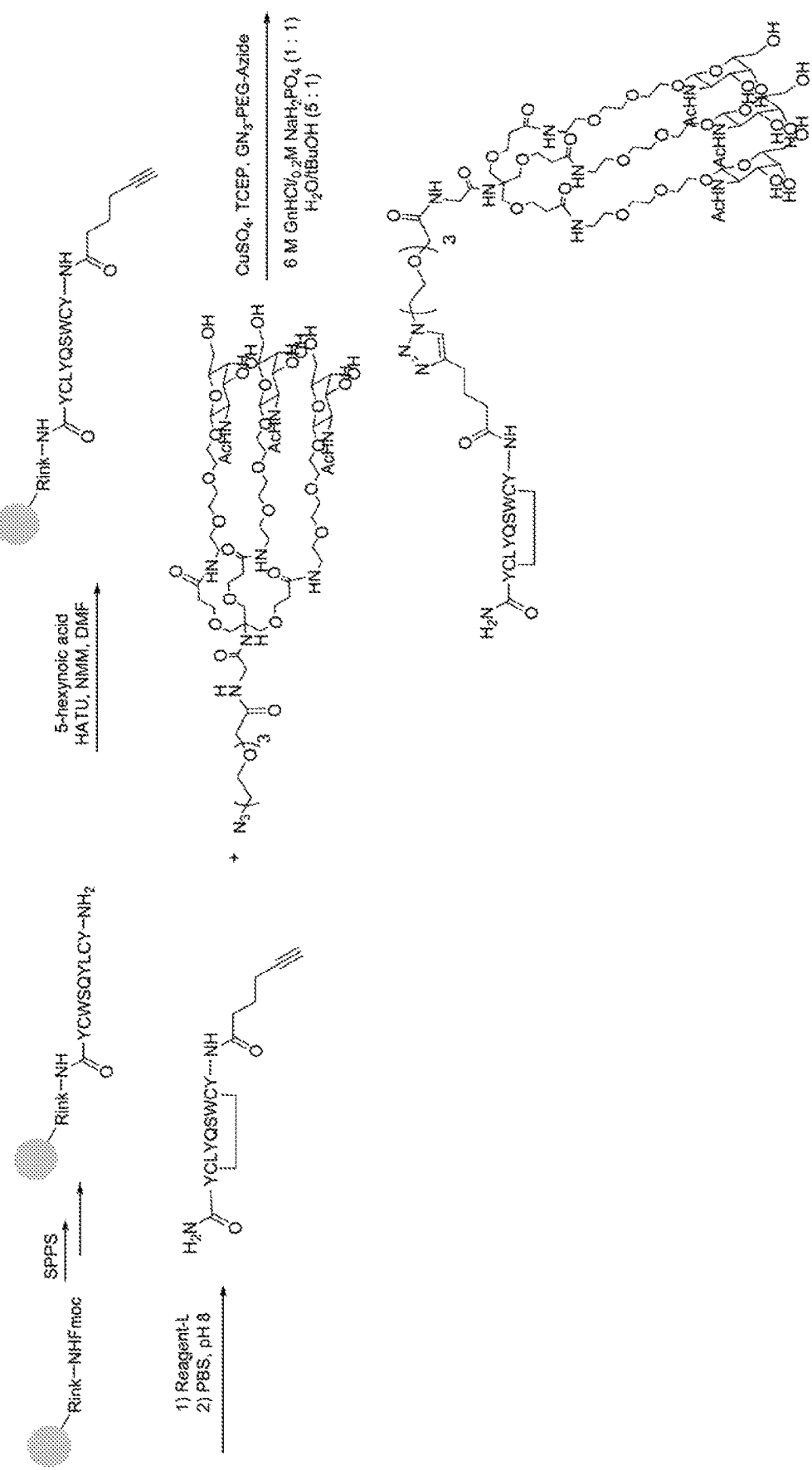
FIG. 75 shows the synthesis of TNF-alpha binding bifunctional molecule YCWSQYLCY-GN3.
Figure 76:
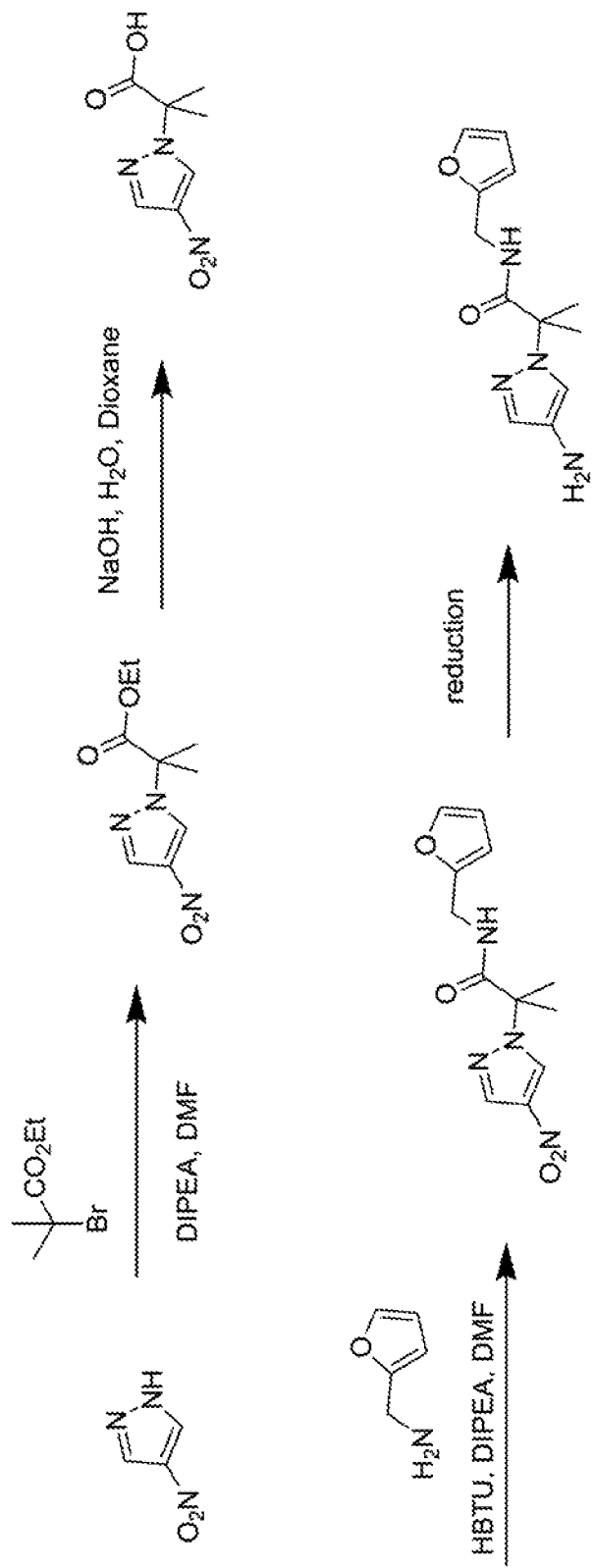
FIG. 76 shows the synthesis of PCSK9 binding bifunctional molecule SBC110424-GN3.
Figure 76:
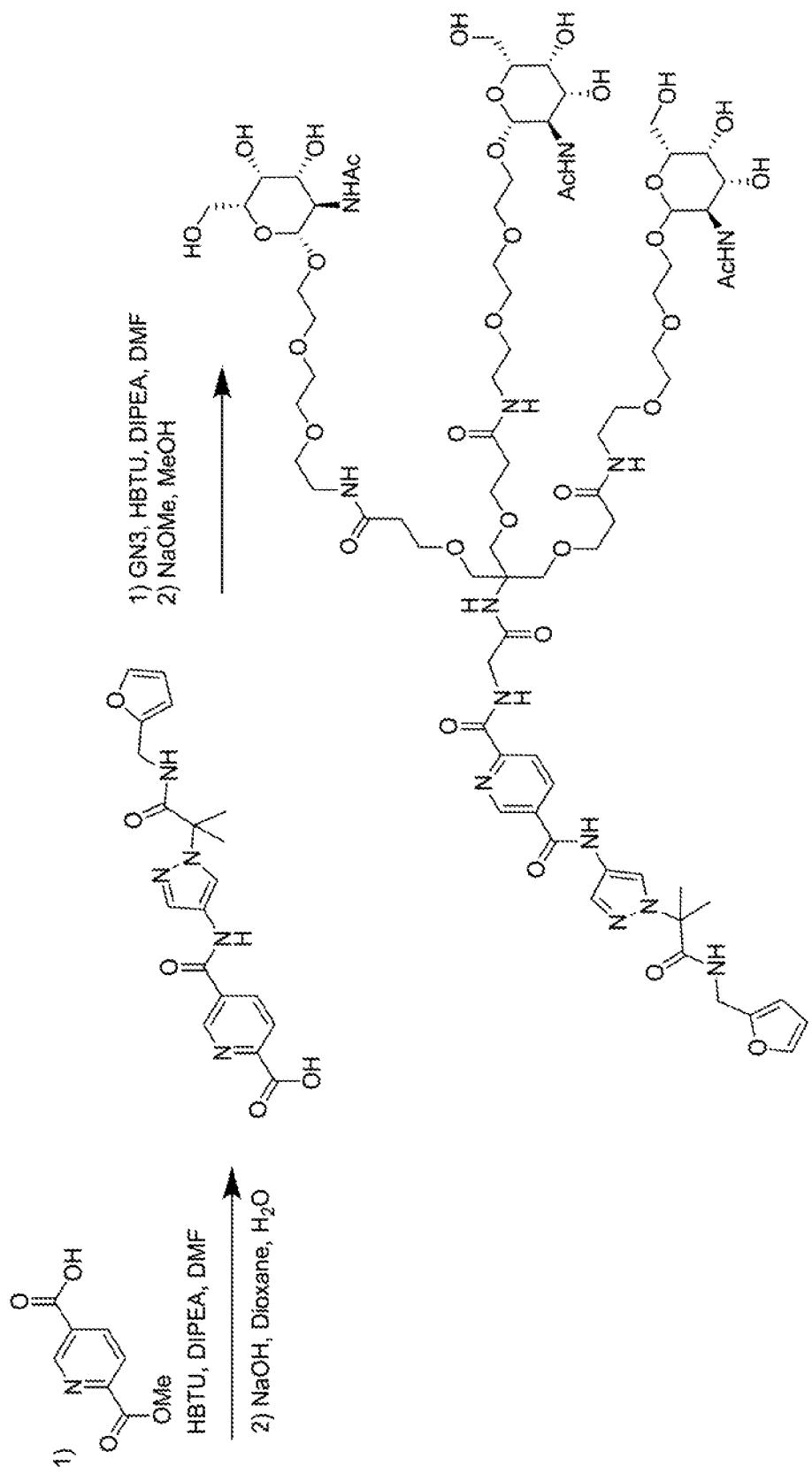
Figure 77:
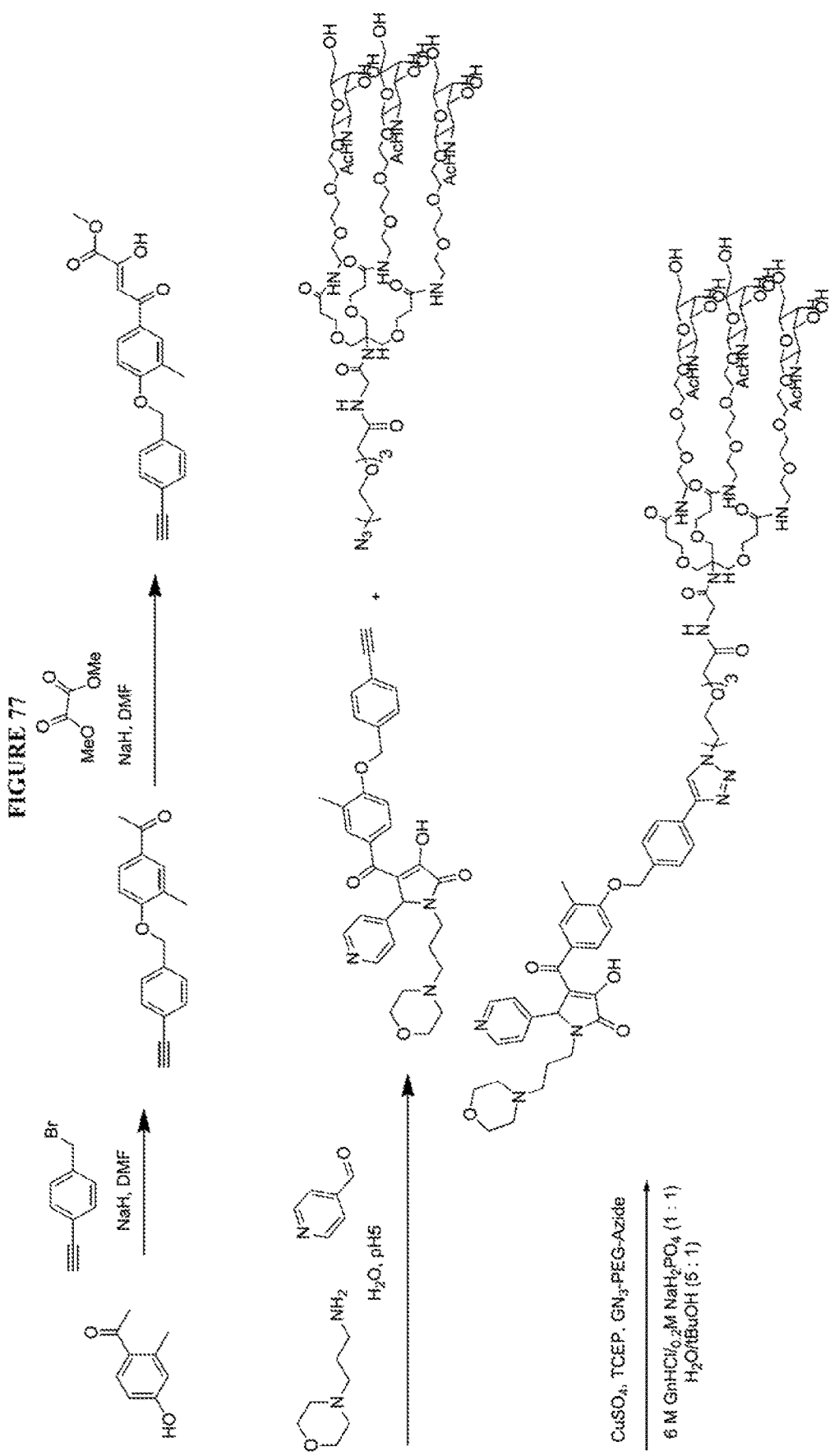
FIG. 77 shows the synthesis of PCSK9 binding bifunctional molecule SBC110076-GN3.
Figure 78:
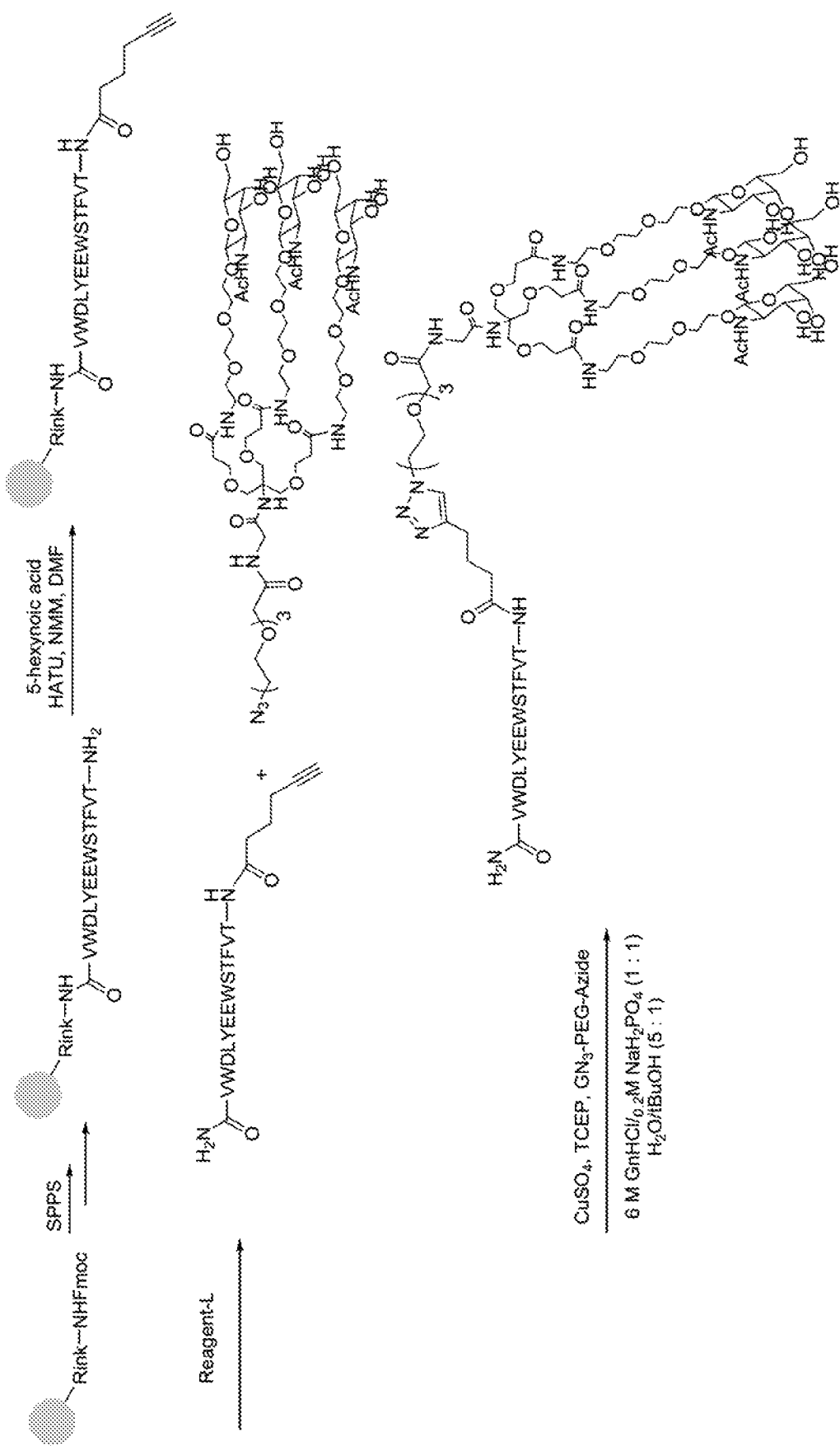
FIG. 78 shows the synthesis of PSCK9 binding bifunctional molecule TVFTSWEEYLDWV-GN3.
Figure 79:
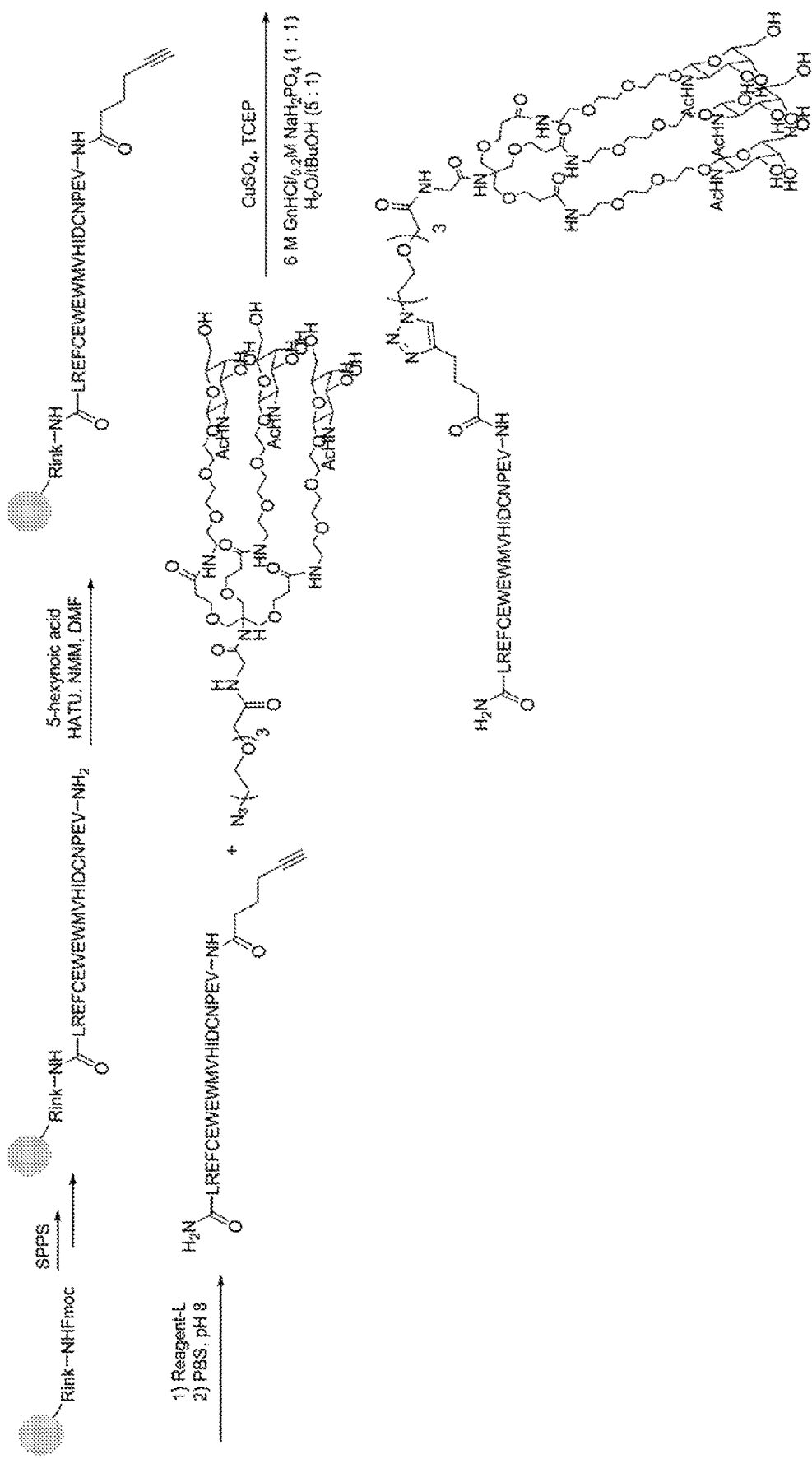
FIG. 79 shows the synthesis of VEGF binding bifunctional molecule VEPNCDIHVMWEWECFERL-GN3.
Figure 80:
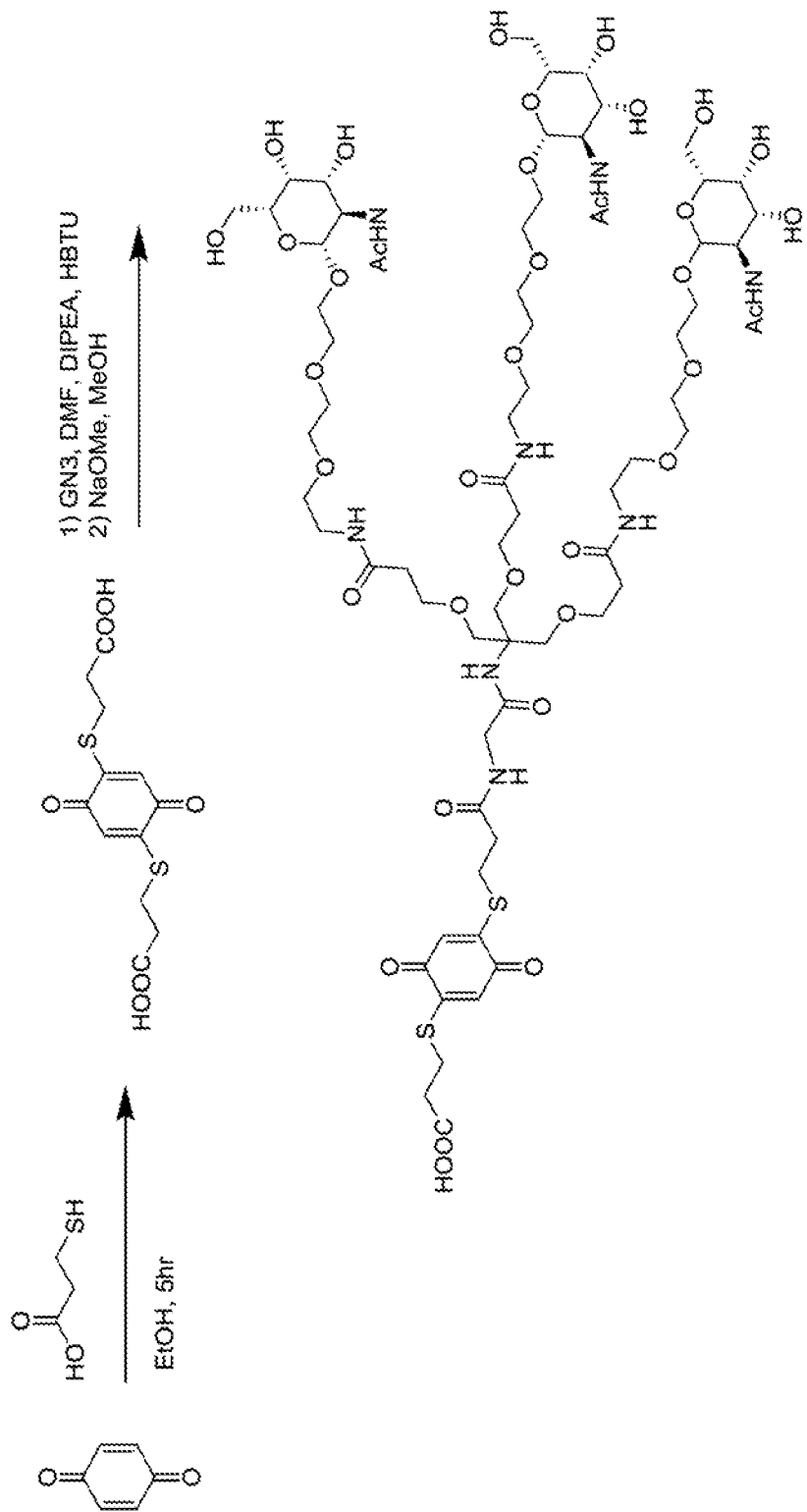
FIG. 80 shows the synthesis of VEGF binding bifunctional molecule VEGFSM-GN3.
Figure 81:
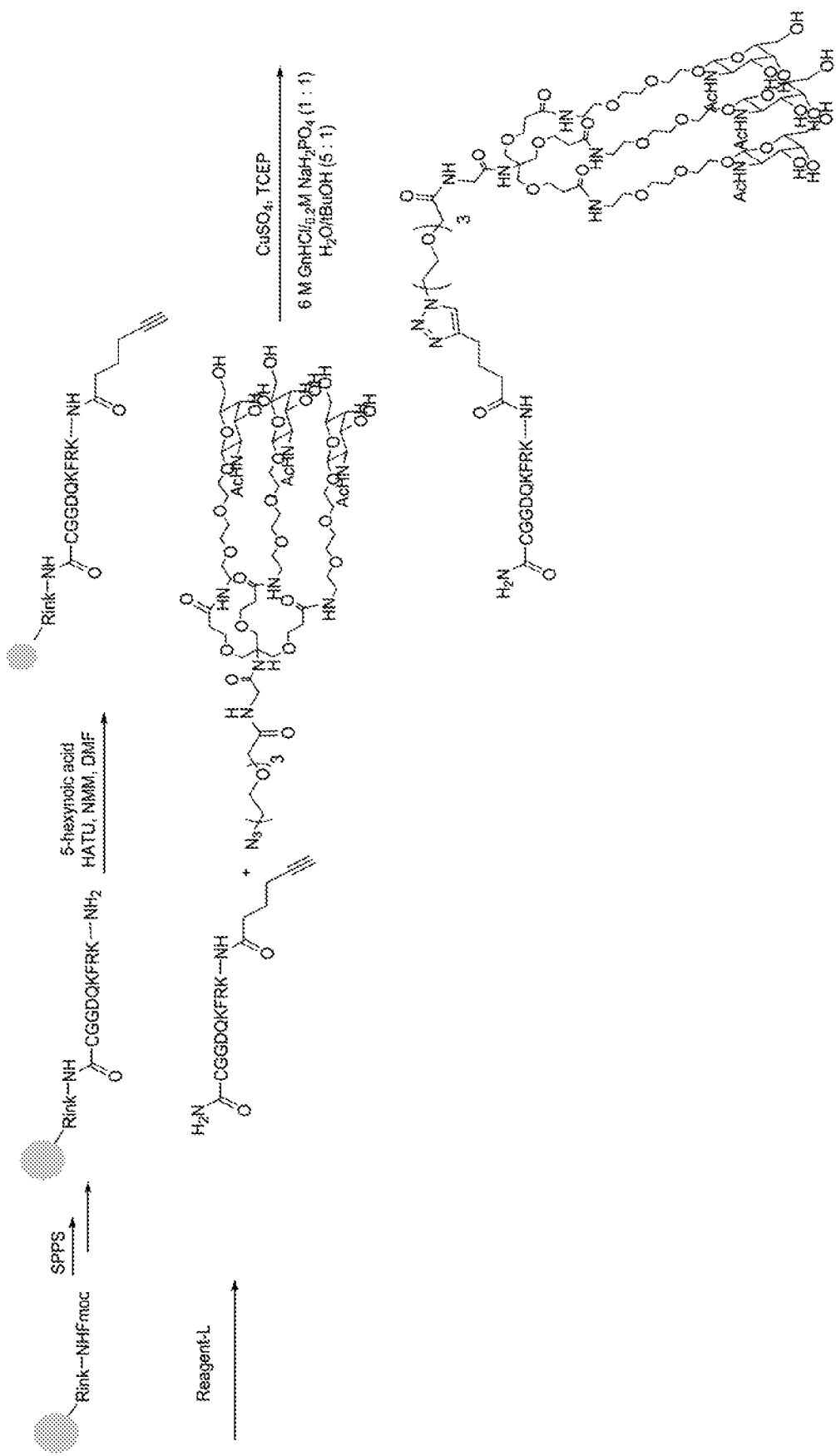
FIG. 81 shows the synthesis of TGF-beta binding bifunctional molecule KRFK-GN3.
Figure 82:
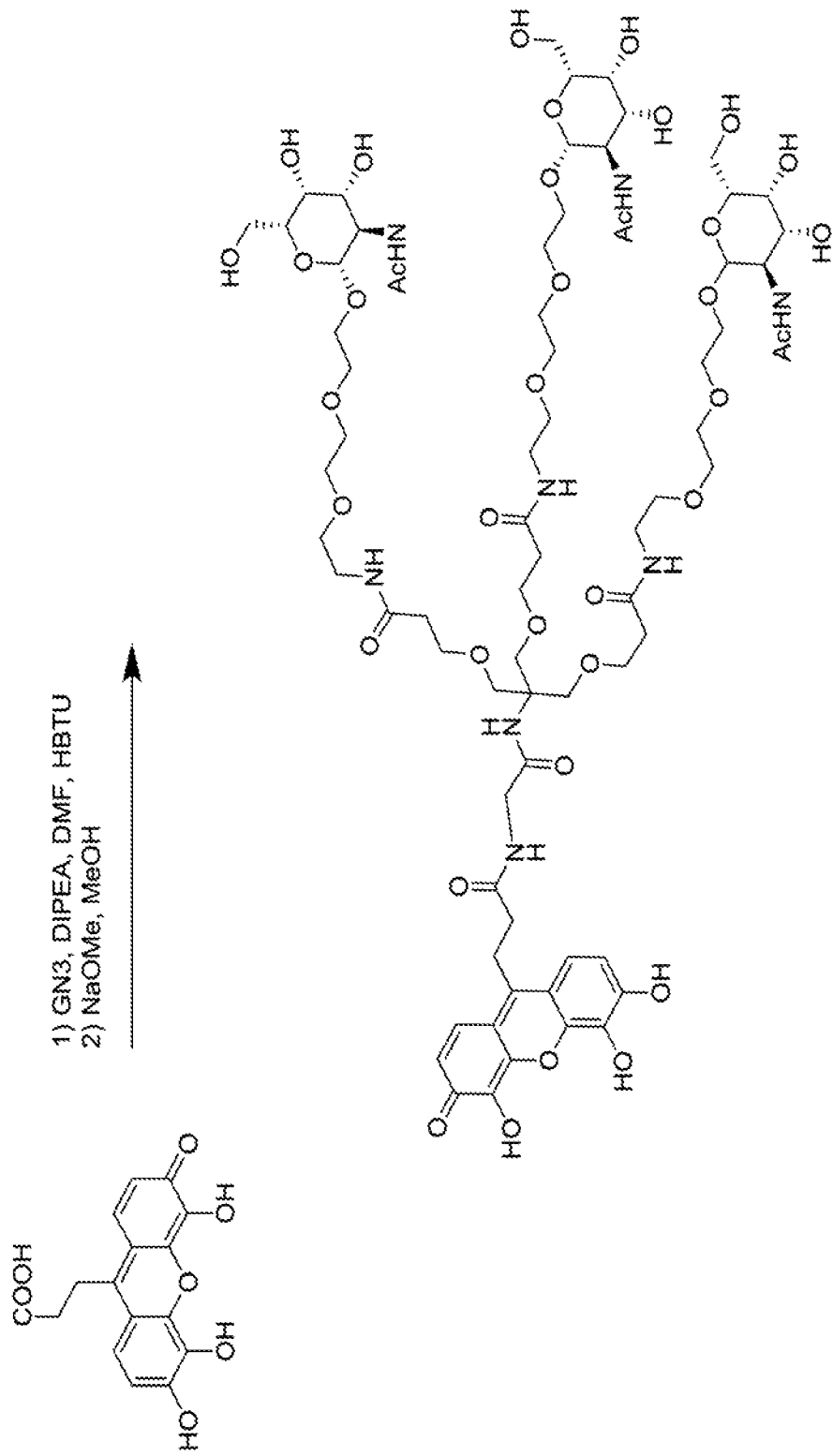
FIG. 82 shows the synthesis of TGF-beta binding bifunctional molecule TGFBSM-GN3.
Figure 83:
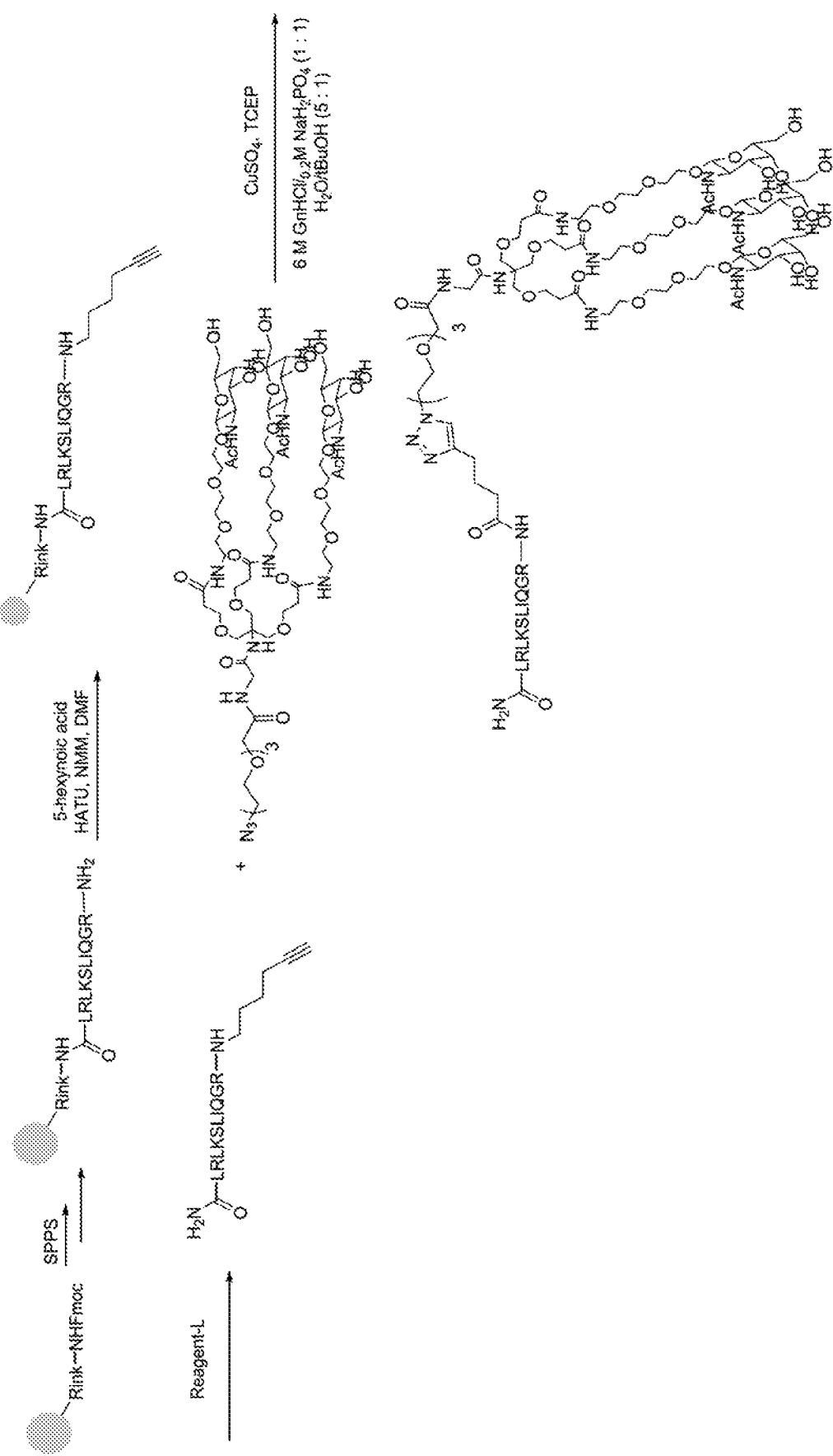
FIG. 83 shows the synthesis of TSP-1 binding bifunctional molecule LSKL-GN3.
Figure 84:
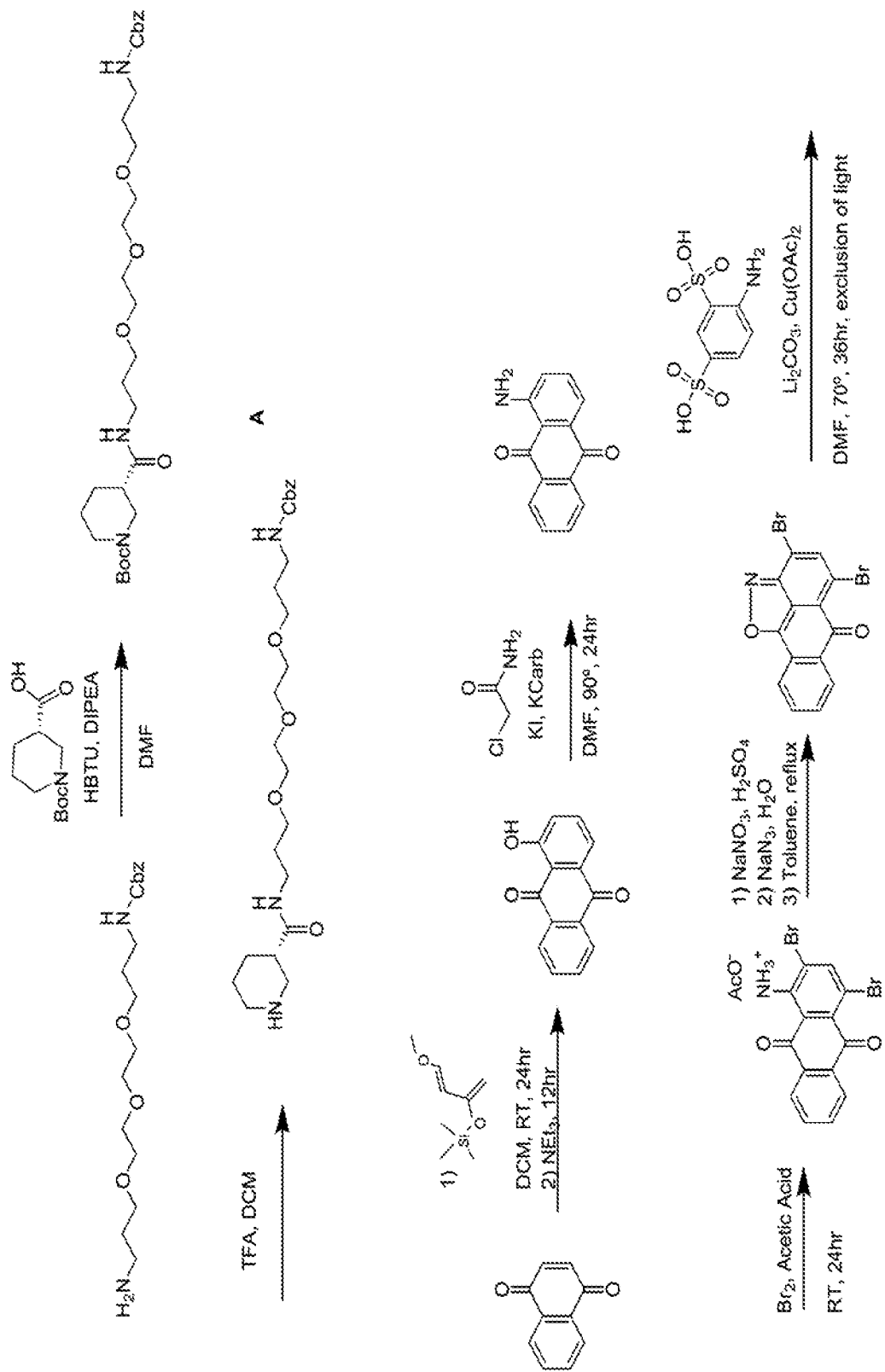
FIG. 84 shows the synthesis of soluble uPAR binding bifunctional molecule uPAR-GN3.
Figure 84:
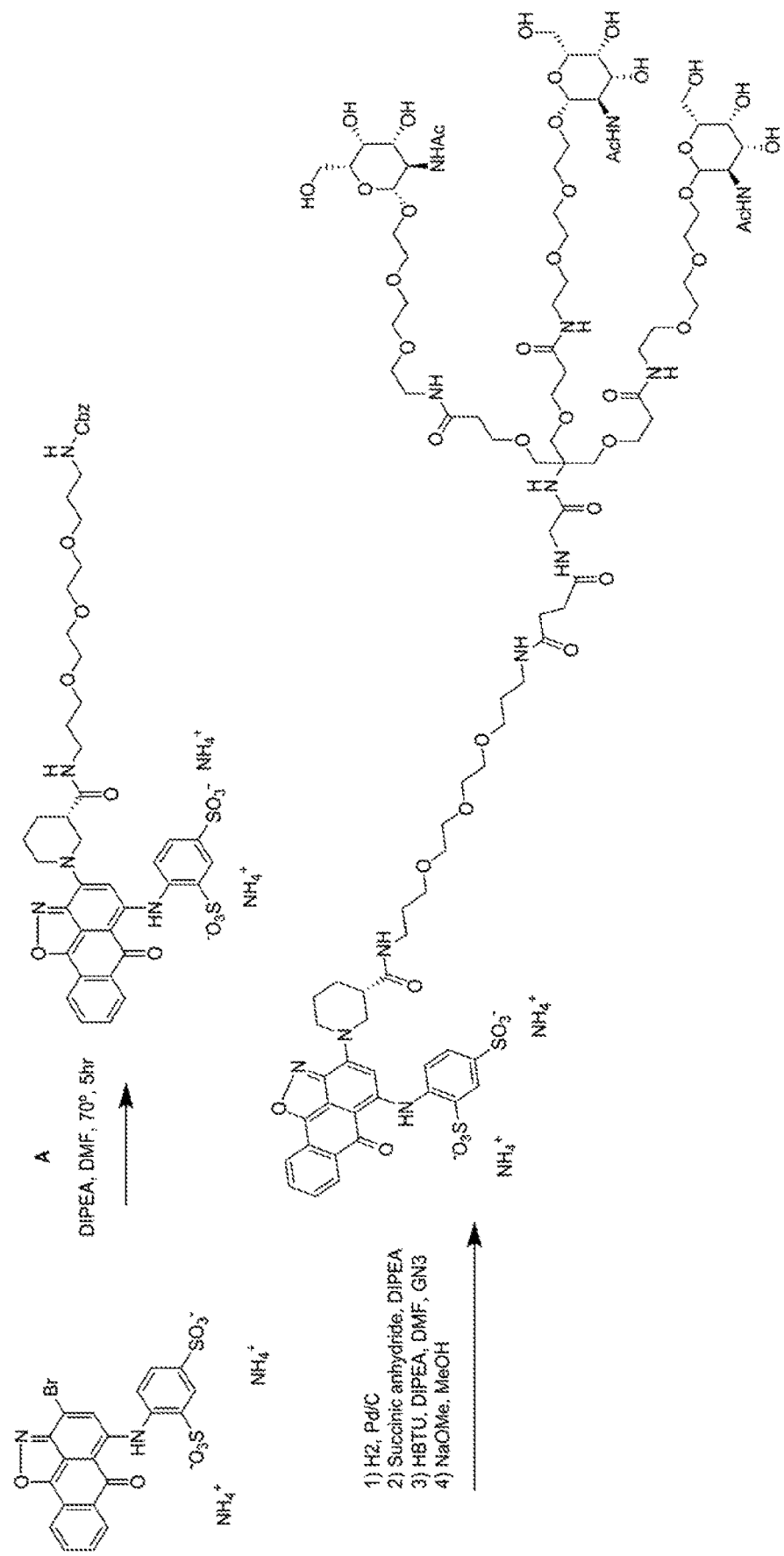
Figure 85:
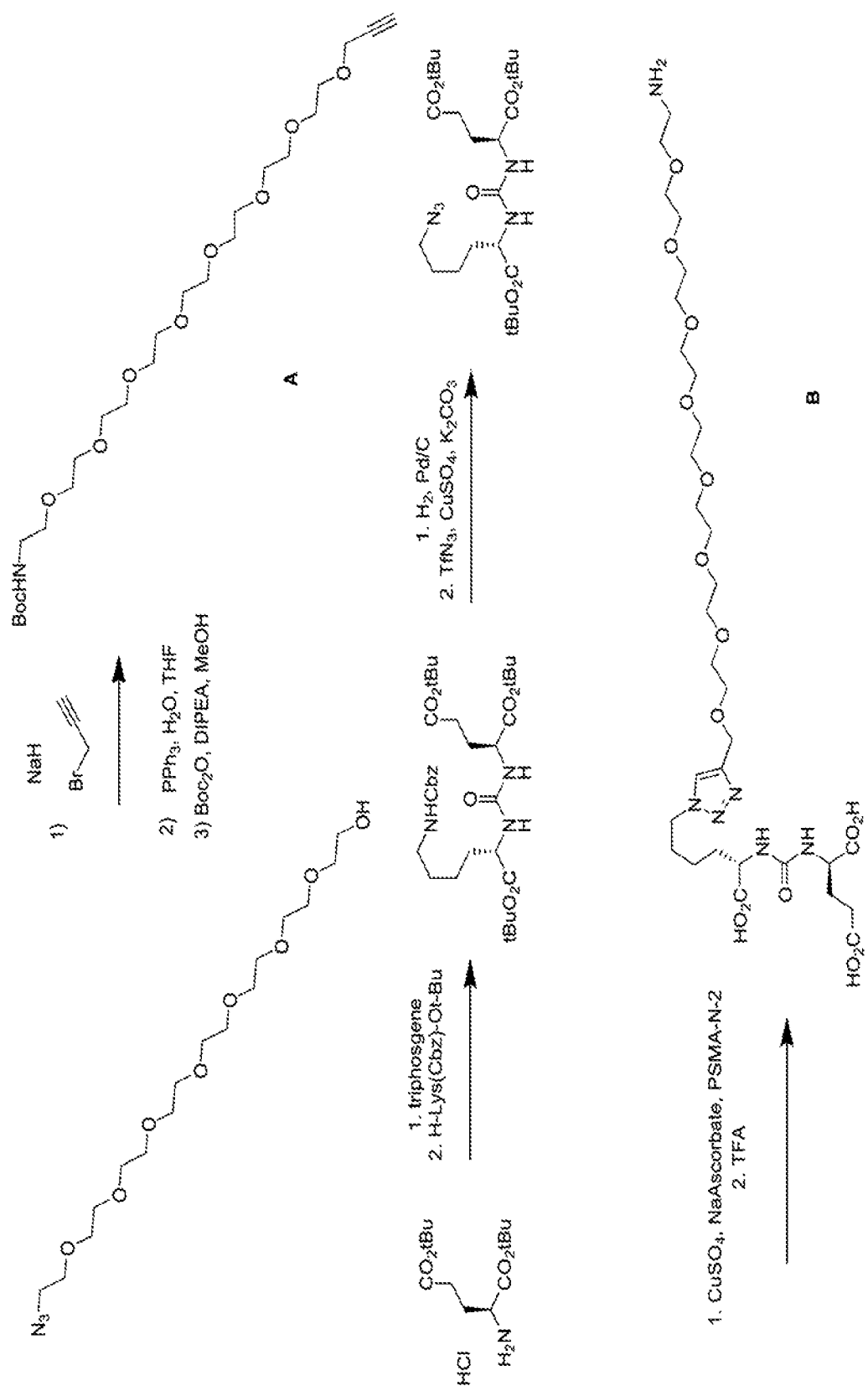
FIG. 85 shows the synthesis of soluble PSMA binding bifunctional molecule PSMA-GN3.
Figure 85:
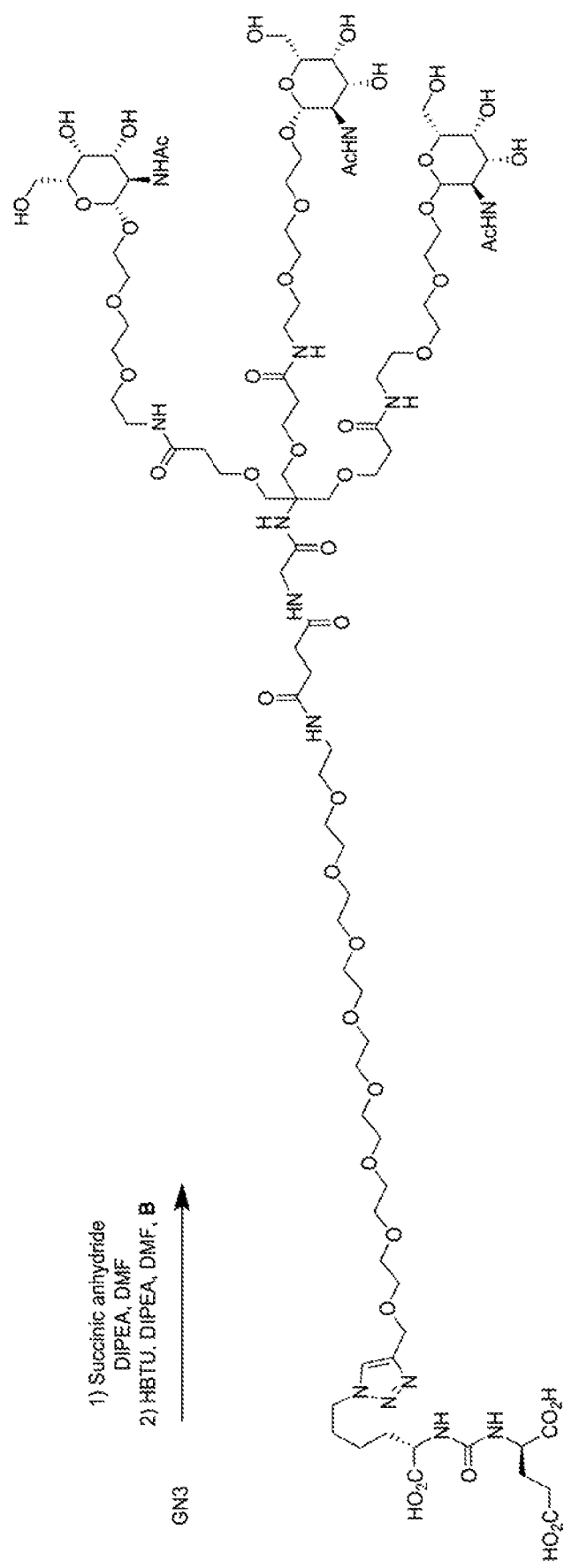
Figure 86:
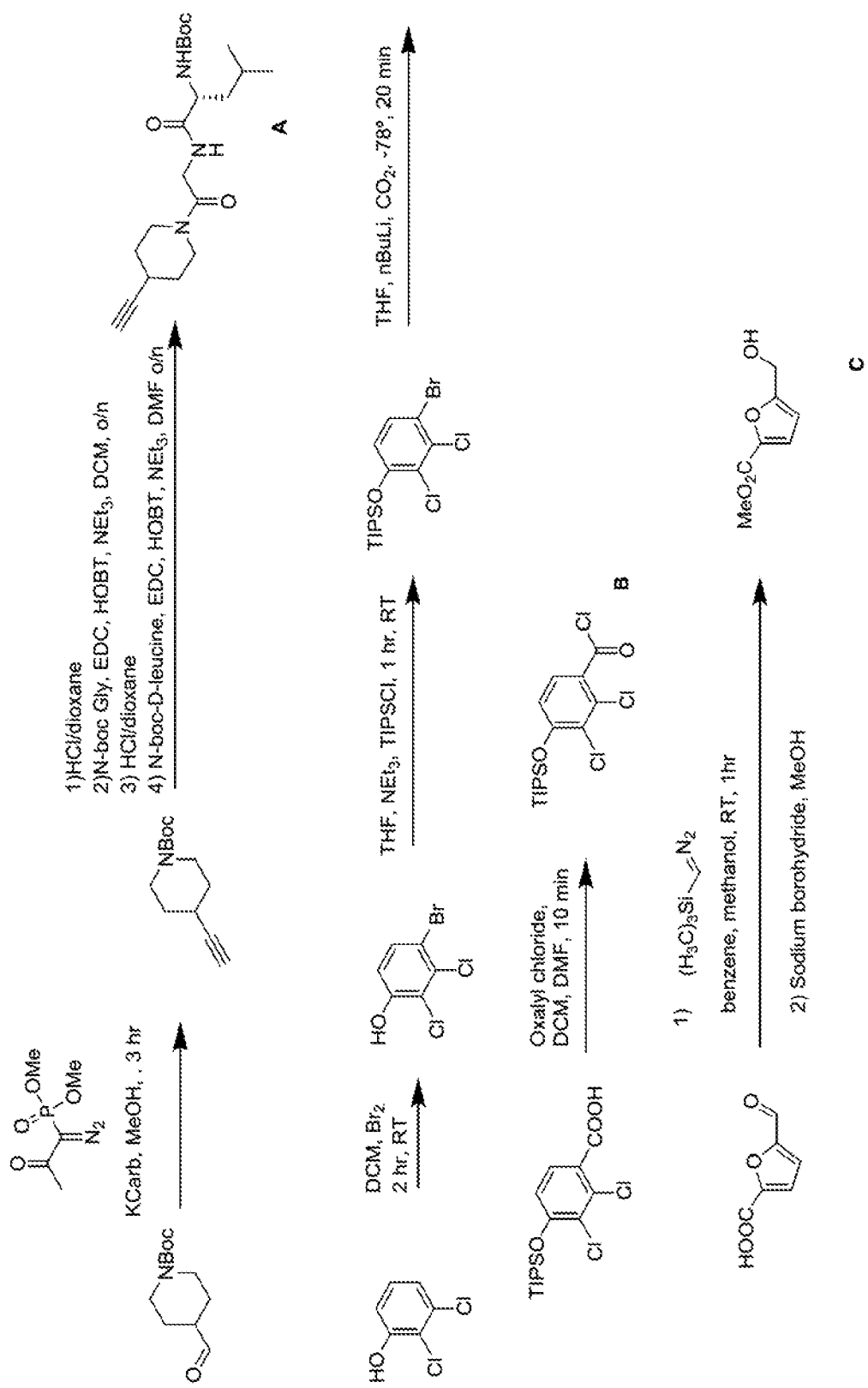
FIG. 86 shows the synthesis of IL-2 binding bifunctional molecule IL2-GN3.
Figure 86:
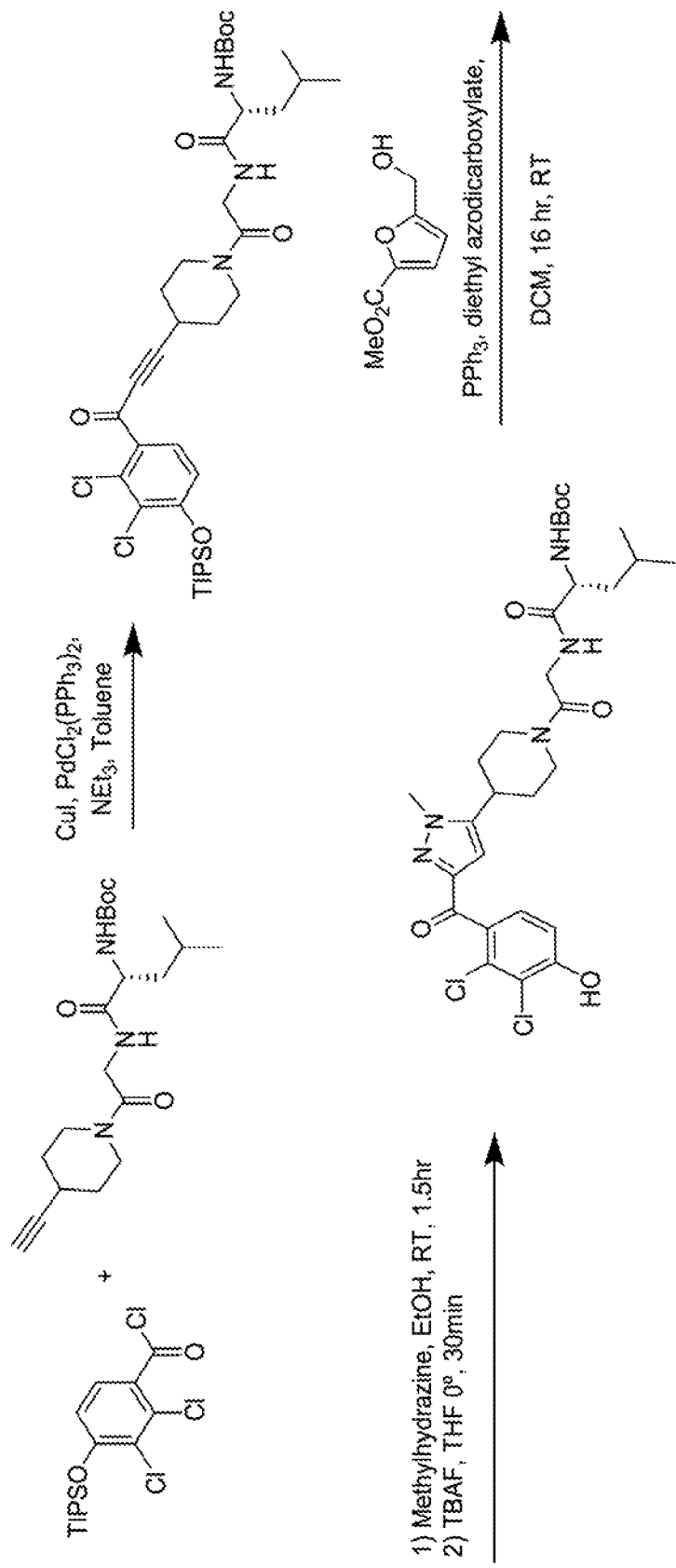
Figure 86:
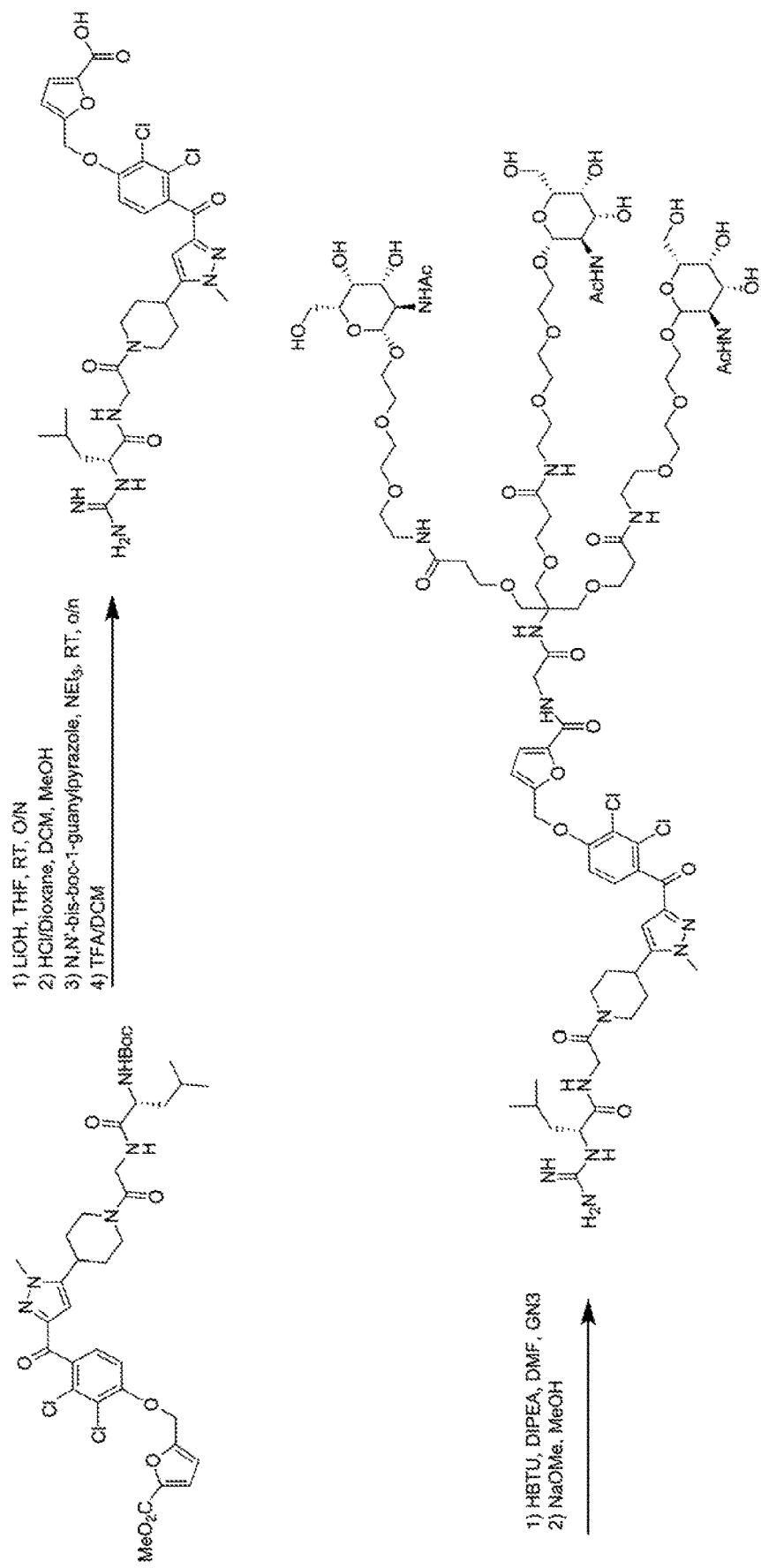
Figure 87:
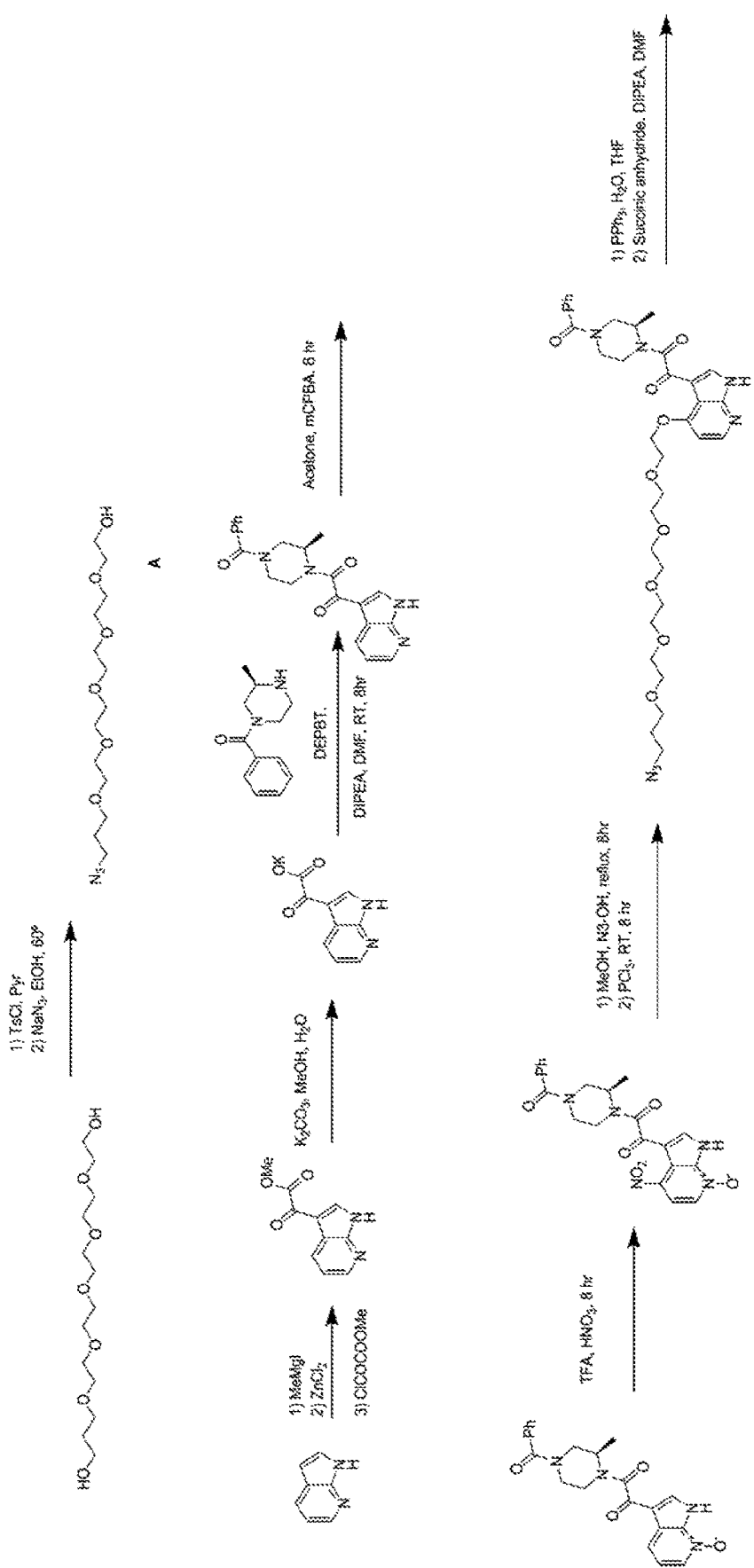
FIG. 87 shows the synthesis of GP120 binding bifunctional molecule BMS378806-GN3.
Figure 87:
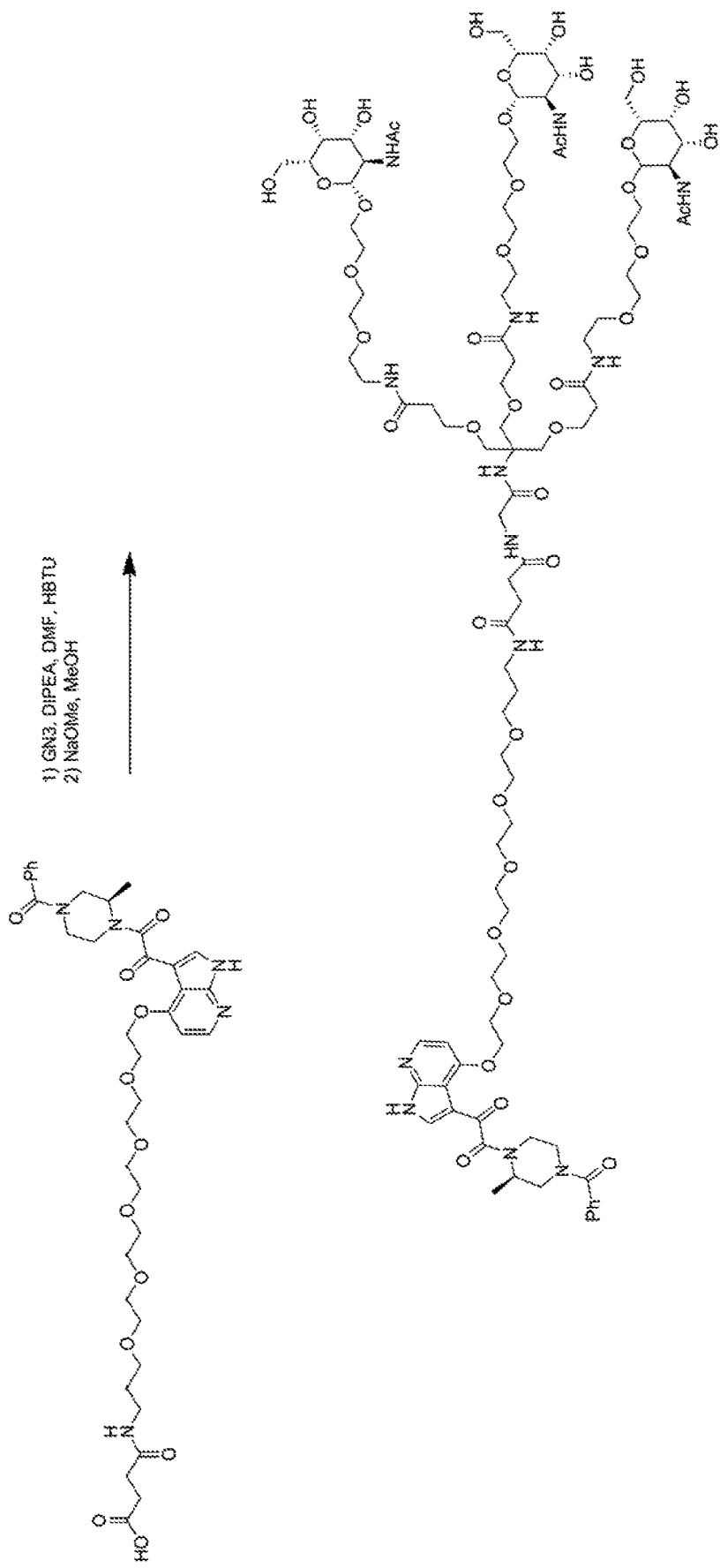
Figure 88:
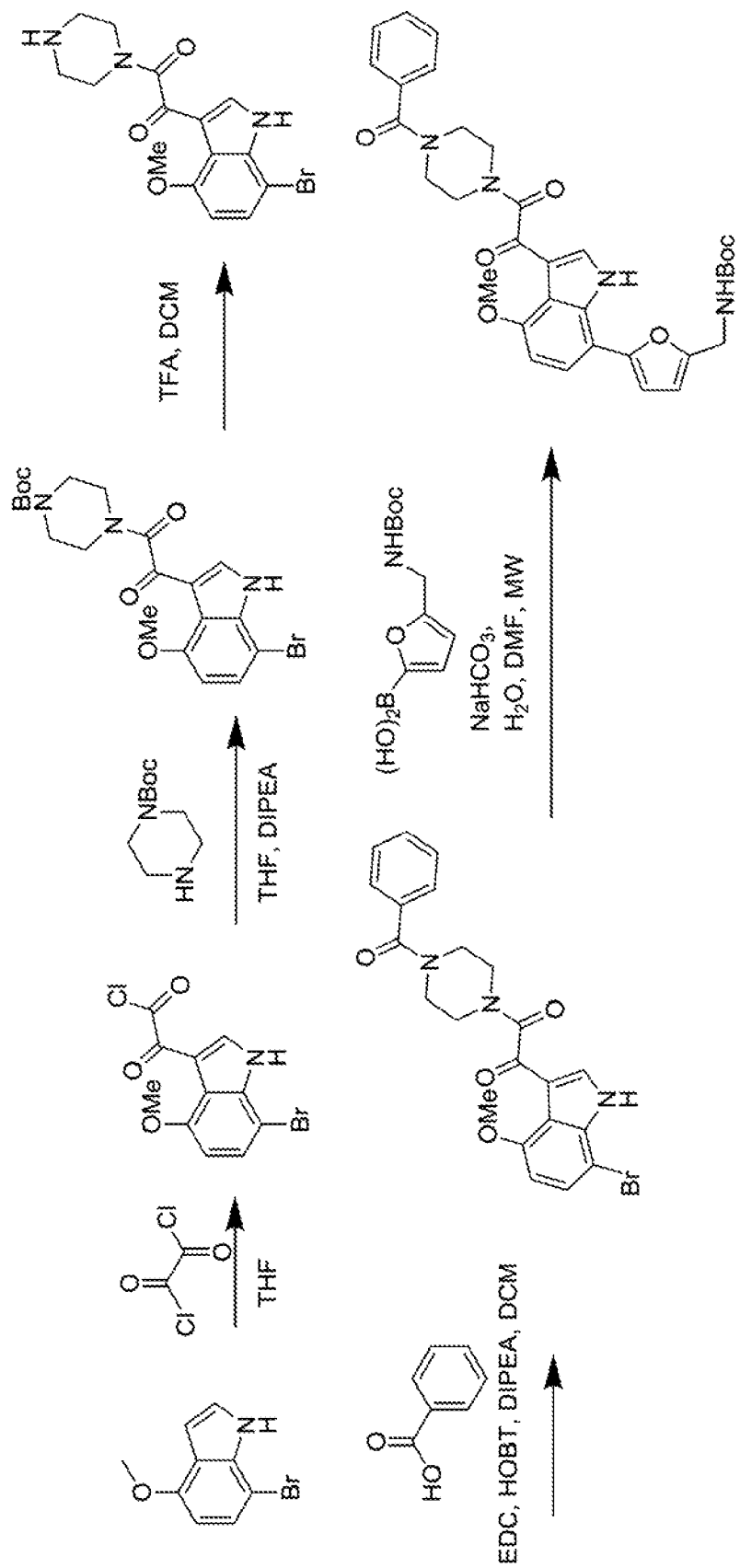
FIG. 88 shows the synthesis of GP120 binding bifunctional molecule CPD7-GN3.
Figure 88:
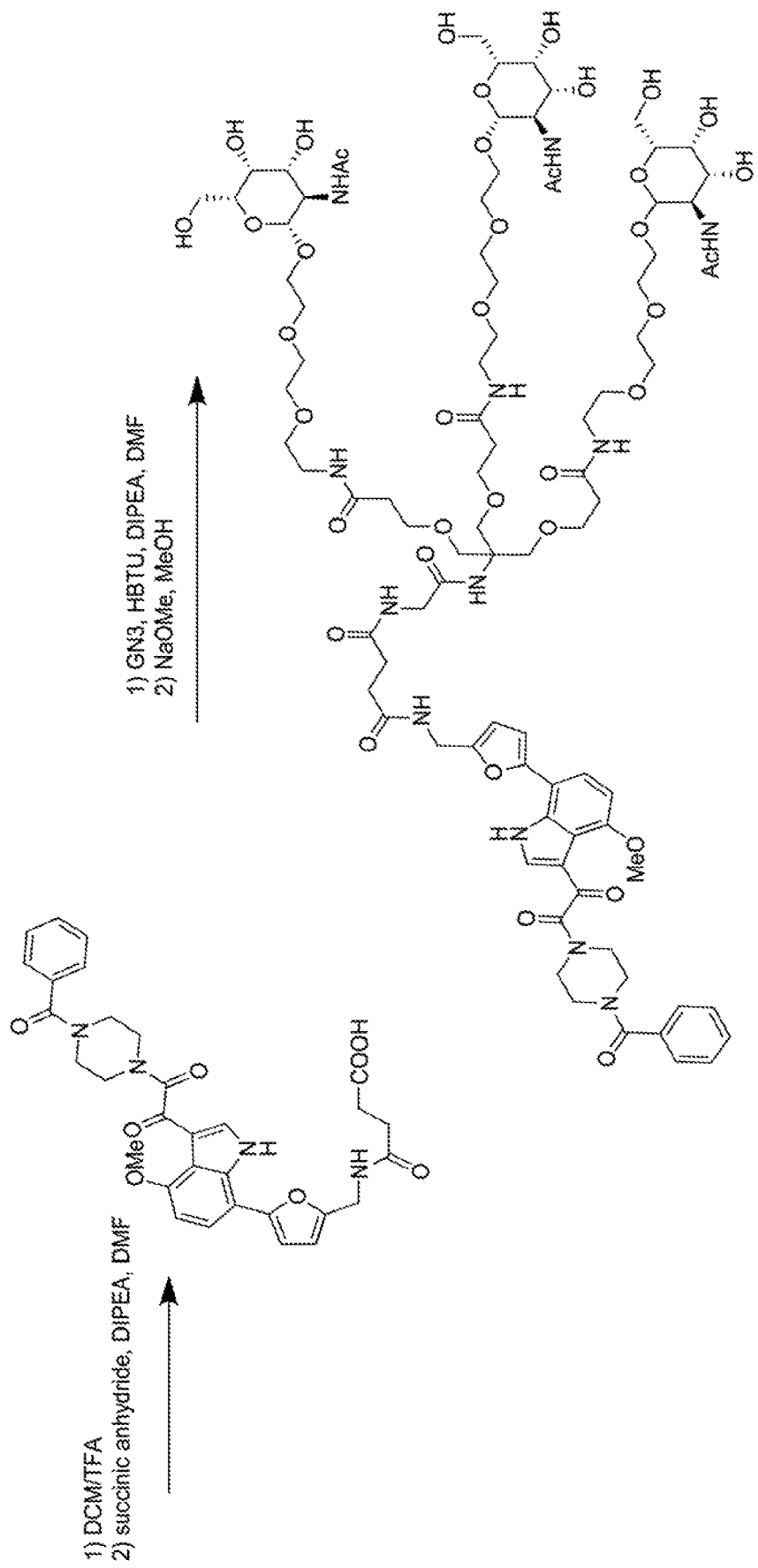
Figure 89:
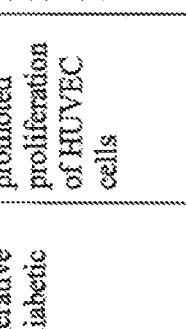
FIG. 89 lists a table of possible target proteins with their indications, examples of in vitro assays, and known binding molecules.
Figure 90:
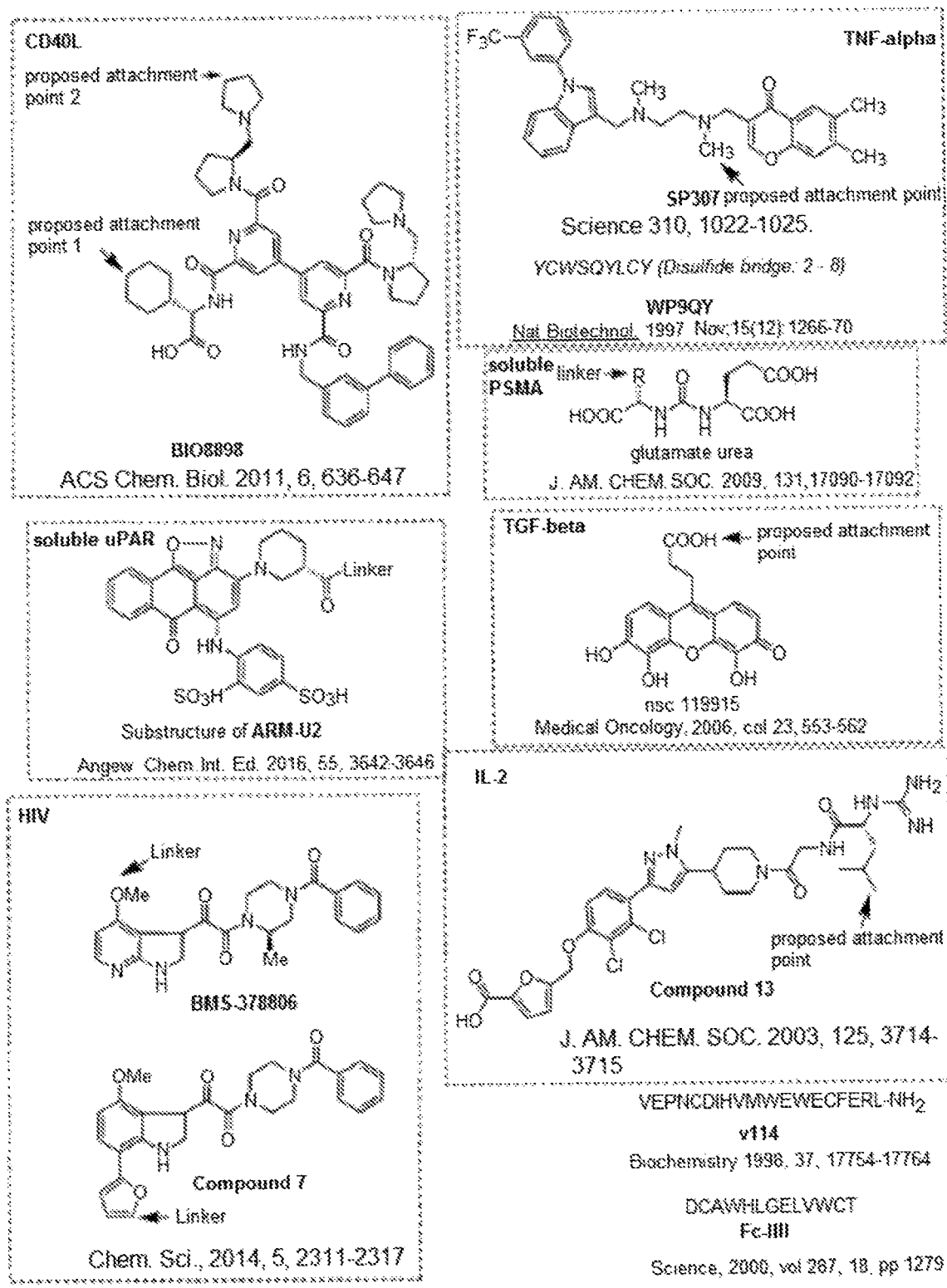
FIG. 90 includes proposed derivatization sites for several ligands that bind target circulating proteins.
Figure 90:
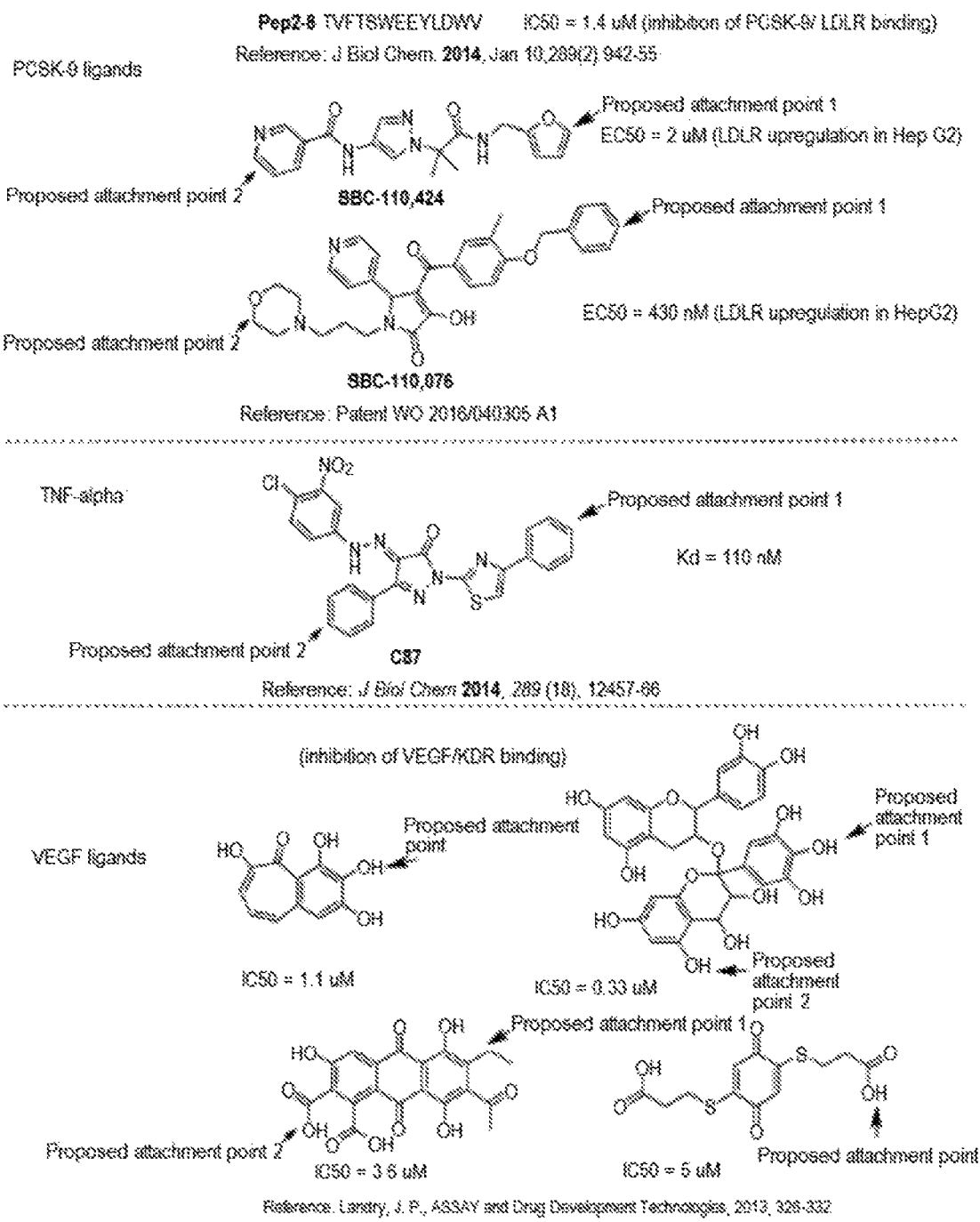

FIG. 52 shows the synthesis of compounds MIF-NVS-PEGN-GN3. PEG compounds were treated with tosyl chloride in the presence of base, then subsequently treated with sodium azide at elevated temperature to give azido alcohols. These intermediates were oxidized using Jones reagent to give carboxylic acid azides. Separately, diethylene glycol was treated with base and propargyl bromide to give an alkynyl alcohol, which was then tosylated in the presence of base and subsequently treated with sodium iodide to give an iodinated intermediate. This iodinated compound was then treated with 4-N-boc-aminophenol in the presence of base, which gave an ether intermediate that was treated with hydrochloric acid in dioxane to give an amino alkyne. This amine was reacted with 2-hydroxy-4-(tert-butyldimethylsiloxy) benzaldehyde in the presence of sodium borohydride to give the cyclic intermediate, which was then treated with TBAF in THF to give the resulting alcohol. CuI-mediated cyclization was then performed between this alkyne and the above-described azide in acetonitrile. The resulting carboxylic acid was reacted with NH2-GN3 as described in previous schemes.

FIGS. 53-66 show the synthesis of a number of MIF-binding compounds with various ASGPRBM moieties. These are synthesized through methods analogous to those laid out above.

FIGS. 70-88 show the synthesis of a number of further bifunctional compounds according to the present invention.

Examples

Proper protein section and turnover is a necessary process for maintaining homeostasis. Newly synthesized proteins targeted for secretion are first trafficked to the endoplasmic reticulum, where they are post-translationally modified with N-linked glycan chains terminating in sialic acids(1). As proteins age, terminal sialic acid residues are removed by circulating endogenous glycosydases(2). This natural protein aging process unmasks galactose and N-acetylgalactose (GalNAc) residues, which bind the asialoglycoprotein receptor (ASGPR) on the surface of hepatocytes(3-5).

The ASGPR is a C-type lectin that removes aged circulating proteins with exposed GalNAc residues from circulation by trafficking them to lysosomes. Multiple galactose or GalNAc residues displayed on the protein surface are necessary for high-affinity binding to—and subsequent endocytosis by—ASGPR(6, 7). Once these proteins are endocytosed, they are released from the ASGPR through depletion of calcium from the endosome and changes in binding site amino acid protonation changes due to a decrease in pH (12); the ASGPR is recycled back to the hepatocyte surface(13). Endocytosed proteins are trafficked to late endosomes, which are fused with lysosomes. Lysosomal proteases then degrade endocytosed proteins, permanently removing them from circulation(14).

Non-glycosylated proteins are not known to be natural target for the ASGPR. One such protein is macrophage inhibitory factor (MIF), a 12.5 kDa protein with possible catalytic activity (15). Genetic depletion or antibody neutralization of MIF has been shown to have positive results in models of sepsis(16), multiple schlorosis(17), rheumatoid arthritis(18), and burn recovery(21). We propose a bifunctional molecule for degrading circulating MIF that takes advantage of ASGPR as an entryway for proteins into the endosomal-lysosomal degradation pathway. The bicyclic ASGPR-binding molecules in MIF-AcF2 and MIF-AcF3 have been reported previously as high affinity binders for the ASGPR (22, 23).

Biological Data

A number of compounds according to the present invention are tested to determine their biological activity. Active compounds are shown in FIGS. 1, 7 and 13 hereof. The results of the biological experiments are described herein below.

FIG. 1 shows representative compounds according to the present invention. Note that the figure discloses compound 3w (negative control for MIF inhibition), MIF-NVS-PEGnGN3, MIFGN3, MIF-PEGnGN3, MIF-AcF3-1, MIF-AcF3-2 and MIF-AcF3-3. Note that n in the PEG linker preferably ranges from 1-12, 1 to 10, 2 to 8, 2 to 6, 2 to 5 or 1, 2, 3 or 4.

Figure 2:
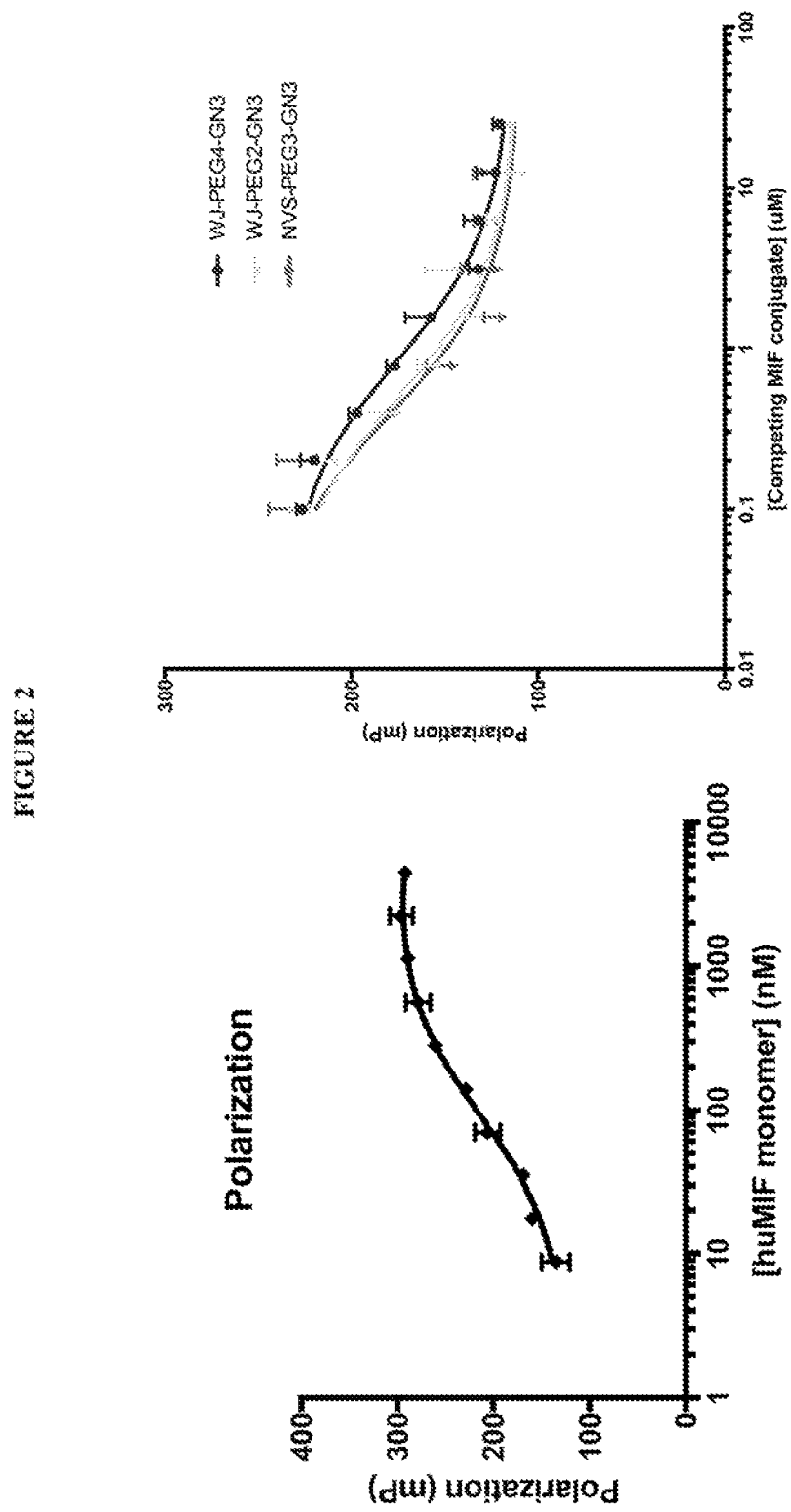
FIG. 2 shows fluorescence polarization data of MIF-FITC binding to human MIF, indicating that our MIF-binding moiety binds MIF. Bifunctional molecules WJ-PEG4-GN3, WJ-PEG2-GN3, and NVS-PEG3-GN3 bound competitively with MIF-FITC, indicating that the bifunctional molecules maintain the ability to bind human MIF.

In an experiment the results of which are shown in FIG. 2, A. fluorescence polarization data of MIF-FITC binding to human MIF indicates that the MIF-binding moiety of the present invention binds MIF. B. Bifunctional molecules WJ-PEG4-GN3, WJ-PEG2-GN3, and NVS-PEG3-GN3 bound competitively with MIF-FITC, indicating that the bifunctional molecules maintain the ability to bind human MIF.

Figure 3:
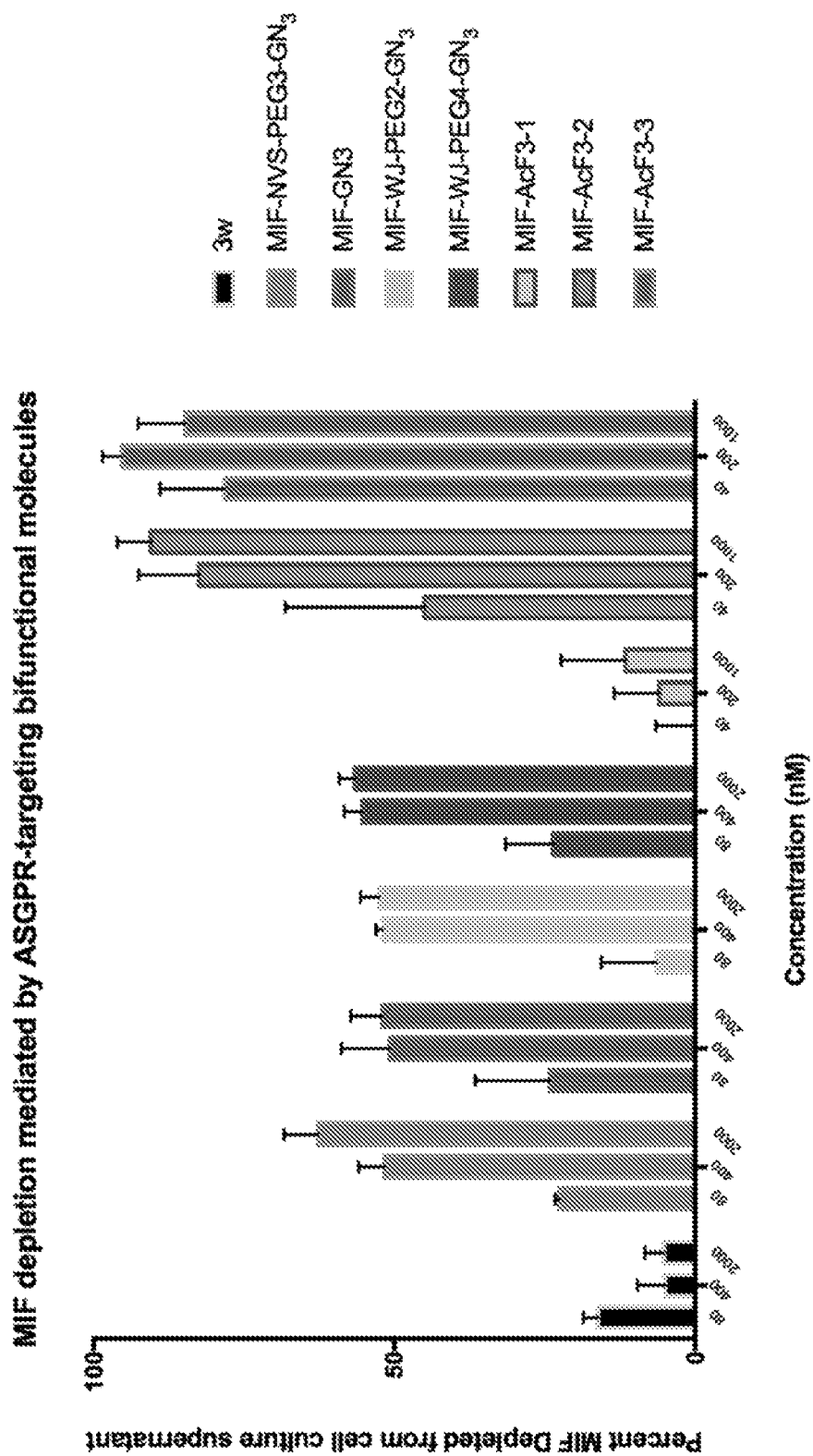
FIG. 3 shows that bifunctional molecules are able to deplete human MIF from the supernatant of culture HepG2 cells.

In an experiment the results of which are presented in FIG. 3, bifunctional molecules were able to deplete human MIF from the supernatant of culture HepG2 cells. Briefly, human MIF (100 nM) was added to cell culture media in the presence of negative control MIF inhibitor 3w as well as bifunctional molecules MIF-NVS-PEGn-GN3, MIF-GN3, MIF-PEGn-Gn3, MIF-AcF3-1, MIF-AcF3-2, and MIF-AcF3-3. All molecules utilized a known MIF-binding ligand. Experiments were performed in 96 well plates (approximate surface area 0.3 cm$^2$). HepG2 cells were grown to 90% confluency in RPMI media, then washed with PBS (2×) and treated with serum-free media (optimem+0.1% BSA, +Pen/Strep) containing 100 nM huMIF (Cayman Chemical) and compounds (when applicable). Compounds were diluted from 1 mM stock solutions in DMSO. After 24 hours, a sample of the supernatant (2 uL) was collected, diluted 1:100, and analyzed for MIF content by sandwich ELISA (and incubated for 24 hours in the presence or absence of compound). Remaining MIF levels were determined by sandwich ELISA (biolegend monoclonal anti-MIF and biotinylated anti-MIF antibodies). Data represents the average of at least 3 biological replicates, and error bars represent a standard deviation. After 24 hours, up to 95.3% of the MIF had been depleted from cell culture media (in the case of MIF-AcF3-3).

Figure 4:
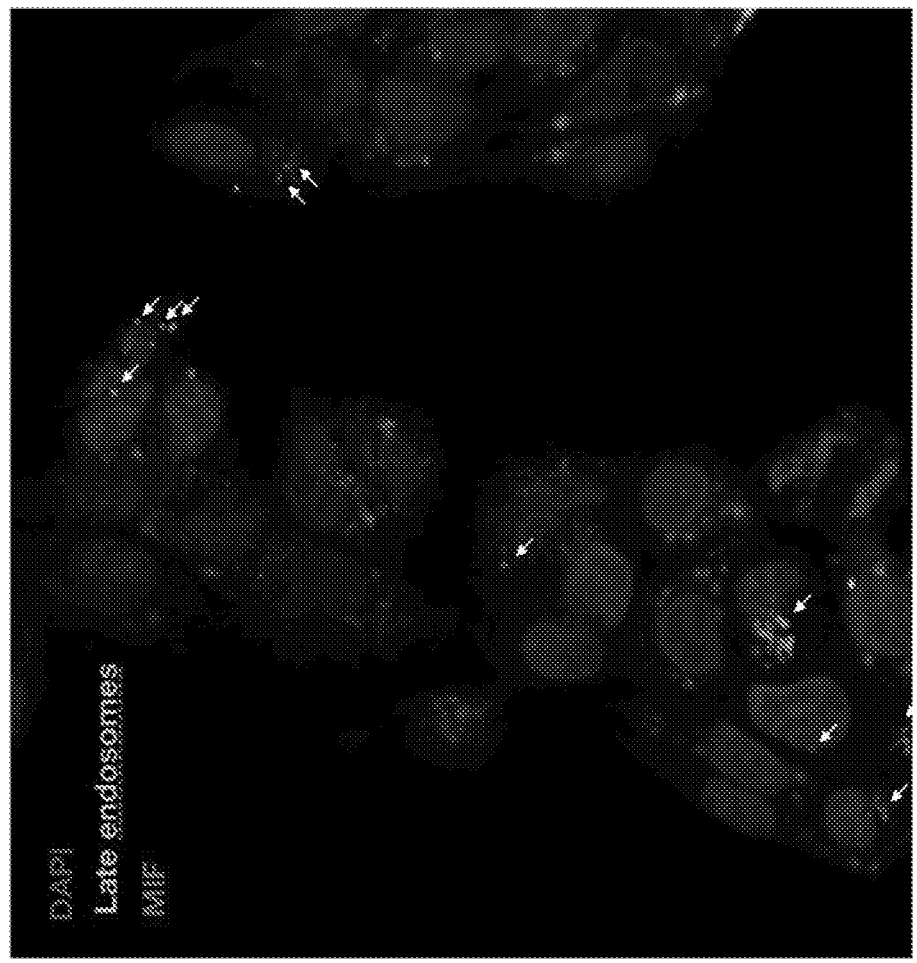
FIG. 4 shows that MIF internalized by HepG2 cells is trafficked to lysosomes.

FIG. 4 shows the results of an experiment to determine whether or not MIF internalized by HepG2 cells is trafficked to lysosomes. In this experiment, cells were incubated with rhuMIF (Cayman) at a concentration of 100 nM with 200 nM MIF-GN3. After 12 hours, cells were fixed with formaldehyde, permeabilized, and probed with anti-Lamp2 antibody (mouse monoclonal, Abcam), polyclonal rabbit anti-MIF antibody (Thermo) and with Alexa-488 labeled anti-mouse antibody and Alexa 568-labeled anti-rabbit antibody, evidencing internalization in lysosomes.

Figure 5:
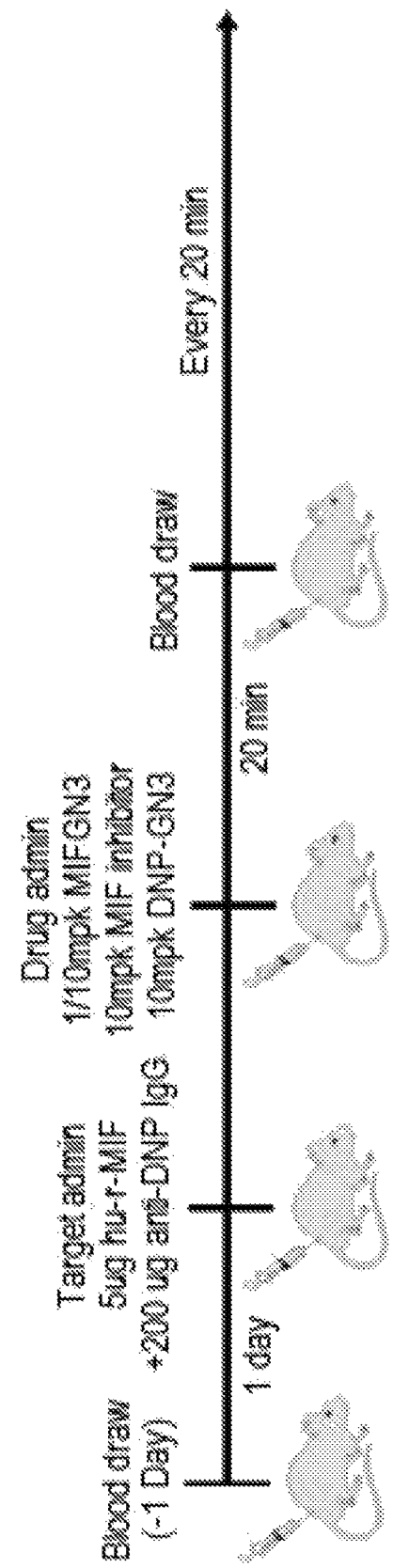
FIG. 5 shows that MIF-GN3 mediates the depletion of injected human MIF from mice.
Figure 5:
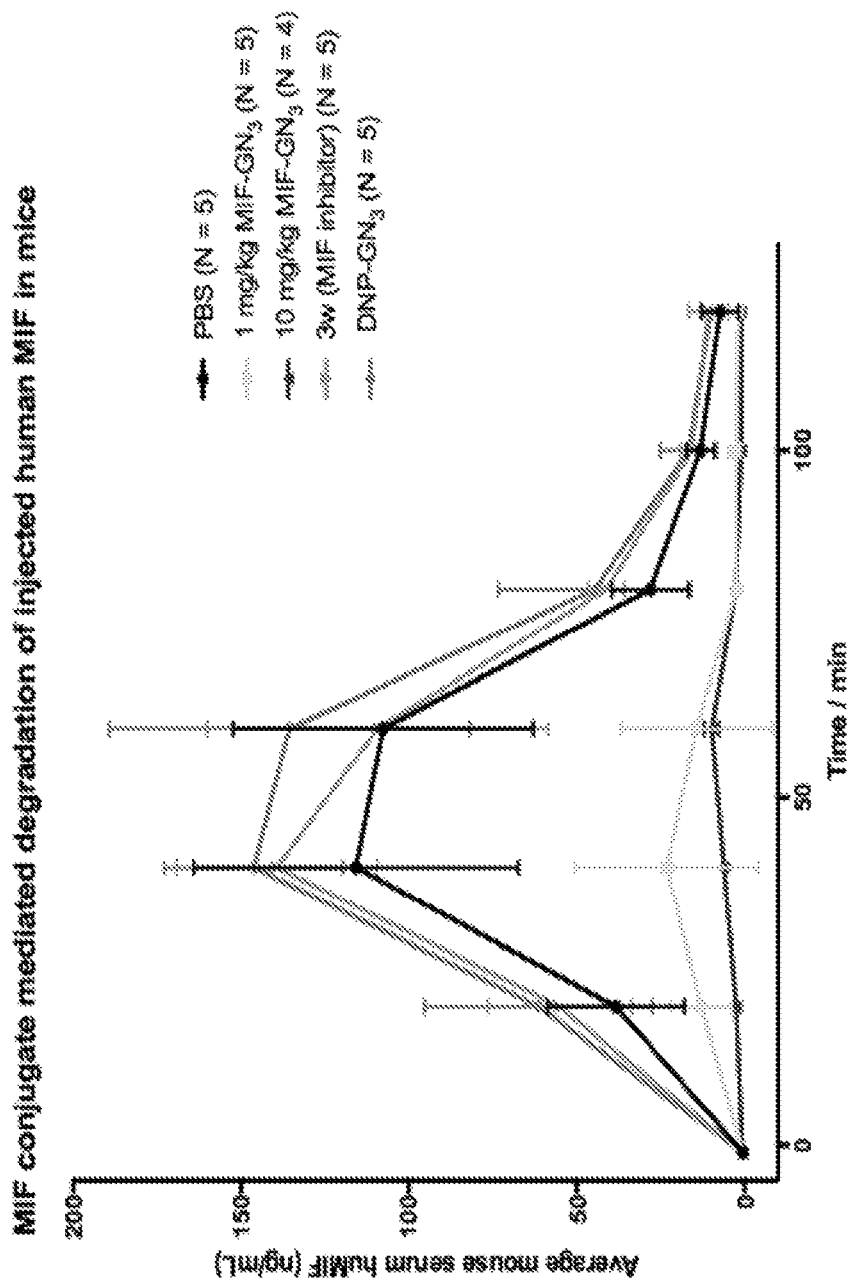
Figure 5:
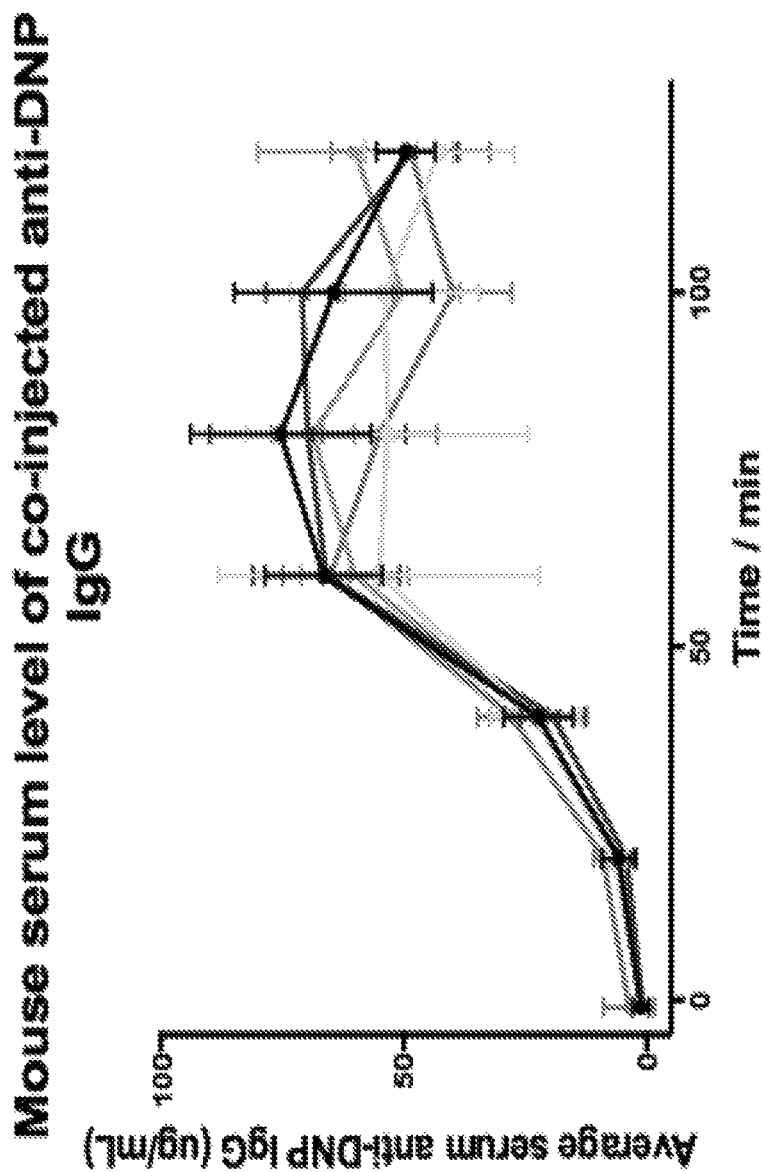

FIG. 5 shows that MIF-GN3 mediates the depletion of injected human MIF from mice. Human MIF has a half-life of approximately 40 minutes in mice. In this experiment, human recombinant MIF (Cayman chemical) was co-injected into mice with an anti-DNP IgG, which was used as an injection positive control. In particular, nude mice were injected with 5 µg recombinant human MIF and 200 µg anti-DNP IgG as an injection control (FIG. 4). MIF-GN3 was then injected at the concentration shown and blood drawn every twenty minutes over the course of two hours. Serum was diluted 1:100 and analyzed for MIF content by sandwich ELISA (biolegend monoclonal anti-MIF and biotinylated anti-MIF antibodies). The levels of the injected IgG were not significantly different between testing groups. In the mice treated with MIF-GN3, a moderate increase in huMIF levels up to 20 ng/ml was seen, while in mice injected with PBS negative control, serum levels of up to 150 ng/ml were observed, evidencing a substantial decrease in huMIF levels as a consequence of the administration of MIF-GN3.

Figure 6:
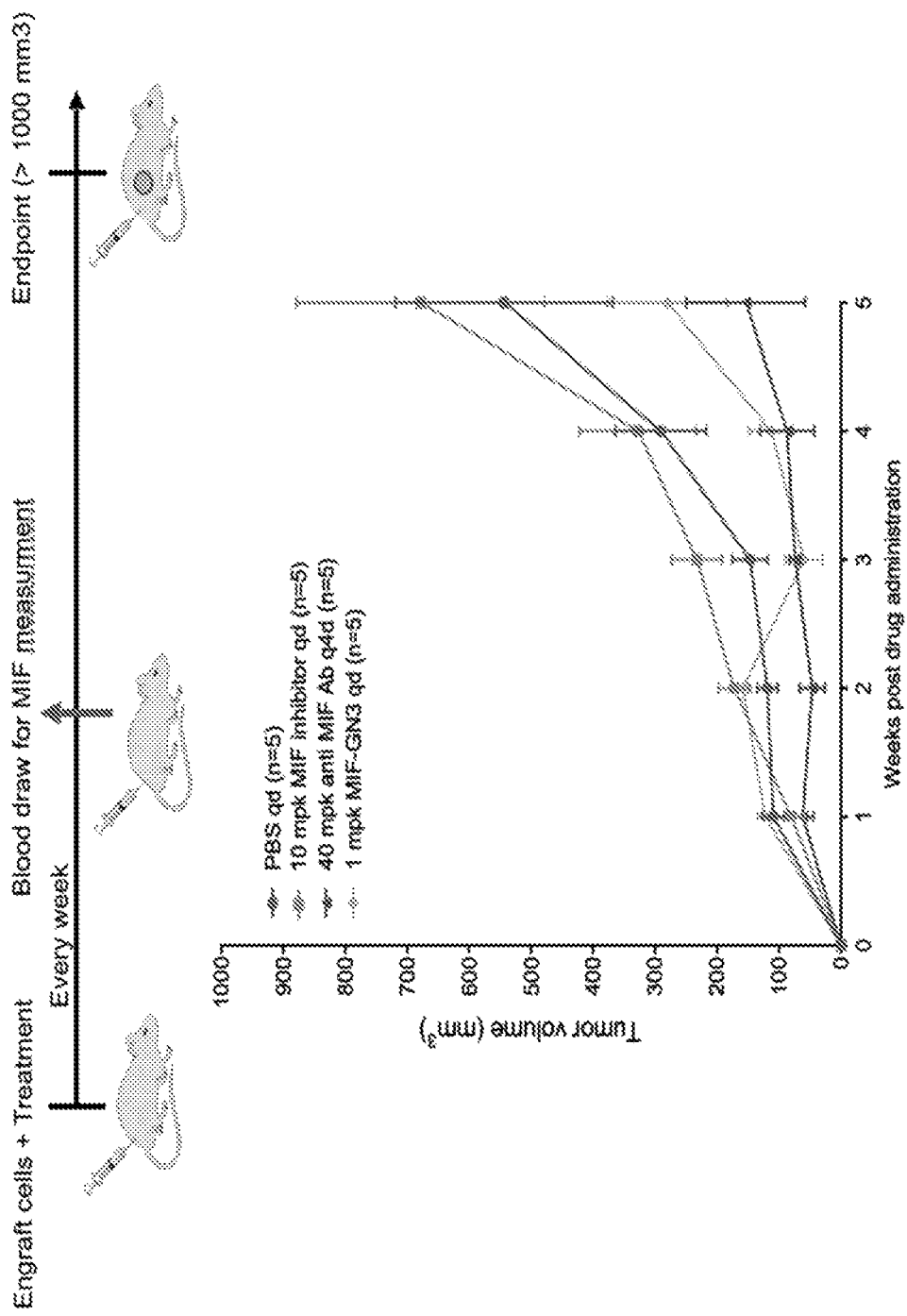
FIG. 6 shows that MIF-GN3 is able to delay tumor growth in a mouse model of prostate cancer.

FIG. 6 shows that MIF-GN3 is able to delay tumor growth in a mouse model of prostate cancer. In this experiment, nude mice were engrafted with PC3 human prostate cancer cells. Treatment was then initiated immediately with either a non-bifunctional MIF inhibitor (3w), an anti-MIF antibody, or MIF-GN3. MIF-GN3 showed a slowing of tumor growth over the course of the experiment, comparable to the MIF-neutralizing antibody. 3w did not inhibit tumor growth, validating the necessity of degrading MIF for therapeutic efficacy.

FIG. 7 shows molecules DNP-GN3 and DNP-AcF3-3, which are bifunctional molecules that bind to anti-DNP IgG and ASGPR. These compounds were used in several of the experiments as described below.

Figure 8:
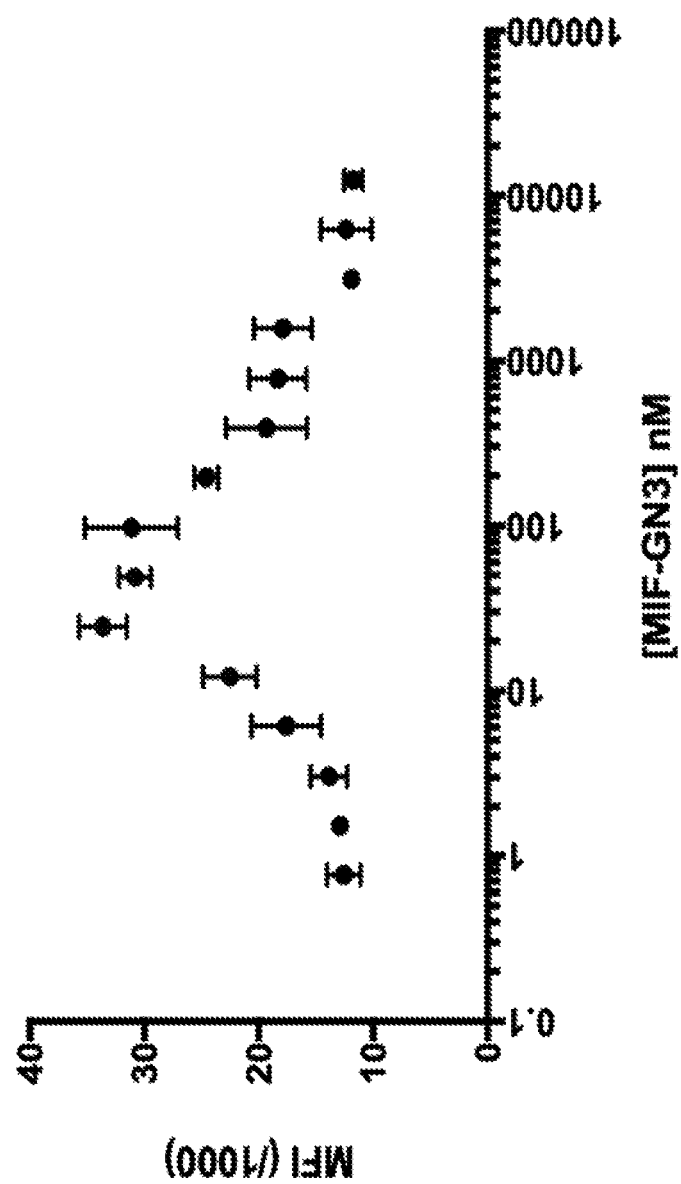
FIG. 8 shows that DNP-GN3 and DNP-AcF3-3 mediate the formation of a ternary complex between HepG2 cells and anti-DNP.
Figure 8:
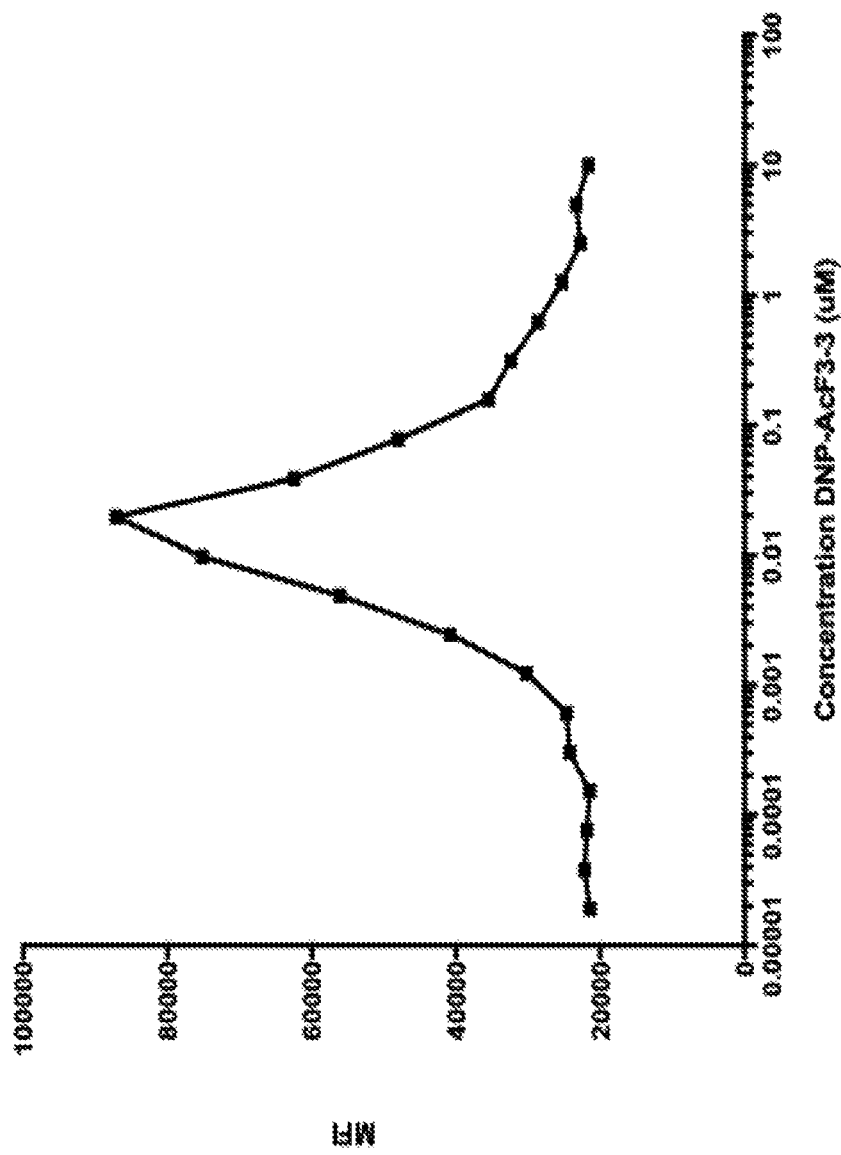

FIG. 8 shows that DNP-GN3 and DNP-AcF3-3 mediate the formation of a ternary complex between HepG2 cells and anti-DNP, thus validating the bifunctional character of the molecules. In this experiment, ASGPR-expressing HepG2 cells were incubated with bifunctional molecules and alexa-488 labeled anti-DNP (Thermo). The readout is mean fluorescence intensity of the cell population. Fluorescence was measured using a flow cytometer.

Figure 9:
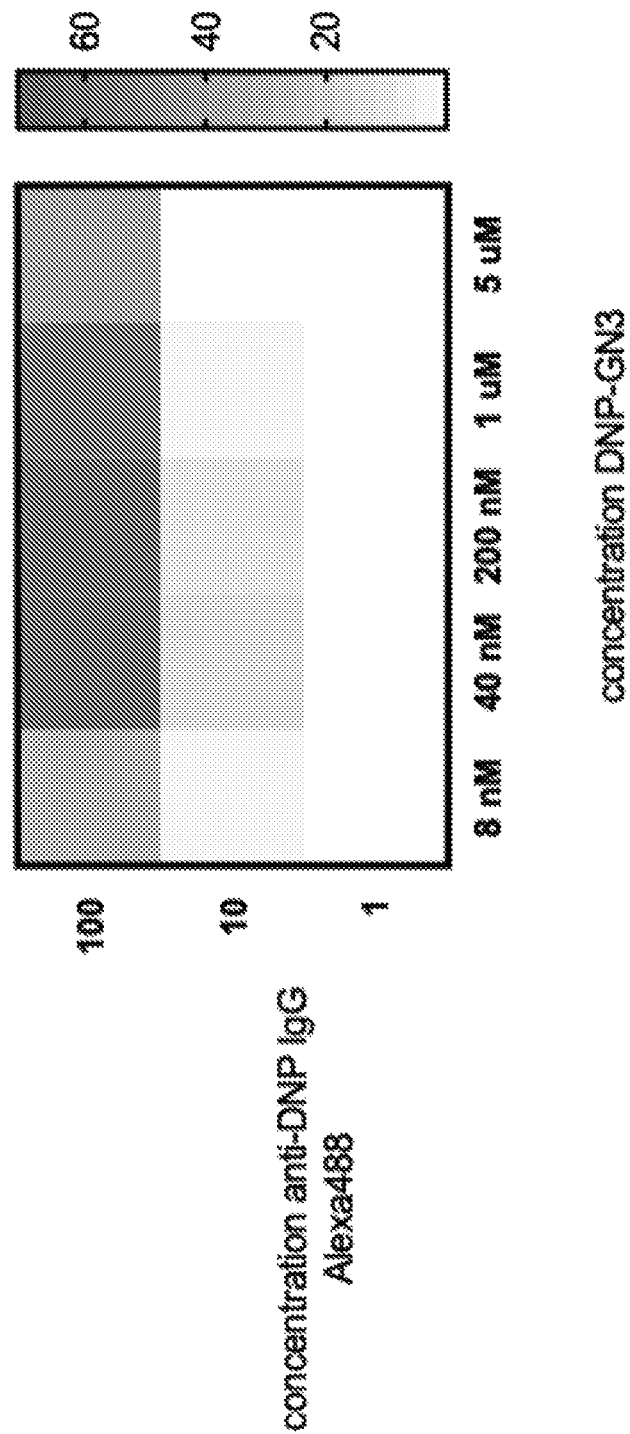
FIG. 9 shows that DNP-GN3 and DNP-AcF3-3 mediate the uptake of alexa 488-labeled anti-DNP by HepG2 cells.
Figure 9:
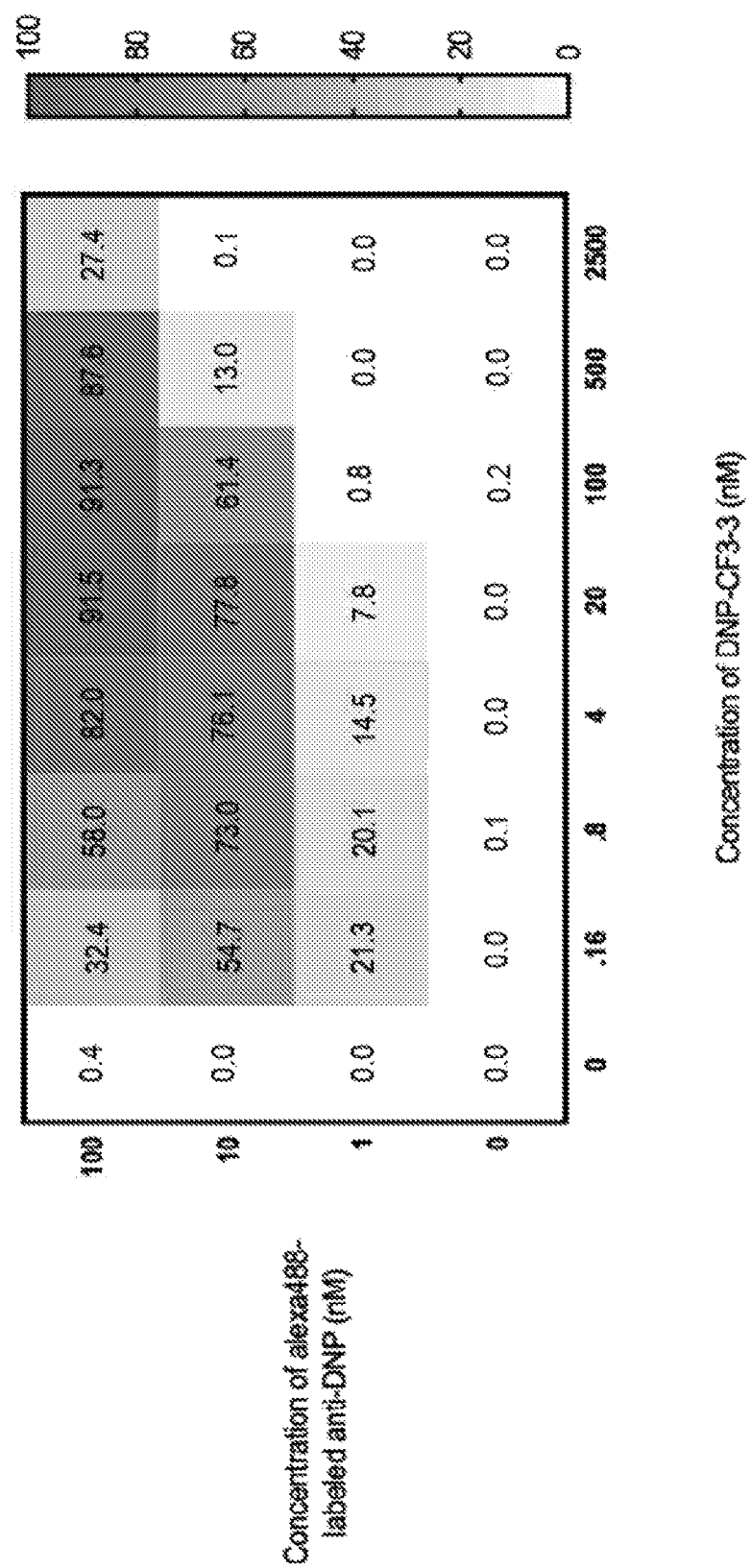

In a further experiment, the results presented in FIG. 9 show that DNP-GN3 and DNP-AcF3-3 mediate the uptake of alexa 488-labeled anti-DNP by HepG2 cells. The assay carried out in this experiment was as is described above for MIF uptake. Readout is percentage of Alexa 488-positive cells after 6 hours. Fluorescence was measured using a flow cytometer.

Figure 10:
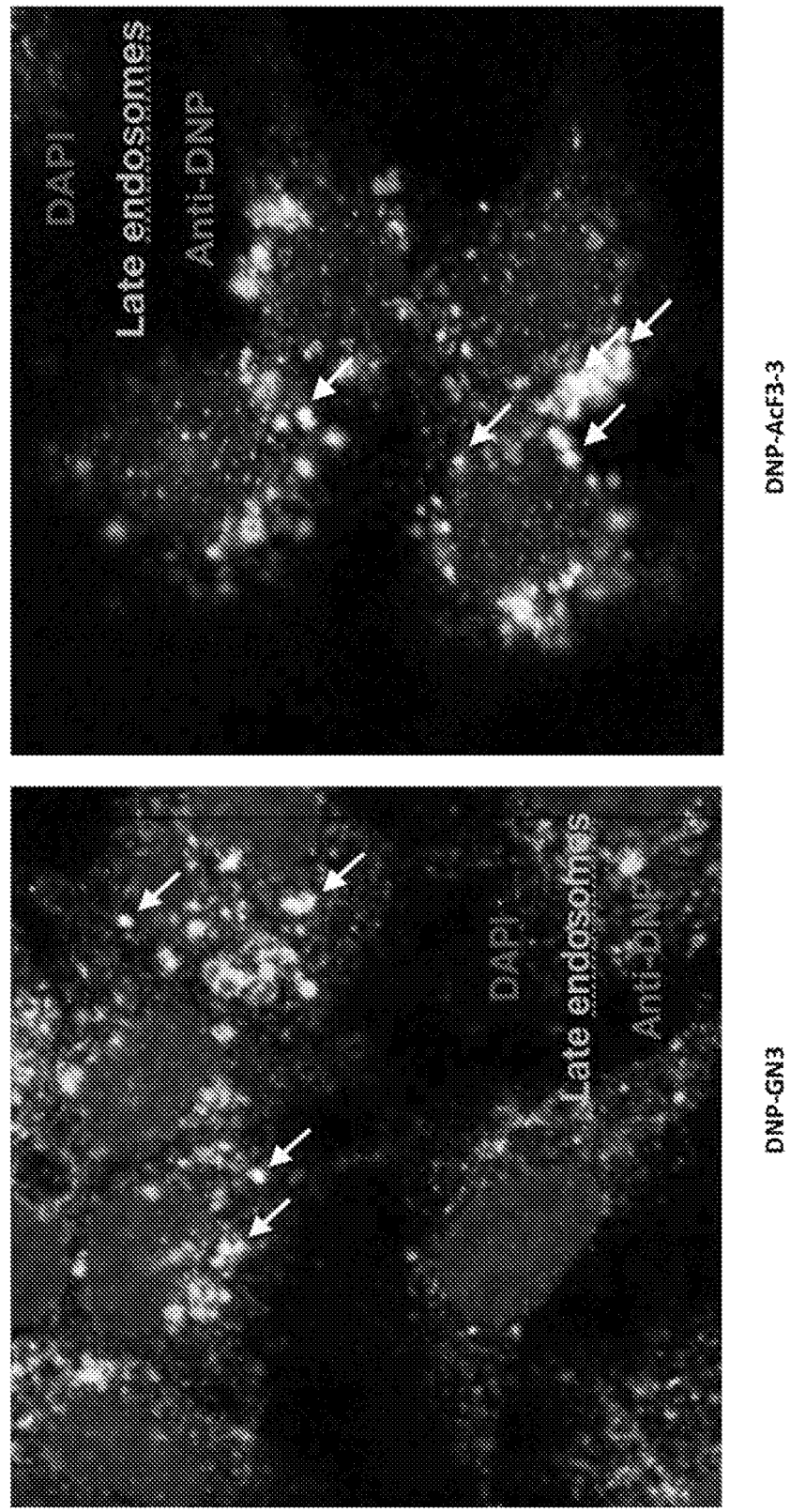
FIG. 10 shows that DNP-GN3 and DNP-AcF3-3 mediate the localization of alexa 568 labeled anti-DNP to late endosomes and lysosomes.

FIG. 10 shows that DNP-GN3 and DNP-AcF3-3 mediate the localization of alexa 568 labeled anti-DNP to late endosomes and lysosomes. This experiment was carried out as described above for the MIF colocalization studies.

Figure 11:
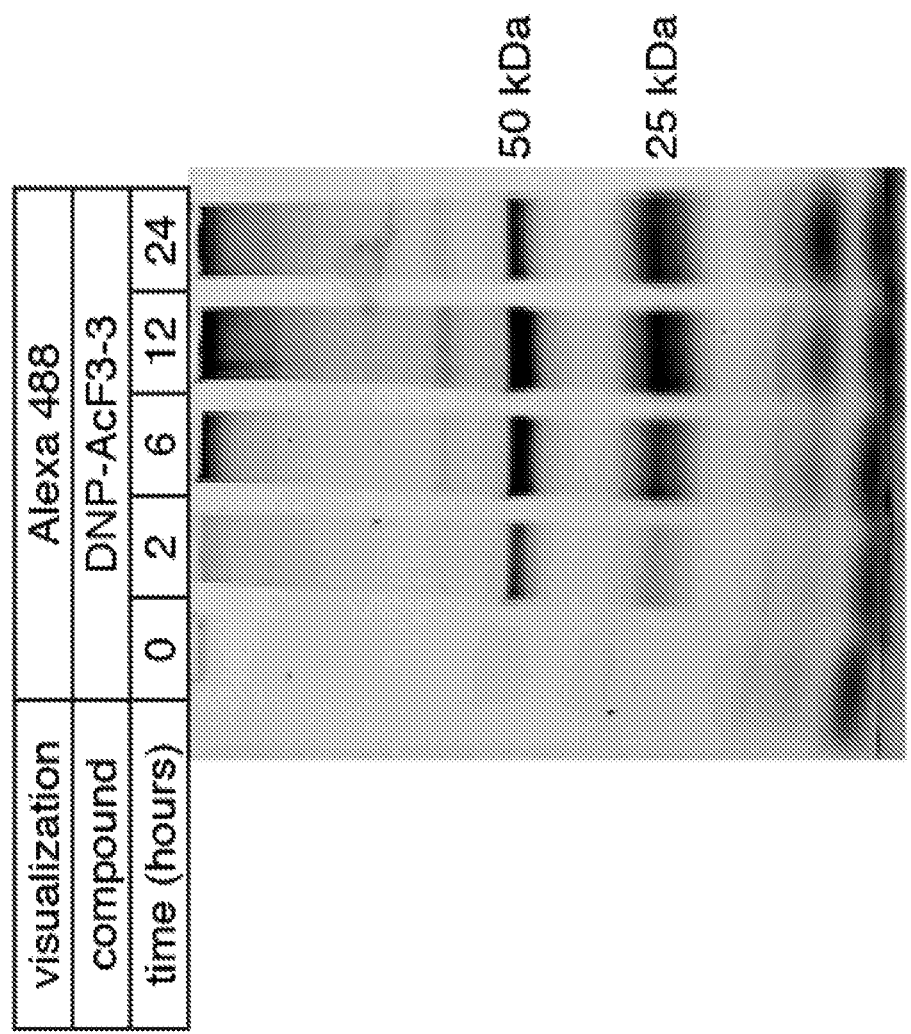
FIG. 11 shows that DNP-AcF3-3 mediates the degradation of alexa 488-labeled anti-DNP in HepG2 cells.

The experimental results presented in FIG. 11 show that DNP-AcF3-3 mediates the degradation of alexa 488-labeled anti-DNP in HepG2 cells. In this experiment, cells were incubated with 1 uM alexa 488-labeled anti-DNP (Thermo) and 200 nM DNP-AcF3-3. Cells were lysed (RIPA in PBS, containing protease inhibitors) at the given time and assayed by SDS-PAGE gel. Readout is fluorescence of protein fragments.

Figure 12:
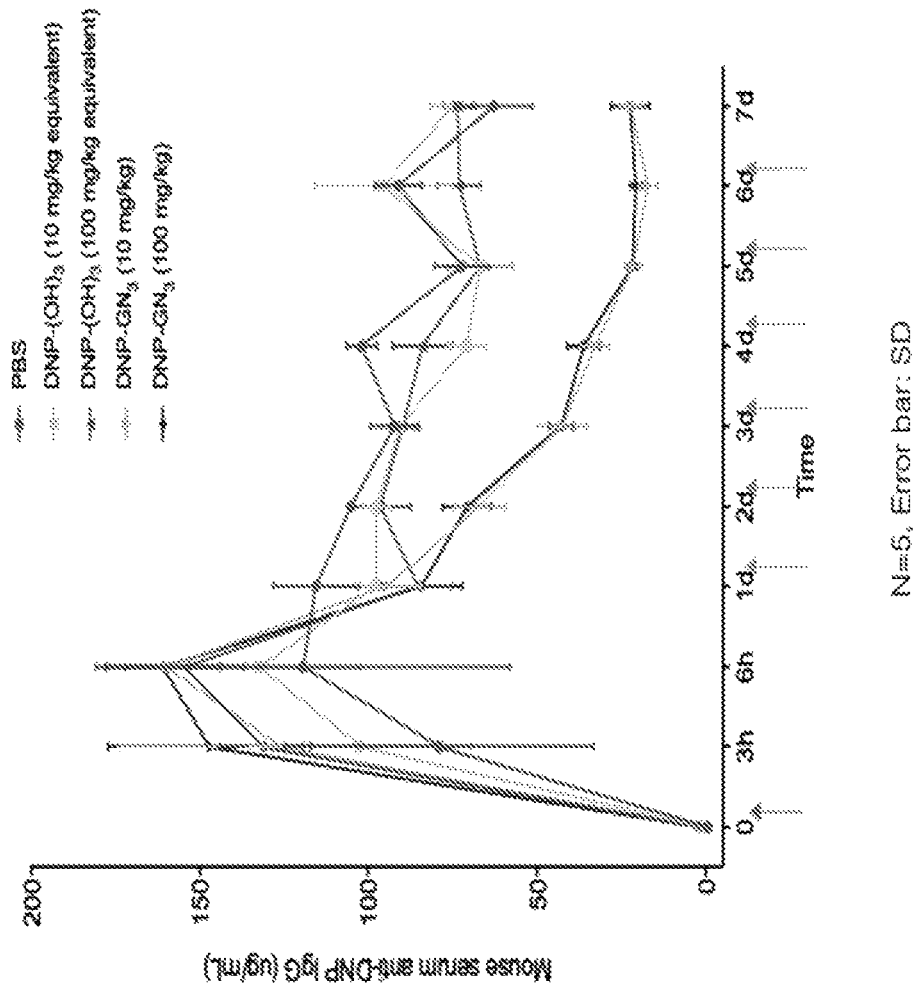
FIG. 12 shows that DNP-GN3 mediates the depletion of anti-DNP from mouse serum.

The results presented in FIG. 12 evidence that DNP-GN3 mediates the depletion of anti-DNP from mouse serum. Mice were injected with anti-DNP on day 0, then treated with the given compounds each day for 6 days. Serum IgG levels were measured by ELISA. DNP-$(OH)_3$ is used as a non-bifunctional control molecule.

FIG. 13 shows the structures of IgG-degrading molecules IBA-GN3, Triazine-GN3, FcIII-GN3, and FcIII-4c-GN3.

Figure 14:
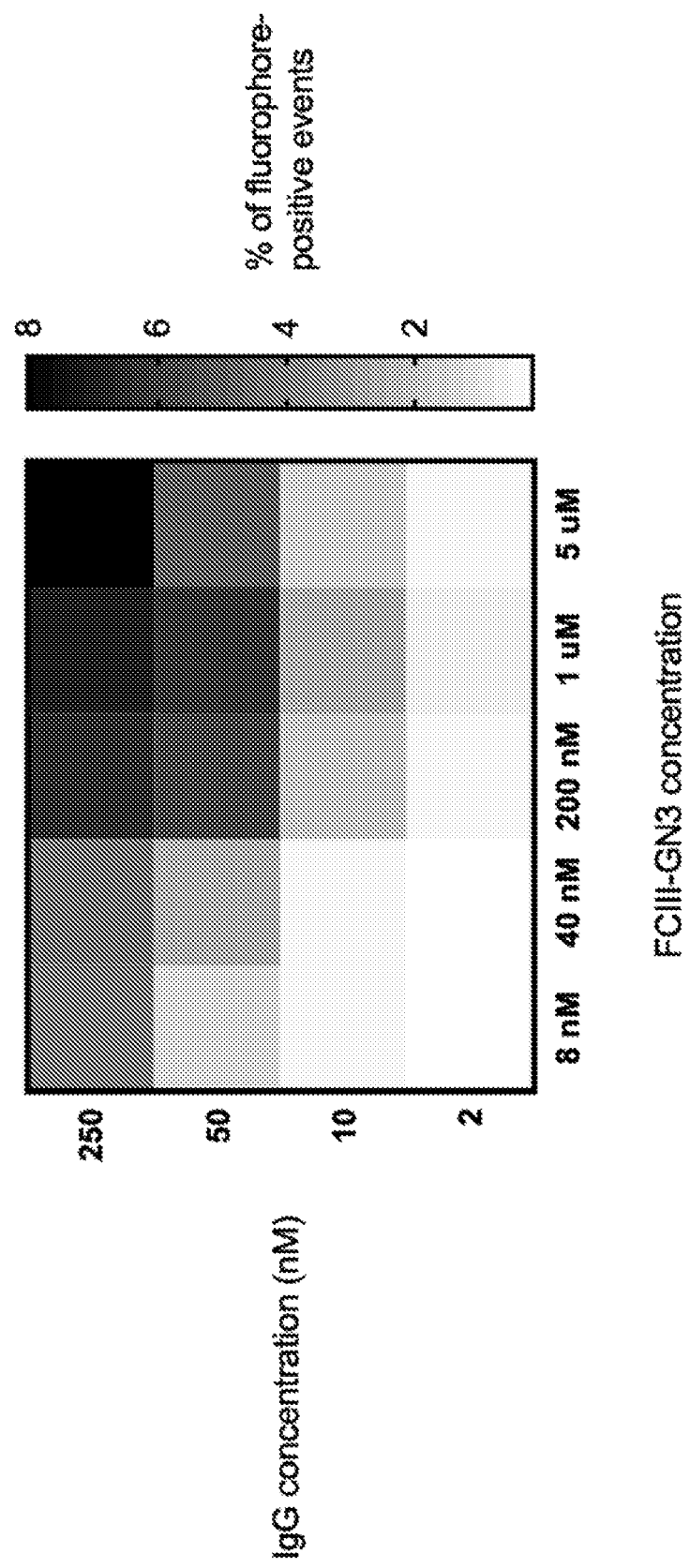
FIG. 14 shows that FcIII-GN3 mediates the uptake of human IgG into HepG2 cells. Experiment performed as described above.

FIG. 14 shows that FcIII-GN3 mediates the uptake of human IgG into HepG2 cells. This experiment was performed as described above.

Figure 15:
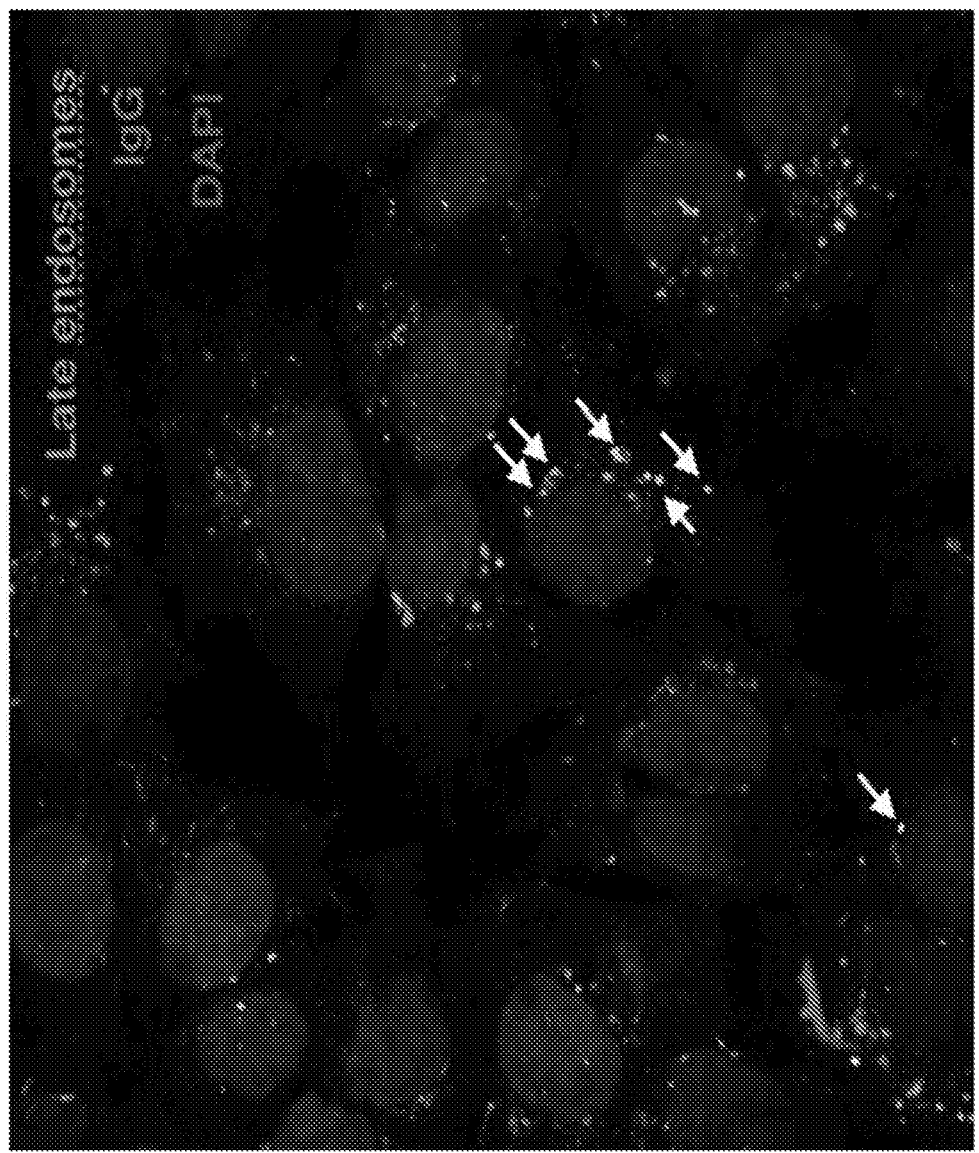
FIG. 15 shows that FcIII-GN3 mediates the localization of IgG to late endosomes in HepG2 cells. Experiment performed as described above.

FIG. 15 shows that FcIII-GN3 mediates the localization of IgG to late endosomes in HepG2 cells. Experiment performed as described above.

Additional Biological Data for Compounds with Varying CRBM Groups

Cells lines are chosen which express the cellular receptor at high levels. These Procedure Compound 31 (1.57 g, 4.42 mmol) was dissolved in DCM (45 mL) and TBAF (5.3 mL, 1M in THF, 5.30 mmol, 1.2 eq) was added dropwise. After 1 minute of stirring 10% citric acid (50 mL) was added and the reaction stirred for 30 minutes. The organic phase was washed with water (1×), dried, and evaporated to give compound 32, which was used in the next step without further purification.

$^1$H NMR (600 MHz, Chloroform-d) δ 8.11-8.00 (m, 1H), 7.51 (d, J=8.4 Hz, 1H), 7.38 (dd, J=9.3, 2.3 Hz, 1H), 7.05 (d, J=2.4 Hz, 1H), 4.15 (p, J=6.6, 6.0 Hz, 3H), 3.43-3.36 (m, 1H), 2.56 (t, J=7.2 Hz, 1H), 2.22-2.14 (m, 1H), 1.73-1.64 (m, 1H), 1.47 (q, J=7.4 Hz, 1H), 1.26 (t, J=7.1 Hz, 2H), 1.02 (t, J=7.3 Hz, 1H).

CNMR: $^{13}$C NMR (151 MHz, cdcl$_3$) δ 173.06, 137.60, 129.91, 128.64, 124.50, 123.18, 122.48, 105.99, 105.58, 77.20, 76.99, 76.77, 67.12, 60.51, 59.14, 30.67, 24.42, 24.22, 19.80, 14.21, 13.69.

HRMS: [M+H]$^+$ Expected 284.129. Found 284.327
MIF-4

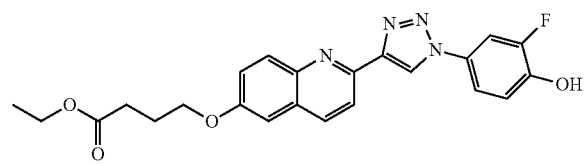 [SMILES: CCOC(=O)CCCOc1ccc2nc(-c3cn(-c4ccc(O)c(F)c4)nn3)ccc2c1]

2-fluoro-4-iodophenol (126 mg, 0.529 mmol) and sodium azide (38 mg, 0.528 mmol, 1.0 eq) were dissolved in DMSO (2.5 mL) and stirred for two hours at 70°. Compound 32 (150 mg, 0.529 mmol, 1 eq), trans-N,N'-dimethylcyclohexane-1,2-diamine (11 mg, 0.079 mmol, 0.15 eq), sodium ascorbate (10 mg, 0.053 mmol, 0.1 eq), copper (I) iodide (15 mg, 0.079 mmol, 0.15 eq), and H$_2$O (2.5 mL) were then added, and the mixture stirred at 70° overnight. The reaction was diluted with ethyl acetate and washed with H$_2$O (1×) and brine (1×). The organic layer was dried over sodium sulfate, evaporated, and purified on silica (DCM/EtOAc) to give compound 33.

$^1$H NMR (600 MHz, DMSO-d$_6$) δ 10.46 (s, 1H), 9.32 (s, 1H), 8.39 (d, J=8.6 Hz, 1H), 8.23 (d, J=8.5 Hz, 1H), 7.95 (dd, J=11.6, 2.6 Hz, 2H), 7.77-7.71 (m, 1H), 7.43 (dd, J=4.8, 2.0 Hz, 2H), 7.16 (t, J=9.0 Hz, 1H), 4.17 (d, J=6.3 Hz, 2H), 4.13-4.07 (m, 3H), 3.17 (d, J=5.2 Hz, 3H), 2.53 (d, J=7.3 Hz, 3H), 2.07 (t, J=6.8 Hz, 2H), 1.19 (d, J=7.1 Hz, 3H), 0.94 (d, J=7.3 Hz, 1H).

$^{13}$C NMR (151 MHz, dmso) δ 172.96, 156.95, 151.95, 150.34, 148.62, 145.98, 143.82, 136.47, 130.40, 129.01, 123.19, 121.83, 119.06, 118.62, 117.31, 109.87, 109.72, 107.12, 67.43, 60.35, 49.03, 40.48, 40.36, 40.22, 40.09, 39.95, 39.81, 39.67, 39.53, 30.61, 24.58, 23.48, 14.56, 13.93.

HRMS: Expected 437.163. Found 437.164.
MIF-5

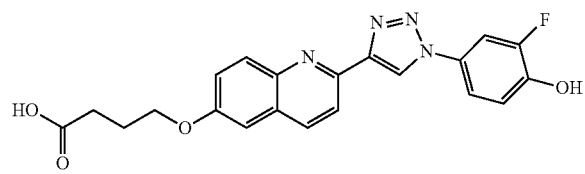 [SMILES: O=C(O)CCCOc1ccc2nc(-c3cn(-c4ccc(O)c(F)c4)nn3)ccc2c1]

Compound 33 (90 mg, 0.206 mmol) was dissolved in dioxane (6 mL) and 2M NaOH (3 mL). The reaction was stirred for 2.5 hours at room temperature, at which time the reaction was diluted with water and the pH adjusted to 3-4 with 1M HCl. The mixture was cooled to 4° and filtered to give compound 34, which was used without further purification.

2. GalNAc Spacer (FIG. 14)

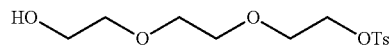 [SMILES: Cc1ccc(S(=O)(=O)OCCOCCOCCO)cc1]

Triethylene glycol (17.5 mL, 19.7 g, 131.13 mmol, 5 eq) was dissolved in DCM (150 mL) and trimethylamine (5.48 mL, 3.98 g, 1.5 eq) and cooled to 0°. TsCl (5.00 g, 26.23 mmol, 1 eq) was then added and the reaction mixture stirred at room temperature for 18 hours. The reaction was diluted into DCM and washed with water (3×) and brine (1×). The organic layer was dried over sodium sulfate and concentrated in vacuo. The crude product was purified on silica (0-5% MeOH in DCM) to give compound 64 (6.89 g, 22.6 mmol) in 85% yield.

$^1$H NMR (400 MHz, Chloroform-d) δ 7.80 (d, J=8.3 Hz, 2H), 7.38-7.30 (m, 2H), 4.23-4.14 (m, 2H), 3.71 (td, J=5.3, 4.3 Hz, 4H), 3.66-3.55 (m, 6H), 2.45 (s, 3H).

$^{13}$C NMR (101 MHz, cdcl$_3$) δ 144.98, 133.09, 129.95, 128.09, 72.58, 70.91, 70.44, 69.28, 68.84, 61.88, 21.76.

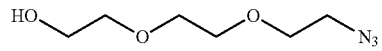

Compound 64 (2.00 g, 6.57 mmol) and sodium azide (0.470 g, 7.23 mmol, 1.1 eq) were dissolved in DMF (40 mL) and stirred overnight at 60°. 25 mL of DMF was then removed by rotary evaporation, and the resulting mixture diluted into water and extracted with ethyl acetate (2×). The organic layers were washed with brine (3×), dried over sodium sulfate, and evaporated. The crude product was purified on silica (0-5% MeOH in DCM) to give compound 65 (932 mg, 5.32 mmol) in 81% yield.

3. GalNAc ASGPR Ligand (FIG. 15)

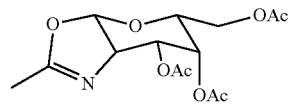

Galactosamine pentaacetate (100 mg, 0.257 mmol) was dissolved in dichloroethane (1 mL) and stirred at room temperature before the addition of TMSOTf (70 uL, 86.0 mg, 0.387 mmol, 1.5 eq). The reaction was stirred at 50° for 90 minutes, then allowed to cool to room temperature and stirred for a further 12 hours. The reaction was poured into ice cold saturated sodium bicarbonate and extracted into DCM. The organic layer was washed with water (2×), dried over sodium sulfate, and evaporated to give compound 66 (0.236 mmol, 77.7 mmol, 92%) as a dark gum, which was used without further purification.
HNMR $^1$H NMR (400 MHz, Chloroform-d) δ 5.98 (d, J=6.8 Hz, 1H), 5.45 (t, J=3.0 Hz, 1H), 4.90 (dd, J=7.4, 3.3 Hz, 1H), 4.29-4.20 (m, 1H), 4.17 (d, J=6.9 Hz, 1H), 4.10 (dd, J=11.1, 5.7 Hz, 1H), 3.99 (td, J=7.1, 1.4 Hz, 1H), 2.11 (s, 3H), 2.05 (m, J=7.6 Hz, 6H).
CNMR
$^{13}$C NMR (101 MHz, cdcl$_3$) δ 170.46, 170.13, 169.78, 166.35, 121.82, 118.64, 101.41, 71.76, 69.44, 65.25, 63.53, 61.56, 46.82, 20.77, 20.68, 20.54, 14.41, 8.64, −0.06.

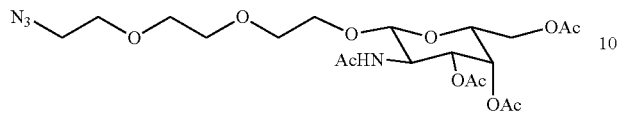

Compound 66 (200 mg, 0.607 mmol) and compound 65 (160 mg, 0.913 mmol, 1.5 eq) were dissolved in 1,2-dichloroethane (5 mL). 4 Å molecular sieves were then added, and the reaction stirred for 30 minutes. TMSOTf (55 uL, 67.5 mg, 0.304 mmol, 0.5 eq) was then added to the mixture, and the reaction stirred overnight. The mixture was diluted into DCM, washed with 1M sodium bicarbonate (1×) and water (1×), then dried over magnesium concentrate and concentrated. The crude oil was purified on silica gel (50-100% EtoAc in DCM) to give compound 67 (245 mg, 0.486 mmol) in 80.1% yield.

$^1$H NMR (400 MHz, Chloroform-d) δ 6.13 (d, J=9.3 Hz, 1H), 5.31 (dd, J=3.4, 1.1 Hz, 1H), 5.05 (dd, J=11.2, 3.4 Hz, 1H), 4.77 (d, J=8.6 Hz, 1H), 4.28-4.04 (m, 3H), 3.93-3.79 (m, 3H), 3.78-3.58 (m, 8H), 3.43 (dt, J=28.2, 4.9 Hz, 4H), 2.15 (s, 3H), 2.04 (s, 3H) 1.98 (s, 3H), 1.97 (s, 3H)

$^{13}$C NMR (101 MHz, cdcl$_3$) δ 170.24, 170.09, 169.99, 101.84, 72.06, 71.27, 70.50, 70.29, 70.27, 70.20, 70.00, 69.98, 69.67, 69.37, 68.18, 66.30, 61.38, 61.17, 50.32, 50.26, 50.11, 22.80, 20.37, 20.31

HRMS: [M+Na]$^+$ 527.207 found 527.203

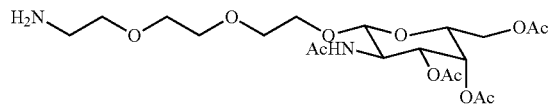 [SMILES: CC(=O)NC1C(OCCOCCOCCN)OC(COC(C)=O)C(OC(C)=O)C1OC(C)=O]

Compound 67 (1.80 g, 3.57 mmol) was dissolved in THF (35 mL). Triphenylphosphine (1.40 g, 5.35 mmol, 1.5 eq) and water (257 uL, 14.28 mmol, 4 eq) were then added and the reaction stirred at room temperature under nitrogen for 36 hours. The solvent was removed and the crude product used in the next step without further purification.

4. Tris Valent Glycine (FIG. 16)

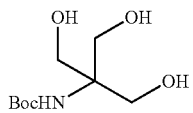

Tris base (5.00 g, 41.3 mmol) was dissolved in dichloromethane (80 mL) and trimethylamine (20 mL). Di-tert-butyl dicarbonate (10.81 g, 49.6 mmol, 1.2 eq) was then added, and the reaction stirred for 4 hours. The mixture was evaporated and the residue portioned between ethyl acetate and water. The organic fraction was washed with water (1×), 1M HCl (2×), saturated sodium bicarbonate (1×), and brine (1×) before drying over sodium sulfate and evaporation to give compound 23 (9.04 g, 40.9 mmol) in 99% yield, which was used without purification in further steps.

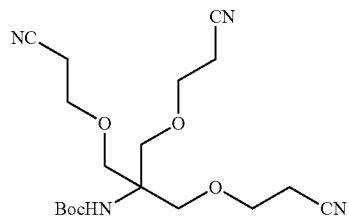 [SMILES: CC(C)(C)OC(=O)NC(COCCC#N)(COCCC#N)COCCC#N]

Compound 27 (9.04 g, 40.9 mmol) was dissolved in a mixture of dioxane (17 mL) and aqueous KOH (4.98 g, 88.7 mmol, 2.46 mL). Acrylonitrile (8.84 mL, 7.16 g, 135.0 mmol, 3.3 eq) was then added dropwise over a period of 2.5 hours, and the reaction stirred under nitrogen for 24 hours. The reaction was neutralized with the addition of 2M HCl (30 mL) and portioned between DCM and water. The organic layer was washed with water (2×) and brine (1×), dried over sodium sulfate, and evaporated. The crude mixture was purified on silica (0-80% EtOAc in hexanes) to give compound 20 (7.87 g, 20.7 mmol) in 59% yield.

HNMR: $^1$H NMR (400 MHz, Chloroform-d) δ 4.84 (s, 1H), 3.73 (s, 6H), 3.65 (t, J=6.1 Hz, 6H), 2.57 (t, J=6.1 Hz, 6H), 1.35 (s, 9H).

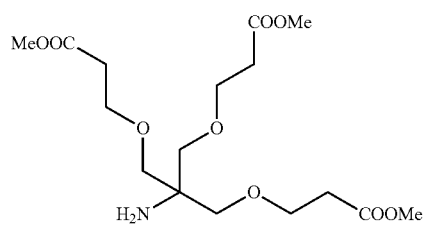

Compound 28 (7.87 g, 20.7 mmol) was dissolved in MeOH (40 mL) and concentrated sulfuric acid (10 mL) was added. The reaction was stirred at reflux under nitrogen for 24 hours, then neutralized with sodium bicarbonate. Methanol was evaporated, and the residue partioned between water and ethyl acetate. The ethyl acetate layer was washed with sodium bicarbonate (1×) and brine (1×), then dried over sodium sulfate. The crude residue was purified on silica (10% MeOH in DCM) to give compound 29 (5.50 g, 14.5 mmol) in 70% yield.

HNMR: $^1$H NMR (400 MHz, Chloroform-d) δ 3.79-3.64 (m, 15H), 3.32 (s, 6H), 2.56 (t, J=6.3 Hz, 6H).

CNMR: $^{13}$C NMR (101 MHz, cdcl$_3$) δ 172.03, 72.52, 66.77, 56.10, 51.62, 34.80.

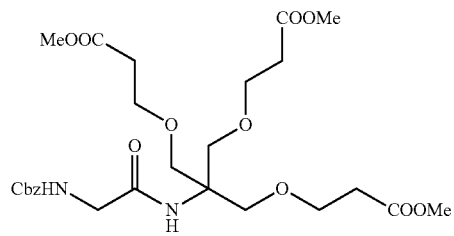 [SMILES: COC(=O)CCOCC(COCCC(=O)OC)(COCCC(=O)OC)NC(=O)CNC(=O)OCc1ccccc1]

Compound 70 (723 mg, 1.90 mmol) was dissolved in MeCN (25 mL). HOBT (291 mg, 1.90 mmol, 1 eq), Cbz-glycine (397 mg, 1.90 mmol, 1 eq), and DCC (392 mg, 1.90 mmol, 1 eq) were then added, and the reaction stirred overnight. MeCN was then evaporated, and the residue adsorbed onto silica and purified using a gradient of 0-75% EtOAc in hexanes. Compound 71 (866 mg, 1.52 mmol) was recovered in 80% yield.

$^1$H NMR (600 MHz, Chloroform-d) δ 7.33 (dd, J=24.9, 4.4 Hz, 5H), 6.33 (s, 1H), 5.55 (s, 1H), 5.12 (s, 2H), 3.86 (d, J=5.1 Hz, 2H), 3.68 (t, J=5.5 Hz, 21H), 3.49 (s, 1H), 2.53 (t, J=6.1 Hz, 6H).

$^{13}$C NMR (151 MHz, cdcl$_3$) δ 172.14, 168.67, 156.32, 136.41, 128.45, 128.05, 127.98, 69.04, 66.85, 66.71, 59.83, 51.69, 44.55, 34.64.

Expected: [M+H]$^+$ 571.250. found 571.243.

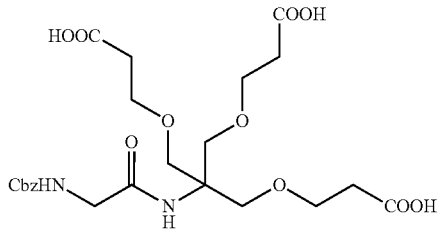 [SMILES: O=C(O)CCOCC(COCCC(=O)O)(COCCC(=O)O)NC(=O)CNC(=O)OCc1ccccc1]

Compound 71 (100 mg, 0.175 mmol) was dissolved in dioxane (2 mL) and 2M NaOH (2 mL). The reaction was stirred for 3 hours, then acidified and extracted twice into ethyl acetate. The organic fraction was washed with 1M HCl, then dried over sodium sulfate and evaporated to give compound 72, which was used in further steps without purification.

5. GalNAc Trivalent (FIG. 17)

Compound 72 (372 mg, 0.704 mmol, 1 eq) was dissolved in DMF (40 mL) and DIPEA (981 uL, 728 mg, 5.632 mmol, 8 eq). HBTU (1.01 g, 2.67 mmol, 3.8 eq) was then added, and the reaction stirred for 10 minutes at room temperature before the addition of compound 68 (1.28 g, 2.67 mmol, 3.8 eq). The reaction was stirred for two hours, then diluted into DCM and washed with H$_3$PO$_4$ (1M, 1×), NaHCO$_3$ (1M, 1×), and brine (1×). The organic layer was dried over sodium sulfate and evaporated onto silica. The residue was purified (0-20% MeOH in DCM) to give compound 73 (831 mg, 0.436 mmol) in 62% yield.

$^1$H NMR (500 MHz, DMSO-d$_6$) δ 7.91 (t, J=5.7 Hz, 3H), 7.80 (d, J=9.2 Hz, 3H), 7.39-7.28 (m, 6H), 7.12 (s, 1H), 5.21 (d, J=3.4 Hz, 3H), 5.02 (s, 2H), 4.97 (dd, J=11.2, 3.4 Hz, 3H), 4.55 (d, J=8.5 Hz, 3H), 4.10-3.99 (m, 9H), 3.92-3.84 (m, 3H), 3.81-3.75 (m, 3H), 3.62-3.46 (m, 35H), 3.39 (t, J=6.1 Hz, 6H), 3.23-3.16 (m, 6H), 2.30 (t, J=6.4 Hz, 6H), 2.10 (s, 9H), 1.99 (s, 9H), 1.89 (s, 9H), 1.77 (s, 9H).

$^{13}$C NMR (126 MHz, dmso) δ 170.40, 170.16, 170.09, 169.79, 169.48, 169.04, 156.60, 137.23, 128.50, 127.94, 127.84, 101.12, 72.50, 70.65, 70.07, 69.93, 69.86, 69.77, 69.59, 69.29, 68.50, 67.51, 66.89, 65.59, 61.63, 60.38, 59.84, 49.50, 43.77, 38.68, 36.01, 22.95, 20.68, 20.62, 20.60.

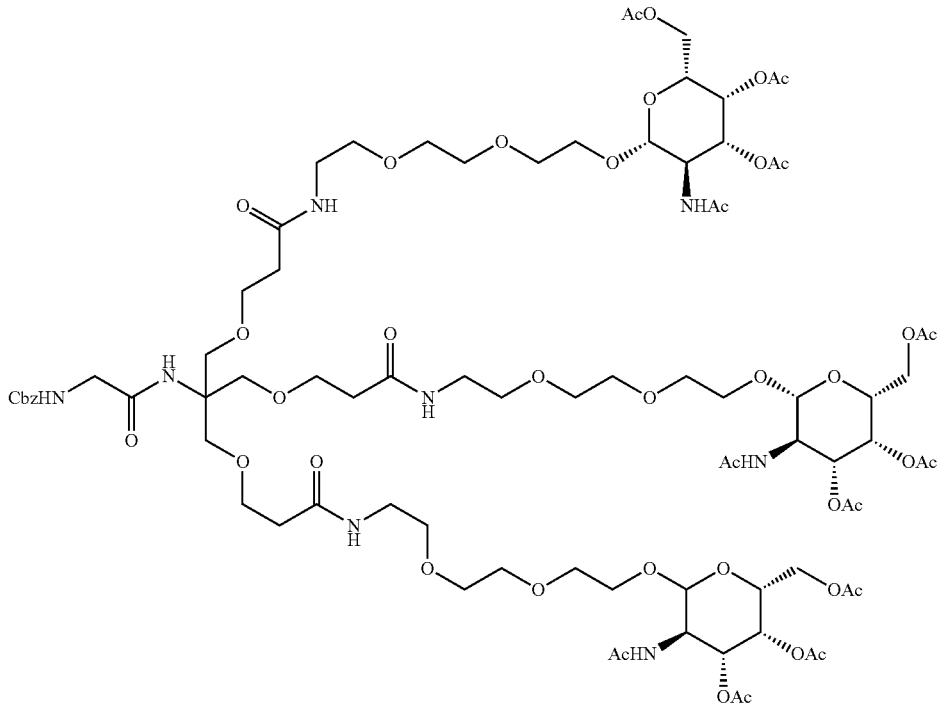 [SMILES: CC(=O)N[C@H]1[C@H](OCCOCCOCCNC(=O)CCOCC(COCCC(=O)NCCOCCOCCOC2O[C@H](COC(C)=O)[C@H](OC(C)=O)[C@H](OC(C)=O)[C@H]2NC(C)=O)(COCCC(=O)NCCOCCOCCO[C@@H]2O[C@H](COC(C)=O)[C@H](OC(C)=O)[C@H](OC(C)=O)[C@H]2NC(C)=O)NC(=O)CNC(=O)OCc2ccccc2)O[C@H](COC(C)=O)[C@H](OC(C)=O)[C@@H]1OC(C)=O]

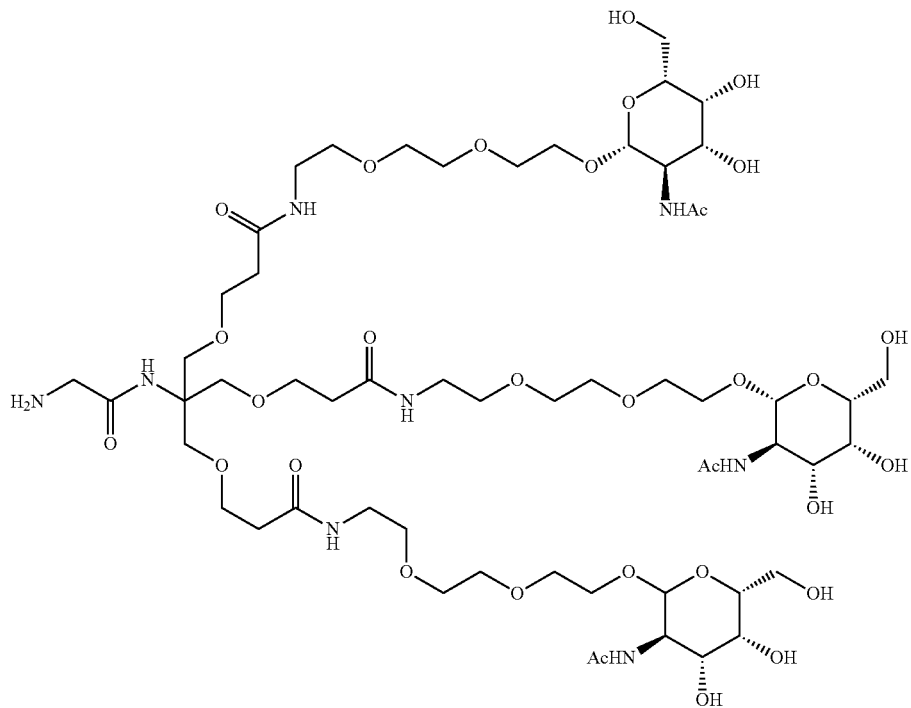 [SMILES: CC(=O)N[C@H]1[C@H](OCCOCCOCCNC(=O)CCOCC(COCCC(=O)NCCOCCOCCOC2O[C@H](CO)[C@H](O)[C@H](O)[C@H]2NC(C)=O)(COCCC(=O)NCCOCCOCCO[C@@H]2O[C@H](CO)[C@H](O)[C@H](O)[C@H]2NC(C)=O)NC(=O)CN)O[C@H](CO)[C@H](O)[C@@H]1O]

Compound 73 (710 mg, 0.372 mmol) was dissolved in dry methanol (90 mL) and cooled to 0° under nitrogen. Pd/C (71.0 mg, 10% w/w) was then added, and the reaction stirred under hydrogen (1 atm) at 0° for 16 hours. Upon completion, the reaction was filtered through celite and methanol evaporated to give compound 74 (657 mg, 0.370 mmol) in 99.5% yield, which was used without further purification.

Compound 74 (441 mg, 0.248 mmol) was dissolved in methanol (15 mL) and cooled to 0°. Sodium methoxide solution (400 uL, 5.4M in MeOH) was then added, and the reaction stirred for 30 minutes. Dowex 50WX8 was then added until the solution was weakly acidic. The resin was filtered off and washed thoroughly with methanol. The combined methanol fractions were evaporated under reduced pressure to give compound 75 (274 mg, 0.196 mmol) in 79% yield. Compound 75 was used in further steps without purification.

6. MIF-GN3 (FIG. 18)

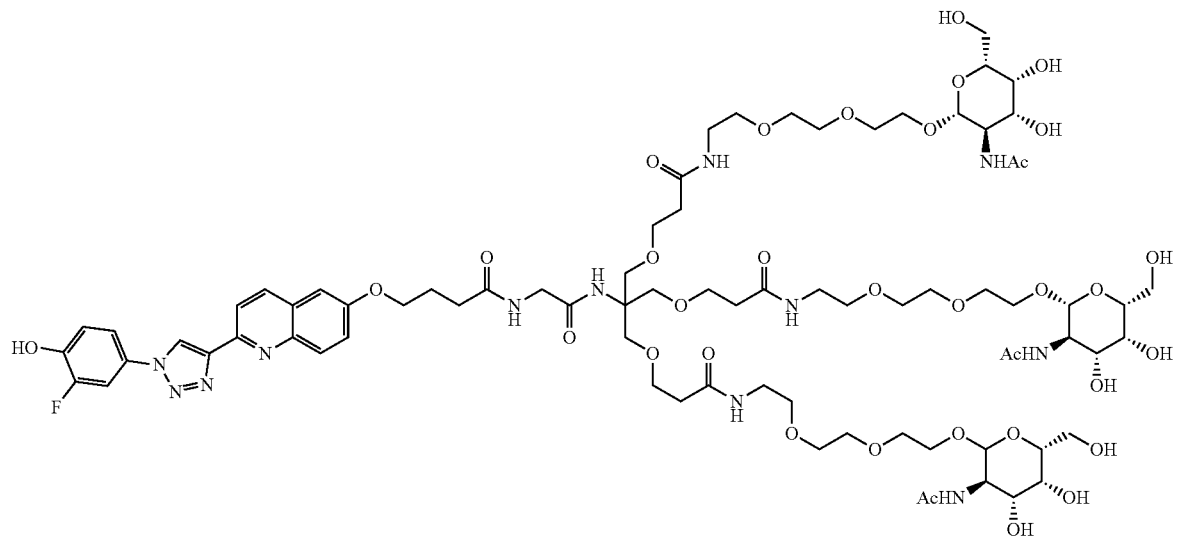 [SMILES: CC(=O)N[C@H]1[C@H](OCCOCCOCCNC(=O)CCOCC(COCCC(=O)NCCOCCOCCOC2O[C@H](CO)[C@H](O)[C@H](O)[C@H]2NC(C)=O)(COCCC(=O)NCCOCCOCCO[C@@H]2O[C@H](CO)[C@H](O)[C@H](O)[C@H]2NC(C)=O)NC(=O)CNC(=O)CCCOc2ccc3nc(-c4cn(-c5ccc(O)c(F)c5)nn4)ccc3c2)O[C@H](CO)[C@H](O)[C@@H]1O]

Compound 34 (23.5 mg, 0.0575 mmol, 1.1 eq) and HATU (20.0 mg, 0.0522 mmol, 1 eq) were dissolved in dry DMF (5 mL) and DIPEA (23.3 uL, 16.9 mg, 0.131 mmol, 2.5 eq) and stirred for 10 minutes at room temperature. Compound 75 (73.0 mg, 0.0522 mmol) was then added, and the reaction stirred for 30 minutes. The mixture was loaded directly onto HPLC and purified (20-30% MeCN in water, 3% TFA) to give compound 76 (12 mg, 0.0067 mmol) in 12.8% yield.

Expected [M+H]$^+$ 1787.801. found 1787.823.

7. Bicyclic ASGPR Spacer (FIG. 19)

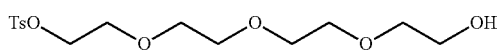 [SMILES: Cc1ccc(S(=O)(=O)OCCOCCOCCOCCO)cc1]

Tetraethylene glycol (50.0 g, 258 mmol) was dissolved in THF (1 mL), cooled to 0°, and stirred. NaOH (1.65 g, 41.3 mmol, 1.6 eq) in water (1 mL) was then added, followed by the dropwise addition of p-toluenesulfonyl chloride (4.92 g, 25.8 mmol, 1 eq) in THF (3 mL). The reaction mixture was stirred at 0° for 4 hours, then diluted into DCM. The organic layer was washed with ice-cold water (2×), brine (1×), and dried over sodium sulfate to give compound 16 (8.84 g, 25.4 mmol, 99% yield), which was used in further steps without purification.

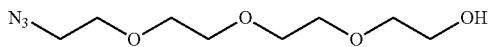 [SMILES: [N-]=[N+]=NCCOCCOCCOCCO]

Compound 16 (8.84 g, 25.4 mmol) was dissolved in 100% ethanol (200 mL) and sodium azide (4.128 g, 63.5 mmol, 2.5 eq) was added. The reaction was heated to reflux for 16 hours, then cooled to room temperature before the addition of water (150 mL). Ethanol was then evaporated under reduced pressure and the product extracted into ethyl acetate (2×). The organic layer was washed with water (1×) and brine (1×), dried over sodium sulfate, and evaporated to give compound 17 (4.82 g, 22.1 mmol) as a yellow oil in 87% yield.

HNMR: $^1$H NMR (400 MHz, Chloroform-d) δ 3.69-3.64 (m, 2H), 3.61 (m, J=4.2 Hz, 10H), 3.57-3.51 (m, 2H), 3.33 (td, J=5.0, 2.3 Hz, 2H), 2.81 (s, 1H).

CNMR: $^{13}$C NMR (101 MHz, cdcl$_3$) δ 72.47, 70.65, 70.63, 70.59, 70.52, 70.28, 69.99, 61.60, 50.59.

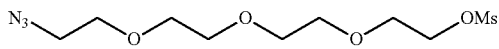 [SMILES: CS(=O)(=O)OCCOCCOCCOCCN=[N+]=[N-]]

Compound 17 (5.00 g, 22.8 mmol) was dissolved in pyridine (50 mL). Methanesulfonyl chloride (3.14 g, 27.4 mmol, 1.2 eq) was then added and the reaction stirred for six hours under nitrogen. The mixture was then diluted into ethyl acetate, washed with water (3×), 0.5M HCl (2×), saturated sodium bicarbonate (1×), and brine (1×), dried over sodium sulfate, and evaporated to give compound 18 (5.71 g, 19.2 mmol) in 84% yield.

HNMR: $^1$H NMR (400 MHz, Chloroform-d) δ 4.41-4.33 (m, 2H), 3.81-3.72 (m, 2H), 3.70-3.59 (m, 10H), 3.38 (t, J=5.0 Hz, 2H), 3.06 (s, 3H).

CNMR: $^{13}$C NMR (101 MHz, cdcl$_3$) δ 70.79, 70.75, 70.71, 70.15, 69.39, 69.11, 50.77, 37.78.

HRMS: Expected 298.107. found 298.105.

8. Bicyclic ASGPR Precursor (FIG. 20)

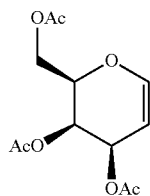 [SMILES: CC(=O)OC[C@H]1OC=C[C@@H](OC(C)=O)[C@H]1OC(C)=O]

Pentaacetyl galactose (25.0 g, 64.0 mmol) was dissolved in 33% HBr in HOAc (30 mL) and stirred under nitrogen for 2 hours. The reaction was diluted into EtOAc (500 mL) and washed with water (3×), saturated sodium bicarbonate (1×), and brine (1×). The organic layer was dried over sodium sulfate and evaporated to give compound 1 as a pale yellow oil in quantitative yield. The compound was used without further purification.

Compound 1 (26.34 g, 64.06 mmol) was dissolved in acetic acid (510 mL) and zinc (67.01 g, 1024 mmol) added. The mixture was stirred vigorously. A solution of CuSO4 (2.96 g, 18.6 mmol) in aqueous NaH2PO4 (128 mL, 0.1M, 1.53 g) was then added, and the reaction stirred for 1 hour. The reaction mixture was filtered over celite and the resulting water/AcOH mixture evaporated to give a white solid. The white solid was dissolved in EtOAc (2×, 300 mL each), water (300 mL), and EtOAc (1×, 300 mL). The layers were separated and the organic layer further washed with water (2×), saturated sodium bicarbonate (2×), and brine (1×). The organic solution was dried over sodium sulfate, evaporated, and purified on silica (15-25% EtOAc in Hexanes) to give compound 2 in 84% yield (14.64 g, 53.76 mmol).

$^1$H NMR (400 MHz, Chloroform-d) δ 6.46 (dd, J=6.3, 1.8 Hz, 1H), 5.54 (qd, J=2.8, 1.2 Hz, 1H), 5.41 (dt, J=4.7, 1.7 Hz, 1H), 4.71 (ddd, J=6.3, 2.7, 1.5 Hz, 1H), 4.33 (ddt, J=7.0, 5.6, 1.4 Hz, 1H), 4.29-4.15 (m, 2H), 2.11 (s, 3H), 2.06 (s, 3H), 2.00 (s, 3H).

$^{13}$C NMR (101 MHz, Chloroform-d) δ 170.33, 170.06, 169.97, 145.30, 98.80, 72.69, 63.82, 63.59, 61.85, 20.66, 20.64, 20.58.

HRMS: [M+Na]$^+$ Expected 295.079. found 295.078.

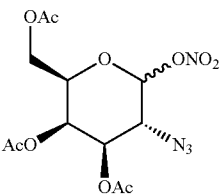

Procedure

Compound 2 (12.0 g, 44 mmol) was dissolved in acetonitrile (250 mL) and cooled to −10°. In a separate nitrogen-flushed flask at −10°, NaN$_3$ (4.3 g, 66 mmol) and ceric ammonium nitrate (87.0 g, 158 mmol) were mixed and stirred vigorously. The solution of compound 2 in acetonitrile was added dropwise via cannula, and the mixture allowed to slowly reach room temperature. The reaction mixture was allowed to stir for a total of 12 hours before dilution with ethyl acetate (500 mL) and washing with water (3×) and brine (1×). The organic layer was dried over sodium sulfate, evaporated, and purified on silica (20-50% EtOAc in Hexanes) to give compound 3 in 79% yield (13.1 g, 34.9 mmol).

¹H NMR (400 MHz, Chloroform-d) δ 6.31 (d, J=4.1 Hz, 1H), 5.60 (d, J=8.8 Hz, 1H), 5.43 (dd, J=3.4, 1.3 Hz, 1H), 5.32 (t, J=3.3 Hz, 1H), 5.16 (dt, J=11.6, 3.4 Hz, 1H), 4.96 (dd, J=10.6, 3.3 Hz, 1H), 4.39-4.28 (m, 1H), 4.14-4.00 (m, 5H), 3.76 (ddd, J=13.5, 9.6, 4.7 Hz, 1H), 2.19-2.05 (m, 6H), 2.05-1.88 (m, 12H).

¹³C NMR (101 MHz, cdcl₃) δ 170.15-169.06, 97.91, 97.79, 96.91, 71.68, 71.45, 69.35, 68.42, 66.98, 66.53, 65.85, 64.75, 61.07, 60.84, 57.38, 55.82, 55.08, 20.31-20.20.

HRMS: [M+Na]⁺ expected 399.076. found 399.073

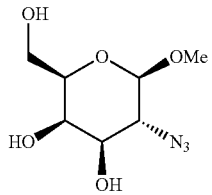 [SMILES: CO[C@@H]1O[C@H](CO)[C@H](O)[C@H](O)[C@H]1N=[N+]=[N-]]

Sodium methoxide solution was prepared from ice-cold dry methanol (50 mL) and sodium hydride (2.296 g, 95.67 mmol) 3 eq) and added to a solution of compound 3 (12.00 g, 31.89 mmol) in dry methanol (100 mL). After thirty minutes of stirring, the reaction was confirmed neutralized by the addition of acetic acid and directly loaded onto silica gel. The reaction mixture was purified over a gradient of 0-20% MeOH in DCM to give compound 4 (6.64 g, 30.3 mmol) in 95% yield.

CNMR:

¹³C NMR (101 MHz, cd₃od) δ 102.60, 100.87, 98.59, 75.65, 74.62, 71.43, 70.41, 68.82, 67.81, 67.69, 67.47, 67.37, 63.73, 62.96, 60.75, 60.43, 59.54, 55.42, 53.69, 45.94.

HRMS: [M+Na]⁺ expected 242.075. found 242.072.

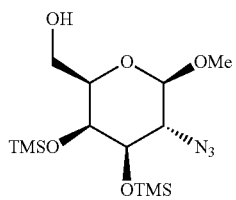

Compound 4 (5.00 g, 22.8 mmol) was dissolved in pyridine (100 mL) and stirred under nitrogen. Trimetylsilylchloride (10.43 mL, 8.929 g, 82.18 mmol, 3.6 eq) was added dropwise and the mixture stirred for 6 hours. The reaction was diluted into ethyl acetate and washed with water (2×) and brine (1×). The organic layer was dried over sodium sulfate and evaporated to give the tri-TMS intermediate. Residual pyridine was removed by coevaporating with toluene (3×). The intermediate was taken up into dry MeOH (45 mL) and cooled to 0° before potassium carbonate (40 mg) was added. The reaction was closely monitored over 1.5 hours and quenched with acetic acid (17 uL) once TLC showed complete consumption of starting material. The product was then dry loaded onto silica and purified with a gradient of 0-50% EtOAc in hexane to give compound 5 (6.55 g, 18.0 mmol) in 79% yield.

¹³C NMR (101 MHz, cdcl₃) δ 103.36, 75.29, 73.71, 72.37, 71.41, 70.94, 70.38, 64.04, 62.49, 62.15, 61.05, 60.36, 57.15, 55.17, 34.60, 31.52, 25.21, 22.59, 20.93, 14.11, 14.05, 0.85, 0.57, 0.55, 0.52, 0.22, 0.14, 0.01, −0.07.

HRMS: [M+Na]⁺ 386.154. found 386.156.

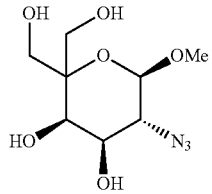 [SMILES: CO[C@@H]1OC(CO)(CO)[C@H](O)[C@H](O)[C@H]1N=[N+]=[N-]]

Compound 5 (7.00 g, 19.3 mmol) was dissolved in DCM (100 mL) and stirred under nitrogen. Dess-Martin periodate (9.82 g, 23.2 mmol, 1.2 eq) was added and the mixture stirred for 2 hours. The reaction was diluted into DCM and washed with water (2×) and brine (1×). The organic layer was dried over sodium sulfate and evaporated to give the intermediate aldehyde.

Compound 6 was dissolved in molecular sieve-dried EtOH (100 mL). Paraformaldehyde (36.50 g, 384.9 mmol, 20 eq) and 21% sodium ethoxide solution (14.5 mL, 38.5 mmol, 2 eq) were added and the reaction stirred for 8 hours. The solvent was evaporated and the product adsorbed onto silica. The product was purified using a gradient of 0-25% MeOH in DCM to afford compound 7 (2.981 g, 11.97 mmol) in 62% yield.

HRMS: [M+Na]⁺ expected 272.086 (+Na), found 272.083.

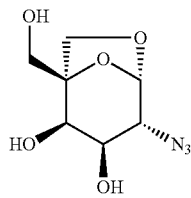

L6-7 (500 mg, 2.00 mmol) was dissolved in water (4.5 mL) and sulfuric acid (0.5 mL). The reaction was sealed in a microwave vial and heated at 100° for 40 minutes. The reaction was cooled to 0°, then diluted with MeOH (10 mL) and neutralized by the addition of concentrated ammonia solution. Salts were filtered off and washed several times with methanol. The filtrate was adsorbed onto silica and purified on a gradient of 0-15% MeOH in DCM to give compound L6-8 (347 mg, 1.60 mmol) in 80% yield.

¹³C NMR (101 MHz, cd₃od) δ 102.70, 85.32, 71.03, 69.59, 69.49, 66.07, 61.85

9. Bicyclic ASGPR Ligand CF3 (FIG. 21)

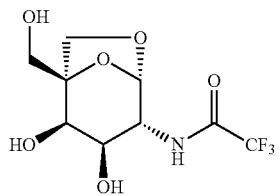 [SMILES: O=C(N[C@H]1[C@H]2OC[C@](CO)(O2)[C@H](O)[C@@H]1O)C(F)(F)F]

Compound (400 mg, 1.84 mmol) was dissolved in methanol (30 mL) and the reaction flask purged with nitrogen. Lindlar's catalyst (40.0 mg, 10 wt %) was then added, and the reaction mixture stirred under a 1 atm hydrogen atmosphere (balloon) for 6 hours. The reaction was filtered over celite and evaporated to give compound 10 (351 mg, 1.84 mmol) in quantitative yield, which was used in the next reaction without further purification.

Compound (351 mg, 1.84 mmol) was dissolved in pyridine (15 mL) and treated with trifluoroacetic anhydride (1.24 mL, 1.85 g, 8.83 mmol, 4.8 eq). The reaction was stirred for 6 hours, then diluted into ethyl acetate and washed with 1M HCl (1×), saturated sodium bicarbonate (1×), and brine (1×). The organic layer was dried over sodium sulfate and evaporated to give compound 11 (1.01 g, 1.75 mmol) in 95% yield, which was used in further steps without purification.

Compound 11 (1.01 g, 1.75 mmol) was dissolved in methanol (25 mL) and dry sodium methoxide (86.2 mg, 1.60 mmol, 4 eq) was added. The reaction was stirred for one hour at room temperature, then neutralized with acetic acid and evaporated onto silica. The crude mixture was purified on silica (0-15% MeOH in DCM) to give compound 12 (482 mg, 1.68 mmol) in 96% yield.

$^1$H NMR (400 MHz, DMSO-$d_6$) δ 9.51 (d, J=6.6 Hz, 1H), 5.15 (s, 1H), 4.98-4.90 (m, 1H), 4.87 (d, J=5.6 Hz, 1H), 4.75-4.70 (m, 1H), 3.86-3.80 (m, 2H), 3.80-3.70 (m, 2H), 3.67-3.54 (m, 3H).

$^{13}$C NMR (101 MHz, dmso) δ 157.47, 157.11, 117.74, 114.87, 100.28, 84.21, 68.77, 68.28, 66.00, 60.51, 55.95, 40.56, 40.35, 40.15, 39.94, 39.73, 39.52, 39.31.

HRMS: [M+H]$^+$ Expected 288.069. found 288.064.

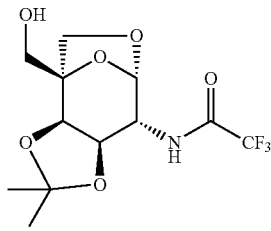 [SMILES: CC1(C)O[C@@H]2[C@@H](NC(=O)C(F)(F)F)[C@H]3OC[C@](CO)(O3)[C@@H]2O1]

Compound 12 (110 mg, 0.383 mmol) was dissolved in DMF (8 mL) and dimethoxypropane (236 uL, 200 mg, 1.92 mmol, 5 eq) and camphorsulfonic acid (45 mg, 0.192 mmol, 0.5 eq) were added. The reaction was stirred at 70° overnight, then DMF evaporated under reduced pressure. The residue was dissolved in ethyl acetate, washed with saturated sodium bicarbonate (1×) and brine (1×), then evaporated onto silica and purified (0-5% MeOH in DCM) to give compound 13 (99.1 mg, 0.303 mmol) in 79% yield.

HNMR:
$^1$H NMR (400 MHz, Chloroform-d) δ 6.87 (d, J=9.0 Hz, 1H), 5.35 (d, J=2.1 Hz, 1H), 4.18-4.11 (m, 2H), 4.11-4.03 (m, 2H), 3.84 (t, J=8.2 Hz, 2H), 3.74 (d, J=7.9 Hz, 1H), 2.66 (d, J=6.6 Hz, 1H), 1.52 (s, 3H), 1.32 (s, 3H).

CNMR:
$^{13}$C NMR (101 MHz, cdcl$_3$) δ 157.87, 157.50, 157.12, 156.75, 119.93, 117.07, 114.21, 112.04, 111.35, 100.22, 81.55, 75.57, 75.00, 68.44, 60.96, 55.16, 27.67, 26.16.

HRMS: [M+H]$^+$ Expected 328.101. found 328.095.

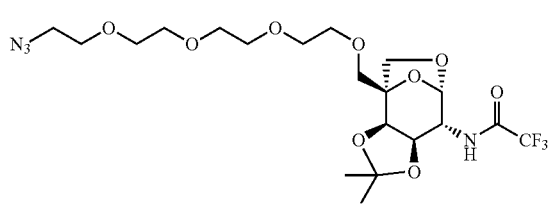 [SMILES: CC1(C)O[C@@H]2[C@@H](NC(=O)C(F)(F)F)[C@H]3OC[C@](COCCOCCOCCOCCN=[N+]=[N-])(O3)[C@@H]2O1]

Compound 13 (99.1 mg, 0.303 mmol) was dissolved in DMF (5 mL) and treated with sodium hydride (8.7 mg, 0.364 mmol, 1.2 eq), then stirred under nitrogen for 15 minutes. Compound 18 (108 mg, 0.364 mmol, 1.2 eq) was then added, and the reaction stirred for 1 hour. The reaction was neutralized by the dropwise addition of acetic acid. The solvent was removed under reduced pressure and the residue taken up into ethyl acetate and washed with brine (4×), and the organic layer was dried over sodium sulfate and evaporated onto silica. The crude mixture was purified on silica (50-100% EtOAc in hexanes) to give compound 14 (131 mg, 0.248 mmol) in 82% yield.

HNMR: $^1$H NMR (400 MHz, DMSO-$d_6$) δ 9.75 (d, J=8.3 Hz, 1H), 5.29 (s, 1H), 4.40 (t, J=6.7 Hz, 1H), 4.30 (d, J=5.9 Hz, 1H), 3.88-3.66 (m, 5H), 3.64-3.48 (m, 14H), 3.39 (t, J=5.0 Hz, 2H), 1.41 (s, 3H), 1.28 (s, 3H).

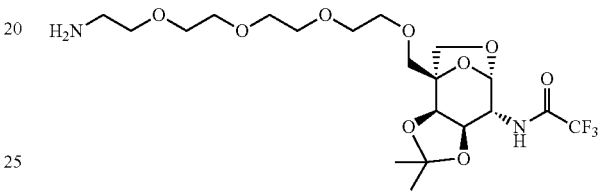

Compound 14 (131 mg, 0.240 mmol) was dissolved in methanol (10 mL) and stirred under a nitrogen atmosphere. Lindlar catalyst (13.1 mg, 10 wt %) was then added, and the reaction stirred for 6 hours under H2 atmosphere (1 atm). The reaction was then filtered over celite and the solvent evaporated to give compound 15 (120 mg, 0.240 mmol) in quantitative yield, which was used without further purification.

HRMS: [M+H]$^+$ Expected 503.222. found 503.223.

10. MIF Binding Divalent (FIG. 23)

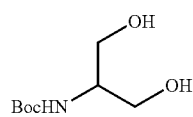

Serinol (2.00 g, 22.0 mmol) was dissolved in dichloromethane (40 mL) and trimethylamine (10 mL). Di-tert-butyl dicarbonate (5.76 g, 26.4 mmol, 1.2 eq) was then added, and the reaction stirred for 4 hours. The mixture was evaporated and the residue portioned between ethyl acetate and water. The organic fraction was washed with water (1×), 1M HCl (2×), saturated sodium bicarbonate (1×), and brine (1×) before drying over sodium sulfate and evaporation to give compound 23 (3.99 g, 20.9 mmol) in 95% yield, which was used without purification in further steps.

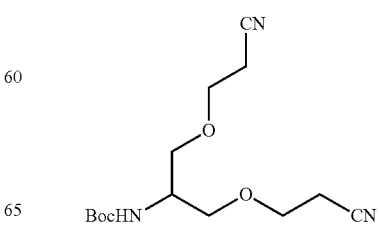

Compound 23 (3.99 g, 20.9 mmol) was dissolved in a mixture of dioxane (12 mL) and aqueous KOH (1.63 g, 29 mmol, 2.4 mL). Acrylonitrile (3.02 mL, 2.44 g, 46.0 mmol, 2.2 eq) was then added dropwise over a period of 2.5 hours, and the reaction stirred under nitrogen for 24 hours. The reaction was neutralized with the addition of 2M HCl (16 mL) and portioned between DCM and water. The organic layer was washed with water (2×) and brine (1×), dried over sodium sulfate, and evaporated. The crude mixture was purified on silica (20-100% EtOAc in hexanes) to give compound 20 (4.96 g, 16.7 mmol) in 80% yield.

HNMR: $^1$H NMR (400 MHz, Chloroform-d) δ 4.91 (d, J=8.9 Hz, 1H), 3.94-3.81 (m, 1H), 3.68 (t, J=6.1 Hz, 4H), 3.65-3.48 (m, 4H), 2.60 (t, J=6.1 Hz, 4H), 1.42 (s, 9H).

CNMR: $^{13}$C NMR (101 MHz, cdcl$_3$) δ 171.11, 155.31, 117.88, 79.70, 69.12, 65.53, 49.24, 28.30, 18.83, 14.16.

ture. Excess sodium bicarbonate was then added, followed by di-tert-butyl dicarbonate (4.37 g, 20.04 mmol, 1.2 eq), and the reaction stirred at room temperature for 6 hours. The cloudy mixture was portioned between water and ethyl acetate, and the organic fraction washed with water (1×), 0.5M HCl (2×), saturated sodium bicarbonate (1×), and brine (1×), dried over sodium sulfate, and evaporated. Compound 20 was purified over a gradient of 0-10% MeOH in DCM on silica, and recovered in 74% yield (4.50 g, 12.4 mmol).

HNMR: $^1$H NMR (400 MHz, Chloroform-d) δ 4.90 (d, J=8.6 Hz, 1H), 3.82 (br s, 1H), 3.70-3.59 (m, 10H), 3.51-3.34 (m, 4H), 2.51 (t, J=6.3 Hz, 4H), 1.38 (s, 9H).

CNMR: $^{13}$C NMR (101 MHz, cdcl$_3$) δ 171.86, 155.34, 79.20, 69.19, 66.41, 51.58, 49.29, 34.75, 28.28.

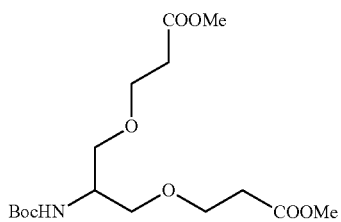 [SMILES: COC(=O)CCOCC(COCCC(=O)OC)NC(=O)OC(C)(C)C]

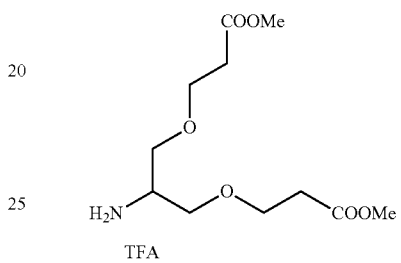

TFA

HNMR:

Compound 24 (4.96 g, 16.7 mmol) was dissolved in methanol (40 mL) and concentrated sulfuric acid (10 mL) was added. The mixture was heated at reflux for 24 hours under a nitrogen atmosphere, then cooled to room tempera- Compound 25 (1.00 g, 2.75 mmol) was dissolved in dry MeOH (10 mL) and TFA (1 mL) and stirred for 15 minutes. Volatiles were evaporated under reduced pressure to give compound 26 as the TFA salt (1.04 g) in quantitative yield.

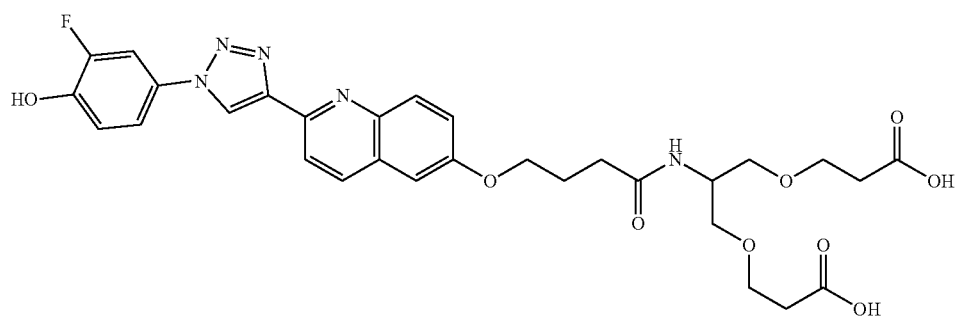 [SMILES: O=C(O)CCOCC(COCCC(=O)O)NC(=O)CCCOc1ccc2nc(-c3cn(-c4ccc(O)c(F)c4)nn3)ccc2c1]

Compound 34 (50.0 mg, 0.123 mmol) was dissolved in DMF (5 mL) and DIPEA (214 uL, 159 mg, 1.23 mmol, 10 eq) and stirred under nitrogen. HBTU (102.4 mg, 0.270 mmol, 2.2 eq) was then added, and the reaction stirred for 15 minutes. Compound 26 (102 mg, 0.270 mmol, 2.2 eq) dissolved in DMF (1 mL) was then added dropwise, and the reaction stirred for 1 hour. The mixture was diluted into ethyl acetate, and washed with 1M HCl (2×) and brine (5×). The organic layer was evaporated to give a gummy residue, which was purified on reverse phase HPLC (35-45% MeCN in water, 0.1% TFA) to give compound 40 (62.6 mg, 0.0959 mmol) in 78% yield.

HRMS: expected 654.258. found 654.259

Compound 40 (62.6 mg, 0.0959 mmol) was dissolved in dioxane (1.8 mL) and 1M NaOH (0.2 mL) was added. The solution was stirred at room temperature for 2 hours, then acidified (pH 3) and evaporated. The residue was resuspended in EtOAc, washed with 1M HCl, and dried over sodium sulfate. The organic layer was evaporated to give compound 41 as an oil (57.6 mg, 0.0921 mmol) in 96% yield, which was used without further purification.

11. MIF Binding Trivalent (FIG. 23)

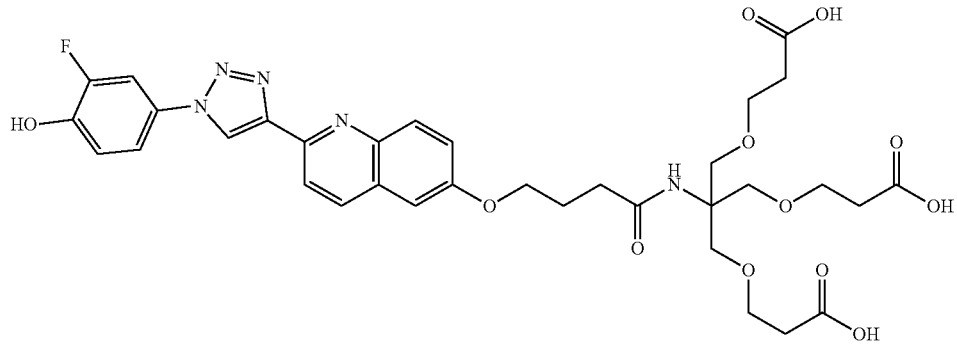 [SMILES: O=C(O)CCOCC(COCCC(=O)O)(COCCC(=O)O)NC(=O)CCCOc1ccc2nc(-c3cn(-c4ccc(O)c(F)c4)nn3)ccc2c1]

Procedure

Compound 34 (50.0 mg, 0.123 mmol) was dissolved in DMF (5 mL) and DIPEA (214 uL, 159 mg, 1.23 mmol, 10 eq) and stirred under nitrogen. HBTU (154 mg, 0.405 mmol, 3.3 eq) was then added, and the reaction stirred for 15 minutes. Compound 29 (200 mg, 0.405 mmol, 3.3 eq) dissolved in DMF (1 mL) was then added dropwise, and the reaction stirred for 1 hour. The mixture was diluted into ethyl acetate, and washed with 1M HCl (2×) and brine (5×). The organic layer was evaporated to give a gummy residue, which was purified on reverse phase HPLC (35-50% MeCN in water, 0.1% TFA) to give compound 44 (79.3 mg, 0.103 mmol) in 84% yield.

HRMS: $[M+H]^+$ expected 770.305. found 770.308.

Compound 44 (79.3 mg, 0.103 mmol) was dissolved in dioxane (1.8 mL) and 1M NaOH (0.2 mL) was added. The solution was stirred at room temperature for 2 hours, then acidified (pH 3) and evaporated. The residue was resuspended in EtOAc, washed with 1M HCl, and dried over sodium sulfate. The organic layer was evaporated to give compound 41 as an oil (68.9 mg, 0.0948 mmol) in 92% yield, which was used without further purification.

12. MIF-AcF3-2 (FIG. 24)

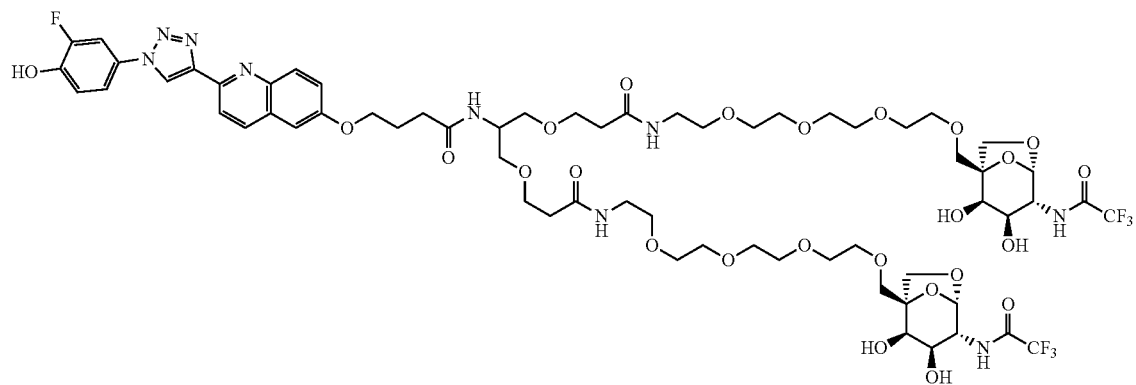 [SMILES: O=C(CCOCC(COCCC(=O)NCCOCCOCCOCCOC[C@@]12CO[C@@H](O1)[C@H](NC(=O)C(F)(F)F)[C@@H](O)[C@H]2O)NC(=O)CCCOc1ccc2nc(-c3cn(-c4ccc(O)c(F)c4)nn3)ccc2c1)NCCOCCOCCOCCOC[C@@]12CO[C@@H](O1)[C@H](NC(=O)C(F)(F)F)[C@@H](O)[C@H]2O]

Compound 41 (57.6 mg, 0.0921 mmol) was dissolved in DMF (1.8 mL) and DIPEA (0.2 mL). HBTU (84.0 mg, 0.222 mmol, 2.4 eq) was then added, and the reaction stirred for 15 minutes before the addition of compound 15 (111 mg, 0.222 mmol, 2.4 eq). The reaction was stirred for 1 hour, then evaporated to give a red residue which was used in the next reaction without purification.

Compound 42 (crude, 0.0921 mmol scale) was dissolved in 1M HCl (1 mL) and stirred for 2 hours. The reaction was purified directly by HPLC (20-40% MeCN in H2O, +3% TFA) to give compound 43 (44.66 mg, 0.0295 mmol) in 32% yield.

Expected (H) 1514.570. found 1514.561.

13. MIF-AcF3-3 (FIG. 25)

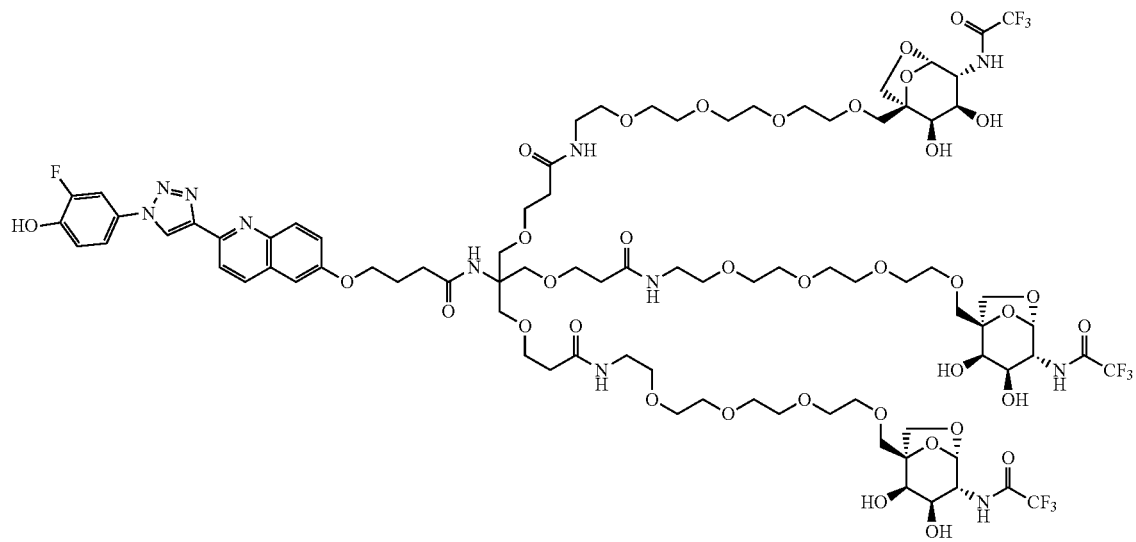 [SMILES: O=C(CCOCC(COCCC(=O)NCCOCCOCCOCCOC[C@@]12CO[C@@H](O1)[C@H](NC(=O)C(F)(F)F)[C@@H](O)[C@H]2O)(COCCC(=O)NCCOCCOCCOCCOC[C@@]12CO[C@@H](O1)[C@H](NC(=O)C(F)(F)F)[C@@H](O)[C@H]2O)NC(=O)CCCOc1ccc2nc(-c3cn(-c4ccc(O)c(F)c4)nn3)ccc2c1)NCCOCCOCCOCCOC[C@@]12CO[C@@H](O1)[C@H](NC(=O)C(F)(F)F)[C@@H](O)[C@H]2O]

Compound 45 (68.9 mg, 0.0948 mmol) was dissolved in DMF (1.8 mL) and DIPEA (0.2 mL). HBTU (126 mg, 0.333 mmol, 3.6 eq) was then added, and the reaction stirred for 15 minutes before the addition of compound 15 (167 mg, 0.333 mmol, 3.6 eq). The reaction was stirred for 1 hour, then evaporated to give a reddish residue which was used in the next reaction without purification.

Procedure

Compound 38 (crude, 0.0948 mmol scale) was dissolved in 1M HCl (1 mL) and stirred for 2 hours. The reaction was purified directly by HPLC (20-40% MeCN in H2O, +3% TFA) to give compound 39 (78.1 mg, 0.0379 mmol) in 40% yield.

Expected (2H, /2) 1030.891 Found 1030.903

Synthesis of MIF-AcF2-3, MIF-Ac-3, MIF-Et-3

Set forth in FIGS. 26-29 are the chemical syntheses of MIF-AcF2-3, MIF-Ac-3, MIF-Et-3 and MIF-EtF3-3 produced using analogous methods to those presented above with minor variation.

Set forth in FIGS. 30-66 and 70-88 are chemical synthetic schemes which provide additional compounds according to the present invention. The schemes in these FIGURES evidence the exemplary synthetic chemistry which can be used to synthesis compounds according to the present invention.

Chemistry for all Peptides

N-Linked Non-Cyclized Peptides, C-Amide Terminating. Without Amine-Containing (Side-Chain) Amino Acids.

Peptides are synthesized on 200 umol scale using Rink amide resin. Standard fmoc amino acids with sidechains protected using acid-labile protecting groups are utilized for all couplings. Between each deprotection, coupling, and capping reaction resin was washed 5× with DMF, 5× with DCM, and 5× with DMF. Resin is Fmoc deprotected (20% piperidine in DMF, 2×3 minute incubations on rotator) and is coupled to the first amino acid (4 eq oxyma, 4 eq Fmoc-protected amino acid, 4 eq DIC in DMF) overnight. The resin is then washed and treated with 10% acetic anhydride in pyridine to cap any unreacted amines (10 minutes on rotator). The resulting resin-amino acid conjugate is Fmoc deprotected as described above and coupled to the next amino acids (4 eq oxyma, 4 eq Fmoc-protected amino acid, 4 eq DIC in DMF) for 40 minutes. The resin is then capped as above. Subsequent iterative deprotection, coupling and capping steps provide the final peptides. Following the last amino acid, {2-[2-(Fmoc-amino)ethoxy]ethoxy}acetic acid is coupled to the peptide and Fmoc deprotected to give an N terminal amine. Peptides are cleaved from resin using 90% TFA, 5% TIPS, 5% water (2 hr treatment), ether precipitated, and purified using RPHPLC to 95% purity, then reacted with carboxylic acids to provide the bifunctional compounds. Alternatively, these peptides are treated with succinic anhydride to afford a terminal carboxylic acid for coupling with amines; azidoacetic acid to generate a terminal alkyne; or 5-hexynoic acid to generate a terminal alkyne. Copper-mediated cross coupling is used in the case of terminal azides or alkynes to give triazole-linked bifunctional molecules.

N-Linked Disulfide Cyclized Peptides, C-Amide Terminating. Without Amine-Containing (Sidechain) Amino Acids.

As above, but following cleavage from resin the peptides are then resuspended in PBS pH 8, MeOH/ammonium bicarbonate, or another acceptable buffer to provide the oxidized peptide containing a disulfide. Alternatively, iodine is used to oxidatively cyclize the peptides.

N-Linked Non-Cyclized Peptides, C-Amide Terminating. With Amine-Containing (Sidechain) Amino Acids.

As above, but amino acids containing amines are protected on their sidechains with Cbz which is removed under reductive conditions (H$_2$, Pd/C) at a later step in the synthesis.

N-Linked Disulfide Cyclized Peptides, C-Amide Terminating. With Amine-Containing (Sidechain) Amino Acids.

As above, but amino acids containing amines are protected on their sidechains with Cbz which is removed under reductive conditions (H$_2$, Pd/C) at a later step in the synthesis. Following cleavage from resin the peptides are then resuspended in PBS pH 8, MeOH/ammonium bicarbonate, or another acceptable buffer to provide the oxidized peptide containing a disulfide. Alternatively, iodine is used to oxidatively cyclize the peptides.

C-Linked Non-Cyclized Peptides. Without Carboxylic Acid-Containing (Sidechain) Amino Acids.

Peptides are synthesized on 200 umol scale using 2-chlorotrityl resin. Standard fmoc amino acids with sidechains protected using acid-labile protecting groups are utilized for all couplings. Between each deprotection, coupling, and capping reaction resin was washed 5× with DMF, 5× with DCM, and 5× with DMF. Resin is treated with 4 eq 2,4,6-collidine in DCM with the first amino acid (4 eq) of the sequence overnight. The resin is then capped by treatment with methanol in DIPEA/DCM for 1 hr at RT. The amino acid is then deprotected (20% piperidine in DMF, 2×3 minute incubations on rotator) and is coupled to the first amino acid (4 eq oxyma, 4 eq Fmoc-protected amino acid, 4 eq DIC in DMF) overnight. The resin is then washed and treated with 10% acetic anhydride in pyridine to cap any unreacted amines (10 minutes on rotator). The resulting resin-amino acid conjugate is Fmoc deprotected as described above and coupled to the next amino acids (4 eq oxyma, 4 eq Fmoc-protected amino acid, 4 eq DIC in DMF) for 40 minutes. The resin is then capped as above. Subsequent iterative deprotection, coupling and capping steps provide the final peptides. Following the last amino acid, peptides are optionally capped with acetic anhydride, propionic anhydride, or another suitable activated acid. Peptides are cleaved from resin using hexafluoroisopropanol (20%) in DCM for 1.5 hr at room temperature and ether precipitated. Peptides are then purified using RPHPLC to 95% purity, then reacted with carboxylic acids to provide the bifunctional compounds. Alternatively, these peptides are treated with N-boc-ethylenediamine and subsequently HCl/DCM to afford a terminal amine for coupling with carboxylic acids. Alternatively, these peptides are treated with 3-azidopropan-1-amine under standard coupling conditions (HBTU, DIPEA, DMF) to generate a terminal azide. Alternatively, these peptides are treated with 4-pentyn-1-amine under standard amide coupling conditions (HBTU, DIPEA, DMF) to give a C terminal alkyne. Copper-mediated cross coupling is used in the case of terminal azides or alkynes to give triazole-linked bifunctional molecules.

C-Linked Disulfide Cyclized Peptides. Without Carboxylic Acid-Containing (Sidechain) Amino Acids.

As above, but following cleavage from resin the peptides are then resuspended in PBS pH 8, MeOH/ammonium bicarbonate, or another acceptable buffer to provide the oxidized peptide containing a disulfide. Alternatively, iodine is used to oxidatively cyclize the peptides.

C-Linked Non-Cyclized Peptides. With Carboxylic Acid-Containing (Sidechain) Amino Acids.

As above, but amino acids containing carboxylic acids are protected on their sidechains with Bz which is removed under reductive conditions ($H_2$, Pd/C) at a later step in the synthesis.

C-Linked Disulfide Cyclized Peptides. With Carboxylic Acid-Containing (Sidechain) Amino Acids.

As above, but amino acids containing carboxylic acids are protected on their sidechains with Bz which is removed under reductive conditions ($H_2$, Pd/C) at a later step in the synthesis. Following cleavage from resin the peptides are then resuspended in PBS pH 8, MeOH/ammonium bicarbonate, or another acceptable buffer to provide the oxidized peptide containing a disulfide. Alternatively, iodine is used to oxidatively cyclize the peptides.

REFERENCES

1. Stöve S, Welte T, Wagner T, Kola A, Klos A, Bautsch W, et al. Circulating complement proteins in patients with sepsis or systemic inflammatory response syndrome. Clinical and diagnostic laboratory immunology. 1996; 3(2):175-83.
2. Chuang T-Y, Chang H-T, Chung K—P, Cheng H—S, Liu C—Y, Liu Y—C, et al. High levels of serum macrophage migration inhibitory factor and interleukin 10 are associated with a rapidly fatal outcome in patients with severe sepsis. International Journal of Infectious Diseases. 2014; 20:13-7.
3. Henderson B, Pockley A G. Proteotoxic stress and circulating cell stress proteins in the cardiovascular diseases. Cell Stress and Chaperones. 2012; 17(3):303-11.
4. Leander K, Malarstig A, van't Hooft F M, Hyde C, Hellénius M-L, Troutt J S, et al. Circulating proprotein convertase subtilisin/kexin type 9 (PCSK9) predicts future risk of cardiovascular events independently of established risk factors. Circulation. 2016; 133(13):1230-9.
5. Benham A M. Protein secretion and the endoplasmic reticulum. Cold Spring Harbor perspectives in biology. 2012; 4 (8):a012872.
6. Yang W H, Aziz P V, Heithoff D M, Mahan M J, Smith J W, Marth J D. An intrinsic mechanism of secreted protein aging and turnover. Proceedings of the National Academy of Sciences. 2015; 112(44): 13657-62.
7. Winkelhake J L, Nicolson G. Aglycosylantibody. Effects of exoglycosidase treatments on autochthonous antibody survival time in the circulation. Journal of Biological Chemistry. 1976; 251(4):1074-80.
8. Sarkar M, Liao J, Kabat E A, Tanabe T, Ashwell G. The binding site of rabbit hepatic lectin. Journal of Biological Chemistry. 1979; 254(9):3170-4.
9. Ashwell G, Harford J. Carbohydrate-specific receptors of the liver. Annual review of biochemistry. 1982; 51(1): 531-54.
10. Connolly D T, Townsend R, Kawaguchi K, Bell W, Lee Y C. Binding and endocytosis of cluster glycosides by rabbit hepatocytes. Evidence for a short-circuit pathway that does not lead to degradation. Journal of Biological Chemistry. 1982; 257(2):939-45.
11. Lee R T, Lee Y C. Affinity enhancement by multivalent lectin-carbohydrate interaction. Glycoconjugate journal. 2000; 17(7-9):543-51.
12. Wragg S, Drickamer K. Identification of amino acid residues that determine pH dependence of ligand binding to the asialoglycoprotein receptor during endocytosis. Journal of Biological Chemistry. 1999; 274(50):35400-6.
13. Schwartz A, Fridovich S, Lodish H. Kinetics of internalization and recycling of the asialoglycoprotein receptor in a hepatoma cell line. Journal of Biological Chemistry. 1982; 257(8):4230-7.
14. Wall D A, Wilson G, Hubbard A L. The galactose-specific recognition system of mammalian liver: the route of ligand internalization in rat hepatocytes. Cell. 1980; 21(1):79-93.
15. Watarai H, Nozawa R, Tokunaga A, Yuyama N, Tomas M, Hinohara A, et al. Posttranslational modification of the glycosylation inhibiting factor (GIF) gene product generates bioactive GIF. Proceedings of the National Academy of Sciences. 2000; 97(24): 13251-6.
16. Calandra T, Echtenacher B, Le Roy D, Pugin J, Metz C N, Hültner L, et al. Protection from septic shock by neutralization of macrophage migration inhibitory factor. Nature medicine. 2000; 6(2):164-70.
17. Benedek G, Meza-Romero R, Jordan K, Zhang Y, Nguyen H, Kent G, et al. MIF and D-DT are potential disease severity modifiers in male MS subjects. Proceedings of the National Academy of Sciences. 2017; 114(40): E8421-E9.
18. Kim K—W, Kim H—R. Macrophage migration inhibitory factor: a potential therapeutic target for rheumatoid arthritis. The Korean journal of internal medicine. 2016; 31(4):634.
19. Hussain F, Freissmuth M, Völkel D, Thiele M, Douillard P, Antoine G, et al. Human anti-macrophage migration inhibitory factor antibodies inhibit growth of human prostate cancer cells in vitro and in vivo. Molecular cancer therapeutics. 2013; 12(7):1223-34.
20. Reidy T, Rittenberg A, Dwyer M, D'Ortona S, Pier G, Gadjeva M. Homotrimeric macrophage migration inhibitory factor (MIF) drives inflammatory responses in the corneal epithelium by promoting caveolin-rich platform assembly in response to infection. Journal of Biological Chemistry. 2013; 288(12):8269-78.
21. Willis M S, Carlson D L, DiMaio J M, White M D, White D J, Adams G A, et al. Macrophage migration inhibitory factor mediates late cardiac dysfunction after burn injury. American Journal of Physiology-Heart and Circulatory Physiology. 2005; 288(2):H795-H804.
22. Sanhueza, C. A.; Baksh, M. M.; Thuma, B.; Roy, M. D.; Dutta, S.; Préville, C.; Chrunyk, B. A.; Beaumont, K.; Dullea, R.; Ammirati, M., Efficient Liver Targeting by Polyvalent Display of a Compact Ligand for the Asialoglycoprotein Receptor. Journal of the American Chemical Society 2017, 139 (9), 3528-3536.
23. Maschitti, V., Patent WO 2015/177668 A1 2015.
24. Schwartz A, Fridovich S E, Knowles B B, Lodish H. Characterization of the asialoglycoprotein receptor in a continuous hepatoma line. Journal of Biological Chemistry. 1981; 256(17):8878-81.
25. Geuze H J, Slot J W, Strous G J, Lodish H F, Schwartz A L. Intracellular site of asialoglycoprotein receptor-ligand uncoupling: double-label immunoelectron microscopy during receptor-mediated endocytosis. Cell. 1983; 32(1):277-87.

The invention claimed is:

1. A compound according to the structure:

wherein:

[CPBM] is selected from the group consisting of:

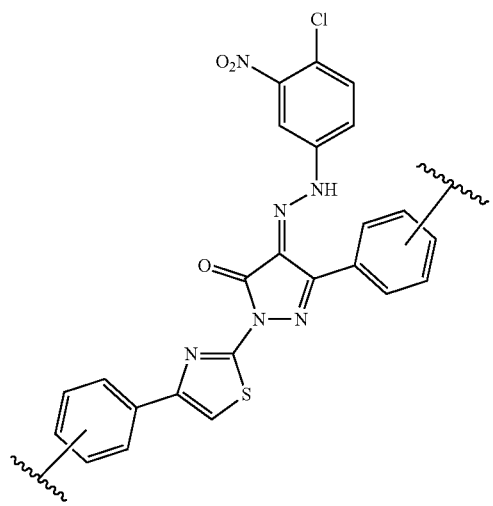

,

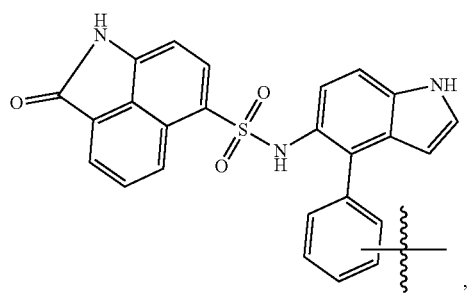

,

-continued

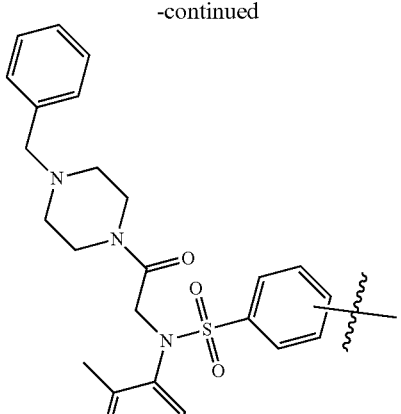

,

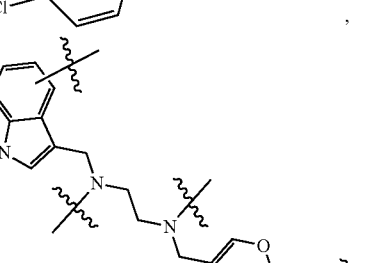

, and

, wherein the [CPBM] is covalently bonded to [CON] at a single position indicated by

[CRBM] is:

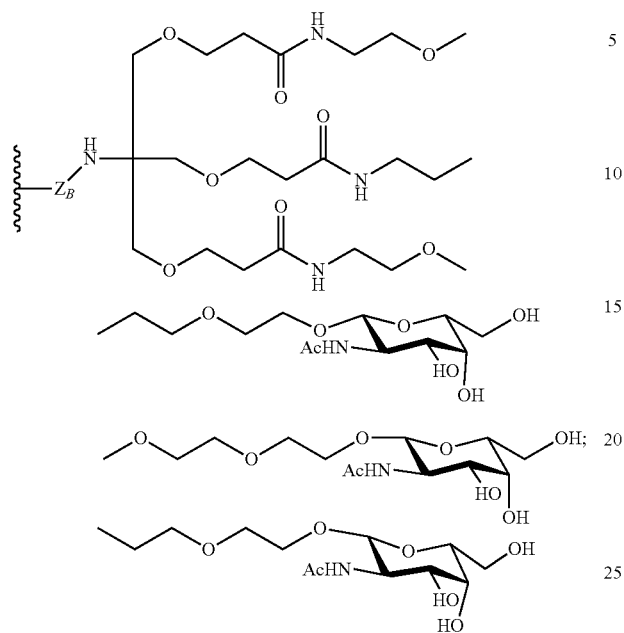

wherein:
- $Z_B$ is absent, —(CH$_2$)$_{IM}$—, —C(O)—(CH$_2$)$_{IM}$—, or —C(O)—(CH$_2$)$_{IM}$—NR$_M$—;
- $R_M$ is H or C$_1$-C$_3$ alkyl optionally substituted with one or two hydroxyl groups; and
- each occurrence of IM is independently 0, 1, 2, 3, 4, or 5;

each occurrence of [CON] is independently selected from the group consisting of:

a) a group selected from the group consisting of:

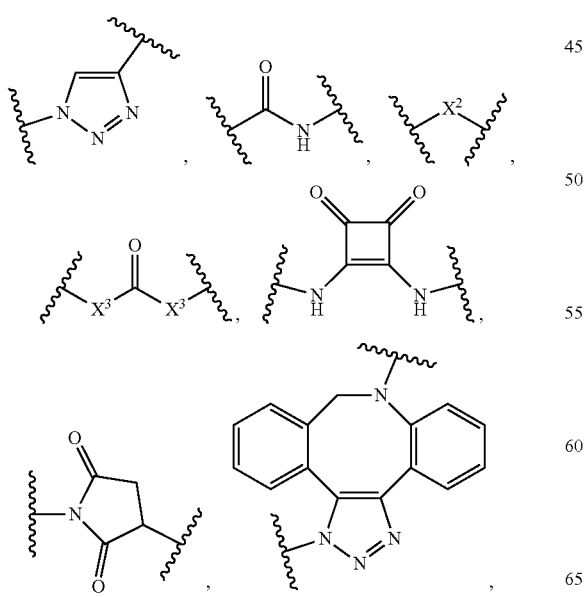

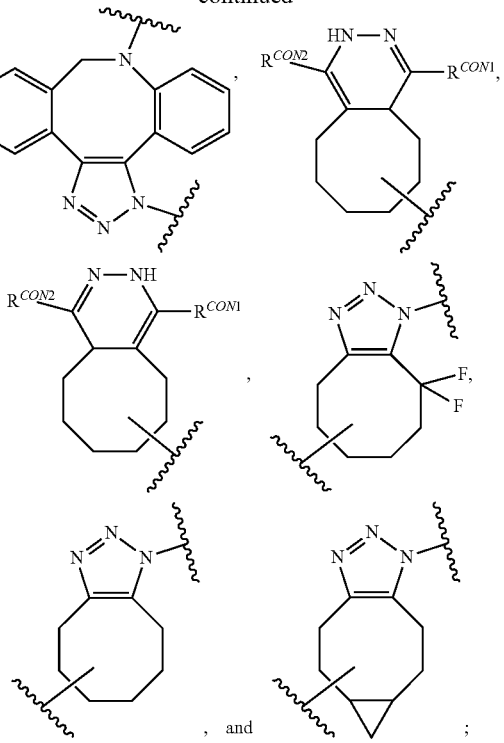

wherein:
- one of R$^{CON1}$ and R$^{CON2}$ is a bond, and the other is H or methyl;
- each occurrence of X$^2$ is independently —CH$_2$—, —O—, —S—, —N(R$^4$)—, —C(O)—, —S(O)—, —S(O)$_2$—, —S(O)$_2$O—, —OS(O)$_2$—, or —OS(O)$_2$O—;
- each occurrence of X$^3$ is independently —O—, —S—, or —N(R$^4$)—;
- each occurrence of R$^4$ is independently H, C$_1$-C$_3$ alkyl, C$_1$-C$_3$ alkanol, or —C(O)(C$_1$-C$_3$ alkyl);

b) a group according to the structure:

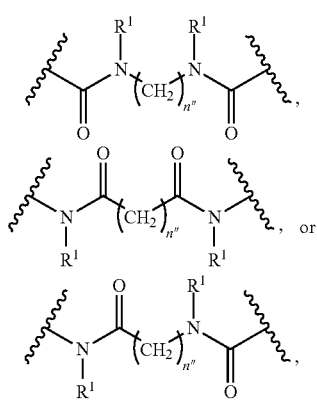

wherein:
- each occurrence of R$^1$ is independently H or C$_1$-C$_3$ alkyl; and
- each occurrence of n" is independently 0, 1, 2, 3, 4, 5, 6, 7, or 8;

c) a group according to the structure:

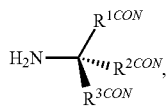

wherein:
$R^{1CON}$, $R^{2CON}$, and $R^{3CON}$ are each independently H, —(CH$_2$)$_{MC1}$—, —(CH$_2$)$_{MC1a}$C(O)$_{XA}$(NR$^4$)$_{XA}$—(CH$_2$)$_{MC1a}$—, —(CH$_2$)$_{MC1a}$(NR$^4$)$_{XA}$C(O)$_{XA}$—(CH$_2$)$_{MC1a}$—, or —(CH$_2$)$_{MC1a}$O—(CH$_2$)$_{MC1}$—C(O)NR$^4$—,
with the proviso that $R^{1CON}$, $R^{2CON}$, and $R^{3CON}$ are not simultaneously H;
each MC1 is independently 1, 2, 3, or 4;
each MC1a is independently 0, 1, 2, 3, or 4;
each XA is independently 0 or 1; and
each $R^4$ is independently H, C$_1$-C$_3$ alkyl, C$_1$-C$_3$ alkanol, or —C(O)(C$_1$-C$_3$ alkyl),
with the proviso that MC1a and XA in a group are not all simultaneously 0;

each occurrence of [LINKER] is independently:
i) a polyethyleneglycol linker having from 1 to 12 ethylene glycol residues,
ii) a polypropylene glycol or polypropylene-co-polyethylene glycol linker containing 1 to 100 alkylene glycol units,
iii) a group according to the structure:

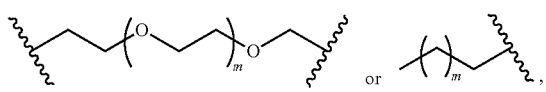

wherein m is independently 1, 2, 3, 4, 5, 6, 7, 8, 9, 10, 11, 12, 13, 14, or 15;
iv) a group according to the structure:

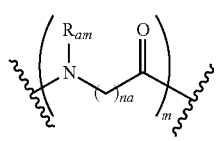

wherein:
$R_{am}$ is H or C$_1$-C$_3$ alkyl optionally substituted with one or two hydroxyl groups;
na is 1, 2, 3, 4, 5, 6, 7, 8, 9, 10, 11, 12, 13, 14, or 15; and
m is an integer from 1 to 100;
v) a group according to the formula:

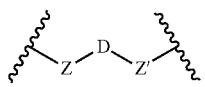

wherein:
Z and Z' are each independently a bond, —(CH$_2$)$_i$—O—, —(CH$_2$)$_i$—S—, —(CH$_2$)$_i$—N(R)—,

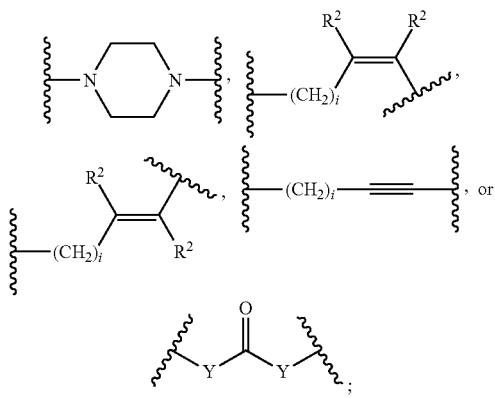

wherein:
the (CH$_2$)$_i$ group, if present in Z or Z', is bonded to [CON], [CPBM], or [CRBM];
each R is independently H, C$_1$-C$_3$ alkyl, or C$_1$-C$_3$ alkanol;
each $R^2$ is independently H or C$_1$-C$_3$ alkyl;
each Y is independently a bond, —O—, —S—, or —N(R)—;
each i is independently 1, 2, 3, 4, 5, 6, 7, 8, 9, or 10;
D is a bond, —(CH$_2$)$_i$—Y—C(O)—Y—(CH$_2$)$_i$—, —(CH$_2$)$_{m'}$—, or —[(CH$_2$)$_n$—X$^1$]$_j$—, with the proviso that Z, Z', and D are not each simultaneously bonds, wherein:
each i is independently 1, 2, 3, 4, 5, 6, 7, 8, 9, or 10;
j is 1, 2, 3, 4, 5, 6, 7, 8, 9, or 10;
m' is 1, 2, 3, 4, 5, 6, 7, 8, 9, or 10;
n is 1, 2, 3, 4, 5, 6, 7, 8, 9, or 10;
$X^1$ is —O—, —S—, or —N(R)—;
R is H, C$_1$-C$_3$ alkyl, or C$_1$-C$_3$ alkanol;
vi) a group according to the structure:

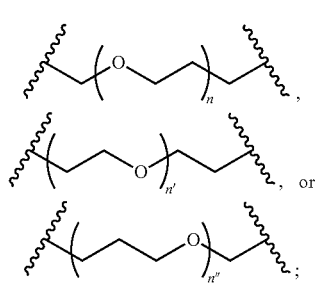

wherein:
n is an integer from 1 to 25;
n' is an integer from 1 to 25; and
n" is 0, 1, 2, 3, 4, 5, 6, 7, or 8;

vii) a group of formula: PEG-[CON]-PEG,
wherein each PEG is independently at each occurrence 1 to 12 ethylene glycol residues and [CON] is

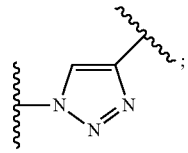 [SMILES: *c1cn(*)nn1];

k' is 1;
j' is 1, 2, or 3;
h and h' are each independently 1, 2, 3, 4, 5, or 6;
$i_L$ is 0, 1, 2, or 3;
or a salt, stereoisomer, or solvate thereof.

2. The compound of claim 1, wherein j', h, h', and $i_L$ are each independently 1, 2, or 3.

3. The compound of claim 1,
wherein [CPBM] is

4. The compound of claim 1, wherein [LINKER] is:

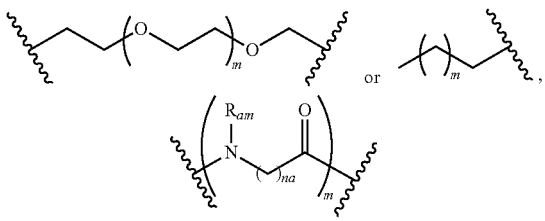

wherein:
each m is independently 1, 2, 3, 4, 5, 6, 7, 8, 9, 10, 11, 12, 13, 14, or 15;
na is 1, 2, 3, 4, 5, 6, 7, 8, 9, 10, 11, 12, 13, 14, or 15; and
$R_{am}$ is H or $C_1$-$C_3$ alkyl optionally substituted with one or two hydroxyl groups.

5. The compound of claim 1, wherein [LINKER] is:

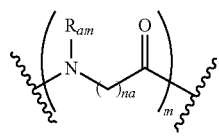

wherein:
$R_{am}$ is H or $C_1$-$C_3$ alkyl optionally substituted with one or two hydroxyl groups;

na is 1, 2, 3, 4, 5, 6, 7, 8, 9, 10, 11, 12, 13, 14, or 15; and
m is an integer from 1 to 100; or
wherein [LINKER] is:

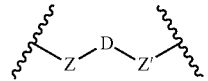

wherein:
Z and Z' are each independently a bond, —$(CH_2)_i$—O—, —$(CH_2)_i$—S—, —$(CH_2)_i$—N(R)—,

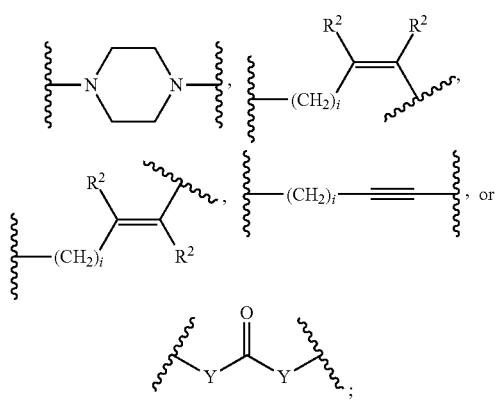

wherein:
the $(CH_2)_i$ group, if present in Z or Z', is bonded to [CON], [CPBM], or [CRBM];
each R is H, $C_1$-$C_3$ alkyl, or $C_1$-$C_3$ alkanol;
each $R^2$ is independently H or $C_1$-$C_3$ alkyl;
each Y is independently a bond, —O—, —S—, or —N(R)—;
each i is independently 1, 2, 3, 4, 5, 6, 7, 8, 9, or 10;
D is
$(CH_2)_j$—Y—C(O)—Y—$(CH_2)_j$—, —$(CH_2)_{m'}$—, —$[(CH_2)_n$—$X^1]_j$—, or a bond,
with the proviso that Z, Z', and D are not each simultaneously bonds;
wherein:
each i is independently 1, 2, 3, 4, 5, 6, 7, 8, 9, or 10;
j is 1, 2, 3, 4, 5, 6, 7, 8, 9, or 10;
m' is 1, 2, 3, 4, 5, 6, 7, 8, 9, or 10;
n is 1, 2, 3, 4, 5, 6, 7, 8, 9, or 10;
$X^1$ is —O—, —S—, or —N(R)—;
each Y is independently a bond, O, S, or N—R;
R is H, $C_1$-$C_3$ alkyl, or $C_1$-$C_3$ alkanol.

6. The compound of claim 1, wherein [LINKER] is:

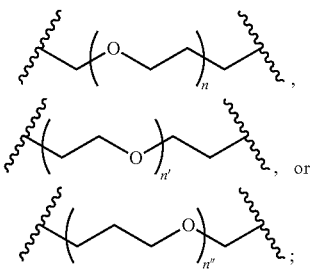

wherein:
  n is an integer from 1 to 25;
  n' is an integer from 1 to 25;
  n" is 0, 1, 2, 3, 4, 5, 6, 7, or 8; or
wherein [LINKER] is:
  PEG-[CON]-PEG,
  wherein each occurrence of PEG is independently 1-12 ethylene glycol residues and [CON] is

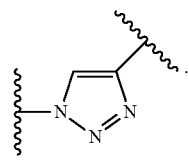 [SMILES: *c1cn(*)nn1]

7. The compound of claim 1, wherein [CON] is:
a) a moiety selected from the group consisting of:

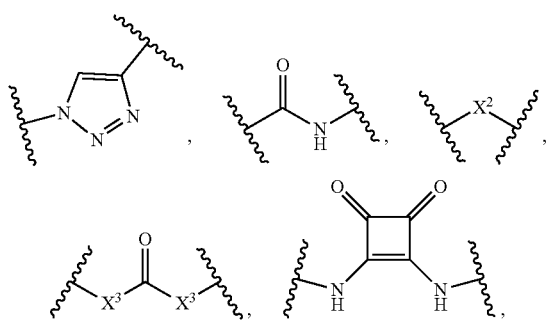

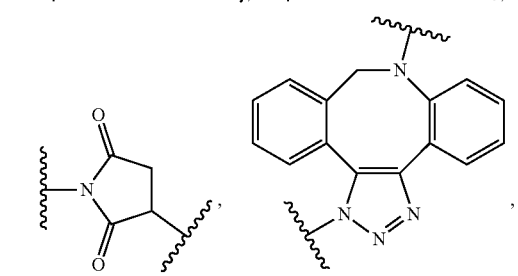

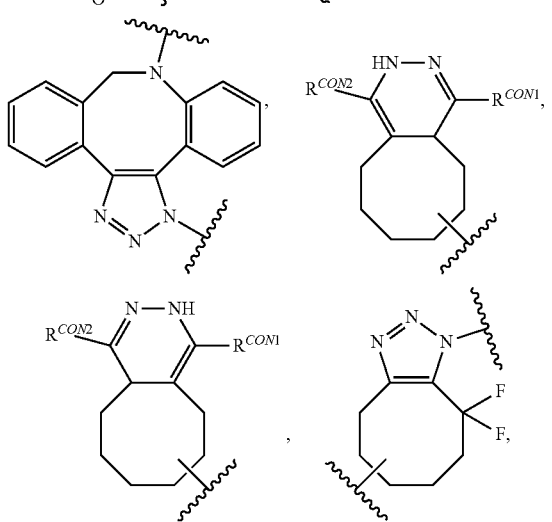

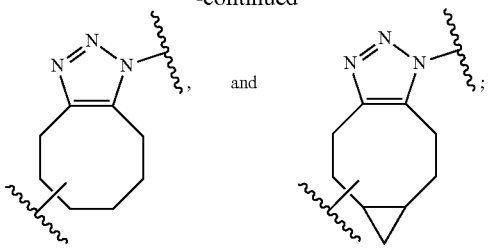

wherein:
  one of $R^{CON1}$ and $R^{CON2}$ is a bond and the other is H or methyl;
  $X^2$ is —$CH_2$—, —O—, —S—, —N($R^4$)—, —C(O)—, —S(O)—, —S(O)$_2$—, —S(O)$_2$O—, —OS(O)$_2$—, or —OS(O)$_2$O;
  each occurrence of $X^3$ is independently —O—, —S—, or —N($R^4$)—;
  each occurrence of $R^4$ is independently H, $C_1$-$C_3$ alkyl, $C_1$-$C_3$ alkanol, or —C(O)($C_1$-$C_3$ alkyl); or
b)

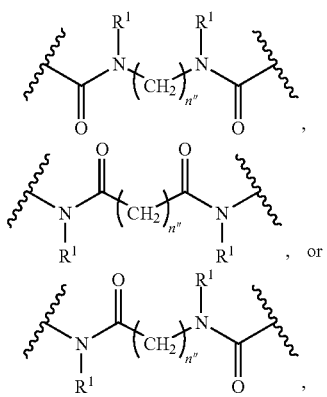

wherein:
  each occurrence of $R^1$ is independently H or $C_1$-$C_3$ alkyl; and
  n" is independently 0, 1, 2, 3, 4, 5, 6, 7, or 8; or
c) a group according to the structure:

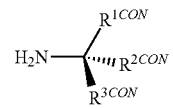

wherein:
  $R^{1CON}$, $R^{2CON}$, and $R^{3CON}$ are each independently H, —$(CH_2)_{MC1}$—, —$(CH_2)_{MC1a}$C(O)$_{XA}$(N$R^4$)$_{XA}$—$(CH_2)_{MC1a}$-, —$(CH_2)_{MC1a}$(N$R^4$)$_{XA}$C(O)$_{XA}$—$(CH_2)_{MC1a}$-, or —$(CH_2)_{MC1a}$O—$(CH_2)_{MC1}$—C(O)N$R^4$—,
  with the proviso that $R^1$CON, $R^2$CON and $R^3$CON are not simultaneously H;
  each MC1 is independently 0, 1, 2, 3, or 4;
  each MC1a is independently 0, 1, 2, 3, or 4;
  each XA is independently 0 or 1; and
  each $R^4$ is independently H, $C_1$-$C_3$ alkyl, $C_1$-$C_3$ alkanol, or —C(O)($C_1$-$C_3$ alkyl),
  with the proviso that MC1a and XA in a group are not all simultaneously 0.

8. A compound selected from the group consisting of
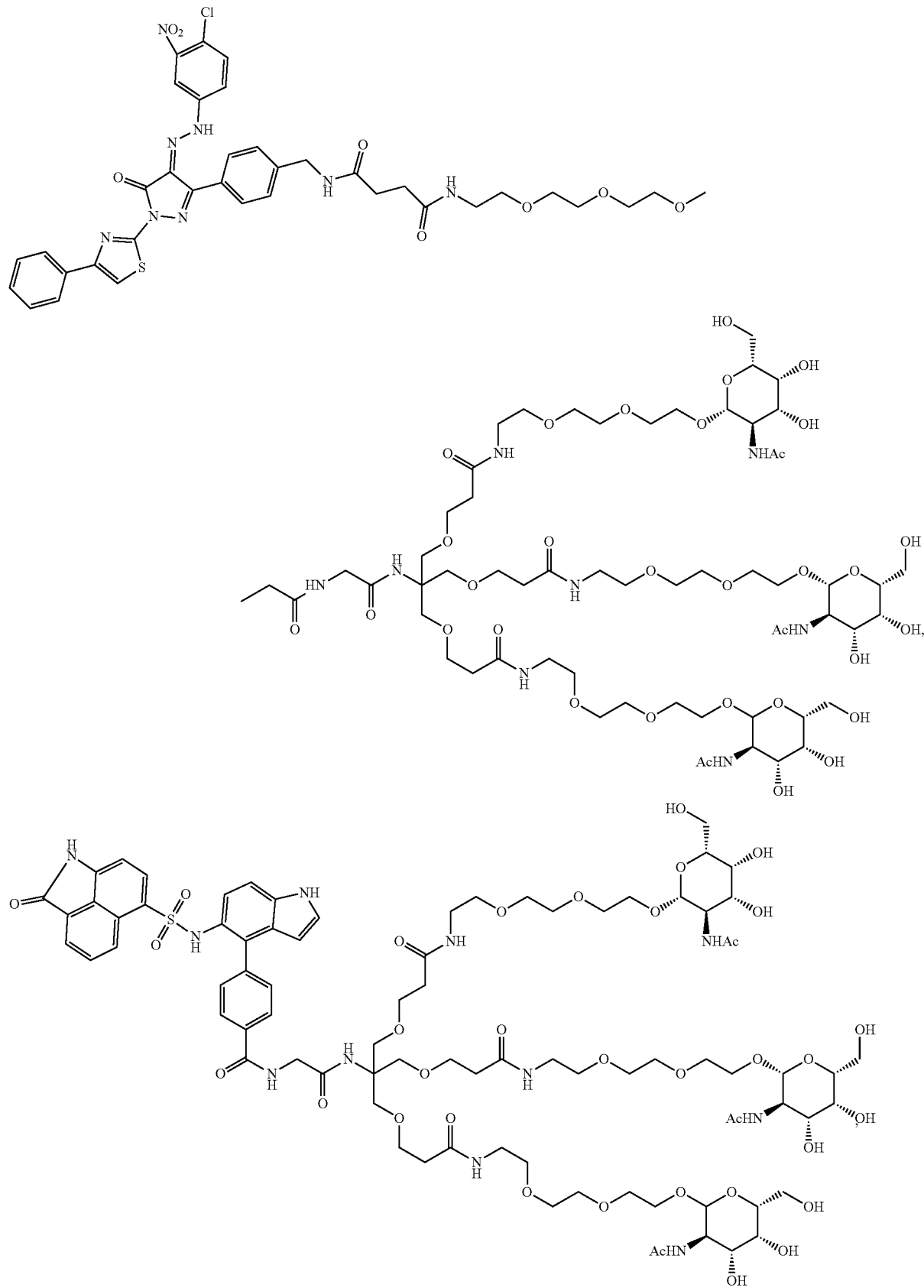

-continued
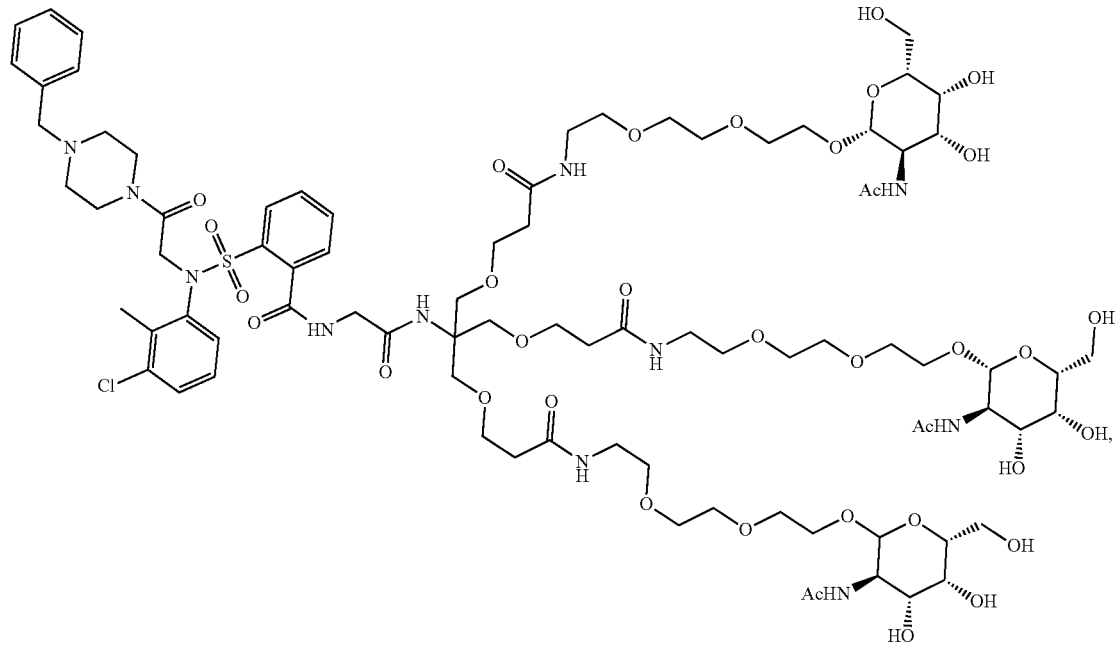

153
154
-continued
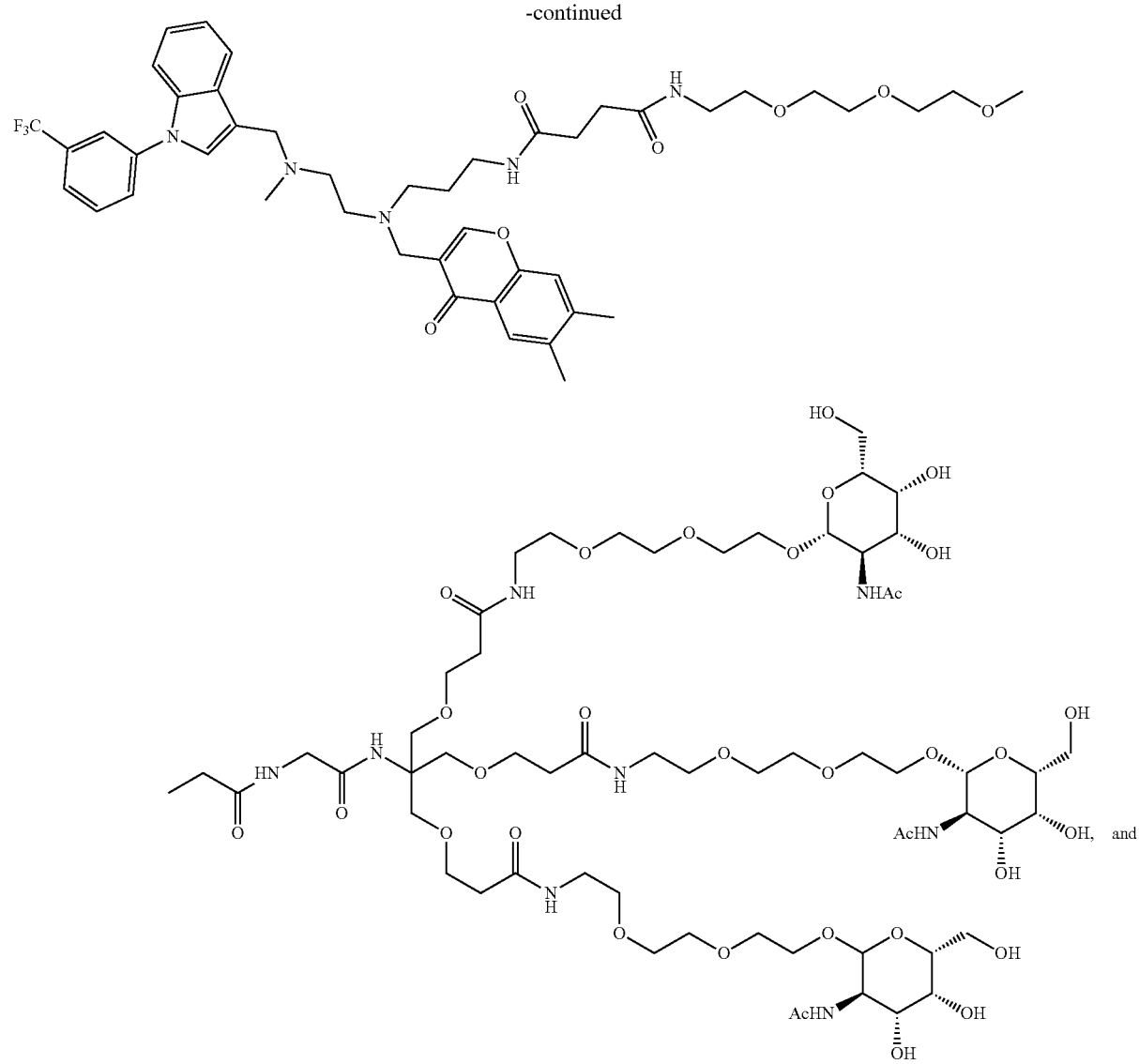
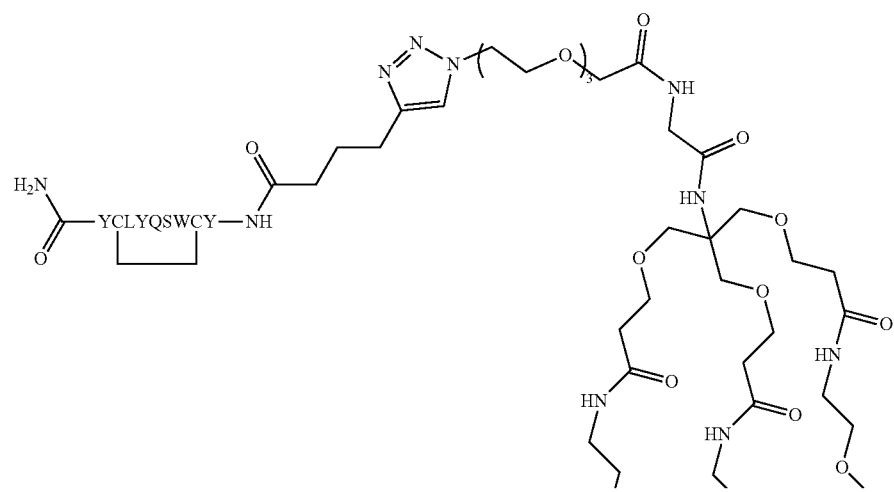

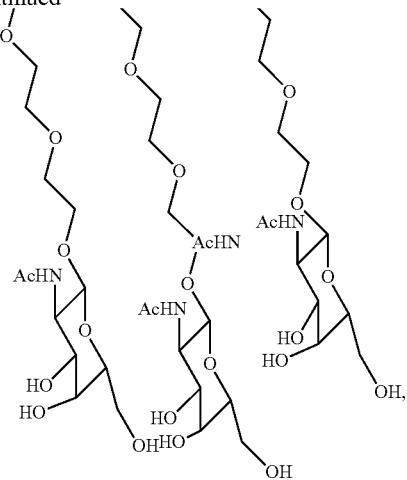

or a salt, stereoisomer, or solvate thereof.

9. A pharmaceutical composition comprising:
a therapeutically effective amount of the compound of claim 1; and
at least one pharmaceutically acceptable carrier or excipient.

10. A method of removing excess circulating tumor necrosis factor alpha (TNF-alpha) protein in subject in need thereof, or treating or ameliorating a disease state or condition in a subject in need thereof, wherein the disease state or condition is selected from the group consisting of rheumatoid arthritis, Crohn's disease, ulcerative colitis, psoriatic arthritis, psoriasis, ankylosing spondylitis, and juvenile rheumatoid arthritis, the method comprising:
administering to the subject a therapeutically effective amount of a compound having the structure:

wherein:
[CPBM] is selected from the group consisting of:

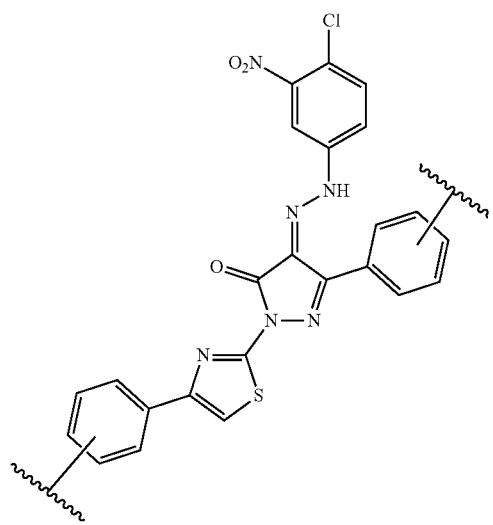

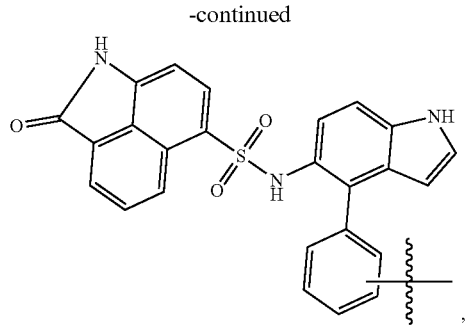

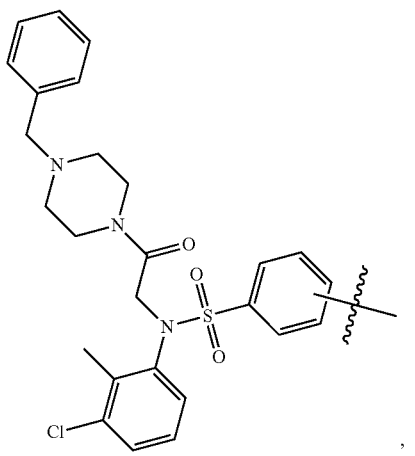

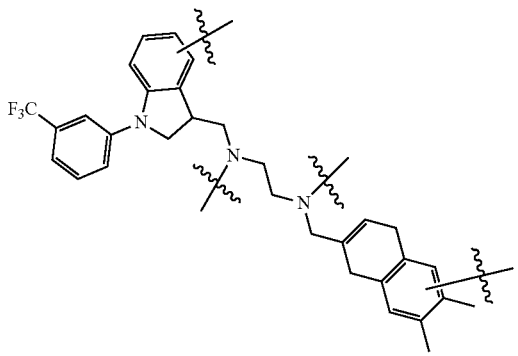

, and

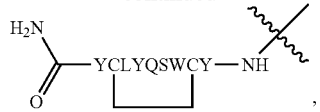

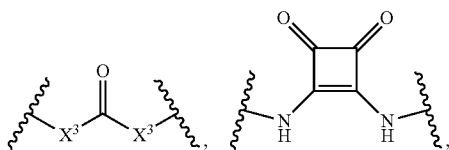

wherein the [CPBM] is covalently bonded to [CON] at a single position indicated by

[CRBM] is:

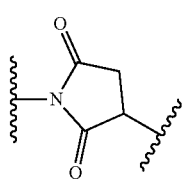

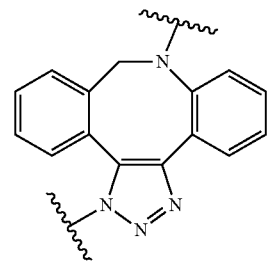

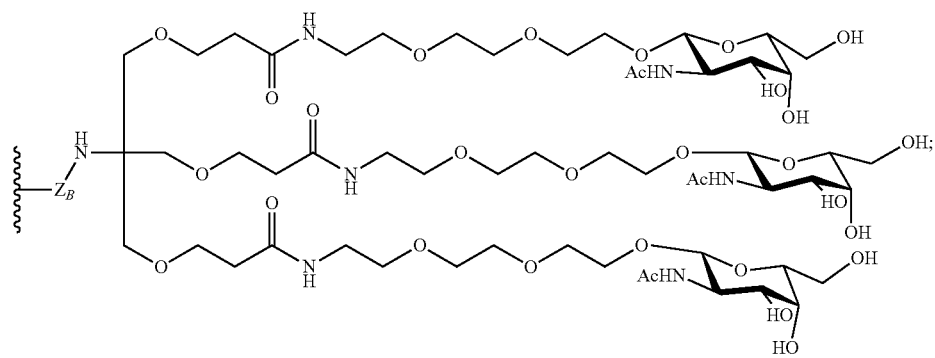

wherein:
- $Z_B$ is absent, —$(CH_2)_{IM}$—, —C(O)—$(CH_2)_{IM}$—, or —C(O)—$(CH_2)_{IM}$—$NR_M$—;
- $R_M$ is H or $C_1$-$C_3$ alkyl optionally substituted with one or two hydroxyl groups; and
- each occurrence of IM is independently 0, 1, 2, 3, 4, or 5;

each occurrence of [CON] is independently selected from the group consisting of:

a) a group selected from the group consisting of:

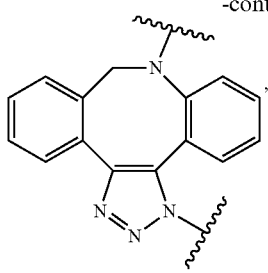

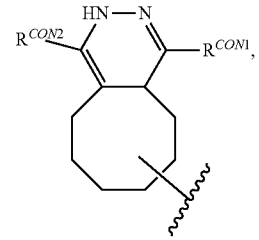

-continued

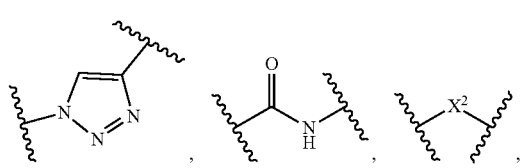

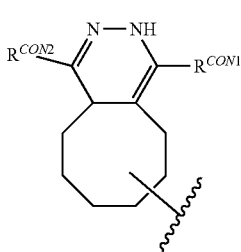

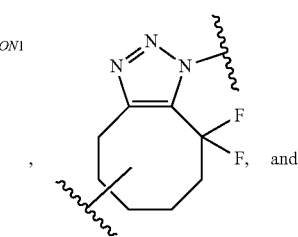

, and

-continued

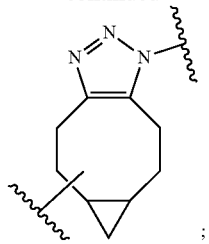
;

wherein:
one of $R^{CON1}$ and $R^{CON2}$ is a bond, and the other is H or methyl;
each occurrence of $X^2$ is independently —CH$_2$—, —O—, —S—, —N(R$^4$)—, —C(O)—, —S(O)—, —S(O)$_2$—, —S(O)$_2$O—, —OS(O)$_2$—, or —OS(O)$_2$O—;
each occurrence of $X^3$ is independently —O—, —S—, or —N(R$^4$)—;
each occurrence of $R^4$ is independently H, $C_1$-$C_3$ alkyl, $C_1$-$C_3$ alkanol, or —C(O)(C$_1$-C$_3$ alkyl);

b) a group according to the structure:

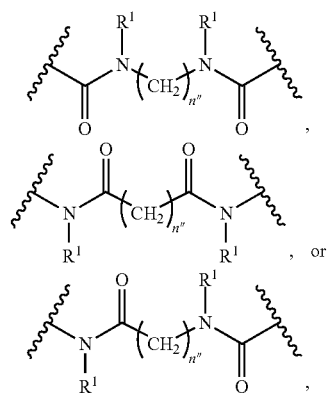

wherein:
each occurrence of $R^1$ is independently H or $C_1$-$C_3$ alkyl; and
each occurrence of n" is independently 0, 1, 2, 3, 4, 5, 6, 7, or 8;

c) a group according to the structure:

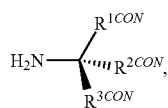

wherein:
$R^{1CON}$, $R^{2CON}$, and $R^{3CON}$ are each independently H, —(CH$_2$)$_{MC1}$—, —(CH$_2$)$_{MC1a}$—, —(CH$_2$)$_{MC1a}$C(O)$_{XA}$(NR$^4$)$_{XA}$—(CH$_2$)$_{MC1a}$—, —(CH$_2$)$_{MC1a}$(NR$^4$)$_{XA}$C(O)$_{XA}$—(CH$_2$)$_{MC1a}$—, or —(CH$_2$)$_{MC1a}$—(CH$_2$)$_{MC1}$—C(O)NR$^4$—,
with the proviso that $R^{1CON}$, $R^{2CON}$, and $R^3$CON are not simultaneously H;
each MC1 is independently 1, 2, 3, or 4;
each MC1a is independently 0, 1, 2, 3, or 4;
each XA is independently 0 or 1; and
each $R^4$ is independently H, $C_1$-$C_3$ alkyl, $C_1$-$C_3$ alkanol, or —C(O)(C$_1$-C$_3$ alkyl),
with the proviso that MC1a and XA in a group are not all simultaneously 0;

each occurrence of [LINKER] is independently:
i) a polyethyleneglycol linker having from 1 to 12 ethylene glycol residues,
ii) a polypropylene glycol or polypropylene-co-polyethylene glycol linker containing 1 to 100 alkylene glycol units,
iii) a group according to the structure:

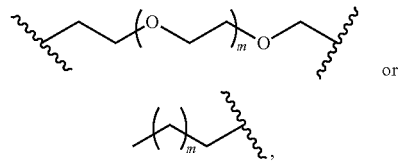 or wherein m is independently 1, 2, 3, 4, 5, 6, 7, 8, 9, 10, 11, 12, 13, 14, or 15;

iv) a group according to the structure:

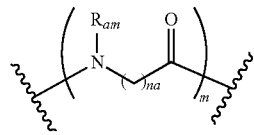

wherein:
$R_{am}$ is H or $C_1$-$C_3$ alkyl optionally substituted with one or two hydroxyl groups;
na is 1, 2, 3, 4, 5, 6, 7, 8, 9, 10, 11, 12, 13, 14, or 15; and
m is an integer from 1 to 100;

v) a group according to the formula:

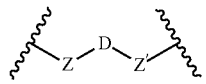

wherein:
Z and Z' are each independently a bond, —(CH$_2$)$_i$—O—, —(CH$_2$)$_i$—S—, —(CH$_2$)$_i$—N(R)—,

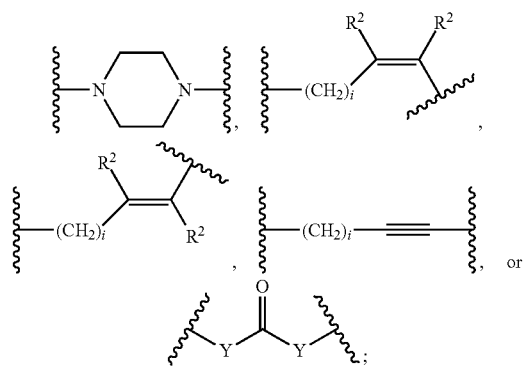

wherein:

the $(CH_2)_i$ group, if present in Z or Z', is bonded to [CON], [CPBM], or [CRBM];

each R is independently H, $C_1$-$C_3$ alkyl, or $C_1$-$C_3$ alkanol;

each $R^2$ is independently H or $C_1$-$C_3$ alkyl;

each Y is independently a bond, —O—, —S—, or —N(R)—;

each i is independently 1, 2, 3, 4, 5, 6, 7, 8, 9, or 10;

D is a bond, —$(CH_2)_i$—Y—C(O)—Y—$(CH_2)_j$—, —$(CH_2)_{m'}$—, or —$[(CH_2)_n$—$X^1]_j$—, with the proviso that Z, Z', and D are not each simultaneously bonds, wherein:

each i is independently 1, 2, 3, 4, 5, 6, 7, 8, 9, or 10;

j is 1, 2, 3, 4, 5, 6, 7, 8, 9, or 10;

m' is 1, 2, 3, 4, 5, 6, 7, 8, 9, or 10;

n is 1, 2, 3, 4, 5, 6, 7, 8, 9, or 10;

$X^1$ is —O—, —S—, or —N(R)—;

R is H, $C_1$-$C_3$ alkyl, or $C_1$-$C_3$ alkanol;

vi) a group according to the structure:

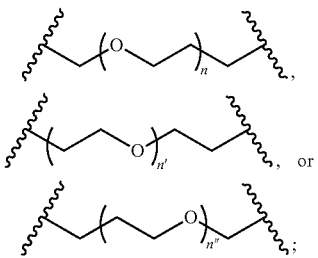

wherein:

n is an integer from 1 to 25;

n' is an integer from 1 to 25; and n" is 0, 1, 2, 3, 4, 5, 6, 7, or 8;

vii) a group of formula: PEG-[CON]-PEG, wherein each PEG is independently at each occurrence 1 to 12 ethylene glycol residues and [CON] is

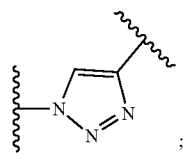 [SMILES: *c1cn(*)nn1]

k' is 1;

j' is 1, 2, or 3;

h and h' are each independently 1, 2, 3, 4, 5, or 6;

$i_L$ is 0, 1, 2, or 3;

or a salt, stereoisomer, or solvate thereof.

11. The method of claim 10, further comprising administering to the subject at least one bioactive agent selected from the group consisting of: everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, AZD2171, batabulin, ofatumumab, zanolimumab, edotecarin, tetrandrine, rubitecan, tesmilifene, oblimersen, ticilimumab, ipilimumab, gossypol, Bio III, 131-I-TM-601, ALT-110, BIO 140, CC 8490, cilengitide, gimatecan, IL13-PE38QQR, INO 1001, $IPdR_1$ KRX-0402, lucanthone, LY317615, neuradiab, vitespan, RTA 744, SDX 102, talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, camptothecin, PEG-labeled irinotecan, tamoxifen, toremifene citrate, anastrozole, exemestane, letrozole, diethylstilbestrol, estradiol, estrogen, conjugated estrogen, bevacizumab, IMC-IC11, CHIR-258, 3-[5-(methylsulfonylpiperadinemethyl)-indolyl-quinolone, vatalanib, AG-013736, AVE-0005, pyro-Glu-His-Trp-Ser-Tyr-D-Ser(But)-Leu-Arg-Pro-Azgly-NH2 acetate $[C_{59}H_{84}N_{18}O_{14} \cdot (C_2H_4O_2)_x$, where x is 1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714, TAK-165, HKI-272, erlotinib, lapatanib, canertinib, ABX-EGF antibody, erbitux, EKB-569, PKI-166, GW-572016, lonafarnib, BMS-214662, tipifarnib, amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxvurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab, erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HNR—3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-trans retinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, vemurafenib, a PD-L1 inhibitor, a PD-1 inhibitor, and a CTLA-4 inhibitor.

12. The method of claim 11, wherein the at least one bioactive agent is administered consecutively or concurrently with the compound, or wherein the at least one bioactive agent is co-formulated with the compound.

13. The method of claim 10, wherein the compound is administered to the subject as a pharmaceutical composition further comprising a pharmaceutically acceptable carrier, additive, or excipient.

14. The method of claim 10, wherein the compound is administered to the subject by a route selected from the group consisting of oral, inhalation, topical, rectal, nasal, buccal, vaginal, via an implanted reservoir, subcutaneous, intravenous, intramuscular, intra-articular, intra-synovial, intrasternal, intrathecal, intrahepatic, intralesional, and intracranial.

15. The method of claim 10, wherein the compound is administered to the subject by a route selected from the group consisting of oral and intravenous.

16. The method of claim 10, wherein the therapeutically effective amount of the compound is about 0.01 to about 200 mg/kg.

* * * * *

SEQUENCE LISTING

<160> NUMBER OF SEQ ID NOS: 95

<210> SEQ ID NO 1
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1

Thr Trp Lys Thr Ser Arg Ile Ser Ile Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 2

Phe Gly Arg Leu Val Ser Ser Ile Arg Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 3

Glu Pro Ile His Arg Ser Thr Leu Thr Ala Leu Leu
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 4

Ala Pro Ala Arg
1

<210> SEQ ID NO 5
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 5

His Trp Arg Gly Trp Val
1               5

<210> SEQ ID NO 6
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 6

His Tyr Phe Lys Phe Asp
1               5

```
<210> SEQ ID NO 7
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 7

His Phe Arg Arg His Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa = citrulline

<400> SEQUENCE: 8

His Trp Xaa Gly Trp Val
1               5

<210> SEQ ID NO 9
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Ala and Glu of Lys-lactic acid-Glu form a ring
<220> FEATURE:
<221> NAME/KEY: misc_feature
<222> LOCATION: (2)..(2)
<223> OTHER INFORMATION: Ser is N-acylated
<220> FEATURE:
<221> NAME/KEY: misc_feature
<222> LOCATION: (8)..(8)
<223> OTHER INFORMATION: C(=O)OH of Lys bonds to lactic acid-Glu

<400> SEQUENCE: 9

Ala Ser Arg Trp His Tyr Phe Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Ala and Glu of Lys-lactic acid-Glu form a ring
<220> FEATURE:
<221> NAME/KEY: misc_feature
<222> LOCATION: (2)..(2)
<223> OTHER INFORMATION: Xaa = N-aceylated 2,3-diaminopropionic acid
<220> FEATURE:
<221> NAME/KEY: misc_feature
<222> LOCATION: (8)..(8)
<223> OTHER INFORMATION: C(=O)OH of Lys bonds to lactic acid-Glu

<400> SEQUENCE: 10

Ala Xaa Arg Trp His Tyr Phe Lys
```

```
<210> SEQ ID NO 11
<211> LENGTH: 7
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Met HN2 is substituted with glutaric acid
<220> FEATURE:
<221> NAME/KEY: misc_feature
<222> LOCATION: (1)..(7)
<223> OTHER INFORMATION: Glutaric acid forms a ring between Lys and Met

<400> SEQUENCE: 11

Met Trp Phe Arg His Tyr Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 12

Asn Lys Phe Arg Gly Lys Tyr Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 13

Asn Ala Arg Lys Phe Tyr Lys Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 14

Phe Tyr Trp His Cys Leu Asp Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 15

Phe Tyr Cys His Trp Ala Leu Glu
1               5

<210> SEQ ID NO 16
<211> LENGTH: 8
<212> TYPE: PRT
```

```
<213> ORGANISM: Artificial Sequence
<220> FEATURE:
<223> OTHER INFORMATION: Chemically Synthesized

<400> SEQUENCE: 16

Phe Tyr Cys His Thr Ile Asp Glu
1               5

<210> SEQ ID NO 17
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 17

Arg Arg Gly Trp
1

<210> SEQ ID NO 18
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 18

Lys His Arg Phe Asn Lys Asp
1               5

<210> SEQ ID NO 19
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-acetylated
<220> FEATURE:
<221> NAME/KEY: misc_feature
<222> LOCATION: (11)..(11)
<223> OTHER INFORMATION: Xaa = neorleucine
<220> FEATURE:
<221> NAME/KEY: misc_feature
<222> LOCATION: (17)..(17)
<223> OTHER INFORMATION: terminus is C(=O)NH2

<400> SEQUENCE: 19

Val Lys Phe Asn Lys Pro Phe Val Phe Leu Xaa Ile Glu Gln Asn Thr
1               5                   10                  15

Lys

<210> SEQ ID NO 20
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 20

Val Lys Phe Asn Lys Pro Phe Val Phe Leu Met Ile Glu Gln Asn Thr
1               5                   10                  15

Lys

<210> SEQ ID NO 21
```

```
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 21

Thr Trp Pro Lys His Phe Asp Lys His Thr Phe Tyr Ser Ile Leu Lys
1               5                   10                  15

Leu Gly Lys His
            20

<210> SEQ ID NO 22
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 22

Thr Phe Phe Tyr Gly Gly Ser Arg Gly Lys Arg Asn Asn Phe Lys Thr
1               5                   10                  15

Glu Glu Tyr

<210> SEQ ID NO 23
<211> LENGTH: 30
<212> TYPE: PRT
<213> ORGANISM: Artificial Sequence
<220> FEATURE:
<223> OTHER INFORMATION: Chemically Synthesized

<400> SEQUENCE: 23

Leu Arg Lys Leu Arg Lys Arg Leu Leu Arg Asp Ala Asp Asp Leu Leu
1               5                   10                  15

Arg Lys Leu Arg Lys Arg Leu Leu Arg Asp Ala Asp Asp Leu
            20                  25                  30

<210> SEQ ID NO 24
<211> LENGTH: 20
<212> TYPE: PRT
<213> ORGANISM: Artificial Sequence
<220> FEATURE:
<223> OTHER INFORMATION: Chemically Synthesized

<400> SEQUENCE: 24

Thr Glu Glu Leu Arg Val Arg Leu Ala Ser His Leu Arg Lys Leu Arg
1               5                   10                  15

Lys Arg Leu Leu
            20

<210> SEQ ID NO 25
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 25

Glu Ala Lys Ile Glu Lys His Asn His Tyr Gln Lys Gln Leu Glu Ile
1               5                   10                  15

Ala His Glu Lys Leu Arg
            20

<210> SEQ ID NO 26
```

```
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 26

Thr Phe Phe Tyr Gly Gly Ser Arg Gly Lys Arg Asn Asn Phe Lys Thr
1               5                   10                  15

Glu Glu Tyr

<210> SEQ ID NO 27
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Cys is a D-amino acid
<220> FEATURE:
<221> NAME/KEY: misc_feature
<222> LOCATION: (1)..(8)
<223> OTHER INFORMATION: Cys and Pen form a ring
<220> FEATURE:
<221> NAME/KEY: misc_feature
<222> LOCATION: (3)..(3)
<223> OTHER INFORMATION: Xaa = thiazolidine-4-carboxylic acid
<220> FEATURE:
<221> NAME/KEY: misc_feature
<222> LOCATION: (8)..(8)
<223> OTHER INFORMATION: Xaa = Penicillamine

<400> SEQUENCE: 27

Cys Met Xaa Arg Leu Arg Gly Xaa
1               5

<210> SEQ ID NO 28
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Cys and Cys form a ring

<400> SEQUENCE: 28

Cys Met Pro Arg Leu Arg Gly Cys
1               5

<210> SEQ ID NO 29
<211> LENGTH: 12
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(9)
<223> OTHER INFORMATION: Cys and Cys form a ring

<400> SEQUENCE: 29

His Leu Asp Cys Met Pro Arg Gly Cys Phe Arg Asn
1               5                   10

<210> SEQ ID NO 30
<211> LENGTH: 9
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 30

Cys Gln Val Lys Ser Met Pro Arg Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 31

Cys Thr Thr Pro Met Pro Arg Leu Cys
1               5

<210> SEQ ID NO 32
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 32

Cys Lys Ala Pro Gln Met Pro Arg Cys
1               5

<210> SEQ ID NO 33
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 33

Cys Leu Asn Pro Ser Met Pro Arg Cys
1               5

<210> SEQ ID NO 34
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 34

Cys Leu Val Ser Ser Met Pro Arg Cys
1               5
```

```
<210> SEQ ID NO 35
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 35

Cys Leu Gln Pro Met Pro Arg Leu Cys
1               5

<210> SEQ ID NO 36
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 36

Cys Pro Val Ser Ser Met Pro Arg Cys
1               5

<210> SEQ ID NO 37
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 37

Cys Gln Ser Pro Met Pro Arg Leu Cys
1               5

<210> SEQ ID NO 38
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(9)
<223> OTHER INFORMATION: Cys and Cys form a ring

<400> SEQUENCE: 38

Cys Leu Thr Pro Met Pro Arg Leu Cys
1               5

<210> SEQ ID NO 39
<211> LENGTH: 15
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (5)..(12)
<223> OTHER INFORMATION: Cys and Cys form a ring
```

```
<400> SEQUENCE: 39

Asp Ser Gly Leu Cys Met Pro Arg Leu Arg Gly Cys Asp Pro Arg
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 40

Thr Pro Ser Ala His Ala Met Ala Leu Gln Ser Leu Ser Val Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-acetylated
<220> FEATURE:
<221> NAME/KEY: misc_feature
<222> LOCATION: (5)..(12)
<223> OTHER INFORMATION: Cys and Cys form a ring
<220> FEATURE:
<221> NAME/KEY: misc_feature
<222> LOCATION: (15)..(15)
<223> OTHER INFORMATION: terminus is C(=O)NH2

<400> SEQUENCE: 41

Asp Ser Gly Leu Cys Met Pro Arg Leu Arg Gly Cys Asp Pro Arg
1               5                   10                  15

<210> SEQ ID NO 42
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Cys and Cys form a ring
<220> FEATURE:
<221> NAME/KEY: misc_feature
<222> LOCATION: (1)..(1)
<223> OTHER INFORMATION: N-propionylated
<220> FEATURE:
<221> NAME/KEY: misc_feature
<222> LOCATION: (8)..(8)
<223> OTHER INFORMATION: terminus is (C=O)NH2

<400> SEQUENCE: 42

Cys Met Pro Arg Leu Arg Gly Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Cys and Cys form a ring
```

```
<220> FEATURE:
<221> NAME/KEY: misc_feature
<222> LOCATION: (1)..(1)
<223> OTHER INFORMATION: N-propionylated D-amino acid
<220> FEATURE:
<221> NAME/KEY: misc_feature
<222> LOCATION: (8)..(8)
<223> OTHER INFORMATION: terminus is C(=O)NH2

<400> SEQUENCE: 43

Cys Met Pro Arg Leu Arg Gly Cys
1               5

<210> SEQ ID NO 44
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Propionylated D-amino acid
<220> FEATURE:
<221> NAME/KEY: misc_feature
<222> LOCATION: (1)..(8)
<223> OTHER INFORMATION: Cys and Pen form a ring
<220> FEATURE:
<221> NAME/KEY: misc_feature
<222> LOCATION: (3)..(3)
<223> OTHER INFORMATION: Xaa = thiazolidine-4-carboxylic acid
<220> FEATURE:
<221> NAME/KEY: misc_feature
<222> LOCATION: (8)..(8)
<223> OTHER INFORMATION: Xaa = penacillamine, terminus is C(=O)NH2

<400> SEQUENCE: 44

Cys Met Xaa Arg Leu Arg Gly Xaa
1               5

<210> SEQ ID NO 45
<211> LENGTH: 7
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(7)
<223> OTHER INFORMATION: Cys and Cys form a ring
<220> FEATURE:
<221> NAME/KEY: misc_feature
<222> LOCATION: (1)..(1)
<223> OTHER INFORMATION: N-acetylated
<220> FEATURE:
<221> NAME/KEY: misc_feature
<222> LOCATION: (7)..(7)
<223> OTHER INFORMATION: terminus is C(=O)NH2

<400> SEQUENCE: 45

Cys Met Pro Arg Leu Gly Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Cys and Cys form a ring
```

```
<220> FEATURE:
<221> NAME/KEY: misc_feature
<222> LOCATION: (1)..(1)
<223> OTHER INFORMATION: N-acetylated D-amino acid
<220> FEATURE:
<221> NAME/KEY: misc_feature
<222> LOCATION: (8)..(8)
<223> OTHER INFORMATION: terminus is C(=O)NH2

<400> SEQUENCE: 46

Cys Met Pro Arg Leu Arg Gly Cys
1               5

<210> SEQ ID NO 47
<211> LENGTH: 9
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-acetylated
<220> FEATURE:
<221> NAME/KEY: misc_feature
<222> LOCATION: (2)..(9)
<223> OTHER INFORMATION: Pen and Cys form a ring
<220> FEATURE:
<221> NAME/KEY: misc_feature
<222> LOCATION: (2)..(2)
<223> OTHER INFORMATION: Xaa = Penicillamine
<220> FEATURE:
<221> NAME/KEY: misc_feature
<222> LOCATION: (4)..(4)
<223> OTHER INFORMATION: Xaa = thiazolidine-4-carboxylic acid
<220> FEATURE:
<221> NAME/KEY: misc_feature
<222> LOCATION: (9)..(9)
<223> OTHER INFORMATION: terminus is C(=O)NH2

<400> SEQUENCE: 47

Asp Xaa Met Xaa Arg Leu Arg Gly Cys
1               5

<210> SEQ ID NO 48
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-propionylated D-amino acid
<220> FEATURE:
<221> NAME/KEY: misc_feature
<222> LOCATION: (1)..(8)
<223> OTHER INFORMATION: Cys and Pen form a ring
<220> FEATURE:
<221> NAME/KEY: misc_feature
<222> LOCATION: (3)..(3)
<223> OTHER INFORMATION: Xaa = thiazolidine-4-carboxylic acid
<220> FEATURE:
<221> NAME/KEY: misc_feature
<222> LOCATION: (8)..(8)
<223> OTHER INFORMATION: Xaa = Penicillamine, terminus is C(=O)NH2

<400> SEQUENCE: 48

Cys Met Xaa Arg Leu Arg Gly Xaa
1               5

<210> SEQ ID NO 49
<211> LENGTH: 8
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-propionylated
<220> FEATURE:
<221> NAME/KEY: misc_feature
<222> LOCATION: (1)..(8)
<223> OTHER INFORMATION: Cys and Pen form a ring
<220> FEATURE:
<221> NAME/KEY: misc_feature
<222> LOCATION: (3)..(3)
<223> OTHER INFORMATION: Xaa = thiazolidine-4-carboxylic acid
<220> FEATURE:
<221> NAME/KEY: misc_feature
<222> LOCATION: (7)..(7)
<223> OTHER INFORMATION: Xaa = Sarcosine
<220> FEATURE:
<221> NAME/KEY: misc_feature
<222> LOCATION: (8)..(8)
<223> OTHER INFORMATION: Xaa = Penicillamine, terminus is C(=O)NH2

<400> SEQUENCE: 49

Cys Met Xaa Arg Leu Arg Xaa Xaa
1               5

<210> SEQ ID NO 50
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-propionylated D-amino acid
<220> FEATURE:
<221> NAME/KEY: misc_feature
<222> LOCATION: (1)..(8)
<223> OTHER INFORMATION: Cys and Cys form ring
<220> FEATURE:
<221> NAME/KEY: misc_feature
<222> LOCATION: (3)..(3)
<223> OTHER INFORMATION: Xaa = Pipecolic group
<220> FEATURE:
<221> NAME/KEY: misc_feature
<222> LOCATION: (7)..(7)
<223> OTHER INFORMATION: Xaa = Sarcosine
<220> FEATURE:
<221> NAME/KEY: misc_feature
<222> LOCATION: (8)..(8)
<223> OTHER INFORMATION: terminus is C(=O)NH2

<400> SEQUENCE: 50

Cys Met Xaa Arg Leu Arg Xaa Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-propionylated D-amino acid
<220> FEATURE:
<221> NAME/KEY: misc_feature
<222> LOCATION: (1)..(8)
<223> OTHER INFORMATION: Cys and Pen form a ring
<220> FEATURE:
```

```
<221> NAME/KEY: misc_feature
<222> LOCATION: (3)..(3)
<223> OTHER INFORMATION: Xaa = Pipecolic group
<220> FEATURE:
<221> NAME/KEY: misc_feature
<222> LOCATION: (8)..(8)
<223> OTHER INFORMATION: Xaa = penacillamine, terminus is C(=O)NH2

<400> SEQUENCE: 51

Cys Met Xaa Arg Leu Arg Gly Xaa
1               5

<210> SEQ ID NO 52
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-propionylated D-amino acid
<220> FEATURE:
<221> NAME/KEY: misc_feature
<222> LOCATION: (1)..(8)
<223> OTHER INFORMATION: Cys and Pen form a ring
<220> FEATURE:
<221> NAME/KEY: misc_feature
<222> LOCATION: (3)..(3)
<223> OTHER INFORMATION: Xaa = Pipecolic group
<220> FEATURE:
<221> NAME/KEY: misc_feature
<222> LOCATION: (7)..(7)
<223> OTHER INFORMATION: Xaa = Sarcosine
<220> FEATURE:
<221> NAME/KEY: misc_feature
<222> LOCATION: (8)..(8)
<223> OTHER INFORMATION: Xaa = penacillamine, terminus is C(=O)NH2

<400> SEQUENCE: 52

Cys Met Xaa Arg Leu Arg Xaa Xaa
1               5

<210> SEQ ID NO 53
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 53

Thr Asp Thr Cys Leu Met Leu Pro Leu Leu Leu Gly Cys Asp Glu Glu
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 54

Asp Pro Ile Cys Trp Tyr Phe Pro Arg Leu Leu Gly Cys Thr Thr Leu
1               5                   10                  15
```

<210> SEQ ID NO 55
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 55

Trp Tyr Pro Cys Tyr Ile Tyr Pro Arg Leu Leu Gly Cys Asp Gly Asp
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 56

Gly Asn Ile Cys Met Leu Ile Pro Gly Leu Leu Gly Cys Ser Tyr Glu
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 57

Val Asn Ser Cys Leu Leu Leu Pro Asn Leu Leu Gly Cys Gly Asp Asp
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 58

Thr Pro Val Cys Ile Leu Leu Pro Ser Leu Leu Gly Cys Asp Thr Gln
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)

```
<223> OTHER INFORMATION: Cys and Cys form a ring

<400> SEQUENCE: 59

Thr Val Leu Cys Ser Leu Trp Pro Glu Leu Leu Gly Cys Pro Pro Glu
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 60

Thr Phe Ser Cys Leu Met Trp Pro Trp Leu Leu Gly Cys Glu Ser Leu
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 61

Phe Gly Thr Cys Tyr Thr Trp Pro Trp Leu Leu Gly Cys Glu Gly Phe
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 62

Ser Leu Phe Cys Arg Leu Leu Thr Pro Val Gly Cys Val Ser Gln
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 63

His Leu Leu Val Leu Pro Arg Gly Leu Leu Gly Cys Thr Thr Leu Ala
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Chemically Synthesized
<220> FEATURE:
```

```
<221> NAME/KEY: misc_feature
<222> LOCATION: (4)..(13)
<223> OTHER INFORMATION: Cys and Cys form a ring

<400> SEQUENCE: 64

Thr Ser Leu Cys Ser Met Phe Pro Asp Leu Leu Gly Cys Phe Asn Leu
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 65

Ser His Pro Cys Gly Arg Leu Pro Met Leu Leu Gly Cys Ala Glu Ser
1               5                   10                  15

<210> SEQ ID NO 66
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 66

Thr Ser Thr Cys Ser Met Val Pro Gly Pro Leu Gly Ala Val Ser Thr
1               5                   10                  15

Trp

<210> SEQ ID NO 67
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 67

Lys Asp Pro Cys Thr Arg Trp Ala Met Leu Leu Gly Cys Asp Gly Glu
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 68

Ile Met Thr Cys Ser Val Tyr Pro Phe Leu Leu Gly Cys Val Asp Lys
1               5                   10                  15

<210> SEQ ID NO 69
<211> LENGTH: 16
<212> TYPE: PRT
```

```
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(13)
<223> OTHER INFORMATION: Cys and Cys form a ring

<400> SEQUENCE: 69

Ile His Ser Cys Ala His Val Met Arg Leu Leu Gly Cys Trp Ser Arg
1               5                   10                  15

<210> SEQ ID NO 70
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-acetylated
<220> FEATURE:
<221> NAME/KEY: misc_feature
<222> LOCATION: (4)..(14)
<223> OTHER INFORMATION: Cys and Cys form a ring
<220> FEATURE:
<221> NAME/KEY: misc_feature
<222> LOCATION: (17)..(17)
<223> OTHER INFORMATION: terminus is C(=O)NH2

<400> SEQUENCE: 70

Gln Arg Phe Cys Thr Gly His Phe Gly Gly Leu Tyr Pro Cys Asn Gly
1               5                   10                  15

Pro

<210> SEQ ID NO 71
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: N-acetylated
<220> FEATURE:
<221> NAME/KEY: misc_feature
<222> LOCATION: (3)..(3)
<223> OTHER INFORMATION: Xaa = Penacillamine
<220> FEATURE:
<221> NAME/KEY: misc_feature
<222> LOCATION: (3)..(13)
<223> OTHER INFORMATION: Pen and Cys form a ring
<220> FEATURE:
<221> NAME/KEY: misc_feature
<222> LOCATION: (9)..(9)
<223> OTHER INFORMATION: Xaa = sarcosine
<220> FEATURE:
<221> NAME/KEY: misc_feature
<222> LOCATION: (10)..(10)
<223> OTHER INFORMATION: Xaa = N-methylleucine
<220> FEATURE:
<221> NAME/KEY: misc_feature
<222> LOCATION: (13)..(13)
<223> OTHER INFORMATION: terminus is C(=O)NH2

<400> SEQUENCE: 71

Arg Phe Xaa Thr Gly His Phe Gly Xaa Xaa Tyr Pro Cys
1               5                   10

<210> SEQ ID NO 72
```

```
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 72

Cys Gly Gly Gly Pro Phe Trp Trp Trp Pro
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 73

Cys Gly Gly Gly His Lys Tyr Leu Arg Trp
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 74

Cys Gly Gly Gly Lys Arg Ile Phe Met Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 75

Cys Gly Gly Gly Lys Trp His Tyr Leu Arg
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 76

Thr His Arg Pro Pro Met Trp Ser Pro Val Trp Pro
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 77

His Ala Ile Tyr Pro Arg His
1               5

<210> SEQ ID NO 78
<211> LENGTH: 12
```

```
<212> TYPE: PRT
<213> ORGANISM: Artificial Sequence
<220> FEATURE:
<223> OTHER INFORMATION: Chemically Synthesized

<400> SEQUENCE: 78

Thr His Arg Pro Pro Met Trp Ser Pro Val Trp Pro
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 79

Thr His Arg Pro Pro Met Trp Ser Pro Val Trp Pro
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 80

Leu Ser Leu Glu Arg Phe Leu Arg Cys Trp Ser Asp Ala Pro Ala
1               5                   10                  15

<210> SEQ ID NO 81
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 81

Leu Glu Arg Phe Leu Arg Cys Trp Ser Asp Ala Pro Ala
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 82

Arg Phe Leu Arg Cys Trp Ser Asp Ala Pro Ala
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 83

Leu Arg Cys Trp Ser Asp Ala Pro Ala
1               5

<210> SEQ ID NO 84
<211> LENGTH: 7
<212> TYPE: PRT
```

```
<213> ORGANISM: Artificial Sequence
<220> FEATURE:
<223> OTHER INFORMATION: Chemically Synthesized

<400> SEQUENCE: 84

Cys Trp Ser Asp Ala Pro Ala
1               5

<210> SEQ ID NO 85
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 85

Asp Trp Phe Lys Ala Phe Tyr Asp Lys Val Ala Glu Lys Phe Lys Glu
1               5                   10                  15
Ala Phe

<210> SEQ ID NO 86
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 86

Glu Ala Lys Ile Glu Lys His Asn His Tyr Gln Lys
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(12)
<223> OTHER INFORMATION: Cys and Cys form a ring
<220> FEATURE:
<221> NAME/KEY: misc_feature
<222> LOCATION: (13)..(13)
<223> OTHER INFORMATION: terminus is C(=O)NH2

<400> SEQUENCE: 87

Asp Cys Ala Trp His Leu Gly Glu Leu Val Trp Cys Thr
1               5                   10

<210> SEQ ID NO 88
<211> LENGTH: 15
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(15)
<223> OTHER INFORMATION: Cys and Cys form a ring
<220> FEATURE:
<221> NAME/KEY: misc_feature
<222> LOCATION: (3)..(13)
<223> OTHER INFORMATION: Cys and Cys form a ring
<220> FEATURE:
<221> NAME/KEY: misc_feature
<222> LOCATION: (15)..(15)
<223> OTHER INFORMATION: terminus is C(=O)NH2

<400> SEQUENCE: 88
```

```
Cys Asp Cys Ala Trp His Leu Gly Glu Leu Val Trp Cys Thr Cys
1               5                   10                  15

<210> SEQ ID NO 89
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 89

Tyr Cys Leu Tyr Gln Ser Trp Cys Tyr
1               5

<210> SEQ ID NO 90
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 90

Thr Val Phe Thr Ser Trp Glu Glu Tyr Leu Asp Trp Val
1               5                   10

<210> SEQ ID NO 91
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 91

Val Glu Pro Asn Cys Asp Ile His Val Met Trp Glu Trp Glu Cys Phe
1               5                   10                  15

Glu Arg Leu

<210> SEQ ID NO 92
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 92

Lys Arg Phe Lys Gln Asp Gly Gly Cys
1               5

<210> SEQ ID NO 93
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 93

Arg Gly Gln Ile Leu Ser Lys Leu Arg Leu
1               5                   10

<210> SEQ ID NO 94
<211> LENGTH: 4
<212> TYPE: PRT
<213> ORGANISM: Artificial Sequence
<220> FEATURE:
<223> OTHER INFORMATION: Chemically Synthesized
```

```
<400> SEQUENCE: 94

Lys Arg Phe Lys
1

<210> SEQ ID NO 95
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 95

Leu Ser Lys Leu
1
```